United States Patent
Chen et al.

(10) Patent No.: US 7,572,809 B2
(45) Date of Patent: Aug. 11, 2009

(54) ISOQUINOLINE AMINOPYRAZOLE DERIVATIVES

(75) Inventors: Li Chen, Shanghai (CN); Guy Georges, Habach (DE); Alfred Mertens, Schriesheim (DE); Xihan Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 211 days.

(21) Appl. No.: 11/637,733

(22) Filed: Dec. 12, 2006

(65) Prior Publication Data

US 2007/0179151 A1    Aug. 2, 2007

(30) Foreign Application Priority Data

Dec. 19, 2005    (EP) .................................. 05027720

(51) Int. Cl.
C07D 403/14    (2006.01)
A61K 31/4709    (2006.01)

(52) U.S. Cl. ........................ 514/307; 546/141; 546/143; 514/309

(58) Field of Classification Search ........................ None
See application file for complete search history.

(56) References Cited

U.S. PATENT DOCUMENTS

2005/0209297 A1    9/2005    Sanner et al.

FOREIGN PATENT DOCUMENTS

| WO | WO 00/44728 | 8/2000 |
|---|---|---|
| WO | WO 02/22601 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 3/2002 |
| WO | WO 02/50065 | 6/2002 |
| WO | WO 02/50066 | 6/2002 |
| WO | WO 02/057259 | 7/2002 |
| WO | WO 02/059111 | 8/2002 |
| WO | WO 02/062789 | 8/2002 |
| WO | WO 02/066461 | 8/2002 |
| WO | WO 02/068415 | 9/2002 |
| WO | WO 02/096905 | 12/2002 |
| WO | WO 2005/002552 | 1/2005 |

*Primary Examiner*—Zinna N Davis
(74) *Attorney, Agent, or Firm*—George W. Johnston; Patricia S. Rocha-Tramaloni; Gene J. Yao

(57) ABSTRACT

The present invention relates to the compounds of formula I:

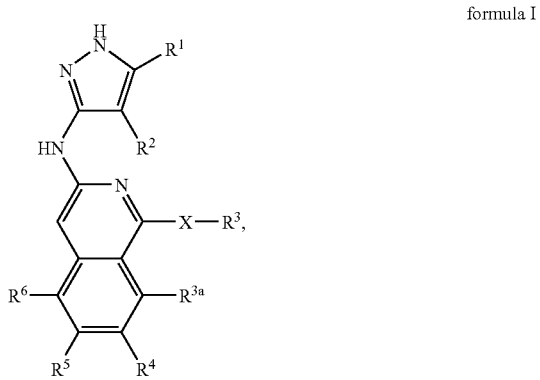

formula I their pharmaceutically acceptable salts or esters, enantiomeric forms, diastereoisomers and racemates, the preparation of such compounds, pharmaceutical compositions containing them and their manufacture, as well as the use of such compounds in the control or prevention of illnesses such as cancer.

74 Claims, No Drawings

ISOQUINOLINE AMINOPYRAZOLE DERIVATIVES

PRIORITY TO RELATED APPLICATIONS

This application claims the benefit of European Application No. 05027720.1, filed Dec. 19, 2005, which is hereby incorporated by reference in its entirety.

The present invention relates to novel isoquinoline aminopyrazole derivatives as protein kinase inhibitors, to a process for their manufacture, pharmaceutical compositions containing them and their manufacture as well as the use of these compounds as pharmaceutically active agents.

BACKGROUND OF THE INVENTION

Protein kinases regulate many different signaling processes by adding phosphate groups to proteins (Hunter, T., Cell 50 (1987) 823-829); particularly serine/threonine kinases phosphorylate proteins on the alcohol moiety of serine or threonine residues. The serine/threonine kinase family includes members that control cell growth, migration, differentiation, gene expression, muscle contraction, glucose metabolism, cellular protein synthesis, and regulation of the cell cycle.

The Aurora kinases are a family of serine/threonine kinases that are believed to play a key role in the protein phosphorylation events that are essential for the completion of essential mitotic events. The Aurora kinase family is made up of three key members: Aurora A, B and C (also known as Aurora-2, Aurora-1 and Aurora-3 respectively). Aurora-1 and Aurora-2 are described in U.S. Pat. No. 6,207,401 of Sugen and in related patents and patent applications, e.g. EP 0 868 519 and EP 1 051 500.

For Aurora A there is increasing evidence that it is a novel proto-oncogene. Aurora A gene is amplified and transcript/protein is highly expressed in a majority of human tumor cell lines and primary colorectal, breast and other tumors. It has been shown that Aurora A overexpression leads to genetic instability shown by amplified centrosomes and significant increase in aneuploidy and transforms Rat1 fibroblasts and mouse NIH3T3 cells in vitro. Aurora A-transformed NIH3T3 cells grow as tumors in nude mice (Bischoff, J. R., and Plowman, G. D., Trends Cell Biol. 9 (1999) 454-459; Giet, R., and Prigent, C., J. Cell Sci. 112 (1999) 3591-3601; Nigg, E. A., Nat. Rev. Mol. Cell. Biol. 2 (2001) 21-32; Adams, R. R., et al., Trends Cell Biol. 11 (2001) 49-54). Moreover, amplification of Aurora A is associated with aneuploidy and aggressive clinical behavior (Sen, S., et al., J. Natl. Cancer Inst. 94 (2002) 1320-1329) and amplification of its locus correlates with poor prognosis for patients with node-negative breast cancer (Isola, J. J., et al., Am. J. Pathology 147 (1995) 905-911). For these reasons it is proposed that Aurora A overexpression contributes to cancer phenotype by being involved in chromosome segregation and mitotic checkpoint control.

Human tumor cell lines depleted of Aurora A transcripts arrest in mitosis. Accordingly, the specific inhibition of Aurora kinase by selective inhibitors is recognized to stop uncontrolled proliferation, re-establish mitotic checkpoint control and lead to apoptosis of tumor cells. In a xenograft model, an Aurora inhibitor therefore slows tumor growth and induces regression (Harrington, E. A., et al., Nat. Med. 10 (2004) 262-267).

Low molecular weight inhibitors for protein kinases are widely known in the state of the art. For Aurora inhibition such inhibitors are based on i.e. quinazoline derivatives (e.g. WO 00/44728), pyrimidine derivatives (e.g. WO 03/077921) imidazole, oxazole and thiazole derivatives (e.g. WO 02/96905 or WO 04/005283).

Aurora kinase inhibitors on the basis of pyrazole derivatives are described e.g. in WO 02/22601; WO 02/22602; WO 02/22603; WO 02/22604; WO 02/22605; WO 02/22606; WO 02/22607; WO 02/22608; WO 02/50065; WO 02/50066; WO 02/057259; WO 02/059111; WO 02/062789; WO 02/066461; WO 02/068415 or WO 2005/002552.

SUMMARY OF THE INVENTION

The present invention relates to tricyclic aminopyrazole derivatives of the general formula I and all pharmaceutically acceptable salts or esters thereof wherein formula I is:

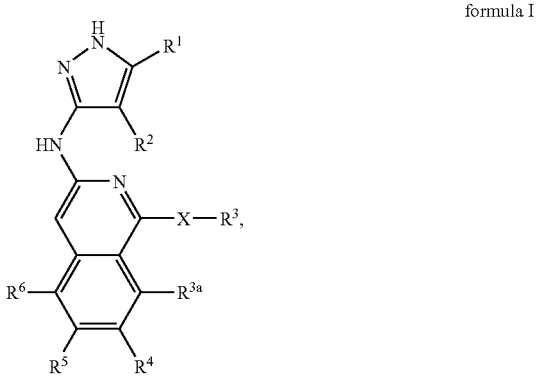

formula I wherein:
(a) $R^1$ is hydrogen, alkyl or cycloalkyl;
(b) $R^2$ is hydrogen or alkyl;
(c) $R^3$ is selected from the group consisting of:
  (1) unsubstituted alkyl,
  (2) alkyl which is substituted one or two times with —C(O)O-alkyl, heteroaryl, phenyl, heterocyclyl or cycloalkyl,
  (3) alkyl wherein one or more —CH$_2$-groups are replaced by oxygen,
  (4) aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR$_2$,
  (5) heteroaryl which is optionally substituted one or more times with alkyl,
  (6) cycloalkyl, and
  (7) heterocyclyl;
(d) $R^{3a}$ is hydrogen, alkyl or alkoxy;
(e) $R^4$ is hydrogen, alkyl, alkoxy, halogen, cyano, —C(O)NR$_2$, —(CH$_2$)$_n$—Y—R$^7$ or -Z-R$^8$;
(f) $R^5$ is hydrogen, alkyl, alkoxy, halogen, cyano, —C(O)NR$_2$, —(CH$_2$)$_n$—Y—R$^7$ or -Z-R$^8$; and $R^6$ is hydrogen, alkyl, alkoxy, halogen or cyano; or alternatively $R^5$ and $R^6$ form together with the carbon atoms to which they are attached a 5- or 6-membered heterocyclic ring;
(g) X is a single bond, —NR—, —O—, —S—, —C(O)— or —C(O)NR—;
(h) Y is —O—, —NR—, —S—, —S(O)$_2$NR—, —NRC(O)—, —NRC(O)O— or —C(O)NR—;
(i) Z is —C(O)—, —O—, a single bond or alkylene;

(j) $R^7$ is cycloalkyl; or alkyl, which is optionally substituted one or more times by alkoxy, hydroxy, alkylsulfonyl, heterocyclyl or —$NR_2$;
(k) $R^8$ is heterocyclyl;
(l) R is hydrogen or alkyl; and
(m) n is 0, 1, 2 or 3.

The compounds according to this invention show activity as protein kinase inhibitors. Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds according to this invention show activity as protein kinase inhibitors, in particular as Aurora family kinase inhibitors, especially as Aurora A kinase inhibitors, and may therefore be useful for the treatment of diseases mediated by said kinase. Aurora A inhibition leads to cell cycle arrest in the G2 phase of the cell cycle and exerts an antiproliferative effect in tumor cell lines. This indicates that Aurora A inhibitors may be useful in the treatment of i.e., hyperproliferative diseases such as cancer and in particular colorectal cancer, breast cancer, lung cancer, prostate cancer, pancreatic cancer, gastric cancer, bladder cancer, ovarian cancer, melanoma, neuroblastoma, cervical cancer, kidney or renal cancers, leukemias or lymphomas. In addition, Aurora A inhibitors may be useful for treating acute-myelogenous leukemia (AML), acute lymphocytic leukemia (ALL) and gastrointestinal stromal tumor (GIST).

The present invention provides the compounds of formula I and their tautomers, pharmaceutically acceptable salts or esters, enantiomeric forms, diastereoisomers and racemates, their use as Aurora kinase inhibitors, the preparation of the above-mentioned compounds, pharmaceutical compositions containing them and their manufacture as well as the use of the above-mentioned compounds in the treatment, control or prevention of illnesses and disorders, especially of the illnesses and disorders as mentioned above like tumors or cancer (e.g. colorectal cancer, breast cancer, lung cancer, prostate cancer, pancreatic cancer, gastric cancer, bladder cancer, ovarian cancer, melanoma, neuroblastoma, cervical cancer, kidney or renal cancers, leukemias or lymphomas) or in the manufacture of corresponding pharmaceutical compositions.

DETAILED DESCRIPTION OF THE INVENTION

1. Definitions

The term "alkyl" as used herein means a saturated, straight-chain or branched-chain hydrocarbon containing from 1 to 6 carbon atoms such as methyl, ethyl, n-propyl, isopropyl, n-butyl, 2-butyl, t-butyl, n-pentyl, or n-hexyl. The alkyl may be substituted or unsubstituted. In preferred embodiments the alkyl contains from 1 to 4 carbon atoms. In particular embodiments, if an alkyl group can be substituted once or twice, such alkyl group is preferably substituted once.

The term "alkyl wherein one or more —$CH_2$-groups are replaced by oxygen" as used herein means a saturated, straight-chain or branched-chain hydrocarbon containing from 3 to 10 carbon atoms wherein one or more —$CH_2$- groups are replaced by oxygen with the proviso that: (1) such alkyl groups are a attached to X in formula I via a carbon atom, and (2) no two adjacent —$CH_2$-groups are replaced by oxygen. Examples of such alkyl groups wherein one or more —$CH_2$-groups are replaced by oxygen include, for example, 2-(2-ethoxy-ethoxy)-ethyl, (2-ethoxy-ethoxy)-methyl, 2-(ethoxy-methoxy)-ethyl, methoxy-ethyl, methoxy-methyl, ethoxy-methyl, [2-(2-ethoxy-ethoxy)-ethoxy]-methyl, 2-[2-(2-ethoxy-ethoxy)-ethoxy]-ethyl and the like. In particular embodiments, the "alkyl wherein one or more —$CH_2$-groups are replaced by oxygen" is preferably a straight-chain hydrocarbon containing 3 to 8 carbon atoms wherein one to three $CH_2$-groups are replaced by oxygen. In a particular preferred embodiment the "alkyl wherein one or more —$CH_2$-groups are replaced by oxygen" is 2-(2-ethoxy-ethoxy)-ethyl.

The term "halogenated alkyl" as used herein means an alkyl group as defined above which is substituted one or more times by halogen. Examples of halogenated alkyls include difluoromethyl, trifluoromethyl, 2,2,2-trifluoroethyl, perfluorethyl, and the like. In particular embodiments the halogenated alkyl is preferably substituted one to six times by halogen, and more preferably one to three times by halogen. In particular preferred embodiments the halogen is fluorine or chlorine; and in a particular preferred embodiment the halogen is fluorine. In a particular preferred embodiment the halogenated alkyl is trifluoromethyl.

The term "halogenated alkoxy" as used herein means an alkoxy group as defined above which is substituted one or more times by halogen. Examples of halogenated alkoxys are difluoromethoxy, trifluoromethoxy, 2,2,2-trifluoroethoxy, perfluoroethoxy and the like. In particular preferred embodiments the halogen is fluorine or chlorine; and in a particular preferred embodiment the halogen is fluorine. In a particular preferred embodiment the halogenated alkoxy is trifluoromethoxy.

The term "alkoxy" as used herein means an alkyl-O— group wherein the alkyl is defined as above. Examples include, for example, methoxy, ethoxy, isopropoxy, n-butoxy, 1-methyl-propoxy, 2-methyl-propoxy and the like.

The term "alkoxy substituted by heterocyclyl or —$NR_2$" as used herein means an alkoxy as defined above which is substituted one or two times by heterocyclyl or by —$NR_2$. Examples include 2-morpholin-4-yl-ethoxy, 2-dimethylamino-ethoxy and the like. In particular preferred embodiments the alkoxy is substituted one time, preferably by morpholinyl.

The term "alkylsulfonyl" as used herein means an alkyl-S$(O)_2$— group wherein the alkyl is defined as above. Examples include methylsulfonyl, ethylsulfonyl, isopropylsulfonyl, n-butylsulfonyl, 1-methyl-propylsulfonyl and the like (preferably methylsulfonyl or ethylsulfonyl).

The term "alkylene" as used herein means a saturated, straight-chain hydrocarbon containing from 1 to 3 carbon atoms such as methylene, ethylene, or trimethylene (1,3-propylene). In particular preferred embodiments the alkylene is a saturated, straight-chain hydrocarbon containing 1 to 2 carbon atoms.

The term "halogen" means fluorine, chlorine, bromine or iodine. In certain preferred embodiments the halogen is fluorine, chlorine or bromine and more preferably fluorine or chlorine.

The term "aryl" means a mono- or bicyclic aromatic ring with 6 to 10 ring carbon atoms. Examples of such aryl groups are phenyl and naphthyl (preferably phenyl). If such aryl is substituted one or more times, it is preferably substituted one to five times, more preferably one to three times, and more preferably one to two times.

The term "heteroaryl" means a mono- or bicyclic aromatic ring with 5 to 10 ring atoms, which contains up to 3 heteroatoms selected independently from the group consisting of N, O and S with the remaining ring atoms being carbon atoms.

Examples of such heteroaryl groups include pyrrolyl, imidazolyl, pyrazolyl, triazolyl, tetrazolyl, furanyl, oxazolyl, isoxazolyl, thienyl, thiazolyl, pyridyl, pyrimidyl, pyridazinyl, pyrazinyl, indolyl, indazolyl, benzimidazolyl, benzothiophenyl, benzofuranyl, quinolyl, isoquinolyl, quinazolinyl and the like (preferably pyridyl, pyrazolyl, thienyl, or benzothiophenyl and more preferably pyridyl, pyrazolyl, or thienyl). In particular preferred embodiments the heteroaryl is a mono- or bicyclic aromatic ring with 5 to 6 ring atoms which preferably contains 1 or 2 heteroatoms. If such heteroaryl is substituted one or more times, it is preferably substituted one to three times, and more preferably one or two times. In one embodiment of the invention such heteroaryl groups are unsubstituted.

The term "cycloalkyl" means a monocyclic saturated hydrocarbon ring with 3 to 7 ring atoms optionally substituted one or more times by alkyl or hydroxy. In particular preferred embodiments the cycloalkyl is a monocyclic saturated hydrocarbon ring with 3 to 6 ring atoms optionally substituted one to three times (preferably one to two times) by alkyl or hydroxyl (preferably by alkyl). In particular preferred embodiments such saturated carbocyclic groups are unsubstituted. Examples of such saturated carbocyclic groups are cyclopropyl, cyclobutyl, cyclopentyl, cyclohexyl, cycloheptyl, 3-methyl-cyclopentyl, 3,3-dimethyl-cyclohexyl, 3-methyl-cyclohexyl, and 2-methyl-cyclohexyl (preferably cyclopropyl, cyclobutyl, cyclopentyl or cyclohexyl).

The term "heterocyclyl" means a saturated, monocyclic ring with 4 to 7 ring atoms which contains up to 3 heteroatoms independently selected from the group consisting of N, O and S with the remaining ring atoms being carbon atoms. Preferably the heterocycyl has 4 to 6 ring atoms and more preferably 5 to 6 ring atoms, which preferably contains 1 or 2 heteroatoms. Preferably at least one heteroatom is nitrogen and the remaining heteroatoms are independently selected from the group consisting of nitrogen, oxygen and sulfur, and such heterocyclyl group is preferably attached to the compound of formula I via the ring nitrogen atom. Such saturated heterocyclyl group can be optionally substituted one to three times (preferably one or two times) by:
  (a) alkyl, which is defined as above (preferably by methyl),
  (b) —C(O)-alkyl (preferably by acetyl),
  (c) oxo,
  (d) —S(O)$_2$-alkyl,
  (e) alkoxy (preferably by methoxy),
  (f) hydroxy,
  (g) alkoxyalkyl, or
  (h) —C(O)NH$_2$.

If such saturated heterocyclyl group are substituted they are preferably substituted one or two times by: (a) alkyl (preferably by methyl); (b) —C(O)-alkyl (preferably by acetyl); (c) oxo; or (d) —S(O)$_2$-alkyl. If the heterocycles in the definition of R$^3$ are substituted they are preferably substituted one or two times by alkyl, —C(O)-alkyl or oxo. If the heterocycles in the definition of R$^7$ and R$^8$ are substituted they are preferably substituted one or two times by: (a) alkyl, which is defined as above (preferably by methyl); (b) —C(O)-alkyl (preferably by acetyl); (c) oxo; (d) —S(O)$_2$-alkyl; (e) alkoxy (preferably by methoxy); (f) hydroxyl; (g) alkoxyalkyl; or (h) —C(O)NH$_2$.

Examples of such saturated heterocyclic groups are oxetanyl, pyrrolidinyl, 2-oxo-pyrrolidin-1-yl, 2-carbamoyl-pyrrolidin-1-yl, morpholinyl, thiomorpholinyl, piperazinyl, N-methyl-piperazinyl, 3,5-dimethyl-piperazin-1-yl, 4-(2-methoxy-ethyl)-piperazin-1-yl, N-acetyl-piperazinyl, N-methylsulfonyl-piperazinyl, 3-oxo-piperazin-1-yl, 2-oxo-piperazin-1-yl, 1,1-Dioxo-1$\lambda^6$-thiomorpholin-4-yl, piperidyl, 4-methoxy-piperidin-1-yl, 4-methoxy-piperidin-1-yl, 2-oxo-piperidin-1-yl, oxazolidinyl, 2-oxo-oxazolidin-3-yl, thiazolidinyl, tetrahydropyranyl, tetrahydrofuranyl and the like. In certain preferred embodiments the heterocyclic group is oxetanyl, pyrrolidinyl, 2-oxo-pyrrolidin-1-yl, 2-carbamoyl-pyrrolidin-1-yl, morpholinyl, piperazinyl, N-methyl-piperazinyl, 3,5-dimethyl-piperazin-1-yl, 4-(2-methoxy-ethyl)-piperazin-1-yl, N-acetyl-piperazinyl, N-methylsulfonyl-piperazinyl, piperidyl, 4-methoxy-piperidin-1-yl, 4-hydroxy-piperidin-1-yl, 2-oxo-piperidin-1-yl, 2-oxo-oxazolidin-3-yl, tetrahydropyranyl or tetrahydrofuranyl; and more preferably morpholinyl, piperazinyl, piperidyl, N-methyl-piperazinyl, N-acetyl-piperazinyl or 2-oxo-oxazolidin-3-yl; and still more preferably morpholinyl. Preferred heterocycles in the definition of R$^3$ are, for example, oxetanyl, morpholinyl, N-acetyl-piperazinyl, piperidyl, 2-oxo-piperidin-1-yl, 2-oxo-oxazolidin-3-yl and tetrahydropyranyl. Preferred heterocycles in the definition of R$^7$ and R$^8$ are, for example, pyrrolidinyl, 2-oxo-pyrrolidin-1-yl, 2-carbamoyl-pyrrolidin-1-yl, morpholinyl, N-methyl-piperazinyl, 3,5-dimethyl-piperazin-1-yl, 4-(2-methoxy-ethyl)-piperazin-1-yl, N-acetyl-piperazinyl, N-methylsulfonyl-piperazinyl, piperidyl, 4-methoxy-piperidin-1-yl, 4-hydroxy-piperidin-1-yl, tetrahydropyranyl and tetrahydrofuranyl.

As used herein the term "5- or 6-membered heterocyclic ring" formed by R$^5$ and R$^6$ together with carbon atoms to which they are attached, means a saturated or unsaturated cyclic hydrocarbon with 5 or 6 ring atoms of which 1 or 2 atoms are replaced by heteroatoms selected from the group consisting of S, N and O with the remaining carbon-atoms, where possible, being optionally substituted one or more times by halogen, preferably with fluorine. In certain embodiments the heteroatoms in said "5 or 6 membered heterocyclic ring" are preferably N or O and the halogen is preferably fluorine. Preferably said "5 or 6 membered heterocyclic ring" is unsubstituted. Examples of such "5- or 6-membered heterocyclic rings", formed by R$^5$ and R$^6$ include [1,4]dioxane or [1,3]dioxolane which form together with the isoquinoline moiety to which they are fused a 2,3-dihydro-1,4-dioxa-7-aza-phenanthrene or a 1,3-dioxa-7-aza-cyclopenta[a]naphthalene.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

As used herein, a "pharmaceutically acceptable carrier" or a "pharmaceutically acceptable adjuvant" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

DETAILED DESCRIPTION

The present invention is directed to the tricyclic aminopyrazole derivatives of general formula I and all pharmaceutically acceptable salts or esters thereof wherein formula I is:

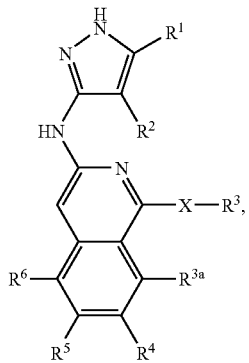

formula I wherein:
(a) $R^1$ is hydrogen, alkyl or cycloalkyl;
(b) $R^2$ is hydrogen or alkyl;
(c) $R^3$ is selected from the group consisting of:
  (1) unsubstituted alkyl,
  (2) alkyl which is substituted one or two times with —C(O)O-alkyl, heteroaryl, phenyl, heterocyclyl or cycloalkyl,
  (3) alkyl wherein one or more —CH$_2$-groups are replaced by oxygen,
  (4) aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR$_2$,
  (5) heteroaryl which is optionally substituted one or more times with alkyl,
  (6) cycloalkyl, and
  (7) heterocyclyl;
(d) $R^{3a}$ is hydrogen, alkyl or alkoxy;
(e) $R^4$ is hydrogen, alkyl, alkoxy, halogen, cyano, —C(O)NR$_2$, —(CH$_2$)$_n$—Y—R$^7$ or -Z-R$^8$;
(f) $R^5$ is hydrogen, alkyl, alkoxy, halogen, cyano, —C(O)NR$_2$, —(CH$_2$)$_n$—Y—R$^7$ or -Z-R$^8$; and $R^6$ is hydrogen, alkyl, alkoxy, halogen or cyano; or alternatively $R^5$ and $R^6$ form together with the carbon atoms to which they are attached a 5- or 6-membered heterocyclic ring;
(g) X is a single bond, —NR—, —O—, —S—, —C(O)— or —C(O)NR—;
(h) Y is —O—, —NR—, —S—, —S(O)$_2$NR—, —NRC(O)—, —NRC(O)O— or —C(O)NR—;
(i) Z is —C(O)—, —O—, a single bond or alkylene;
(j) $R^7$ is cycloalkyl; or alkyl, which is optionally substituted one or more times by alkoxy, hydroxy, alkylsulfonyl, heterocyclyl or —NR$_2$;
(k) $R^8$ is heterocyclyl;
(l) R is hydrogen or alkyl; and
(m) n is 0, 1, 2 or 3.

In certain preferred embodiments:
$R^1$ is preferably hydrogen or alkyl and more preferably alkyl.
$R^2$ is preferably hydrogen.
$R^3$ is preferably selected from the group consisting of:
  (1) unsubstituted alkyl;
  (2) alkyl which is preferably substituted one time with phenyl, heterocyclyl or cycloalkyl; and in a particular preferred embodiment substituted one time with phenyl or cycloalkyl;
  (3) alkyl wherein one or more —CH$_2$-groups are replaced by oxygen;
  (4) aryl which is preferably optionally substituted one to three times with a substituent independently selected from the group consisting of halogen, alkyl, halogenated alkyl, cyano, —C(O)-alkyl, —NH—C(O)-alkyl, and unsubstituted alkoxy;
  (5) heteroaryl which is optionally substituted one or more times with alkyl;
  (6) cyclobutyl, cyclopentyl or cyclohexyl; and
  (7) heterocyclyl, wherein preferably at least one heteroatom is nitrogen and the remaining heteroatoms are selected independently from the group consisting of nitrogen, oxygen and sulfur, and such heterocyclyl group is attached to X via the ring nitrogen atom.
Preferably $R^3$ is unsubstituted alkyl.
$R^{3a}$ is preferably hydrogen or alkoxy.
$R^4$ is preferably hydrogen, halogen (preferably bromine, chlorine or fluorine, and more preferably chlorine or fluorine and more preferably fluorine), alkyl, cyano, —C(O)NR$_2$, —(CH$_2$)$_n$—Y—R$^7$, or -Z-R$^8$.
$R^5$ is preferably hydrogen, alkyl, —C(O)NR$_2$, —(CH$_2$)$_n$—Y—R$^7$ or -Z-R$^8$. If $R^5$ is halogen, the halogen is preferably bromine, chlorine or fluorine, more preferably chlorine or fluorine and more preferably fluorine.
$R^6$ is preferably hydrogen, alkyl or alkoxy.
X is preferably a single bond, —S—, —NR— or —O—; and more preferably a single bond, —NR— or —O— and still more preferably a single bond or —O—.
Y is preferably —O—, —NR— or —C(O)NR—; and more preferably —O— or —C(O)NR—.
Preferably $R^7$ is alkyl which is optionally substituted by alkoxy, hydroxyl, heterocyclyl or —NR$_2$, and more preferably the alkyl is optionally substituted once by alkoxy or heterocyclyl.
$R^8$ is heterocyclyl wherein preferably at least one heteroatom is nitrogen and the remaining heteroatoms are selected independently from the group consisting of nitrogen, oxygen, and sulfur and preferably such heterocyclyl group is attached to the compound of formula I via the ring nitrogen atom.
R is preferably hydrogen.
n is preferably 0 or 1 and in a particular preferred embodiment n is 0.

One embodiment of the invention are the compounds of formula I wherein:
$R^1$ is hydrogen, alkyl or cycloalkyl;
$R^2$ is hydrogen;
$R^3$ is selected from the group consisting of:
  (1) unsubstituted alkyl;
  (2) alkyl which is substituted one or two times with —C(O)O-alkyl, heteroaryl, phenyl, heterocyclyl or cycloalkyl (preferably once with phenyl, heterocyclyl or cycloalkyl);

(3) alkyl wherein one or more —CH$_2$-groups are replaced by oxygen,
(4) aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR$_2$,
(5) heteroaryl which is optionally substituted one or more times with alkyl,
(6) cycloalkyl, and
(7) heterocyclyl;

R$^4$ is hydrogen, alkyl, halogen, cyano, —(CH$_2$)$_n$—Y—R$^7$ or -Z-R$^8$;

R$^5$ is hydrogen, alkyl, halogen, cyano, —(CH$_2$)$_n$—Y—R$^7$ or -Z-R$^8$;

R$^6$ is hydrogen, alkyl, alkoxy, halogen or cyano;

X is a single bond, —NR—, —O—, —S—, —C(O)— or —C(O)NR—;

Y is —O—, —NR—, —S—, —S(O)$_2$NR—, —NRC(O)—, —NRC(O)O— or —C(O)NR—;

Z is —C(O)—;

R$^7$ is alkyl which is optionally substituted one or more times by alkoxy, hydroxy, alkylsulfonyl, heterocyclyl or —NR$_2$;

R$^8$ is heterocyclyl;

R is hydrogen or alkyl; and n is 0, 1, 2 or 3.

Another embodiment of the invention are the compounds of formula I wherein:
R$^5$ is hydrogen, alkyl, alkoxy, halogen, cyano, —(CH$_2$)$_n$—Y—R$^7$ or
-Z-R$^8$;
R$^4$ is hydrogen, alkyl, alkoxy, halogen, cyano, —(CH$_2$)$_n$—Y—R$^7$ or
-Z-R$^8$; and
R$^7$ is alkyl which is optionally substituted one or two times by alkoxy, hydroxy, alkylsulfonyl, heterocyclyl or —NR$_2$.

Another embodiment of the invention are the compounds of formula I wherein R$^2$ is hydrogen.

Another embodiment of the invention are the compounds of formula I wherein R$^1$ is hydrogen or alkyl.

Another embodiment of the invention are the compounds of formula I wherein R$^3$ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR$_2$.

Another embodiment of the invention are the compounds of formula I wherein R$^3$ is heteroaryl which is optionally substituted one or more times with alkyl.

Another embodiment of the invention are the compounds of formula I wherein X is a single bond.

Another embodiment of the invention are the compounds of formula I wherein X is —NR—.

Another embodiment of the invention are the compounds of formula I wherein X is —O—.

Another embodiment of the invention are the compounds of formula I wherein X is —S—.

Another embodiment of the invention are the compounds of formula I wherein X is —C(O)—.

Another embodiment of the invention are the compounds of formula I wherein X is —C(O)NR—.

Another embodiment of the invention are the compounds of formula I wherein X is a single bond, —NR— or —O—.

Another embodiment of the invention are the compounds of formula I wherein X is a single bond, —NR—, —O— or —C(O)NR—; and R is hydrogen.

Another embodiment of the invention are the compounds of formula I wherein:
R$^3$ is selected from the group consisting of:
(1) unsubstituted alkyl;
(2) aryl which is optionally substituted one or more times with halogen, alkyl, halogenated alkyl, halogenated alkoxy, cyano, —C(O)-alkyl, —NH—C(O)-alkyl, —C(O)OH,
—C(O)O-alkyl, unsubstituted alkoxy, alkoxy substituted by heterocyclyl, or —NR$_2$; and
(3) heteroaryl which is optionally substituted one or more times with alkyl; and
X is a single bond.

Another embodiment of the invention are the compounds of formula I wherein:
R$^3$ is selected from the group consisting of:
(1) unsubstituted alkyl,
(2) alkyl which is substituted one or two times with heteroaryl, phenyl, heterocyclyl or cycloalkyl,
(3) alkyl wherein one or more —CH$_2$-groups are replaced by oxygen,
(4) aryl which is optionally substituted one or more times with halogen, alkyl, halogenated alkyl, halogenated alkoxy, cyano, —C(O)-alkyl, —NH—C(O)-alkyl, —C(O)OH,
—C(O)O-alkyl, unsubstituted alkoxy, alkoxy substituted by heterocyclyl, or —NR$_2$,
(5) heteroaryl which is optionally substituted one or more times with alkyl,
(6) cycloalkyl, and
(7) heterocyclyl; and
X is a single bond.

Another embodiment of the invention are the compounds of formula I wherein R$^3$ is unsubstituted alkyl; and X is a single bond.

Another embodiment of the invention are the compounds of formula I wherein:
R$^2$ is hydrogen;
R$^3$ is unsubstituted alkyl; and
X is a single bond.

Such compounds, for example, may be selected from the group consisting of:
(1-Isopropyl-6-methoxy-isoquinolin-3-yl)-(5-methyl-1H-pyrazol-3-yl)-amine;
(5-Cyclopropyl-1H-pyrazol-3-yl)-(1-isopropyl-6,7-dimethoxy-isoquinolin-3-yl)-amine;
[1-Isopropyl-6-(2-methoxy-ethoxy)-isoquinolin-3-yl]-(5-methyl-1H-pyrazol-3-yl)-amine;
[1-Isopropyl-6-(2-morpholin-4-yl-ethoxy)-isoquinolin-3-yl]-(5-methyl-1H-pyrazol-3-yl)-amine;
1-Isopropyl-3-(5-methyl-1H-pyrazol-3-ylamino)-isoquinoline-6-carboxylic acid (3-methoxy-propyl)-amide;
1-{4-[1-Isopropyl-3-(5-methyl-1H-pyrazol-3-ylamino)-isoquinoline-6-carbonyl]-piperazin-1-yl}-ethanone;
(1-Isopropyl-6,7-dimethoxy-isoquinolin-3-yl)-(5-methyl-1H-pyrazol-3-yl)-amine;
(1-Isopropyl-5-methoxy-isoquinolin-3-yl)-(5-methyl-1H-pyrazol-3-yl)-amine;
(1-Ethyl-6-methoxy-isoquinolin-3-yl)-(5-methyl-1H-pyrazol-3-yl)-amine;
(8-Isopropyl-2,3-dihydro-1,4-dioxa-7-aza-phenanthren-6-yl)-(5-methyl-1H-pyrazol-3-yl)-amine;
(1-Isopropyl-6-morpholin-4-yl-isoquinolin-3-yl)-(5-methyl-1H-pyrazol-3-yl)-amine;

[1-Isopropyl-6-(4-methyl-piperazin-1-yl)-isoquinolin-3-yl]-(5-methyl-1H-pyrazol-3-yl)-amine;
[1-Isopropyl-6-methoxy-7-(2-methoxy-ethoxy)-isoquinolin-3-yl]-(5-methyl-1H-pyrazol-3-yl)-amine; and
(1-Isobutyl-6-methoxy-isoquinolin-3-yl)-(5-methyl-1H-pyrazol-3-yl)-amine.

Another embodiment of the invention are the compounds of formula I wherein:
$R^3$ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl or —NR₂; and
X is a single bond.

Such compounds, for example, may be selected from the group consisting of:
(5-Methyl-1H-pyrazol-3-yl)-(1-phenyl-isoquinolin-3-yl)-amine;
[1-(4-Fluoro-phenyl)-isoquinolin-3-yl]-(5-methyl-1H-pyrazol-3-yl)-amine;
4-[3-(5-Methyl-1H-pyrazol-3-ylamino)-isoquinolin-1-yl]-benzonitrile;
[1-(4-Methoxy-phenyl)-isoquinolin-3-yl]-(5-methyl-1H-pyrazol-3-yl)-amine;
(5-Methyl-1H-pyrazol-3-yl)-[1-(4-trifluoromethyl-phenyl)-isoquinolin-3-yl]-amine;
(5-Methyl-1H-pyrazol-3-yl)-(1-p-tolyl-isoquinolin-3-yl)-amine;
[1-(4-Chloro-phenyl)-isoquinolin-3-yl]-(5-methyl-1H-pyrazol-3-yl)-amine;
[1-(3-Chloro-phenyl)-isoquinolin-3-yl]-(5-methyl-1H-pyrazol-3-yl)-amine;
[1-(3-Fluoro-phenyl)-isoquinolin-3-yl]-(5-methyl-1H-pyrazol-3-yl)-amine;
3-[3-(5-Methyl-1H-pyrazol-3-ylamino)-isoquinolin-1-yl]-benzonitrile;
[1-(3-Methoxy-phenyl)-isoquinolin-3-yl]-(5-methyl-1H-pyrazol-3-yl)-amine;
(5-Methyl-1H-pyrazol-3-yl)-[1-(3-trifluoromethyl-phenyl)-isoquinolin-3-yl]-amine;
(5-Methyl-1H-pyrazol-3-yl)-(1-m-tolyl-isoquinolin-3-yl)-amine;
1-{3-[3-(5-Methyl-1H-pyrazol-3-ylamino)-isoquinolin-1-yl]-phenyl}-ethanone;
1-{4-[3-(5-Methyl-1H-pyrazol-3-ylamino)-isoquinolin-1-yl]-phenyl}-ethanone;
[1-(2-Fluoro-phenyl)-isoquinolin-3-yl]-(5-methyl-1H-pyrazol-3-yl)-amine;
[1-(2-Methoxy-phenyl)-isoquinolin-3-yl]-(5-methyl-1H-pyrazol-3-yl)-amine;
[1-(2,4-Difluoro-phenyl)-6,7-dimethoxy-isoquinolin-3-yl]-(5-methyl-1H-pyrazol-3-yl)-amine;
(5-Methyl-1H-pyrazol-3-yl)-(1-naphthalen-2-yl-isoquinolin-3-yl)-amine;
[1-(4-tert-Butyl-phenyl)-isoquinolin-3-yl]-(5-methyl-1H-pyrazol-3-yl)-amine;
[1-(2,4-Difluoro-phenyl)-isoquinolin-3-yl]-(5-methyl-1H-pyrazol-3-yl)-amine;
[1-(3,4-Difluoro-phenyl)-isoquinolin-3-yl]-(5-methyl-1H-pyrazol-3-yl)-amine;
[1-(3,4-Dimethoxy-phenyl)-isoquinolin-3-yl]-(5-methyl-1H-pyrazol-3-yl)-amine;
N-{4-[3-(5-Methyl-1H-pyrazol-3-ylamino)-isoquinolin-1-yl]-phenyl}-acetamide;
(6-Methoxy-1-phenyl-isoquinolin-3-yl)-(5-methyl-1H-pyrazol-3-yl)-amine;
[1-(4-Fluoro-phenyl)-6-methoxy-isoquinolin-3-yl]-(5-methyl-1H-pyrazol-3-yl)-amine;
4-[6-Methoxy-3-(5-methyl-1H-pyrazol-3-ylamino)-isoquinolin-1-yl]-benzonitrile;
[1-(4-Ethoxy-phenyl)-6-methoxy-isoquinolin-3-yl]-(5-methyl-1H-pyrazol-3-yl)-amine;
[6-Methoxy-1-(4-trifluoromethyl-phenyl)-isoquinolin-3-yl]-(5-methyl-1H-pyrazol-3-yl)-amine;
(6-Methoxy-1-p-tolyl-isoquinolin-3-yl)-(5-methyl-1H-pyrazol-3-yl)-amine;
[1-(4-Chloro-phenyl)-6-methoxy-isoquinolin-3-yl]-(5-methyl-1H-pyrazol-3-yl)-amine;
[1-(3-Chloro-phenyl)-6-methoxy-isoquinolin-3-yl]-(5-methyl-1H-pyrazol-3-yl)-amine;
[1-(3-Fluoro-phenyl)-6-methoxy-isoquinolin-3-yl]-(5-methyl-1H-pyrazol-3-yl)-amine;
3-[6-Methoxy-3-(5-methyl-1H-pyrazol-3-ylamino)-isoquinolin-1-yl]-benzonitrile;
[6-Methoxy-1-(3-methoxy-phenyl)-isoquinolin-3-yl]-(5-methyl-1H-pyrazol-3-yl)-amine;
[6-Methoxy-1-(3-trifluoromethyl-phenyl)-isoquinolin-3-yl]-(5-methyl-1H-pyrazol-3-yl)-amine;
(6-Methoxy-1-m-tolyl-isoquinolin-3-yl)-(5-methyl-1H-pyrazol-3-yl)-amine;
1-{3-[6-Methoxy-3-(5-methyl-1H-pyrazol-3-ylamino)-isoquinolin-1-yl]-phenyl}-ethanone;
1-{4-[6-Methoxy-3-(5-methyl-1H-pyrazol-3-ylamino)-isoquinolin-1-yl]-phenyl}-ethanone;
[1-(2-Fluoro-phenyl)-6-methoxy-isoquinolin-3-yl]-(5-methyl-1H-pyrazol-3-yl)-amine;
[6-Methoxy-1-(2-methoxy-phenyl)-isoquinolin-3-yl]-(5-methyl-1H-pyrazol-3-yl)-amine;
(6-Methoxy-1-naphthalen-2-yl-isoquinolin-3-yl)-(5-methyl-1H-pyrazol-3-yl)-amine;
[1-(4-tert-Butyl-phenyl)-6-methoxy-isoquinolin-3-yl]-(5-methyl-1H-pyrazol-3-yl)-amine;
[1-(2,4-Difluoro-phenyl)-6-methoxy-isoquinolin-3-yl]-(5-methyl-1H-pyrazol-3-yl)-amine;
[1-(3,4-Difluoro-phenyl)-6-methoxy-isoquinolin-3-yl]-(5-methyl-1H-pyrazol-3-yl)-amine;
[1-(3,4-Dimethoxy-phenyl)-6-methoxy-isoquinolin-3-yl]-(5-methyl-1H-pyrazol-3-yl)-amine;
N-{4-[6-Methoxy-3-(5-methyl-1H-pyrazol-3-ylamino)-isoquinolin-1-yl]-phenyl}-acetamide;
[1-(2-Fluoro-phenyl)-5-methoxy-isoquinolin-3-yl]-(5-methyl-1H-pyrazol-3-yl)-amine;
[5-Methoxy-1-(3-methoxy-phenyl)-isoquinolin-3-yl]-(5-methyl-1H-pyrazol-3-yl)-amine;
3-[5-Methoxy-3-(5-methyl-1H-pyrazol-3-ylamino)-isoquinolin-1-yl]-benzonitrile;
(5-Methoxy-1-phenyl-isoquinolin-3-yl)-(5-methyl-1H-pyrazol-3-yl)-amine;
[1-(2-Fluoro-phenyl)-7-methoxy-isoquinolin-3-yl]-(5-methyl-1H-pyrazol-3-yl)-amine;
[7-Methoxy-1-(3-methoxy-phenyl)-isoquinolin-3-yl]-(5-methyl-1H-pyrazol-3-yl)-amine;
3-[7-Methoxy-3-(5-methyl-1H-pyrazol-3-ylamino)-isoquinolin-1-yl]-benzonitrile;
(7-Methoxy-1-phenyl-isoquinolin-3-yl)-(5-methyl-1H-pyrazol-3-yl)-amine;
[1-(2,4-Difluoro-phenyl)-5-methoxy-isoquinolin-3-yl]-(5-methyl-1H-pyrazol-3-yl)-amine;
[1-(2,4-Difluoro-phenyl)-7-methoxy-isoquinolin-3-yl]-(5-methyl-1H-pyrazol-3-yl)-amine;
[1-(2-Fluoro-phenyl)-6,7-dimethoxy-isoquinolin-3-yl]-(5-methyl-1H-pyrazol-3-yl)-amine;

[6,7-Dimethoxy-1-(3-methoxy-phenyl)-isoquinolin-3-yl]-(5-methyl-1H-pyrazol-3-yl)-amine;
(6,7-Dimethoxy-1-phenyl-isoquinolin-3-yl)-(5-methyl-1H-pyrazol-3-yl)-amine;
[1-(2-Fluoro-phenyl)-5,6-dimethoxy-isoquinolin-3-yl]-(5-methyl-1H-pyrazol-3-yl)-amine;
[5,6-Dimethoxy-1-(3-methoxy-phenyl)-isoquinolin-3-yl]-(5-methyl-1H-pyrazol-3-yl)-amine;
(5,6-Dimethoxy-1-phenyl-isoquinolin-3-yl)-(5-methyl-1H-pyrazol-3-yl)-amine;
(1-Phenyl-isoquinolin-3-yl)-(1H-pyrazol-3-yl)-amine;
[1-(2-Methoxy-phenyl)-isoquinolin-3-yl]-(1H-pyrazol-3-yl)-amine;
(1H-Pyrazol-3-yl)-[1-(4-trifluoromethyl-phenyl)-isoquinolin-3-yl]-amine;
[1-(3-Fluoro-phenyl)-isoquinolin-3-yl]-(1H-pyrazol-3-yl)-amine;
3-[3-(1H-Pyrazol-3-ylamino)-isoquinolin-1-yl]-benzoic acid ethyl ester;
[1-(4-Fluoro-phenyl)-isoquinolin-3-yl]-(1H-pyrazol-3-yl)-amine;
[1-(3-Methoxy-phenyl)-isoquinolin-3-yl]-(1H-pyrazol-3-yl)-amine;
4-[3-(1H-Pyrazol-3-ylamino)-isoquinolin-1-yl]-benzoic acid;
[1-(2-Fluoro-phenyl)-isoquinolin-3-yl]-(1H-pyrazol-3-yl)-amine;
[1-(3,4-Difluoro-phenyl)-isoquinolin-3-yl]-(1H-pyrazol-3-yl)-amine;
[1-(2,4-Difluoro-phenyl)-isoquinolin-3-yl]-(1H-pyrazol-3-yl)-amine;
(1H-Pyrazol-3-yl)-[1-(3-trifluoromethyl-phenyl)-isoquinolin-3-yl]-amine;
(1-Naphthalen-2-yl-isoquinolin-3-yl)-(1H-pyrazol-3-yl)-amine;
3-[3-(1H-Pyrazol-3-ylamino)-isoquinolin-1-yl]-benzonitrile;
(1H-Pyrazol-3-yl)-(1-p-tolyl-isoquinolin-3-yl)-amine;
(1H-Pyrazol-3-yl)-(1-m-tolyl-isoquinolin-3-yl)-amine;
[1-(4-tert-Butyl-phenyl)-isoquinolin-3-yl]-(1H-pyrazol-3-yl)-amine;
1-{4-[3-(1H-Pyrazol-3-ylamino)-isoquinolin-1-yl]-phenyl}-ethanone;
1-{3-[3-(1H-Pyrazol-3-ylamino)-isoquinolin-1-yl]-phenyl}-ethanone;
[1-(4-Chloro-phenyl)-isoquinolin-3-yl]-(1H-pyrazol-3-yl)-amine;
[1-(3,4-Dimethoxy-phenyl)-isoquinolin-3-yl]-(1H-pyrazol-3-yl)-amine;
[1-(4-Ethoxy-phenyl)-isoquinolin-3-yl]-(1H-pyrazol-3-yl)-amine;
4-[3-(1H-Pyrazol-3-ylamino)-isoquinolin-1-yl]-benzonitrile;
N-{4-[3-(1H-Pyrazol-3-ylamino)-isoquinolin-1-yl]-phenyl}-acetamide;
(6-Methoxy-1-phenyl-isoquinolin-3-yl)-(1H-pyrazol-3-yl)-amine;
[1-(4-Fluoro-phenyl)-6-methoxy-isoquinolin-3-yl]-(1H-pyrazol-3-yl)-amine;
1-{3-[6-Methoxy-3-(1H-pyrazol-3-ylamino)-isoquinolin-1-yl]-phenyl}-ethanone;
1-{4-[6-Methoxy-3-(1H-pyrazol-3-ylamino)-isoquinolin-1-yl]-phenyl}-ethanone;
[1-(2-Fluoro-phenyl)-6-methoxy-isoquinolin-3-yl]-(1H-pyrazol-3-yl)-amine;
[6-Methoxy-1-(3-methoxy-phenyl)-isoquinolin-3-yl]-(1H-pyrazol-3-yl)-amine;
[6-Methoxy-1-(4-trifluoromethyl-phenyl)-isoquinolin-3-yl]-(1H-pyrazol-3-yl)-amine;
[1-(4-Chloro-phenyl)-6-methoxy-isoquinolin-3-yl]-(1H-pyrazol-3-yl)-amine;
3-[6-Methoxy-3-(1H-pyrazol-3-ylamino)-isoquinolin-1-yl]-benzonitrile;
[6-Methoxy-1-(3-trifluoromethyl-phenyl)-isoquinolin-3-yl]-(1H-pyrazol-3-yl)-amine;
[1-(2,4-Difluoro-phenyl)-6-methoxy-isoquinolin-3-yl]-(1H-pyrazol-3-yl)-amine;
[1-(3,4-Difluoro-phenyl)-6-methoxy-isoquinolin-3-yl]-(1H-pyrazol-3-yl)-amine;
[1-(3,5-Difluoro-phenyl)-6-methoxy-isoquinolin-3-yl]-(1H-pyrazol-3-yl)-amine;
[6-Methoxy-1-(2-methoxy-phenyl)-isoquinolin-3-yl]-(1H-pyrazol-3-yl)-amine;
(6-Methoxy-1-p-tolyl-isoquinolin-3-yl)-(1H-pyrazol-3-yl)-amine;
[1-(3-Fluoro-phenyl)-6-methoxy-isoquinolin-3-yl]-(1H-pyrazol-3-yl)-amine;
(6-Methoxy-1-naphthalen-2-yl-isoquinolin-3-yl)-(1H-pyrazol-3-yl)-amine;
[1-(4-Ethoxy-phenyl)-6-methoxy-isoquinolin-3-yl]-(1H-pyrazol-3-yl)-amine;
(6-Methoxy-1-m-tolyl-isoquinolin-3-yl)-(1H-pyrazol-3-yl)-amine;
[1-(3,4-Dimethoxy-phenyl)-6-methoxy-isoquinolin-3-yl]-(1H-pyrazol-3-yl)-amine;
N-{4-[6-Methoxy-3-(1H-pyrazol-3-ylamino)-isoquinolin-1-yl]-phenyl}-acetamide;
(5-Methyl-1H-pyrazol-3-yl)-[6-(2-morpholin-4-yl-ethoxy)-1-phenyl-isoquinolin-3-yl]-amine;
[1-(3-Methoxy-phenyl)-6-(2-morpholin-4-yl-ethoxy)-isoquinolin-3-yl]-(5-methyl-1H-pyrazol-3-yl)-amine;
[1-(2,4-Difluoro-phenyl)-3-(5-methyl-1H-pyrazol-3-ylamino)-isoquinolin-6-yl]-morpholin-4-yl-methanone;
1-(2,4-Difluoro-phenyl)-3-(5-methyl-1H-pyrazol-3-ylamino)-isoquinoline-6-carboxylic acid (3-methoxy-propyl)-amide;
[1-(2,4-Difluoro-phenyl)-6-(2-methoxy-ethoxy)-isoquinolin-3-yl]-(5-methyl-1H-pyrazol-3-yl)-amine;
3-[5,6-Dimethoxy-3-(5-methyl-1H-pyrazol-3-ylamino)-isoquinolin-1-yl]-benzonitrile;
3-[6,7-Dimethoxy-3-(5-methyl-1H-pyrazol-3-ylamino)-isoquinolin-1-yl]-benzonitrile;
{6-Methoxy-1-[3-(2-morpholin-4-yl-ethoxy)-phenyl]-isoquinolin-3-yl}-(5-methyl-1H-pyrazol-3-yl)-amine;
{5-Methoxy-1-[3-(2-morpholin-4-yl-ethoxy)-phenyl]-isoquinolin-3-yl}-(5-methyl-1H-pyrazol-3-yl)-amine;
[1-(4-Fluoro-phenoxy)-6-isopropoky-isoquinolin-3-yl]-(5-methyl-1H-pyrazol-3-yl)-amine; and
{1-[3-(2-Dimethylamino-ethoxy)-phenyl]-isoquinolin-3-yl}-(5-methyl-1H-pyrazol-3-yl)-amine.

Another embodiment of the invention are the compounds of formula I wherein:
R$^3$ is heteroaryl which is optionally substituted one or more times with alkyl; and
X is a single bond.

Such compounds, for example, may be selected from the group consisting of:
(6-Methoxy-1-pyridin-4-yl-isoquinolin-3-yl)-(1H-pyrazol-3-yl)-amine;
(6-Methoxy-1-pyridin-3-yl-isoquinolin-3-yl)-(1H-pyrazol-3-yl)-amine;
[6-Methoxy-1-(1-methyl-1H-pyrazol-4-yl)-isoquinolin-3-yl]-(1H-pyrazol-3-yl)-amine;

(5-Methyl-1H-pyrazol-3-yl)-[1-(4-methyl-thiophen-3-yl)-isoquinolin-3-yl]-amine;
(5-Methyl-1H-pyrazol-3-yl)-(1-thiophen-3-yl-isoquinolin-3-yl)-amine;
(1-Benzo[b]thiophen-3-yl-isoquinolin-3-yl)-(5-methyl-1H-pyrazol-3-yl)-amine;
(5-Methyl-1H-pyrazol-3-yl)-(1-pyridin-3-yl-isoquinolin-3-yl)-amine;
(5-Methyl-1H-pyrazol-3-yl)-(1-pyridin-4-yl-isoquinolin-3-yl)-amine;
(5-Methyl-1H-pyrazol-3-yl)-[1-(1H-pyrazol-4-yl)-isoquinolin-3-yl]-amine;
(5-Methyl-1H-pyrazol-3-yl)-[1-(1-methyl-1H-pyrazol-4-yl)-isoquinolin-3-yl]-amine;
[6-Methoxy-1-(1H-pyrazol-4-yl)-isoquinolin-3-yl]-(1H-pyrazol-3-yl)-amine;
[6-Methoxy-1-(4-methyl-thiophen-3-yl)-isoquinolin-3-yl]-(5-methyl-1H-pyrazol-3-yl)-amine;
(6-Methoxy-1-thiophen-3-yl-isoquinolin-3-yl)-(5-methyl-1H-pyrazol-3-yl)-amine;
(1-Benzo[b]thiophen-3-yl-6-methoxy-isoquinolin-3-yl)-(5-methyl-1H-pyrazol-3-yl)-amine;
N-{4-[6-Methoxy-3-(5-methyl-1H-pyrazol-3-ylamino)-isoquinolin-1-yl]-phenyl}-acetamide;
(6-Methoxy-1-pyridin-3-yl-isoquinolin-3-yl)-(5-methyl-1H-pyrazol-3-yl)-amine;
(6-Methoxy-1-pyridin-4-yl-isoquinolin-3-yl)-(5-methyl-1H-pyrazol-3-yl)-amine;
[6-Methoxy-1-(1H-pyrazol-4-yl)-isoquinolin-3-yl]-(5-methyl-1H-pyrazol-3-yl)-amine;
[6-Methoxy-1-(1-methyl-1H-pyrazol-4-yl)-isoquinolin-3-yl]-(5-methyl-1H-pyrazol-3-yl)-amine;
[5-Methoxy-1-(1-methyl-1H-pyrazol-4-yl)-isoquinolin-3-yl]-(5-methyl-1H-pyrazol-3-yl)-amine;
(5-Methoxy-1-pyridin-3-yl-isoquinolin-3-yl)-(5-methyl-1H-pyrazol-3-yl)-amine;
(5-Methoxy-1-thiophen-3-yl-isoquinolin-3-yl)-(5-methyl-1H-pyrazol-3-yl)-amine;
[7-Methoxy-1-(1-methyl-1H-pyrazol-4-yl)-isoquinolin-3-yl]-(5-methyl-1H-pyrazol-3-yl)-amine;
(7-Methoxy-1-pyridin-3-yl-isoquinolin-3-yl)-(5-methyl-1H-pyrazol-3-yl)-amine;
(7-Methoxy-1-thiophen-3-yl-isoquinolin-3-yl)-(5-methyl-1H-pyrazol-3-yl)-amine;
(1-Benzo[b]thiophen-3-yl-isoquinolin-3-yl)-(1H-pyrazol-3-yl)-amine;
(1H-Pyrazol-3-yl)-(1-thiophen-3-yl-isoquinolin-3-yl)-amine;
(1H-Pyrazol-3-yl)-[1-(1H-pyrazol-4-yl)-isoquinolin-3-yl]-amine;
[1-(1-Methyl-1H-pyrazol-4-yl)-isoquinolin-3-yl]-(1H-pyrazol-3-yl)-amine;
(1H-Pyrazol-3-yl)-(1-pyridin-3-yl-isoquinolin-3-yl)-amine;
(1H-Pyrazol-3-yl)-(1-pyridin-4-yl-isoquinolin-3-yl)-amine;
(6-Methoxy-1-thiophen-3-yl-isoquinolin-3-yl)-(1H-pyrazol-3-yl)-amine;
[6-Methoxy-1-(4-methyl-thiophen-3-yl)-isoquinolin-3-yl]-(1H-pyrazol-3-yl)-amine; and
(1-Benzo[b]thiophen-3-yl-6-methoxy-isoquinolin-3-yl)-(1H-pyrazol-3-yl)-amine.

Another embodiment of the invention are the compounds of formula I wherein:
R³ is alkyl which is substituted one or two times with heteroaryl, phenyl, heterocyclyl or cycloalkyl; and
X is a single bond.

Such compounds, for example, may be selected from the group consisting of:

(6-Methoxy-1-piperidin-1-ylmethyl-isoquinolin-3-yl)-(5-methyl-1H-pyrazol-3-yl)-amine;
1-[6-Methoxy-3-(5-methyl-1H-pyrazol-3-ylamino)-isoquinolin-1-ylmethyl]-piperidin-2-one;
3-[6-Methoxy-3-(5-methyl-1H-pyrazol-3-ylamino)-isoquinolin-1-ylmethyl]-oxazolidin-2-one;
(6-Methoxy-1-pyrazol-1-ylmethyl-isoquinolin-3-yl)-(5-methyl-1H-pyrazol-3-yl)-amine; and
(1-Benzyl-6-methoxy-isoquinolin-3-yl)-(5-methyl-1H-pyrazol-3-yl)-amine.

Another embodiment of the invention are the compounds of formula I wherein R³ is cycloalkyl; and X is a single bond.

Another embodiment of the invention are the compounds of formula I wherein:
R² is hydrogen;
R³ is cycloalkyl; and
X is a single bond.

Such compounds, for example, may be selected from the group consisting of:
(1-Cyclopropyl-6-methoxy-isoquinolin-3-yl)-(5-methyl-1H-pyrazol-3-yl)-amine;
(1-Cyclohexyl-6-methoxy-isoquinolin-3-yl)-(5-methyl-1H-pyrazol-3-yl)-amine; and
(1-Cyclopentyl-6-methoxy-isoquinolin-3-yl)-(5-methyl-1H-pyrazol-3-yl)-amine.

Another embodiment of the invention are the compounds of formula I wherein:
R³ is selected from the group consisting of:
(1) unsubstituted alkyl,
(2) alkyl which is substituted one or two times with —C(O)O-alkyl, phenyl, or heterocyclyl,
(3) aryl which is optionally substituted one or more times with halogen, alkyl, halogenated alkyl, halogenated alkoxy, cyano, —C(O)-alkyl, —NH—C(O)-alkyl, —C(O)OH,
—C(O)O-alkyl, unsubstituted alkoxy, alkoxy substituted by heterocyclyl or —NR₂, and
(4) heteroaryl which is optionally substituted one or more times with alkyl; and
X is —NR—.

Another embodiment of the invention are the compounds of formula I wherein R³ is alkyl which is substituted one time with phenyl; and X is —NR—.

Such compounds, for example, may be selected from the group consisting of:
N¹-Benzyl-N³-(5-methyl-1H-pyrazol-3-yl)-isoquinoline-1,3-diamine; and
N³-(5-Methyl-1H-pyrazol-3-yl)-N¹-((R)-1-phenyl-ethyl)-isoquinoline-1,3-diamine.

Another embodiment of the invention are the compounds of formula I wherein:
R³ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR₂; and
X is —NR—.

Such compounds, for example, may be selected from the group consisting of:
4-[6-Methoxy-3-(5-methyl-1H-pyrazol-3-ylamino)-isoquinolin-1-ylamino]-benzonitrile;
4-[3-(5-Methyl-1H-pyrazol-3-ylamino)-isoquinolin-1-ylamino]-benzonitrile;
N¹-(4-Bromo-phenyl)-6-methoxy-N³-(5-methyl-1H-pyrazol-3-yl)-isoquinoline-1,3-diamine;
N¹-(4-Chloro-phenyl)-6-methoxy-N³-(5-methyl-1H-pyrazol-3-yl)-isoquinoline-1,3-diamine;

N¹-(4-Fluoro-phenyl)-6-methoxy-N³-(5-methyl-1H-pyrazol-3-yl)-isoquinoline-1,3-diamine;
4-[6,7-Dimethoxy-3-(5-methyl-1H-pyrazol-3-ylamino)-isoquinolin-1-ylamino]-benzonitrile;
4-[5,6-Dimethoxy-3-(5-methyl-1H-pyrazol-3-ylamino)-isoquinolin-1-ylamino]-benzonitrile;
N¹-(4-Butoxy-phenyl)-N³-(5-methyl-1H-pyrazol-3-yl)-isoquinoline-1,3-diamine;
N¹-(4-Butoxy-phenyl)-6-methoxy-N³-(5-methyl-1H-pyrazol-3-yl)-isoquinoline-1,3-diamine;
N¹-(4-Butoxy-phenyl)-6-methoxy-N³-(1H-pyrazol-3-yl)-isoquinoline-1,3-diamine;
N¹-(3,4-Dimethoxy-phenyl)-N³-(1H-pyrazol-3-yl)-isoquinoline-1,3-diamine;
N¹-(3,5-Dimethoxy-phenyl)-N³-(1H-pyrazol-3-yl)-isoquinoline-1,3-diamine;
N¹-(3-Ethyl-phenyl)-N³-(5-methyl-1H-pyrazol-3-yl)-isoquinoline-1,3-diamine;
N¹-(3-Ethyl-phenyl)-6-methoxy-N³-(5-methyl-1H-pyrazol-3-yl)-isoquinoline-1,3-diamine;
N¹-(3-Chloro-phenyl)-N³-(5-methyl-1H-pyrazol-3-yl)-isoquinoline-1,3-diamine;
N¹-(3-Chloro-phenyl)-6-methoxy-N³-(5-methyl-1H-pyrazol-3-yl)-isoquinoline-1,3-diamine;
N¹-(3-Ethyl-phenyl)-6-methoxy-N³-(1H-pyrazol-3-yl)-isoquinoline-1,3-diamine;
4-[5-Methoxy-3-(5-methyl-1H-pyrazol-3-ylamino)-isoquinolin-1-ylamino]-benzonitrile;
4-[7-Methoxy-3-(5-methyl-1H-pyrazol-3-ylamino)-isoquinolin-1-ylamino]-benzonitrile;
N³-(5-Methyl-1H-pyrazol-3-yl)-N¹-phenyl-isoquinoline-1,3-diamine; and
N¹-(4-Butoxy-phenyl)-N-(1H-pyrazol-3-yl)-isoquinoline-1,3-diamine.

Another embodiment of the invention are the compounds of formula I wherein:
R³ is heteroaryl, preferably pyridyl, which is optionally substituted one or more times with alkyl; and
X is —NR—.

Such compounds, for example, may be selected from the group consisting of:
N³-(5-Methyl-1H-pyrazol-3-yl)-N¹-pyridin-4-yl-isoquinoline-1,3-diamine;
6-Methoxy-N³-(5-methyl-1H-pyrazol-3-yl)-N¹-pyridin-4-yl-isoquinoline-1,3-diamine;
N³-(1H-Pyrazol-3-yl)-N¹-pyridin-4-yl-isoquinoline-1,3-diamine;
6-Methoxy-N³-(5-methyl-1H-pyrazol-3-yl)-N¹-pyridin-2-yl-isoquinoline-1,3-diamine;
N³-(1H-Pyrazol-3-yl)-N¹-pyridin-2-yl-isoquinoline-1,3-diamine;
N³-(5-Methyl-1H-pyrazol-3-yl)-N¹-pyridin-3-yl-isoquinoline-1,3-diamine; and
6-Methoxy-N³-(5-methyl-1H-pyrazol-3-yl)-N¹-pyridin-3-yl-isoquinoline-1,3-diamine.

Another embodiment of the invention are the compounds of formula I wherein:
R³ is selected from the group consisting of:
(1) unsubstituted alkyl;
(2) alkyl which is substituted one or two times with phenyl or heterocyclyl;
(3) alkyl wherein one or more —CH₂-groups are replaced by oxygen;
(4) aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR₂; and
(5) cycloalkyl; and
X is —O—.

Another embodiment of the invention are the compounds of formula I wherein R³ is selected from the group consisting of:
(1) unsubstituted alkyl;
(2) alkyl which is substituted one or two times with phenyl, heterocyclyl, or cycloalkyl;
(3) alkyl wherein one or more —CH₂-groups are replaced by oxygen;
(4) aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR₂;
(5) cycloalkyl; and
(6) heterocyclyl, preferably selected from oxetanyl and tetrahydrofuranyl; and X is —O—.

Another embodiment of the invention are the compounds of formula I wherein:
R³ is selected from the group consisting of:
(1) alkyl which is substituted one or two times with phenyl, heterocyclyl, or cycloalkyl, and
(2) alkyl wherein one or more —CH₂-groups are replaced by oxygen; and
X is —O—.

Such compounds, for example, may be selected from the group consisting of:
(1-Benzyloxy-isoquinolin-3-yl)-(5-methyl-1H-pyrazol-3-yl)-amine;
{-[2-(2-Ethoxy-ethoxy)-ethoxy]-isoquinolin-3-yl}-(5-methyl-1H-pyrazol-3-yl)-amine;
(5-Methyl-1H-pyrazol-3-yl)-[1-(2-morpholin-4-yl-ethoxy)-isoquinolin-3-yl]-amine;
(5-Methyl-1H-pyrazol-3-yl)-[1-(2-piperidin-1-yl-ethoxy)-isoquinolin-3-yl]-amine;
(1-Benzyloxy-6-methoxy-isoquinolin-3-yl)-(5-methyl-1H-pyrazol-3-yl)-amine;
[6-Methoxy-1-(2-piperidin-1-yl-ethoxy)-isoquinolin-3-yl]-(5-methyl-1H-pyrazol-3-yl)-amine;
{1-[2-(2-Ethoxy-ethoxy)-ethoxy]-6-methoxy-isoquinolin-3-yl}-(5-methyl-1H-pyrazol-3-yl)-amine;
[6-Methoxy-1-(2-morpholin-4-yl-ethoxy)-isoquinolin-3-yl]-(5-methyl-1H-pyrazol-3-yl)-amine;
[1-(4-Methoxy-phenoxy)-5-methyl-isoquinolin-3-yl]-(5-methyl-1H-pyrazol-3-yl)-amine;
(5-Methyl-1H-pyrazol-3-yl)-(1,6,7-trimethoxy-isoquinolin-3-yl)-amine;
(5-Methyl-1H-pyrazol-3-yl)-(1,5,6-trimethoxy-isoquinolin-3-yl)-amine;
(1-Benzyloxy-isoquinolin-3-yl)-(1H-pyrazol-3-yl)-amine;
{1-[2-(2-Ethoxy-ethoxy)-ethoxy]-isoquinolin-3-yl}-(1H-pyrazol-3-yl)-amine;
(1-Benzyloxy-6-methoxy-isoquinolin-3-yl)-(1H-pyrazol-3-yl)-amine; and
(1-Cyclopropylmethoxy-6,7-dimethoxy-isoquinolin-3-yl)-(5-methyl-1H-pyrazol-3-yl)-amine.

Another embodiment of the invention are the compounds of formula I wherein R³ is unsubstituted alkyl; and X is —O—.

Another embodiment of the invention are the compounds of formula I wherein:

R² is hydrogen;
R³ is unsubstituted alkyl; and
X is —O—.

Such compounds, for example, may be selected from the group consisting of:
(1-Methoxy-isoquinolin-3-yl)-(5-methyl-1H-pyrazol-3-yl)-amine;
(1-Isobutoxy-isoquinolin-3-yl)-(5-methyl-1H-pyrazol-3-yl)-amine;
(1-Isopropoxy-isoquinolin-3-yl)-(5-methyl-1H-pyrazol-3-yl)-amine;
(1,6-Dimethoxy-isoquinolin-3-yl)-(5-methyl-1H-pyrazol-3-yl)-amine;
(1-Isobutoxy-6-methoxy-isoquinolin-3-yl)-(5-methyl-1H-pyrazol-3-yl)-amine;
(1-Isopropoxy-isoquinolin-3-yl)-(1H-pyrazol-3-yl)-amine;
(1-Isopropoxy-6-methoxy-isoquinolin-3-yl)-(5-methyl-1H-pyrazol-3-yl)-amine;
(1-Isopropoxy-5-methoxy-isoquinolin-3-yl)-(5-methyl-1H-pyrazol-3-yl)-amine;
(1,5-Dimethoxy-isoquinolin-3-yl)-(5-methyl-1H-pyrazol-3-yl)-amine;
(1-Isopropoxy-7-methoxy-isoquinolin-3-yl)-(5-methyl-1H-pyrazol-3-yl)-amine;
(1,7-Dimethoxy-isoquinolin-3-yl)-(5-methyl-1H-pyrazol-3-yl)-amine;
(1-Methoxy-5-methyl-isoquinolin-3-yl)-(5-methyl-1H-pyrazol-3-yl)-amine;
(1-Isopropoxy-6,7-dimethoxy-isoquinolin-3-yl)-(5-methyl-1H-pyrazol-3-yl)-amine;
(1-Ethoxy-6,7-dimethoxy-isoquinolin-3-yl)-(5-methyl-1H-pyrazol-3-yl)-amine;
(1-Isopropoxy-5,6-dimethoxy-isoquinolin-3-yl)-(5-methyl-1H-pyrazol-3-yl)-amine;
(1-Methoxy-isoquinolin-3-yl)-(1H-pyrazol-3-yl)-amine;
(1-Isobutoxy-isoquinolin-3-yl)-(1H-pyrazol-3-yl)-amine;
(1-Isobutoxy-6-methoxy-isoquinolin-3-yl)-(1H-pyrazol-3-yl)-amine;
(1-Isopropoxy-6-methoxy-isoquinolin-3-yl)-(1H-pyrazol-3-yl)-amine;
(5-Cyclopropyl-1H-pyrazol-3-yl)-(1-ethoxy-6,7-dimethoxy-isoquinolin-3-yl)-amine;
(5-Cyclopropyl-1H-pyrazol-3-yl)-(1-isopropoxy-6,7-dimethoxy-isoquinolin-3-yl)-amine;
[1-Isopropoxy-6-(2-methoxy-ethoxy)-isoquinolin-3-yl]-(5-methyl-1H-pyrazol-3-yl)-amine;
[1-Isopropoxy-6-(2-morpholin-4-yl-ethoxy)-isoquinolin-3-yl]-(5-methyl-1H-pyrazol-3-yl)-amine;
(1-Isopropoxy-5-methyl-isoquinolin-3-yl)-(5-methyl-1H-pyrazol-3-yl)-amine;
[1-Isopropoxy-7-methoxy-6-(2-methoxy-ethoxy)-isoquinolin-3-yl]-(5-methyl-1H-pyrazol-3-yl)-amine;
[1-Isopropoxy-7-methoxy-6-(2-morpholin-4-yl-ethoxy)-isoquinolin-3-yl]-(5-methyl-1H-pyrazol-3-yl)-amine;
[1-Isopropoxy-7-methoxy-6-(tetrahydro-pyran-4-yloxy)-isoquinolin-3-yl]-(5-methyl-1H-pyrazol-3-yl)-amine;
1-Isopropoxy-7-methoxy-3-(5-methyl-1H-pyrazol-3-ylamino)-isoquinoline-6-carboxylic acid (3-methoxy-propyl)-amide;
[1-Isopropoxy-7-methoxy-3-(5-methyl-1H-pyrazol-3-ylamino)-isoquinolin-6-yl]-morpholin-4-yl-methanone;
1-Isopropoxy-7-methoxy-3-(5-methyl-1H-pyrazol-3-ylamino)-isoquinoline-6-carboxylic acid dimethylamide;
(8-Isopropoxy-2,3-dihydro-1,4-dioxa-7-aza-phenanthren-6-yl)-(5-methyl-1H-pyrazol-3-yl)-amine;
[1,6-Diethoxy-7-(2-methoxy-ethoxy)-isoquinolin-3-yl]-(5-methyl-1H-pyrazol-3-yl)-amine;
[1,6-Diisopropoxy-7-(2-methoxy-ethoxy)-isoquinolin-3-yl]-(5-methyl-1H-pyrazol-3-yl)-amine;
[1-Isopropoxy-7-(2-methoxy-ethoxy)-6-(tetrahydro-furan-3-yloxy)-isoquinolin-3-yl]-(5-methyl-1H-pyrazol-3-yl)-amine;
3-[1-Isopropoxy-7-(2-methoxy-ethoxy)-3-(5-methyl-1H-pyrazol-3-ylamino)-isoquinolin-6-yloxy]-propane-1,2-diol;
[1-Isopropoxy-3-(5-methyl-1H-pyrazol-3-ylamino)-isoquinolin-6-yl]-morpholin-4-yl-methanone;
1-Isopropoxy-3-(5-methyl-1H-pyrazol-3-ylamino)-isoquinoline-6-carboxylic acid dimethylamide;
1-Isopropoxy-3-(5-methyl-1H-pyrazol-3-ylamino)-isoquinoline-6-carboxylic acid (3-methoxy-propyl)-amide;
1-Isopropoxy-3-(5-methyl-1H-pyrazol-3-ylamino)-isoquinoline-6-carboxylic acid (3-dimethylamino-propyl)-methyl-amide;
[1-Isopropoxy-3-(5-methyl-1H-pyrazol-3-ylamino)-isoquinolin-6-yl]-piperidin-1-yl-methanone;
[1-Isopropoxy-6-(4-methyl-piperazin-1-yl)-isoquinolin-3-yl]-(5-methyl-1H-pyrazol-3-yl)-amine;
(1-Isopropoxy-6-morpholin-4-yl-isoquinolin-3-yl)-(5-methyl-1H-pyrazol-3-yl)-amine;
(1-Isopropoxy-6-piperidin-1-yl-isoquinolin-3-yl)-(5-methyl-1H-pyrazol-3-yl)-amine;
(1-Isopropoxy-6-pyrrolidin-1-yl-isoquinolin-3-yl)-(5-methyl-1H-pyrazol-3-yl)-amine;
[1-Isopropoxy-6-(4-methyl-piperazin-1-ylmethyl)-isoquinolin-3-yl]-(5-methyl-1H-pyrazol-3-yl)-amine;
(S)-1-[1-Isopropoxy-3-(5-methyl-1H-pyrazol-3-ylamino)-isoquinolin-6-ylmethyl]-pyrrolidine-2-carboxylic acid amide;
(1-Isopropoxy-6-methoxy-5-methyl-isoquinolin-3-yl)-(5-methyl-1H-pyrazol-3-yl)-amine;
(7-Fluoro-1-isopropoxy-6-methoxy-isoquinolin-3-yl)-(5-methyl-1H-pyrazol-3-yl)-amine;
(5-Cyclopropyl-1H-pyrazol-3-yl)-(7-fluoro-1-isopropoxy-6-methoxy-isoquinolin-3-yl)-amine;
[1-Isopropoxy-6-methoxy-7-(2-morpholin-4-yl-ethoxy)-isoquinolin-3-yl]-(5-methyl-1H-pyrazol-3-yl)-amine;
(7-Fluoro-1-isopropoxy-6-morpholin-4-yl-isoquinolin-3-yl)-(5-methyl-1H-pyrazol-3-yl)-amine;
1-[7-Fluoro-1-isopropoxy-3-(5-methyl-1H-pyrazol-3-ylamino)-isoquinolin-6-yl]-pyrrolidin-2-one;
(5-Chloro-1-isopropoxy-6,7-dimethoxy-isoquinolin-3-yl)-(5-methyl-1H-pyrazol-3-yl)-amine;
(5-Chloro-1,6-diisopropoxy-7-methoxy-isoquinolin-3-yl)-(5-methyl-1H-pyrazol-3-yl)-amine;
(6-Bromo-1-isopropoxy-isoquinolin-3-yl)-(5-methyl-1H-pyrazol-3-yl)-amine;
1-Isopropoxy-3-(5-methyl-1H-pyrazol-3-ylamino)-isoquinoline-6-carboxylic acid diethylamide;
1-Isopropoxy-3-(5-methyl-1H-pyrazol-3-ylamino)-isoquinoline-6-carboxylic acid isopropylamide;
1-Isopropoxy-3-(5-methyl-1H-pyrazol-3-ylamino)-isoquinoline-6-carboxylic acid cyclohexyl-methyl-amide;
[1-Isopropoxy-3-(5-methyl-1H-pyrazol-3-ylamino)-isoquinolin-6-yl]-(4-methyl-piperazin-1-yl)-methanone;
1-Isopropoxy-3-(5-methyl-1H-pyrazol-3-ylamino)-isoquinoline-6-carboxylic acid methyl-(2-piperidin-1-yl-ethyl)-amide;
1-{4-[1-Isopropoxy-3-(5-methyl-1H-pyrazol-3-ylamino)-isoquinoline-6-carbonyl]-piperazin-1-yl}-ethanone;
1-Isopropoxy-3-(5-methyl-1H-pyrazol-3-ylamino)-isoquinoline-6-carboxylic acid methyl-(3-piperidin-1-yl-propyl)-amide;

[1-Isopropoxy-3-(5-methyl-1H-pyrazol-3-ylamino)-isoquinolin-6-yl]-(4-methanesulfonyl-piperazin-1-yl)-methanone;
1-Isopropoxy-3-(5-methyl-1H-pyrazol-3-ylamino)-isoquinoline-6-carboxylic acid methyl-(tetrahydro-pyran-2-ylmethyl)-amide;
(3,5-Dimethyl-piperazin-1-yl)-[1-isopropoxy-3-(5-methyl-1H-pyrazol-3-ylamino)-isoquinolin-6-yl]-methanone;
[1-Isopropoxy-3-(5-methyl-1H-pyrazol-3-ylamino)-isoquinolin-6-yl]-[4-(2-methoxy-ethyl)-piperazin-1-yl]-methanone;
[1-Isopropoxy-3-(5-methyl-1H-pyrazol-3-ylamino)-isoquinolin-6-yl]-(4-methoxy-piperidin-1-yl)-methanone;
(4-Hydroxy-piperidin-1-yl)-[1-isopropoxy-3-(5-methyl-1H-pyrazol-3-ylamino)-isoquinolin-6-yl]-methanone;
[1-Isopropoxy-3-(5-methyl-1H-pyrazol-3-ylamino)-isoquinolin-6-yl]-pyrrolidin-1-yl-methanone;
(7-Bromo-1-isopropoxy-6-methoxy-isoquinolin-3-yl)-(5-methyl-1H-pyrazol-3-yl)-amine;
(7-Bromo-1-isopropoxy-isoquinolin-3-yl)-(5-methyl-1H-pyrazol-3-yl)-amine;
[1-Isopropoxy-6-methoxy-7-(2-methoxy-ethoxy)-isoquinolin-3-yl]-(5-methyl-1H-pyrazol-3-yl)-amine;
[1-Isopropoxy-6,7-bis-(2-methoxy-ethoxy)-isoquinolin-3-yl]-(5-methyl-1H-pyrazol-3-yl)-amine;
(1-Isopropoxy-6,8-dimethoxy-isoquinolin-3-yl)-(5-methyl-1H-pyrazol-3-yl)-amine;
1-Isopropoxy-6-methoxy-3-(5-methyl-1H-pyrazol-3-ylamino)-isoquinoline-7-carboxylic acid dimethylamide;
1-Isopropoxy-6-methoxy-3-(5-methyl-1H-pyrazol-3-ylamino)-isoquinoline-7-carbonitrile;
[1-Isopropoxy-6-methoxy-7-(2-piperidin-1-yl-ethoxy)-isoquinolin-3-yl]-(5-methyl-1H-pyrazol-3-yl)-amine; and
1-[1-Isopropoxy-3-(5-methyl-1H-pyrazol-3-ylamino)-isoquinolin-6-yl]-pyrrolidin-2-one.

Another embodiment of the invention are the compounds of formula I wherein:
R³ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR₂; and
X is —O—.
Such compounds, for example, may be selected from the group consisting of:
[1-(4-Methoxy-phenoxy)-isoquinolin-3-yl]-(5-methyl-1H-pyrazol-3-yl)-amine;
(5-Methyl-1H-pyrazol-3-yl)-(1-phenoxy-isoquinolin-3-yl)-amine;
[1-(4-Fluoro-phenoxy)-isoquinolin-3-yl]-(5-methyl-1H-pyrazol-3-yl)-amine;
(5-Methyl-1H-pyrazol-3-yl)-(1-p-tolyloxy-isoquinolin-3-yl)-amine;
4-[3-(5-Methyl-1H-pyrazol-3-ylamino)-isoquinolin-1-yloxy]-benzonitrile;
[1-(4-Chloro-phenoxy)-isoquinolin-3-yl]-(5-methyl-1H-pyrazol-3-yl)-amine;
(5-Methyl-1H-pyrazol-3-yl)-(1-m-tolyloxy-isoquinolin-3-yl)-amine;
[1-(3-Fluoro-phenoxy)-isoquinolin-3-yl]-(5-methyl-1H-pyrazol-3-yl)-amine;
[1-(3-Chloro-phenoxy)-isoquinolin-3-yl]-(5-methyl-1H-pyrazol-3-yl)-amine;
[1-(3-Methoxy-phenoxy)-isoquinolin-3-yl]-(5-methyl-1H-pyrazol-3-yl)-amine;
(5-Methyl-1H-pyrazol-3-yl)-(1-o-tolyloxy-isoquinolin-3-yl)-amine;
[1-(2-Fluoro-phenoxy)-isoquinolin-3-yl]-(5-methyl-1H-pyrazol-3-yl)-amine;
[1-(2-Chloro-phenoxy)-isoquinolin-3-yl]-(5-methyl-1H-pyrazol-3-yl)-amine;
[1-(2-Methoxy-phenoxy)-isoquinolin-3-yl]-(5-methyl-1H-pyrazol-3-yl)-amine;
3-[3-(5-Methyl-1H-pyrazol-3-ylamino)-isoquinolin-1-yloxy]-benzonitrile;
(5-Methyl-1H-pyrazol-3-yl)-[1-(3-trifluoromethyl-phenoxy)-isoquinolin-3-yl]-amine;
[6-Methoxy-1-(4-methoxy-phenoxy)-isoquinolin-3-yl]-(5-methyl-1H-pyrazol-3-yl)-amine;
(6-Methoxy-1-phenoxy-isoquinolin-3-yl)-(5-methyl-1H-pyrazol-3-yl)-amine;
[1-(4-Fluoro-phenoxy)-6-methoxy-isoquinolin-3-yl]-(5-methyl-1H-pyrazol-3-yl)-amine;
(6-Methoxy-1-p-tolyloxy-isoquinolin-3-yl)-(5-methyl-1H-pyrazol-3-yl)-amine;
4-[6-Methoxy-3-(5-methyl-1H-pyrazol-3-ylamino)-isoquinolin-1-yloxy]-benzonitrile;
[1-(4-Chloro-phenoxy)-6-methoxy-isoquinolin-3-yl]-(5-methyl-1H-pyrazol-3-yl)-amine;
(6-Methoxy-1-m-tolyloxy-isoquinolin-3-yl)-(5-methyl-1H-pyrazol-3-yl)-amine;
[1-(3-Fluoro-phenoxy)-6-methoxy-isoquinolin-3-yl]-(5-methyl-1H-pyrazol-3-yl)-amine;
[1-(3-Chloro-phenoxy)-6-methoxy-isoquinolin-3-yl]-(5-methyl-1H-pyrazol-3-yl)-amine;
[6-Methoxy-1-(3-methoxy-phenoxy)-isoquinolin-3-yl]-(5-methyl-1H-pyrazol-3-yl)-amine;
(6-Methoxy-1-o-tolyloxy-isoquinolin-3-yl)-(5-methyl-1H-pyrazol-3-yl)-amine;
[1-(2-Fluoro-phenoxy)-6-methoxy-isoquinolin-3-yl]-(5-methyl-1H-pyrazol-3-yl)-amine;
[1-(2-Chloro-phenoxy)-6-methoxy-isoquinolin-3-yl]-(5-methyl-1H-pyrazol-3-yl)-amine;
[1-(4-Methoxy-phenoxy)-isoquinolin-3-yl]-(1H-pyrazol-3-yl)-amine;
N-{4-[6-Methoxy-3-(5-methyl-1H-pyrazol-3-ylamino)-isoquinolin-1-yloxy]-phenyl}-acetamide;
N-{4-[3-(5-Methyl-1H-pyrazol-3-ylamino)-isoquinolin-1-yloxy]-phenyl}-acetamide;
N-{4-[5-Methoxy-3-(5-methyl-1H-pyrazol-3-ylamino)-isoquinolin-1-yloxy]-phenyl}-acetamide;
N-{4-[7-Methoxy-3-(5-methyl-1H-pyrazol-3-ylamino)-isoquinolin-1-yloxy]-phenyl}-acetamide;
[5-Methoxy-1-(4-methoxy-phenoxy)-isoquinolin-3-yl]-(5-methyl-1H-pyrazol-3-yl)-amine;
(5-Methoxy-1-phenoxy-isoquinolin-3-yl)-(5-methyl-1H-pyrazol-3-yl)-amine;
[1-(4-Fluoro-phenoxy)-5-methoxy-isoquinolin-3-yl]-(5-methyl-1H-pyrazol-3-yl)-amine;
(5-Methoxy-1-p-tolyloxy-isoquinolin-3-yl)-(5-methyl-1H-pyrazol-3-yl)-amine;
4-[5-Methoxy-3-(5-methyl-1H-pyrazol-3-ylamino)-isoquinolin-1-yloxy]-benzonitrile;
[1-(4-Chloro-phenoxy)-5-methoxy-isoquinolin-3-yl]-(5-methyl-1H-pyrazol-3-yl)-amine;
[7-Methoxy-1-(4-methoxy-phenoxy)-isoquinolin-3-yl]-(5-methyl-1H-pyrazol-3-yl)-amine;
(7-Methoxy-1-phenoxy-isoquinolin-3-yl)-(5-methyl-1H-pyrazol-3-yl)-amine;
[1-(4-Fluoro-phenoxy)-7-methoxy-isoquinolin-3-yl]-(5-methyl-1H-pyrazol-3-yl)-amine;
N-{4-[6-Methoxy-3-(1H-pyrazol-3-ylamino)-isoquinolin-1-yloxy]-phenyl}-acetamide;

4-[7-Methoxy-3-(5-methyl-1H-pyrazol-3-ylamino)-isoquinolin-1-yloxy]-benzonitrile;
[1-(4-Chloro-phenoxy)-7-methoxy-isoquinolin-3-yl]-(5-methyl-1H-pyrazol-3-yl)-amine;
(5-Methyl-1-phenoxy-isoquinolin-3-yl)-(5-methyl-1H-pyrazol-3-yl)-amine;
[1-(4-Fluoro-phenoxy)-5-methyl-isoquinolin-3-yl]-(5-methyl-1H-pyrazol-3-yl)-amine;
(5-Methyl-1H-pyrazol-3-yl)-(5-methyl-1-p-tolyloxy-isoquinolin-3-yl)-amine;
[1-(4-Chloro-phenoxy)-5-methyl-isoquinolin-3-yl]-(5-methyl-1H-pyrazol-3-yl)-amine;
(6,7-Dimethoxy-1-phenoxy-isoquinolin-3-yl)-(5-methyl-1H-pyrazol-3-yl)-amine;
[1-(4-Fluoro-phenoxy)-6,7-dimethoxy-isoquinolin-3-yl]-(5-methyl-1H-pyrazol-3-yl)-amine;
N-{4-[3-(1H-Pyrazol-3-ylamino)-isoquinolin-1-yloxy]-phenyl}-acetamide;
N-{4-[6,7-Dimethoxy-3-(5-methyl-1H-pyrazol-3-ylamino)-isoquinolin-1-yloxy]-phenyl}-acetamide;
(5,6-Dimethoxy-1-phenoxy-isoquinolin-3-yl)-(5-methyl-1H-pyrazol-3-yl)-amine;
[1-(4-Fluoro-phenoxy)-5,6-dimethoxy-isoquinolin-3-yl]-(5-methyl-1H-pyrazol-3-yl)-amine;
4-[5,6-Dimethoxy-3-(5-methyl-1H-pyrazol-3-ylamino)-isoquinolin-1-yloxy]-benzonitrile;
[1-(4-Chloro-phenoxy)-5,6-dimethoxy-isoquinolin-3-yl]-(5-methyl-1H-pyrazol-3-yl)-amine;
N-{4-[5,6-Dimethoxy-3-(5-methyl-1H-pyrazol-3-ylamino)-isoquinolin-1-yloxy]-phenyl}-acetamide;
(1H-Pyrazol-3-yl)-(1-m-tolyloxy-isoquinolin-3-yl)-amine;
(1H-Pyrazol-3-yl)-(1-p-tolyloxy-isoquinolin-3-yl)-amine;
(1H-Pyrazol-3-yl)-(1-o-tolyloxy-isoquinolin-3-yl)-amine;
[1-(3-Methoxy-phenoxy)-isoquinolin-3-yl]-(1H-pyrazol-3-yl)-amine;
[1-(2-Methoxy-phenoxy)-isoquinolin-3-yl]-(1H-pyrazol-3-yl)-amine;
[1-(2-Fluoro-phenoxy)-isoquinolin-3-yl]-(1H-pyrazol-3-yl)-amine;
[1-(3-Fluoro-phenoxy)-isoquinolin-3-yl]-(1H-pyrazol-3-yl)-amine;
3-[3-(1H-Pyrazol-3-ylamino)-isoquinolin-1-yloxy]-benzonitrile;
4-[3-(1H-Pyrazol-3-ylamino)-isoquinolin-1-yloxy]-benzonitrile;
[1-(4-Chloro-phenoxy)-isoquinolin-3-yl]-(1H-pyrazol-3-yl)-amine;
[1-(3-Chloro-phenoxy)-isoquinolin-3-yl]-(1H-pyrazol-3-yl)-amine;
[1-(2-Chloro-phenoxy)-isoquinolin-3-yl]-(1H-pyrazol-3-yl)-amine;
(1-Phenoxy-isoquinolin-3-yl)-(1H-pyrazol-3-yl)-amine;
[1-(4-Fluoro-phenoxy)-isoquinolin-3-yl]-(1H-pyrazol-3-yl)-amine;
(6-Methoxy-1-phenoxy-isoquinolin-3-yl)-(1H-pyrazol-3-yl)-amine;
[1-(4-Fluoro-phenoxy)-6-methoxy-isoquinolin-3-yl]-(1H-pyrazol-3-yl)-amine;
[1-(3-Fluoro-phenoxy)-6-methoxy-isoquinolin-3-yl]-(1H-pyrazol-3-yl)-amine;
[1-(2-Fluoro-phenoxy)-6-methoxy-isoquinolin-3-yl]-(1H-pyrazol-3-yl)-amine;
(6-Methoxy-1-p-tolyloxy-isoquinolin-3-yl)-(1H-pyrazol-3-yl)-amine;
(6-Methoxy-1-m-tolyloxy-isoquinolin-3-yl)-(1H-pyrazol-3-yl)-amine;
[6-Methoxy-1-(4-methoxy-phenoxy)-isoquinolin-3-yl]-(1H-pyrazol-3-yl)-amine;
[6-Methoxy-1-(3-methoxy-phenoxy)-isoquinolin-3-yl]-(1H-pyrazol-3-yl)-amine;
[1-(4-Chloro-phenoxy)-6-methoxy-isoquinolin-3-yl]-(1H-pyrazol-3-yl)-amine;
[1-(3-Chloro-phenoxy)-6-methoxy-isoquinolin-3-yl]-(1H-pyrazol-3-yl)-amine;
[1-(4-Fluoro-phenoxy)-3-(5-methyl-1H-pyrazol-3-ylamino)-isoquinolin-6-yl]-morpholin-4-yl-methanone; and
[1-(4-Fluoro-phenoxy)-6,8-dimethoxy-isoquinolin-3-yl]-(5-methyl-1H-pyrazol-3-yl)-amine.

Another embodiment of the invention are the compounds of formula I wherein $R^3$ is cycloalkyl; and X is —O—.

Another embodiment of the invention are the compounds of formula I wherein:
$R^2$ is hydrogen;
$R^3$ is cycloalkyl; and
X is —O—.

Such compounds, for example, may be selected from the group consisting of:
(1-Cyclohexyloxy-isoquinolin-3-yl)-(5-methyl-1H-pyrazol-3-yl)-amine;
(1-Cyclohexyloxy-6-methoxy-isoquinolin-3-yl)-(5-methyl-1H-pyrazol-3-yl)-amine;
(1-Cyclopentyloxy-6,7-dimethoxy-isoquinolin-3-yl)-(5-methyl-1H-pyrazol-3-yl)-amine;
(1-Cyclobutoxy-6,7-dimethoxy-isoquinolin-3-yl)-(5-methyl-1H-pyrazol-3-yl)-amine;
(1-Cyclobutoxy-6,7-dimethoxy-isoquinolin-3-yl)-(5-cyclopropyl-1H-pyrazol-3-yl)-amine;
[1-Cyclobutoxy-6-methoxy-7-(2-methoxy-ethoxy)-isoquinolin-3-yl]-(5-methyl-1H-pyrazol-3-yl)-amine;
1-Cyclobutoxy-6-methoxy-3-(5-methyl-1H-pyrazol-3-ylamino)-isoquinoline-7-carboxylic acid dimethylamide;
1-Cyclopentyloxy-6-methoxy-3-(5-methyl-1H-pyrazol-3-ylamino)-isoquinoline-7-carboxylic acid dimethylamide; and
(1-Cyclobutoxy-6-methoxy-isoquinolin-3-yl)-(5-methyl-1H-pyrazol-3-yl)-amine.

Another embodiment of the invention are the compounds of formula I wherein:
$R^3$ is heterocyclyl, preferably selected from oxetanyl and tetrahydrofuranyl; and
X is —O—.

Another embodiment of the invention are the compounds of formula I wherein:
$R^2$ is hydrogen;
$R^3$ is heterocyclyl, preferably selected from oxetanyl and tetrahydrofuranyl; and
X is —O—.

Such compounds, for example, may be selected from the group consisting of:
{6,7-Dimethoxy-1-[(R)-(tetrahydro-furan-3-yl)oxy]-isoquinolin-3-yl}-(5-methyl-1H-pyrazol-3-yl)-amine;
{6,7-Dimethoxy-1-[(S)-(tetrahydro-furan-3-yl)oxy]-isoquinolin-3-yl}-(5-methyl-1H-pyrazol-3-yl)-amine;
[6,7-Dimethoxy-1-(tetrahydro-furan-3-yloxy)-isoquinolin-3-yl]-(5-methyl-1H-pyrazol-3-yl)-amine;
[6-Methoxy-7-(2-methoxy-ethoxy)-1-(tetrahydro-furan-3-yloxy)-isoquinolin-3-yl]-(5-methyl-1H-pyrazol-3-yl)-amine;
[6-Methoxy-7-(2-methoxy-ethoxy)-1-(oxetan-3-yloxy)-isoquinolin-3-yl]-(5-methyl-1H-pyrazol-3-yl)-amine; and
6-Methoxy-3-(5-methyl-1H-pyrazol-3-ylamino)-1-(tetrahydro-furan-3-yloxy)-isoquinoline-7-carbonitrile.

Another embodiment of the invention are the compounds of formula I wherein:
R³ is selected from the group consisting of:
(1) alkyl which is substituted one or two times with —C(O)O-alkyl, phenyl, heterocyclyl or cycloalkyl,
(2) aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR₂;
X is —S—.

Another embodiment of the invention are the compounds of formula I wherein:
R³ is selected from the group consisting of:
(1) alkyl which is substituted one time with —C(O)O-alkyl; and
(2) aryl which is optionally substituted one or more times with halogen, alkyl or unsubstituted alkoxy; and
X is —S—.

Such compounds, for example, may be selected from the group consisting of:
(5-Methyl-1H-pyrazol-3-yl)-(1-phenylsulfanyl-isoquinolin-3-yl)-amine;
[1-(3-Methoxy-phenylsulfanyl)-isoquinolin-3-yl]-(5-methyl-1H-pyrazol-3-yl)-amine;
[6-Methoxy-1-(3-methoxy-phenylsulfanyl)-isoquinolin-3-yl]-(5-methyl-1H-pyrazol-3-yl)-amine;
[1-(4-Chloro-phenylsulfanyl)-isoquinolin-3-yl]-(5-methyl-1H-pyrazol-3-yl)-amine;
[1-(4-Chloro-phenylsulfanyl)-6-methoxy-isoquinolin-3-yl]-(5-methyl-1H-pyrazol-3-yl)-amine;
[1-(3-Fluoro-phenylsulfanyl)-isoquinolin-3-yl]-(5-methyl-1H-pyrazol-3-yl)-amine;
[1-(3-Fluoro-phenylsulfanyl)-6-methoxy-isoquinolin-3-yl]-(5-methyl-1H-pyrazol-3-yl)-amine;
[1-(4-Fluoro-phenylsulfanyl)-isoquinolin-3-yl]-(5-methyl-1H-pyrazol-3-yl)-amine;
[1-(4-Fluoro-phenylsulfanyl)-6-methoxy-isoquinolin-3-yl]-(5-methyl-1H-pyrazol-3-yl)-amine;
[1-(2-Fluoro-phenylsulfanyl)-isoquinolin-3-yl]-(5-methyl-1H-pyrazol-3-yl)-amine;
[1-(2-Fluoro-phenylsulfanyl)-6-methoxy-isoquinolin-3-yl]-(5-methyl-1H-pyrazol-3-yl)-amine;
(6-Methoxy-1-phenylsulfanyl-isoquinolin-3-yl)-(5-methyl-1H-pyrazol-3-yl)-amine;
(5-Methyl-1H-pyrazol-3-yl)-(1-p-tolylsulfanyl-isoquinolin-3-yl)-amine;
(6-Methoxy-1-p-tolylsulfanyl-isoquinolin-3-yl)-(5-methyl-1H-pyrazol-3-yl)-amine;
(5-Methyl-1H-pyrazol-3-yl)-(1-m-tolylsulfanyl-isoquinolin-3-yl)-amine;
(6-Methoxy-1-m-tolylsulfanyl-isoquinolin-3-yl)-(5-methyl-1H-pyrazol-3-yl)-amine;
[1-(3-Chloro-phenylsulfanyl)-isoquinolin-3-yl]-(5-methyl-1H-pyrazol-3-yl)-amine;
[1-(3-Chloro-phenylsulfanyl)-6-methoxy-isoquinolin-3-yl]-(5-methyl-1H-pyrazol-3-yl)-amine;
[1-(2-Chloro-phenylsulfanyl)-isoquinolin-3-yl]-(5-methyl-1H-pyrazol-3-yl)-amine;
[1-(2-Chloro-phenylsulfanyl)-6-methoxy-isoquinolin-3-yl]-(5-methyl-1H-pyrazol-3-yl)-amine; and
[3-(5-Methyl-1H-pyrazol-3-ylamino)-isoquinolin-1-ylsulfanyl]-acetic acid ethyl ester.

Another embodiment of the invention are the compounds of formula I wherein R³ is heterocyclyl; and X is —C(O)—.
Such compounds, for example, may be selected from the group consisting of:

[6-Methoxy-3-(5-methyl-1H-pyrazol-3-ylamino)-isoquinolin-1-yl]-morpholin-4-yl-methanone;
1-{4-[6-Methoxy-3-(5-methyl-1H-pyrazol-3-ylamino)-isoquinoline-1-carbonyl]-piperazin-1-yl}-ethanone; and
[6-Methoxy-3-(5-methyl-1H-pyrazol-3-ylamino)-isoquinolin-1-yl]-piperidin-1-yl-methanone.

Another embodiment of the invention are the compounds of formula I wherein:
R³ is selected from the group consisting of:
(1) unsubstituted alkyl,
(2) alkyl which is substituted one or two times with phenyl or cycloalkyl,
(3) aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR₂, and
(4) cycloalkyl; and
X is —C(O)NR—.

Another embodiment of the invention are the compounds of formula I wherein:
R³ is selected from the group consisting of:
(1) unsubstituted alkyl,
(2) alkyl which is substituted one or two times with phenyl or cycloalkyl,
(3) aryl, and
(4) cycloalkyl; and
X is —C(O)NR—.

Such compounds, for example, may be selected from the group consisting of:
6-Methoxy-3-(5-methyl-1H-pyrazol-3-ylamino)-isoquinoline-1-carboxylic acid cyclopropylmethyl-amide;
6-Methoxy-3-(5-methyl-1H-pyrazol-3-ylamino)-isoquinoline-1-carboxylic acid dimethylamide;
6-Methoxy-3-(5-methyl-1H-pyrazol-3-ylamino)-isoquinoline-1-carboxylic acid phenylamide;
6-Methoxy-3-(5-methyl-1H-pyrazol-3-ylamino)-isoquinoline-1-carboxylic acid cyclohexylamide;
6-Methoxy-3-(5-methyl-1H-pyrazol-3-ylamino)-isoquinoline-1-carboxylic acid benzylamide; and
6-Methoxy-3-(5-methyl-1H-pyrazol-3-ylamino)-isoquinoline-1-carboxylic acid cyclopropylamide.

Another embodiment of the invention are the compounds of formula I wherein:
R³ is selected from the group consisting of:
(1) unsubstituted alkyl,
(2) alkyl which is substituted one or two times with phenyl or heterocyclyl,
(3) alkyl wherein one or more —CH₂-groups are replaced by oxygen,
(4) aryl which is optionally substituted one or more times with halogen, alkyl, halogenated alkyl, halogenated alkoxy, cyano, —C(O)-alkyl, —NH—C(O)-alkyl, —C(O)OH,
—C(O)O-alkyl, unsubstituted alkoxy, alkoxy substituted by heterocyclyl, or —NR₂,
(5) heteroaryl which is optionally substituted one or more times with alkyl, and
(6) cycloalkyl; and
X is a single bond, —NR— or —O—.

Another embodiment of the invention are the compounds of formula I wherein R³ is unsubstituted alkyl, cycloalkyl or heterocyclyl.

Another embodiment of the invention are the compounds of formula I wherein:
R³ is unsubstituted alkyl, cycloalkyl or heterocyclyl; and
X is a single bond or —O—.

Another embodiment of the invention are the compounds of formula I wherein:
R$^3$ is unsubstituted alkyl, cycloalkyl or heterocyclyl; and
X is —O—.

Another embodiment of the invention are the compounds of formula I wherein R$^3$ is unsubstituted alkyl or cycloalkyl.

Another embodiment of the invention are the compounds of formula I wherein:
R$^3$ is unsubstituted alkyl or cycloalkyl; and
X is a single bond or —O—.

Another embodiment of the invention are the compounds of formula I wherein:
R$^3$ is unsubstituted alkyl or cycloalkyl; and
X is a single bond.

Another embodiment of the invention are the compounds of formula I wherein R$^3$ is unsubstituted alkyl.

Another embodiment of the invention are the compounds of formula I wherein:
R$^3$ is unsubstituted alkyl; and
X is —O—.

Another embodiment of the invention are the compounds of formula I wherein:
R$^3$ is unsubstituted alkyl; and
X is a single bond or —O—.

Another embodiment of the invention are the compounds of formula I wherein R$^3$ is cycloalkyl.

Another embodiment of the invention are the compounds of formula I wherein:
R$^3$ is cycloalkyl; and
X is a single bond.

Another embodiment of the invention are the compounds of formula I wherein:
R$^3$ is cycloalkyl; and
X is —O—.

Another embodiment of the invention are the compounds of formula I wherein:
R$^3$ is cycloalkyl; and
X is a single bond or —O—.

Another embodiment of the invention are the compounds of formula I wherein R$^3$ is heterocyclyl.

Another embodiment of the invention are the compounds of formula I wherein:
R$^3$ is heterocyclyl; and
X is —O—.

Another embodiment of the invention are the compounds of formula I wherein:
R$^3$ is heterocyclyl; and
X is a single bond or —O—.

Another embodiment of the invention are the compounds of formula I wherein:
Y is —O— or —C(O)NR—; and
R$^7$ is alkyl which is optionally substituted one time by alkoxy or heterocyclyl.

Another embodiment of the invention are the compounds of formula I wherein:
Y is —O— or —C(O)NR—;
R$^7$ is alkyl which is optionally substituted one time by alkoxy or heterocyclyl; and
n is 0 or 1.

Another embodiment of the invention are the compounds of formula I wherein n is 0 or 1.

Another embodiment of the invention are the compounds of formula I wherein n is 0.

Another embodiment of the invention are the compounds of formula I wherein R$^6$ is hydrogen, alkyl or alkoxy.

Another embodiment of the invention are the compounds of formula I wherein R$^5$ is hydrogen, —(CH$_2$)$_n$—Y—R$^7$ or -Z-R$^8$;

Another embodiment of the invention are the compounds of formula I wherein R$^4$ is hydrogen, —(CH$_2$)$_n$—Y—R$^7$ or -Z-R$^8$;

Another embodiment of the invention are the compounds of formula I wherein R$^6$ is hydrogen.

Another embodiment of the invention are the compounds of formula I wherein R$^5$ is hydrogen.

Another embodiment of the invention are the compounds of formula I wherein R$^4$ is hydrogen.

Another embodiment of the invention are the compounds of formula I wherein R$^4$ and R$^6$ are both hydrogen.

Another embodiment of the invention are the compounds of formula I wherein R$^5$ and R$^6$ are both hydrogen.

Another embodiment of the invention are the compounds of formula I wherein R$^4$ and R$^5$ are both hydrogen.

Another embodiment of the invention are the compounds of formula I wherein R$^4$, R$^5$ and R$^6$ are all hydrogen.

Another embodiment of the invention are the compounds of formula I wherein R is hydrogen.

Another embodiment of the invention are the compounds of formula I wherein R$^6$ is alkyl or alkoxy.

Another embodiment of the invention are the compounds of formula I wherein R$^6$ is alkoxy.

Another embodiment of the invention are the compounds of formula I wherein R$^5$ is alkoxy.

Another embodiment of the invention are the compounds of formula I wherein R$^4$ is alkoxy.

Another embodiment of the invention are the compounds of formula I wherein R$^5$ or R$^6$ are alkoxy.

Another embodiment of the invention are the compounds of formula I wherein R$^5$ and R$^6$ are alkoxy.

Another embodiment of the invention are the compounds of formula I wherein R$^4$ or R$^5$ are alkoxy.

Another embodiment of the invention are the compounds of formula I wherein R$^4$ and R$^5$ are alkoxy.

Another embodiment of the invention are the compounds of formula I wherein R$^4$, R$^5$ or R$^6$ are alkoxy.

Another embodiment of the invention are the compounds of formula I wherein:
R$^1$ is hydrogen, alkyl or cycloalkyl;
R$^2$ is hydrogen or alkyl (preferably hydrogen);
R$^3$ is selected from the group consisting of:
  (1) unsubstituted alkyl,
  (2) alkyl which is substituted one time with phenyl, heterocyclyl or cycloalkyl,
  (3) alkyl wherein one or more —CH$_2$-groups are replaced by oxygen,
  (4) aryl which is optionally substituted one to three times with a substituent independently selected from the group consisting of halogen, alkyl, halogenated alkyl, cyano, —C(O)-alkyl, —NH—C(O)-alkyl, and unsubstituted alkoxy,
  (5) heteroaryl which is optionally substituted one or more times with alkyl,
  (6) cycloalkyl; and
  (7) heterocyclyl, wherein preferably at least one heteroatom is nitrogen and the remaining heteroatoms are selected independently from the group consisting of nitrogen, oxygen and sulfur, and such heterocyclyl group is attached via the ring nitrogen atom;
R$^{3a}$ is hydrogen or alkoxy;
R$^4$ is hydrogen, halogen, alkyl, cyano, —C(O)NR$_2$, —(CH$_2$)$_n$—Y—R$^7$ or -Z-R$^8$;

$R^5$ is hydrogen, alkyl, —C(O)$NR_2$, —$(CH_2)_n$—Y—$R^7$ or -Z-$R^8$;

$R^6$ is hydrogen, alkyl or alkoxy;

X is a single bond, —S—, —NR— or —O—;

Y is —O— or —C(O)NR—;

Z is —C(O)—, —O—, a single bond or alkylene;

$R^7$ is cycloalkyl, or alkyl which is optionally substituted once or twice by alkoxy, hydroxy, heterocyclyl or —$NR_2$, (preferably alkyl which is optionally substituted once or twice by alkoxy, hydroxy, heterocyclyl or —$NR_2$);

$R^8$ is heterocyclyl;

R is hydrogen or alkyl; and n is 0 or 1 (preferably 0).

Another embodiment of the invention are the compounds of formula I wherein:

$R^3$ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —$NR_2$;

X is —O—;

$R^4$ and $R^6$ are hydrogen; and $R^5$ is alkoxy.

Another embodiment of the invention are the compounds of formula I wherein:

$R^3$ is heteroaryl (preferably pyridyl) which is optionally substituted one or more times with alkyl;

X is —NR—;

$R^4$ and $R^6$ are hydrogen; and $R^5$ is alkoxy.

Another embodiment of the invention are the compounds of formula I wherein:

$R^3$ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —$NR_2$;

X is a single bond;

$R^4$ is hydrogen; and $R^5$ and $R^6$ are alkoxy.

Another embodiment of the invention are the compounds of formula I wherein:

$R^3$ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —$NR_2$;

X is a single bond;

$R^1$ is alkyl;

$R^2$ is hydrogen;

$R^4$ and $R^6$ are hydrogen; and $R^5$ is alkoxy.

It will be understood that the above embodiments may be combined to form additional embodiments of the invention.

The compounds of formula I may be prepared by any process known to be applicable to the preparation of chemically-related compounds. Such preparation is included within the present invention.

One embodiment of the invention is a process for the preparation of the compounds of formula I comprising the steps of:

(a) reacting a compound of formula II:

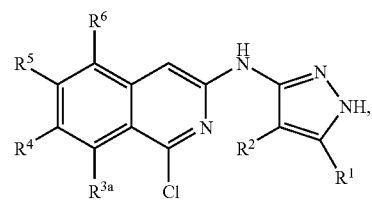

formula II wherein $R^1$, $R^2$, $R^{3a}$, $R^4$, $R^5$ and $R^1$ have the significance given above for formula I; with a compound of formula III:

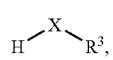

formula III wherein $R^3$ has the significance given above for formula I and X is a single bond, —NR—, —O— or —S—;

to obtain the compounds of formula I:

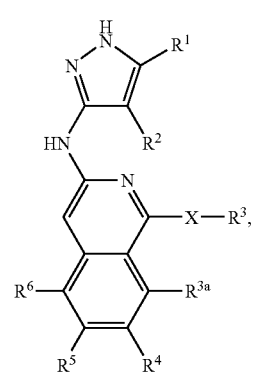

formula I wherein $R^1$ to $R^6$ have the significance given above for formula I and X is a single bond, —NR—, —O— or —S—, (b) optionally isolating said compound of formula I from the reaction mixture, and (c) optionally converting said compound into a pharmaceutically acceptable salt or ester.

One embodiment of the invention is a process for the preparation of the compounds of formula I comprising the steps of:

(a) reacting a compound of formula IIa:

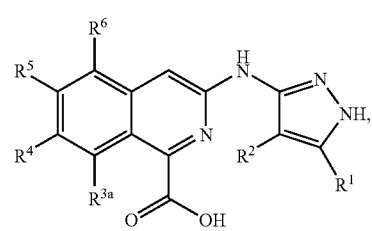

formula IIa wherein $R^1$, $R^2$, $R^{3a}$, $R^4$, $R^5$ and $R^1$ have the significance given above for formula I; with a compound of formula IIIa:

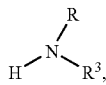

formula IIIa wherein R and $R^3$ have the significance given above for formula I and X is —C(O)NR—;

to obtain the compounds of formula I:

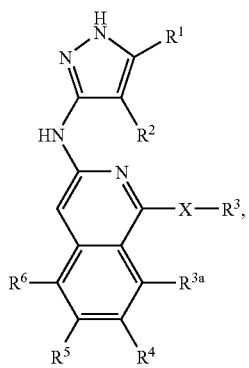

formula Ia wherein $R^1$ to $R^6$ and R have the significance given above for formula I and X is —C(O)NR—;

(b) optionally isolating said compound of formula I from the reaction mixture, and (c) optionally converting said compound into a pharmaceutically acceptable salt or ester.

The compounds of formula I, or a pharmaceutically acceptable salt or ester thereof, which are the subject of the present invention, may be prepared by any process known to be applicable to the preparation of chemically-related compounds. Such processes, when used to prepare a compound of the formula I, or a pharmaceutically-acceptable salt or ester thereof, are illustrated by the following representative schemes 1 to 3 and the examples in which, unless otherwise stated, X, Y, Z, $R^1$, $R^2$, $R^3$, $R^{3a}$, $R^4$, $R^5$, $R^6$, $R^7$, $R^8$, R and n have the meaning given previously for formula I. Necessary starting materials may be obtained by standard procedures of organic chemistry. The preparation of such starting materials is described within the accompanying examples or in the literature cited below with respect to scheme 1 to 4. Alternatively, necessary starting materials are obtainable by analogous procedures to those illustrated which are within the ordinary skill of an organic chemist.

Reaction Scheme 1

The compounds of the present invention may be prepared by any conventional means. In Reaction Scheme 1, a compound of formula IV in which $R^1$ is hydrogen, halogen, alkoxy, alkyl, substituted alkyl or cyano, is either a known compound or can be prepared by standard methodology. The compound of formula IV is treated with a nitrosation reagent (for example butyl nitrite) in a solvent (such as ether or methanol) under an acid catalysis to obtain a compound of formula V. Conversion of formula V to an acid of formula VI can be carried out using p-toluenesulfonyl chloride in aqueous sodium hydroxide. Condensation of the acid of formula VI with a compound of formula VII can be conducted under microwave irradiation (Kappe, C. Oliver, Angew. Chem. Int. Ed. 43 (2004) 6250-6284), for example heating of VI and VII in acetic acid under microwave irradiation directly leads to a compound of formula VIII. The cyclized compound of formula VIII can be converted to the corresponding chloride of formula IX by treatment with a halogenation agent such as phosphorous oxytrichloride under microwave irradiation.

Reaction Scheme 1

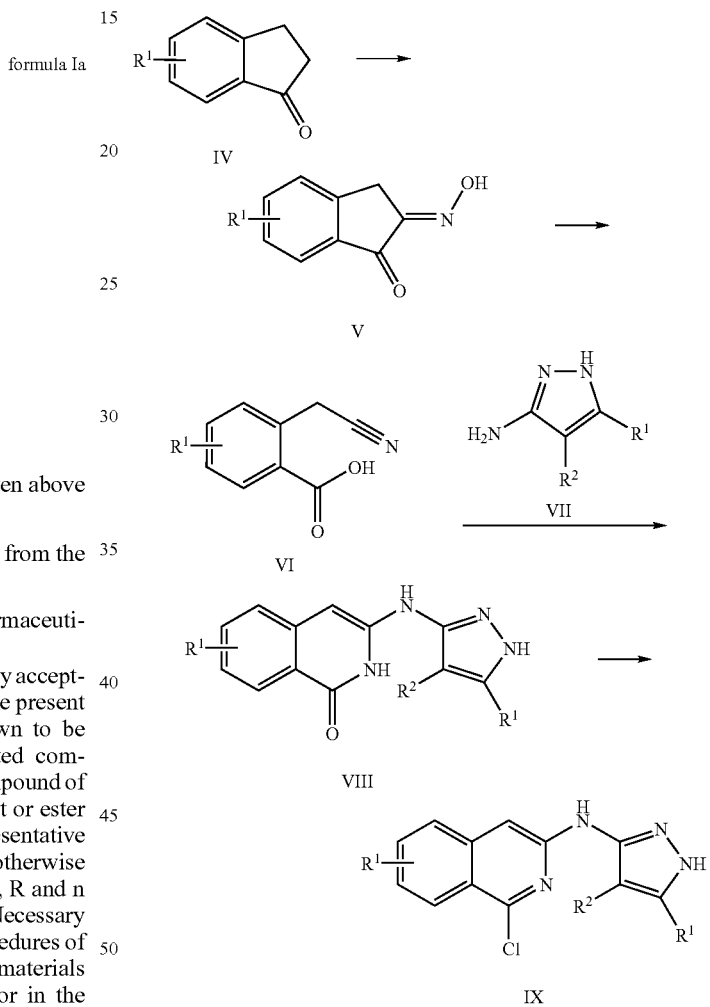

In reaction scheme 1, $R^1$ and $R^2$ have the meaning given previously formula I and $R^1$ is hydrogen, halogen alkoxy, alkyl, substituted alkyl or cyano.

Reaction Scheme 2

The process for the conversion of the compounds of formula IX into compounds of the invention is shown in Reaction Scheme 2. Treatment of the compounds of formula IX with $NaOR^{II}$, or $NaSR^{II}$, in which $R^{II}$ is optionally a substituted alkyl or a optionally substituted aryl at a temperature between $80°$ C and $200°$ C under a conventional heating method or under microwave irradiation resulted in a compound of formula X, wherein X is —O— or —S—. $NaOR^{II}$ or NaSR$^{II}$, can be prepared (e.g. in situ) from the corresponding alcohol or thiol HOR$^{II}$ or HSR$^{II}$ using basic conditions. Suzuki coupling (Mongin, F., Rebstock, A., Trecourt, F., Queguiner, G., Marsais, F., J. Org. Chem. 69 (2004) 6766-6771) of IX with R$^{III}$B(OH)$_2$ in which R$^{III}$ is a optionally substituted aryl or a optionally substituted heteroaryl under a conventional heating method or under microwave irradiation directly leads to a compound of formula XI. The Compound of formula XII can be prepared by Buchwald-Hartwig amination of IX with R$^{IV}$NH$_2$ in which R$^{IV}$ is a optionally substituted aryl or a optionally substituted heteroaryl under conventional conditions or microwave irradiation (Jonckers, T. M., Maes, B. W., Lemiere, G. F., Dommisse, R., Tetrahedron 57 (2001) 7027-7034). To prepare the compound of formula XIII starting from the chloro-isoquinoline of formula IX a three step procedure is necessary. First an ester group is introduced at the chloro-position using carbonmonoxide and isopropanol under autoclave conditions under heating in the presence of Pd(OAc)$_2$, Pd(PPh$_3$)$_4$, Cs$_2$CO$_3$ and 1,3-bis(diphenylphosphino)propane (DPPP) (for alternative conditions see e.g Blaser, H.-U., et al, 68 J. Org. Chem.(2003) 3725-3728, Adamczyk, M., et al, Tetrahedron 58 (2002) 6951-6964 or Henegar, K. E., et al, 62 J. Org. Chem.(1997) 6588-6597). Then, in a second step the ester is saponified, typically in an alcoholic solution of KOH or NaOH yielding the corresponding carboxylic acid. In the third step such carboxylic acid is activated, for example, with 1-hydroxybenzotriazole (HOBt), 1,1'-carbonyldiimidazole (CDI), 1-ethyl-3-[3-dimethylaminopropyl]carbodiimide hydrochloride (EDCI), oxalyl chloride and the like, and reacted with R$^V$R$^{VI}$NH, wherein R$^V$ is a optionally substituted alkyl and R$^{VI}$ is a alkyl or hydrogen, or alternatively R$^V$ and R$^{VI}$ form a heterocyclyl group together with the nitrogen atom to which they are attached, to obtain the compounds of formula XIII.

substituted aryl, R$^{III}$ and R$^{IV}$ are optionally substituted aryls or optionally substituted heteroaryls, R$^V$ is a optionally substituted alkyl and R$^{VI}$ is an alkyl or hydrogen, or alternatively R$^V$ and R$^{VI}$ form a heterocyclyl group together with the nitrogen atom to which they are attached, and X is —O— or —S—.

Reaction Scheme 3

To prepare either the compounds of formula XV, wherein R$^{VII}$ is a optionally substituted alkyl, or the compounds of formula XVII, wherein R$^V$ is a optionally substituted alkyl and R$^{VI}$ is an alkyl or hydrogen, or alternatively R$^V$ and R$^{VI}$ form a heterocyclyl group together with the nitrogen atom to which they are attached, firstly the compound of formula X, wherein R$^1$ is methoxy and which is named Xa, is converted to a compound of formula XIV by ether cleavage with a de-methylation reagent, for example 48% HBr. Alkylation of XIV with R$^{VII}$Br or R$^{VII}$Cl under a conventional method directly leads to a compound of formula XV. The compound of formula XIV can also be converted to its trifluoromethanesulfonate XVI under a conventional method e.g. by reaction with trifluoromethanesulfonic acid anhydride, then XVI can be readily converted to a compound of formula XVII by using a transition-metal-catalyzed carbonylation reaction (Wannberg, J., Larhed, M. J., J. Org. Chem. 68 (2003) 5750-5753). This reaction can be carried out by reaction of the compound of formula XVI with Mo(CO)$_6$ and R$^V$R$^{VI}$NH in the presence of DBU as a base and palladium acetate as a catalyst at a temperature of from 110$^O$ C to 180$^O$ C. under microwave irradiation.

To prepare the compounds of formula XVIII, wherein R$^{VIII}$ is an N-containing heterocyclyl which is attached via the nitrogen, the triflate derivatives of formula XVI are either

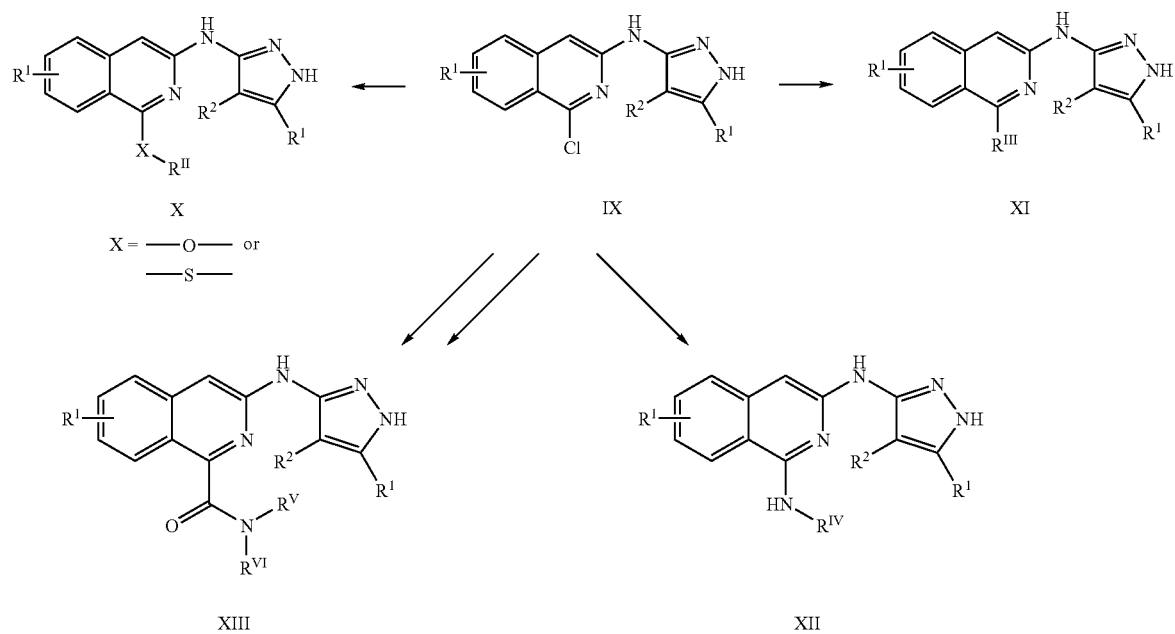

Reaction Scheme 2

In reaction scheme 2, R$^1$ and R$^2$ have the meaning given previously for formula I and R$^1$ is hydrogen, halogen or alkoxy, R$^{II}$ is a optionally substituted alkyl or a optionally directly reacted with the respective N-containing heterocycle like morpholine, piperidine, pyrrolidine, N-methyl-piperazine, and the like, in inert solvents like N-Methylpyridone (NMP), at temperatures of from 150° C to 250° C under microwave irradiation. Alternatively the triflate derivatives of formula XVI are reacted with the respective N-containing heterocycle in a palladium catalyzed Buchwald type reaction using e.g. $Pd_2(dba)_3$, Xantphos and $K_3PO_4$ in inert solvents like dioxane, N,N-dimethylformamide (DMF), NMP and the like at temperatures from 80° C. to 140° C.

To prepare the compounds of formula XIX, wherein $R^{IX}$ is a substituted alkyl or a heterocyclyl which is attached via the nitrogen, the hydroxy derivatives of formula XIV are reacted with substituted alkyl-halides or heterocyclyl-halides such as e.g. 2-bromoethyl methyl ether, N-(2-Chloroethyl)-morpholine, 4-chloro-tetrahydropyran and the like, in the presence of a base such as sodium hydride, triethylamine, N,N-diisopropylethylamine and the like, at temperatures between 0° C. and 180° C. (eventually under microwave irradiation), in an inert solvent like DMF, THF, NMP, dichlormethane and the like.

tuted alkyl, $R^{VIII}$ is a N-containing heterocyclyl which is attached via the nitrogen and $R^{IX}$ is a substituted alkyl or a heterocyclyl.

Reaction Scheme 4

To prepare either the compounds of formula XVIIa, wherein $R^X$ is a optionally substituted alkyl or cycloalkyl and $R^{XI}$ is a alkyl or hydrogen, or alternatively wherein $R^X$ and $R^{XI}$ form a heterocyclyl group together with the nitrogen atom to which they are attached, firstly the bromo derivative of formula XX (preparation according to schemes 1 and 2) is converted to a isopropanol-ester derivative of formula XXI by a palladium catalyzed reaction under pressure and heating in the presence of carbonmonoxide (CO) and isopropanol using e.g. $Pd(OAc)_2$, $Pd(PPh_3)_4$, 1,3-bis(diphenylphosphino)propane (DPPP) and $Cs_2CO_3$ in DMF. Saponification of this ester

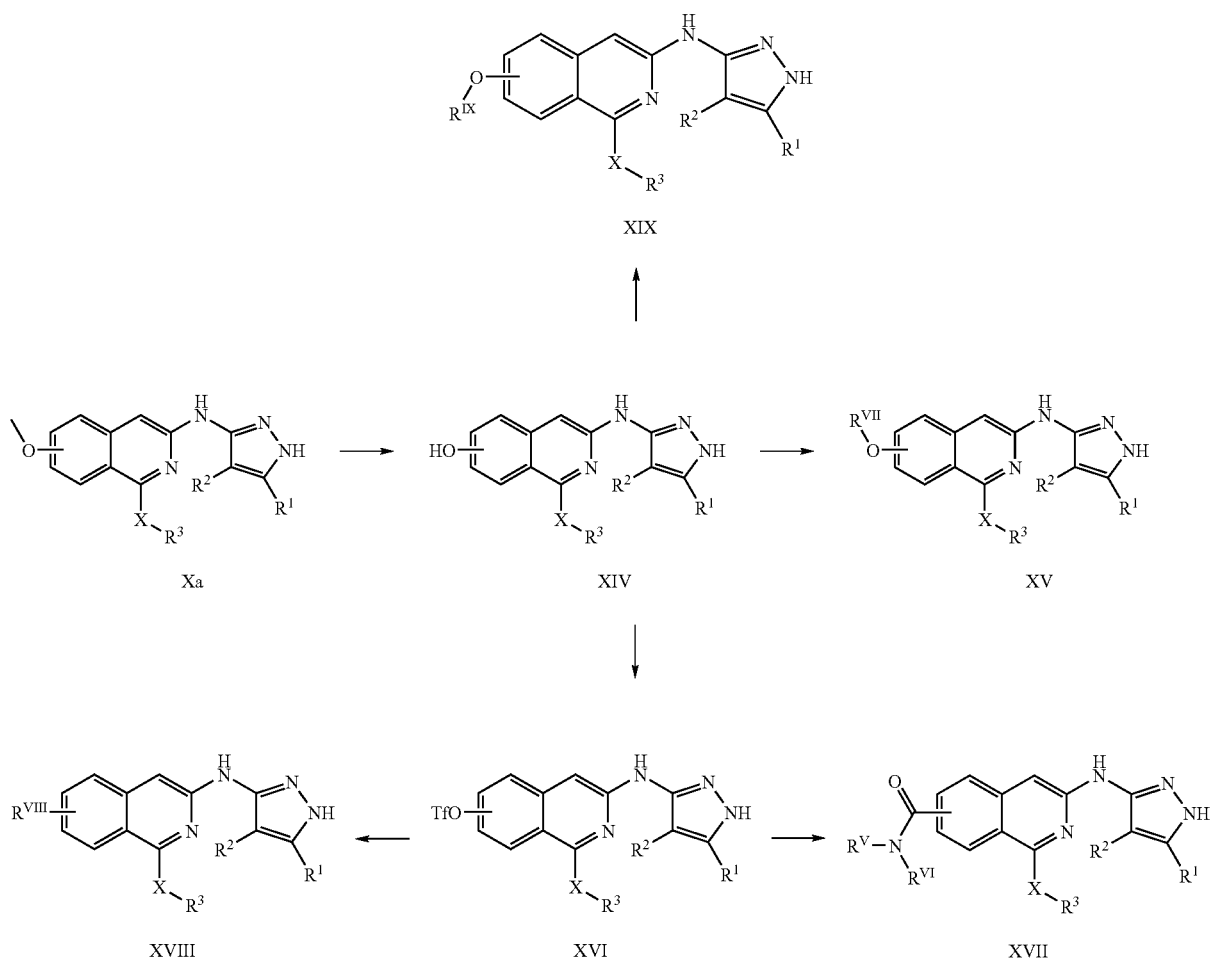

Reaction Scheme 3

In reaction scheme 3, $R^1$, $R^2$, $R^3$ and X have the meaning given previously for formula I and $R^V$ is a optionally substituted alkyl and $R^{VI}$ is alkyl or hydrogen, or alternatively $R^V$ and $R^{VI}$ form a heterocyclyl group together with the nitrogen atom to which they are attached, $R^{VII}$ is a optionally substi- (e.g. with KOH in methanol) yields the corresponding carboxylic acid of formula of XXII. This carboxylic acid derivative can then be activated (e.g. as acid chloride or in situ with e.g. 1-ethyl-3-(3-dimethylaminopropyl)carbodiimide (EDCI) and 1-hydroxybenzotriazole (HOBt) or any other suitable activation method) and then reacted with either an amine (e.g. diethylamine, N-methyl-cyclohexyl, etc.) or the respective N-containing heterocycle in the presence of a base like sodium hydride, triethylamine, N,N-diisopropylethylamine, 4-(dimethylamino)-pyridine (DMAP) and the like at temperatures between 0° C. and 100° C. in inert solvents.

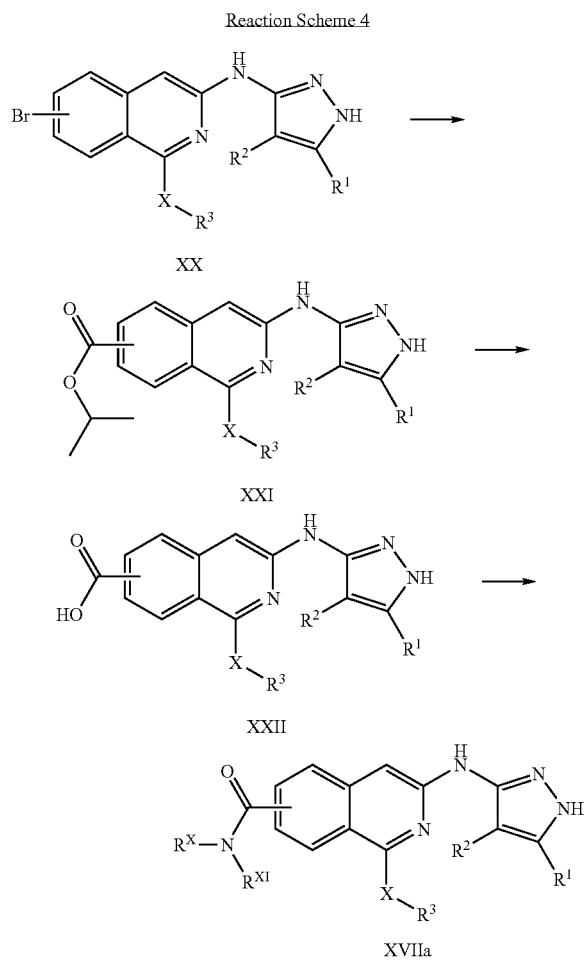

In reaction scheme 3, $R^1$, $R^2$, $R^3$ and X have the meaning given previously for formula I and $R^X$ is a optionally substituted alkyl, cycloalkyl or hydrogen and $R^{XI}$ is alkyl or hydrogen, or alternatively $R^V$ and $R^{VI}$ form a heterocyclyl group together with the nitrogen atom to which they are attached, and $R^{VII}$ is a optionally substituted alkyl.

The compounds according to the present invention may exist in the form of their pharmaceutically acceptable salts or esters. The term "pharmaceutically acceptable salt" refers to conventional acid-addition salts that retain the biological effectiveness and properties of the compounds of formula I and are formed from suitable non-toxic organic or inorganic acids. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g. Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

The compounds of formula I can contain one or more chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases (HPLC: High Performance Liquid Chromatography) which are commercially available.

Pharmacological Activity

The compounds of formula I and their pharmaceutically acceptable salts or esters possess valuable pharmacological properties. It has been found that said compounds show activity as inhibitors of the Aurora kinase family and also show anti-proliferative activity. Consequently the compounds of the present invention are useful in the therapy and/or prevention of illnesses with known over-expression of kinases of the Aurora family preferably Aurora A, especially in the therapy and/or prevention of illnesses mentioned above. The activity of the present compounds as inhibitors of the Aurora kinase family is demonstrated by the following biological assay:

$IC_{50}$ Determination for Inhibitors of Aurora A Kinase

Assay Principle

Aurora A is a Serine Threonine Kinase Involved in Spindle Assembly and Chromosome Segregation.

The assay is a typically ELISA-type assay where substrate (GST-Histone H3) is coupled to the assay-plate and is phosphorylated by the kinase. Phosphorylation is detected by a mouse anti-Phosphopeptid mAb and an HRP-labeled anti-mouse pAb. The assay is validated for $IC_{50}$-determination.

Kinase activities were measured by Enzyme-Linked Immunosorbent Assay (ELISA): Maxisorp 384-well plates (Nunc) were coated with recombinant fusion protein comprising residues 1-15 of HistoneH3 fused to the N-terminus of Glutathione-S-Transferase. Plates were then blocked with a solution of 1 mg/mL I-block (Tropix cat# T2015—highly purified form of casein) in phosphate-buffered saline. Kinase reactions were carried out in the wells of the ELISA plate by combining an appropriate amount of mutant Aurora A kinase with test compound and 30 μM ATP. The reaction buffer was 10× Kinase Buffer (Cell Signaling cat # 9802) supplemented with 1 μg/mL I-block. Reactions were stopped after 40 minutes by addition of 25 mM EDTA (ethylenediaminetetraacetic acid). After washing, substrate phosphorylation was detected by addition of anti-phospho-Histone H3 (Ser 10) 6G3 mAb (Cell Signaling cat #9706) and sheep anti-mouse pAb-HRP (Amersham cat# NA931V), followed by colorimetric development with TMB (3,3',5,5'-tetramethylbenzidine from Kirkegaard & Perry Laboratories). After readout of the absorbance, $IC_{50}$ values were calculated using a non-linear curve fit (XLfit® software (ID Business Solution Ltd., Guilford, Surrey, UK)).

TABLE 1

Results:

| Example No. | IC50 Aurora A kinase inhibition [μM] |
|---|---|
| 14 | 0.066 |
| 23 | 1.657 |
| 59 | 0.039 |
| 99 | 1.463 |
| 110 | 0.822 |
| 117 | 0.021 |
| 135 | 0.653 |
| 162 | 0.330 |
| 183 | 0.390 |
| 201 | 0.047 |
| 221 | 0.615 |
| 241 | 0.946 |
| 248 | 3.437 |
| 265 | 2.966 |
| 275 | 0.043 |
| 284 | 0.259 |
| 292 | 0.241 |
| 299 | 0.297 |
| 305 | 0.497 |
| 311 | 0.210 |
| 10, 11, 15, 16, 21, 26, 27, 32, 36, 38, 39, 41, 44, 47, 50, 51, 53, 55, 57, 60, 61, 64, 68, 71, 74, 78, 81, 89, 92, 97, 109, 120, 122, 126, 130, 131, 136, 138, 143, 148, 149, 151, 152, 156, 159, 164, 171, 176, 179, 188, 189, 192, 198, 207, 216, 220, 222, 225, 233, 236, 240, 255, 261, 269, 273, 274, 278, 281, 288, 294, 297, 300, 303, 309, 312, 315, 317, 318, 319, 321 | 0.001-15.0 |

Antiproliferative Activity

The activity of the present compounds as antiproliferative agents is demonstrated by the following biological assay:

Viability Assay in HCT 116 Cells

A viability assay was performed using the CellTiter-Glo® Luminescent Cell Viability Assay (see Promega Corporation's Technical Bulletin No. 288, pp. 1-11 [revised February, 2004] which is hereby incorporated by reference in its entirety). This assay is a homogeneous method of determining the number of viable cells in culture based on quantitation of the ATP present, an indicator of metabolically active cells. The assay is designed for use with multiwell formats, making it ideal for automated high-throughput screening (HTS), cell proliferation and cytotoxicity assays. The homogeneous assay procedure involves adding a single reagent (containing luciferase, luciferan substrate, and buffer) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The above-referenced assay generates a "glow-type" luminescent signal, produced by the luciferase reaction, which has a half-life generally greater than five hours, depending on cell type and medium used. The extended half-life eliminates the need to use reagent injectors and provides flexibility for continuous or batch mode processing of multiple plates. The unique homogeneous format avoids errors that may be introduced by other ATP measurement methods that require multiple steps.

HCT 116 cells (human colon carcinoma, ATCC-No. CCl-247) were cultivated in RPMI 1640 medium with GlutaMAX™ I (cell culture media that contains L-Alanyl-L-Glutamine [a stabilized form/source of L-Glutamine] from Invitrogen, Cat-No. 61870-010), 5% Fetal Calf Serum (FCS, Sigma Cat-No. F4135 (FBS)); 100 Units/ml penicillin/100 μg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 μM to 0.0015 μM (10 concentrations, 1:3 diluted). After 5 days the viability assay was performed according to the instructions of the manufacturer. In brief: the cell-plate was equilibrated to room temperature for approximately 30 minutes and then the CellTiter-Glo™ reagent (which contains luciferase, luciferan substrate, and buffer) was added. The contents were carefully mixed for 15 minutes to induce cell lysis. After 45 minutes the luminescent signal was measured in Victor 2, (scanning multiwell spectrophotometer, Wallac).

Details:

1st. Day:

Medium: RPMI 1640 with GlutaMAX™ I (Invitrogen, Cat-No. 61870), 5% FCS (Sigma Cat.-No. F4135), Pen/Strep (Invitrogen, Cat No. 15140).

HCT116 (ATCC-No. CCl-247): 1000 cells in 60 μl per well of 384 well plate (Greiner 781098, μClear-plate white)

After seeding incubate plates 24 h at 37° C., 5% $CO_2$

2nd. Day: Induction (Treatment with Compounds, 10 Concentrations):

In order to achieve a final concentration of 30 μM as highest concentration 3.5 μl of 10 mM compound stock solution were added directly to 163 μl media. Then step e) of the dilution procedure described below, was followed.

In order to achieve the second highest to the lowest concentrations, a serial dilution with dilution steps of 1:3 was followed according to the procedure (a-e) as described here below:

a) for the second highest concentration add 10 μl of 10 mM stock solution of compound to 20 μl dimethylsulfoxide (DMSO)

b) dilute 8×1:3 (always 10 μl to 20 μl DMSO) in this DMSO dilution row (results in 9 wells with concentrations from 3333.3 μM to 0.51 μM)

c) dilute each concentration 1:47.6 (3.5 μl compound dilution to 163 μl media)

e) add 10 μl of every concentration to 60 μl media in the cell plate resulting in final concentration of DMSO: 0.3% in every well and resulting in 10 final concentration of compounds ranging from 30 μM to 0.0015 μM.

Each compound is tested in triplicate.

Incubate 120 h (5 days) at 37° C., 5% $CO_2$

Analysis:

Add 30 μl CellTiter-Glo™ Reagent ((which contains luciferase, luciferan substrate, and buffer) (lyophilized) purchased from Promega) per well, shake 15 minutes at room temperature incubate further 45 minutes at room temperature without shaking Measurement:

Victor 2 scanning multiwell spectrophotometer (Waflac), Luminescence mode (0.5 sec/read, 477 nm)

Determine IC50 using a non-linear curve fit (XLfit® software (ID Business Solution Ltd., Guilford, Surrey, UK))

With all compounds a significant inhibition of HCT 116 cell viability was detected, which is exemplified by the compounds shown in Table 2.

TABLE 2

Results:

| Example No. | IC50 HCT 116 [µM] |
|---|---|
| 11 | 1.826 |
| 12 | 3.32 |
| 16 | 1.934 |
| 21 | 5.67 |
| 28 | 0.999 |
| 33 | 3.242 |
| 39 | 1.384 |
| 53 | 3.505 |
| 56 | 0.636 |
| 67 | 1.37 |
| 77 | 1.939 |
| 94 | 2.541 |
| 117 | 0.666 |
| 125 | 0.51 |
| 131 | 3.931 |
| 140 | 2.609 |
| 159 | 1.899 |
| 164 | 5.306 |
| 183 | 4.015 |
| 194 | 3.44 |
| 202 | 1.411 |
| 220 | 3.167 |
| 252 | 3.874 |
| 263 | 1.544 |
| 275 | 0.995 |
| 288 | 1.294 |
| 294 | 1.785 |
| 300 | 1.529 |
| 302 | 3.073 |
| 306 | 1.575 |
| 312 | 3.76 |
| 318 | 3.108 |
| 10, 13, 20, 23, 32, 36, 37, 40, 44, 47, 51, 57, 60, 69, 72, 81, 84, 85, 87, 89, 92, 132, 137, 142, 144, 151, 158, 165, 166, 173, 180, 185, 187, 191, 198, 201, 204, 210, 215, 217, 238, 243, 249, 253, 271, 273, 274, 278, 279 283, 292, 298, 299, 311, 314, 321 | 0.01-15.00 |

Pharmaceutical compositions containing a compound of the present invention or a pharmaceutically acceptable salt or ester thereof and a pharmaceutically acceptable carrier are provided by the present invention, as is a process for their production, which comprises bringing one or more compounds of the present invention and/or pharmaceutically acceptable salts or esters and, if desired, one or more other therapeutically valuable substances into a galenical administration form together with one or more pharmaceutically acceptable carriers.

In accordance with the invention the compounds of the present invention as well as their pharmaceutically acceptable salts or esters are useful in the control or prevention of illnesses. Based on their Aurora kinase inhibition and their antiproliferative activity, said compounds are useful for the treatment of diseases such as cancer in humans or animals and for the production of corresponding pharmaceutical compositions. The dosage depends on various factors such as manner of administration, species, age and/or individual state of health.

An embodiment of the invention are the compounds according to formula I for the use as pharmaceutical agents.

An embodiment of the invention is a pharmaceutical composition, containing one or more compounds according to formula I, together with pharmaceutically acceptable carriers.

Another embodiment of the invention is a pharmaceutical composition containing one or more compounds of formula I as active ingredients together with pharmaceutically acceptable adjuvants for the treatment of diseases mediated by an inappropriate activation of Aurora family kinases.

Another embodiment of the invention is a pharmaceutical composition, containing one or more compounds according to formula I, for the inhibition of tumor growth.

Another embodiment of the invention is a pharmaceutical composition containing one or more compounds of formula I as active ingredients together with pharmaceutically acceptable adjuvants for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is a pharmaceutical composition containing one or more compounds of formula I as active ingredients together with pharmaceutically acceptable adjuvants for the treatment of acute-myelogenous leukemia (AML, acute lymphocytic leukemia (ALL) and gastrointestinal stromal tumor (GIST).

Another embodiment of the invention is the use of one or more compounds of formula I for the manufacture of pharmaceutical compositions for the treatment of diseases mediated by an inappropriate activation of Aurora family kinases.

Another embodiment of the invention is the use of a compound according to formula I, for the manufacture of corresponding pharmaceutical compositions for the inhibition of tumor growth.

Another embodiment of the invention is the use of a compound according to formula I, for the manufacture of corresponding pharmaceutical compositions for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of corresponding pharmaceutical compositions for the treatment of acute-myelogenous leukemia (AML, acute lymphocytic leukemia (ALL) and gastrointestinal stromal tumor (GIST).

Another embodiment of the invention is the use of the compounds of formula I as Aurora A kinase inhibitors.

Another embodiment of the invention is a method for the treatment of a disease mediated by an inappropriate activation of src family tyrosine kinases, comprising administering, to a patient in need thereof, a therapeutically effective amount of a compound according to claim 1

Another embodiment of the invention is the use of the compounds of formula I as anti-proliferating agents.

Another embodiment of the invention is the use of one or more compounds of formula I for the treatment of cancer.

The compounds according to this invention and their pharmaceutically acceptable salts or esters cane be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or it's salts and the like can be used as carriers for tablets, coated tablets, dragées and hard gelatine capsules. Suitable carriers for soft gelatine capsules are, for example, vegetable oils, waxes, fats, semi-solid and liquid polyols and the like. However, depending on the nature of the active substance, carriers may not be required for some soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical composition may, for example, comprise the following:

| a) Tablet Formulation (Wet Granulation): | | | | |
|---|---|---|---|---|
| Item | Ingredients | | Mg/tablet | | |
| 1. | Compound of formula I | 5 | 25 | 100 | 500 |
| 2. | Lactose Anhydrous DTG (direct tabletting grade) | 125 | 105 | 30 | 150 |
| 3. | Sta-Rx 1500 (pre-gelatinized starch powder) | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

| b) Capsule Formulation: | | | | |
|---|---|---|---|---|
| Item | Ingredients | | mg/capsule | | |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:

1. Mix items 1, 2 and 3 in a suitable mixer for 30 minutes.

2. Add items 4 and 5 and mix for 3 minutes.

3. Fill into a suitable capsule.

The following examples and references are provided to aid the understanding of the present invention, the true scope of which is set forth in the appended claims. It is understood that modifications can be made in the procedures set forth without departing from the spirit of the invention.

EXAMPLES

Synthesis of Intermediates

Example 1

(1-Chloro-isoquinolin-3-yl)-(5-methyl-1H-pyrazol-3-yl)-amine

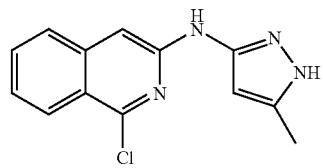

a) Preparation of indan-1,2-dione-2-oxime

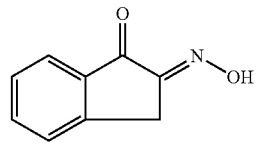

To a solution of 1-indanone (19.5 g, 0.15 mol) in 200 ml of ether was added 15 ml of concentrated HCl, then a solution of n-butylnitrite (18.75 ml, 0.16 mol) in 50 ml of ether at room temperature. The resulting mixture was stirred for 2 h, the precipitate was collected and dried to yield a white solid (15.4 g, 65% yield). LC-MS: 162 (MH$^+$)

b) Preparation of 2-cyanomethyl-benzoic acid

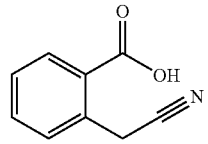

Indan-1,2-dione-2-oxime (35 g, 0.22 mol) was added to a solution of 402.5 ml 8% NaOH, and the mixture was heated to 50° C. Then p-toluenesulfonyl chloride (54.25, 0.28 mol) was added in portions to the mixture, and the mixture was heated at 80° C. for 15 min. After cooled to room temperature, the precipitate was removed from the mixture. The filtrate was acidified with concentrated HCl to pH=3-4 and the precipitate was collected and dried to give colorless solid (26 g, 74% yield). LC-MS: 162 (MH$^+$)

c) Preparation of 3-(5-methyl-1H-pyrazol-3-ylamino)-2H-isoquinolin-1-one

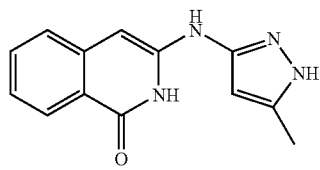

2-Cyanomethyl-benzoic acid (1.61 g, 0.01 mol), 3-amino-5-methylpyrazol (1 g, 0.01 mol) and acetic acid (15 ml) were sealed in a bottle. The mixture was heated at 130° C. for 20 minutes under microwave irradiation. The mixture was concentrated, and the residue was dissolved in 5 ml methanol (MeOH). The resulting solution was added dropwise to 200 ml water. After stirred for 1 hour, the solid was collected, and dried to give product (1.8 g, 75% yield). LC-MS: 241 (MH$^+$)

d) Preparation of (1-chloro-isoquinolin-3-yl)-(5-methyl-1H-pyrazol-3-yl)-amine

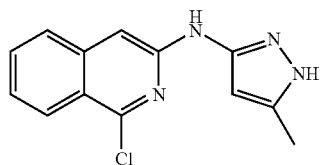

3-(5-Methyl-1H-pyrazol-3-ylamino)-2H-isoquinolin-1-one (7.4 g, 0.03 mol) and POCl$_3$ (80 ml) were sealed in 4 bottles (20 ml). The mixture was heated at 130° C. for 15 minutes under microwave irradiation. The mixture was concentrated, and the residue was treated with 15 ml MeOH. The mixture was stirred for 2 hours at room temperature, and the solid was collected and dried to give desired product (4.7 g, 61% yield). LC-MS: 259 (MH$^+$)

Example 2

(1-Chloro-6-methoxy-isoquinolin-3-yl)-(5-methyl-1H-pyrazol-3-yl)-amine

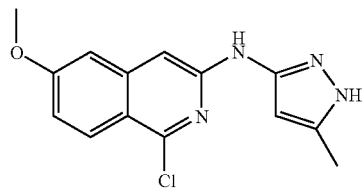

a) Preparation of 5-methoxy-indan-1,2-dione-2-oxime

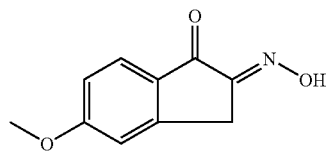

To a solution of 5-methoxy-1-indanone (25 g, 0.15 mol) in 300 ml MeOH was added 15 ml concentrated HCl, and then n-butylnitrite (19.5 ml, 0.17 mol) in 50 ml MeOH at 40° C. The solution was stirred for 2 hours during which time a precipitate was formed. The precipitate was collected and dried to yield a white solid (22.3 g, 75% yield). LC-MS: 192 (MH$^+$)

b) Preparation of 2-Cyanomethyl-4-methoxy-benzoic acid

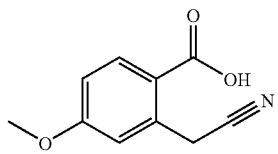

5-Methoxy-indan-1,2-dione-2-oxime (22 g, 0.12 mol) was added to a solution of 230 ml 8% NaOH. The mixture was heated to 50° C., and then p-toluenesulfonyl chloride (30 g, 0.16 mol) was added in portions. The mixture was heated at 80° C. for 15 min. After cooled to room temperature, the precipitate was removed, and the filtrate was acidified with concentrated HCl to pH=3-4. The precipitate was collected and dried to give colorless solid (22 g, 100% yield). LC-MS: 192 (MH$^+$)

c) Preparation of 6-methoxy-3-(5-methyl-1H-pyrazol-3-ylamino)-2H-isoquinolin-1-one

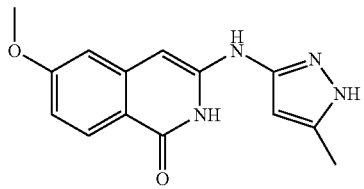

2-Cyanomethyl-4-methoxy-benzoic acid (1.91 g, 0.01 mol), 3-amino-5-methylpyrazol (1 g, 0.01 mol) and acetic acid (15 ml) were sealed in bottle (20 ml). The mixture was heated at 130° C. for 20 minutes under microwave irradiation. The mixture was concentrated and the residue was dissolved in 5 ml MeOH. The solution was added dropwise to 200 ml water. After stirred for 1 hour, solid was collected and dried to give product (2.24 g, 82% yield). LC-MS: 271 (MH$^+$)

d) Preparation of (1-chloro-6-methoxy-isoquinolin-3-yl)-(5-methyl-1H-pyrazol-3-yl)-amine

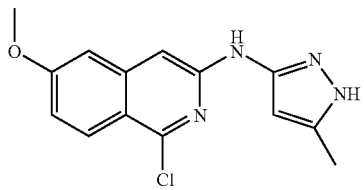

6-Methoxy-3-(5-methyl-1H-pyrazol-3-ylamino)-2H-isoquinolin-1-one (4.7 g, 0.017 mol) and POCl$_3$ (60 ml) were sealed in 3 different bottles (20 ml). The mixture was heated at 150° C. for 15 minutes under microwave irradiation. The mixture was concentrated, and the residue was treated with 15 ml MeOH, stirred for 2 hours at room temperature. The solid was collected and dried to give product (3.4 g, 68% yield). LC-MS: 289 (MH⁺)

Example 3

(1-Chloro-isoquinolin-3-yl)-(1H-pyrazol-3-yl)-amine

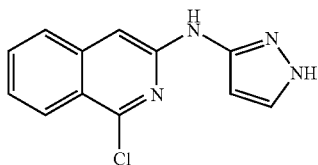

a) Preparation of 3-(1H-pyrazol-3-ylamino)-2H-isoquinolin-1-one

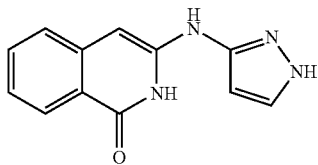

2-Cyanomethyl-benzoic acid (1.61 g, 0.01 mol), 3-amino-pyrazole (1 g, 0.01 mol), acetic acid (15 ml), were sealed in a bottle (20 ml). The mixture was heated at 130° C. for 20 minutes under microwave irradiation. The mixture was concentrated and the residue was dissolved in 5 ml MeOH. The solution was added dropwise to 200 ml water. After stirred for 1 hour, solid was collected and dried to give product (1.8 g, 75% yield). LC-MS: 227 (MH⁺)

b) Preparation of (1-chloro-isoquinolin-3-yl)-(1H-pyrazol-3-yl)-amine

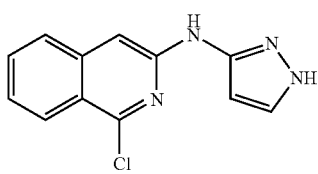

3-(1H-Pyrazol-3-ylamino)-2H-isoquinolin-1-one (7.4 g, 0.03 mol) and POCl₃ (80 ml) were sealed in 4 different bottles (20 ml). The mixture was heated at 130° C. for 15 minutes under microwave irradiation. The mixture was concentrated, the residue was treated with 15 ml MeOH and stirred for 2 hours at room temperature. The solid was collected and dried to give product (4.7 g, 61% yield). LC-MS: 245(MH⁺)

Example 4

(1-Chloro-6-methoxy-isoquinolin-3-yl)-(1H-pyrazol-3-yl)-amine

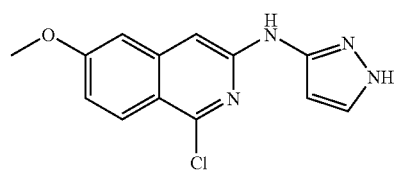

a) Preparation of 6-methoxy-3-(1H-pyrazol-3-ylamino)-2H-isoquinolin-1-one

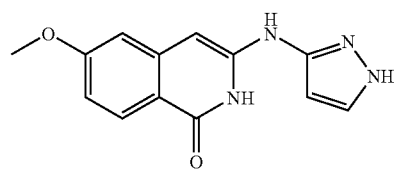

2-Cyanomethyl-4-methoxy-benzoic acid (1.91 g, 0.01 mol), 3-amino-pyrazole (1 g, 0.01 mol) and acetic acid (15 ml) were sealed in a bottle (20 ml). The mixture was heated at 130° C. for 20 minutes under microwave irradiation. The mixture was concentrated and the residue was dissolved in 5 ml MeOH. The solution was added dropwise to 200 ml water. After stirred for 1 hour, solid was collected and dried to give product (2.24 g, 82% yield). LC-MS:

b) Preparation of (1-chloro-6-methoxy-isoquinolin-3-yl)-(1H-pyrazol-3-yl)-amine

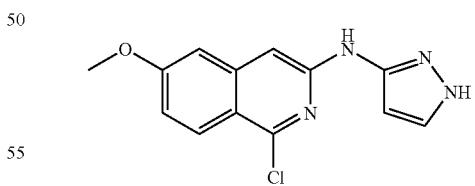

6-Methoxy-3-(1H-pyrazol-3-ylamino)-2H-isoquinolin-1-one (4.7 g, 0.017 mol) and POCl₃ (60 ml) were sealed in 3 different bottles (20 ml). The mixture was heated at 150° C. for 15 minutes under microwave irradiation. The mixture was concentrated, the residue was treated with 15 ml MeOH and stirred for 2 hours at room temperature. The solid was collected and dried to give product (3.4 g, 68% yield). LC-MS: 275 (MH⁺)

Example 5

(1-Chloro-5-methoxy-isoquinolin-3-yl)-(5-methyl-1H-pyrazol-3-yl)-amine

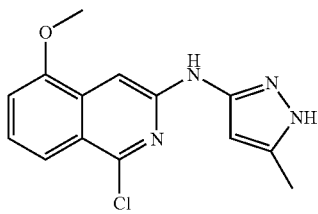

a) Preparation of 4-methoxy-indan-1,2-dione-2-oxime

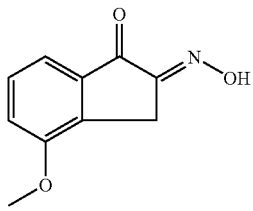

Similar procedure as described in example 2a was used, starting from 4-methoxy-1-indanone to give 4-methoxy-indan-1,2-dione-2-oxime. LC-MS: m/e 192 (MH$^+$). LC-MS: 192 (MH$^{30}$)

b) Preparation of 2-cyanomethyl-3-Methoxy-benzoic acid

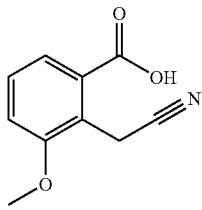

Similar procedure as described in example 2b was used, starting from 4-methoxy-indan-1,2-dione-2-oxime to give 2-cyanomethyl-3-methoxy-benzoic acid. LC-MS: m/e 192 (MH$^+$).

c) Preparation of 5-methoxy-3-(5-methyl-1H-pyrazol-3-ylamino)-2H-isoquinolin-1-one

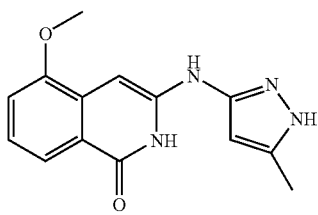

Similar procedure as described in example 2c was used, starting from 2-cyanomethyl-3-Methoxy-benzoic acid to give 5-methoxy-3-(5-methyl-1H-pyrazol-3-ylamino)-2H-isoquinolin-1-one. LC-MS: m/e 271 (MH$^+$).

d) Preparation of (1-chloro-5-methoxy-isoquinolin-3-yl)-(5-methyl-1H-pyrazol-3-yl)-amine

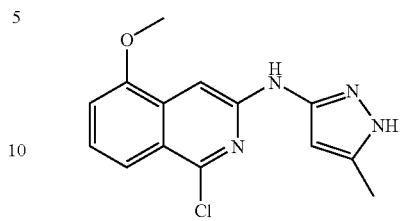

Similar procedure as described in example 2d was used, starting from 5-methoxy-3-(5-methyl-1H-pyrazol-3-ylamino)-2H-isoquinolin-1-one to give (1-chloro-5-methoxy-isoquinolin-3-yl)-(5-methyl-1H-pyrazol-3-yl)-amine. LC-MS: m/e 289 (MH$^+$).

Example 6

(1-Chloro-7-methoxy-isoquinolin-3-yl)-(5-methyl-1H-pyrazol-3-yl)-amine

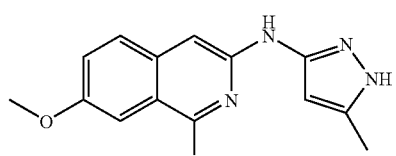

a) Preparation of 6-methoxy-indan-1,2-dione 2-oxime

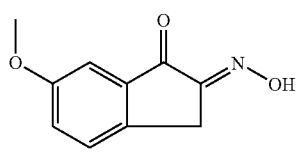

Similar procedure as described in example 2a was used, starting from 6-methoxy-1-indanone to give 6-methoxy-indan-1,2-dione 2-oxime. LC-MS: m/e 192 (MH$^+$).

b) Preparation of 2-cyanomethyl-5-Methoxy-benzoic acid

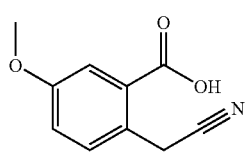

Similar procedure as described in example 2b was used, starting from 6-methoxy-indan-1,2-dione-2-oxime to give 2-cyanomethyl-5-Methoxy-benzoic acid. LC-MS: m/e 192 (MH$^+$).

c) Preparation of 7-methoxy-3-(5-methyl-1H-pyrazol-3-ylamino)-2H-isoquinolin-1-one

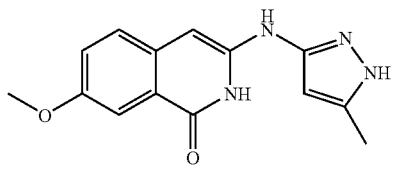

Similar procedure as described in example 2c was used, starting from 2-cyanomethyl-5-methoxy-benzoic acid to give 7-methoxy-3-(5-methyl-1H-pyrazol-3-ylamino)-2H-isoquinolin-1-one. LC-MS: m/e 271 (MH$^+$).

d) Preparation of (1-chloro-7-methoxy-isoquinolin-3-yl)-(5-methyl-1H-pyrazol-3-yl)-amine

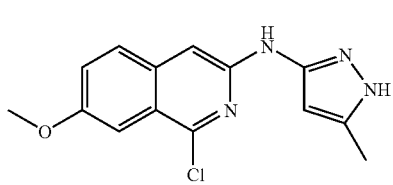

Similar procedure as described in example 2d was used, starting from 7-methoxy-3-(5-methyl-1H-pyrazol-3-ylamino)-2H-isoquinolin-1-one to give (1-chloro-7-methoxy-isoquinolin-3-yl)-(5-methyl-1H-pyrazol-3-yl)-amine. LC-MS: m/e 289 (MH$^+$).

Example 7

(1-Chloro-6,7-dimethoxy-isoquinolin-3-yl)-(5-methyl-1H-pyrazol-3-yl)-amine

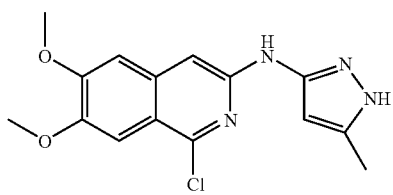

a) Preparation of 5,6-dimethoxy-indan-1,2-dione-2-oxime

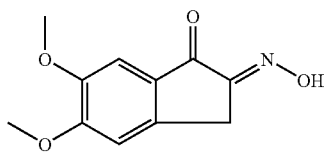

Similar procedure as described in example 2a was used, starting from 5,6-dimethoxy-1-indanone to give 5,6-dimethoxy-indan-1,2-dione-2-oxime. LC-MS: m/e 222 (MH$^+$).

b) Preparation of 2-cyanomethyl-4,5-dimethoxy-benzoic acid

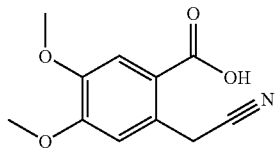

Similar procedure as described in example 2b was used, starting from 5,6-dimethoxy-indan-1,2-dione 2-oxime to give 2-cyanomethyl-4,5-dimethoxy-benzoic acid. LC-MS: m/e 222 (MH$^+$).

c) Preparation of 6,7-dimethoxy-3-(5-methyl-1H-pyrazol-3-ylamino)-2H-isoquinolin-1-one

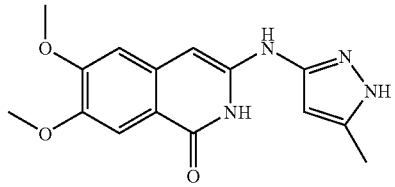

Similar procedure as described in example 2c was used, starting from 2-cyanomethyl-4,5-dimethoxy-benzoic acid to give 6,7-dimethoxy-3-(5-methyl-1H-pyrazol-3-ylamino)-2H-isoquinolin-1-one. LC-MS: m/e 301 (MH$^+$).

d) Preparation of (1-chloro-6,7-dimethoxy-isoquinolin-3-yl)-(5-methyl-1H-pyrazol-3-yl)-amine

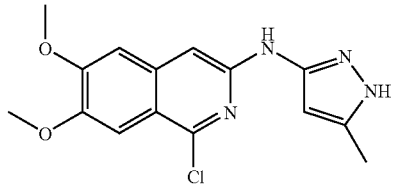

Similar procedure as described in example 2d was used, starting from 6,7-dimethoxy-3-(5-methyl-1H-pyrazol-3-ylamino)-2H-isoquinolin-1-one to give (1-chloro-6,7-dimethoxy-isoquinolin-3-yl)-(5-methyl-1H-pyrazol-3-yl)-amine. LC-MS: m/e 319 (MH$^+$).

Example 8

(1-Chloro-5,6-dimethoxy-isoquinolin-3-yl)-(5-methyl-1H-pyrazol-3-yl)-amine

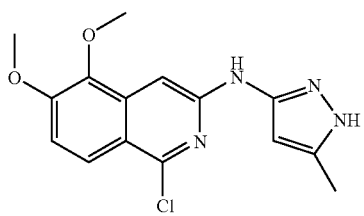

a) Preparation of 4,5-dimethoxy-indan-1,2-dione-2-oxime

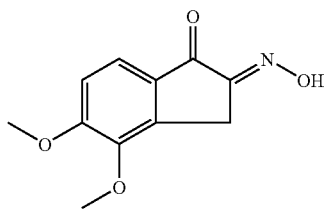

Similar procedure as described in example 2a was used, starting from 5,6-dimethoxy-1-indanone to give 4,5-dimethoxy-indan-1,2-dione 2-oxime. LC-MS: m/e 222 (MH$^+$).

b) Preparation of 2-cyanomethyl-3,4-dimethoxy-benzoic acid

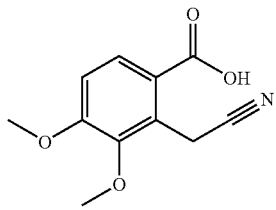

Similar procedure as described in example 2b was used, starting from 4,5-dimethoxy-indan-1,2-dione-2-oxime to give 2-cyanomethyl-3,4-dimethoxy-benzoic acid. LC-MS: m/e 222 (MH$^+$).

c) Preparation of 5,6-dimethoxy-3-(5-methyl-1H-pyrazol-3-ylamino)-2H-isoquinolin-1-one

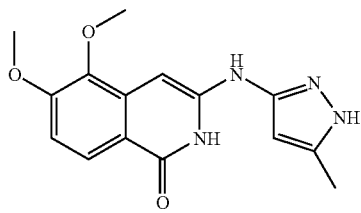

Similar procedure as described in example 2c was used, starting from 2-cyanomethyl-3,4-dimethoxy-benzoic acid to give 5,6-dimethoxy-3-(5-methyl-1H-pyrazol-3-ylamino)-2H-isoquinolin-1-one. LC-MS: m/e 301 (MH$^+$).

d) Preparation of (1-chloro-5,6-dimethoxy-isoquinolin-3-yl)-(5-methyl-1H-pyrazol-3-yl)-amine

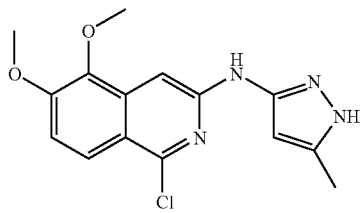

Similar procedure as described in example 2d was used, starting from 5,6-dimethoxy-3-(5-methyl-1H-pyrazol-3-ylamino)-2H-isoquinolin-1-one to give (1-chloro-5,6-dimethoxy-isoquinolin-3-yl)-(5-methyl-1H-pyrazol-3-yl)-amine. LC-MS: m/e 319 (MH$^+$).

Example 9

(1-Chloro-5-methyl-isoquinolin-3-yl)-(5-methyl-1H-pyrazol-3-yl)-amine

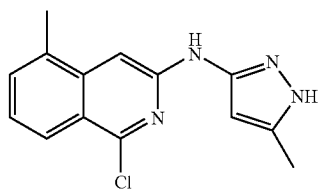

a) Preparation of 4-methyl-indan-1,2-dione 2-oxime

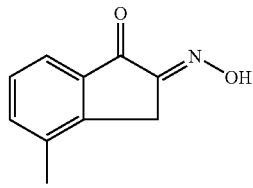

Similar procedure as described in example 2a was used, starting from 4-methyl-1-indanone to give 4-methyl-indan-1,2-dione 2-oxime. LC-MS: m/e 176 (MH$^+$).

b) Preparation of 2-cyanomethyl-3-methyl-benzoic acid

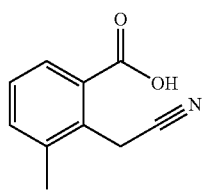

Similar procedure as described in example 2b was used, starting from 4-methyl-indan-1,2-dione 2-oxime to give 2-cyanomethyl-4-methyl-benzoic acid. LC-MS: m/e 176 (MH$^+$).

c) Preparation of 5-methyl-3-(5-methyl-1H-pyrazol-3-ylamino)-2H-isoquinolin-1-one

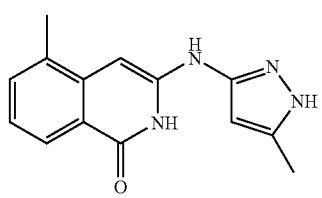

Similar procedure as described in example 2c was used, starting from 2-cyanomethyl-4-methyl-benzoic acid to give 5-methyl-3-(5-methyl-1H-pyrazol-3-ylamino)-2H-isoquinolin-1-one. LC-MS: m/e 255 (MH$^+$).

d) Preparation of (1-chloro-5-methyl-isoquinolin-3-yl)-(5-methyl-1H-pyrazol-3-yl)-amine

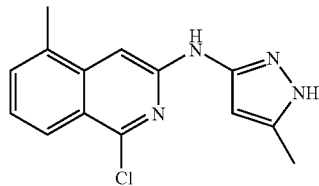

Similar procedure as described in example 2d was used, starting from 5-methyl-3-(5-methyl-1H-pyrazol-3-ylamino)-2H-isoquinolin-1-one to give (1-chloro-5-methyl-isoquinolin-3-yl)-(5-methyl-1H-pyrazol-3-yl)-amine. LC-MS: m/e 273 (MH+).

Example 9A

6-Methoxy-3-(5-methyl-1H-pyrazol-3-ylamino)-isoquinoline-1-carboxylic acid

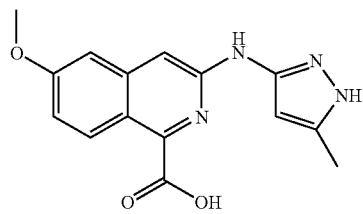

a) Preparation of 6-methoxy-3-(5-methyl-1H-pyrazol-3-ylamino)-isoquinoline-1-carboxylic acid isopropyl ester

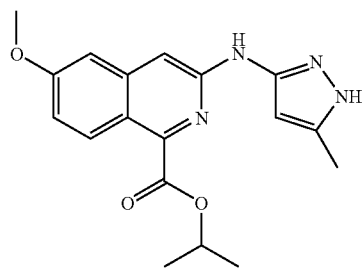

A mixture of (1-chloro-6-methoxy-isoquinolin-3-yl)-(5-methyl-1H-pyrazol-3-yl)-amine (1.4 g), Propan-2-ol (100 ml), Pd(OAc)$_2$ (60 mg), 1,3-bis(diphenylphosphino)propane (DPPP) (200 mg), Cs$_2$CO$_3$ (4 g), N,N-dimethylformamide (DMF) (50 ml) and Tetrakis(triphenylphosphine)palladium (0) (30 mg) was sealed in high-pressure bottle under 30 psi of CO and stirred for 2 hours at room temperature. Then the mixture was heated at 50° C. for 2 hours, and then the mixture was heated at 95° C. overnight.

After cooled to room temperature, the precipitate was filtered off, and the filtrate was concentrated, the residue was purified by flash column chromatography to give 0.7 g of 6-methoxy-3-(5-methyl-1H-pyrazol-3-ylamino)-isoquinoline-1-carboxylic acid isopropyl ester. LC-MS: 341 (MH+)

b) Preparation of 6-methoxy-3-(5-methyl-1H-pyrazol-3-ylamino)-isoquinoline-1-carboxylic acid

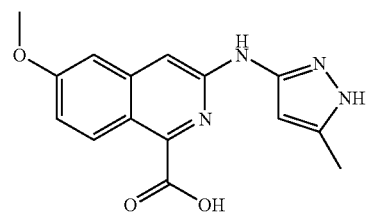

A mixture of 6-methoxy-3-(5-methyl-1H-pyrazol-3-ylamino)-isoquinoline-1-carboxylic acid isopropyl ester (0.7 g), 1M KOH (10 ml) and methanol (30 ml) was stirred at room temperature overnight, and then it was concentrated. The residue was acidified to pH=1 by 1M HCl and yielded 0.42 g of crude 6-methoxy-3-(5-methyl-1H-pyrazol-3-ylamino)-isoquinoline-1-carboxylic acid. LC-MS: 299 (MH+).

Example 9B (1-Chloro-7-fluoro-6-methoxy-isoquinolin-3-yl)-(5-methyl-1H-pyrazol-3-yl)-amine

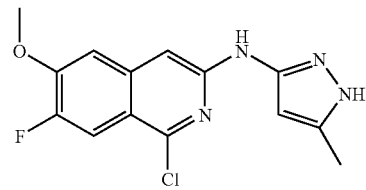

a) Preparation of 3-(4-Fluoro-3-methoxy-phenyl)-acrylic acid

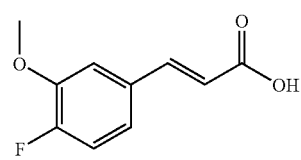

A mixture of 4-Fluoro-3-methoxy-benzaldehyde (6.16 g, 40 mmol), and malonic acid (6.24 g, 60 mmol) in pyridine (30 ml) and piperidine (1 ml) was heated at 120° C. for 2 hrs. The mixture was cooled to room temperature and neutralized with concentrated HCl to PH<3, the white solid was collected and dried to give 7.6 g of product (97% yield). LC-MS: m/e 195 (M−1)

b) Preparation of 3-(4-Fluoro-3-methoxy-phenyl)-propionic acid

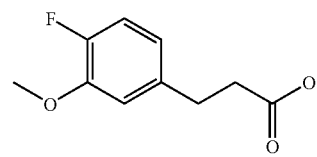

3-(4-Fluoro-3-methoxy-phenyl)-acrylic acid (6.2 g, 31.6 mmol) and Pd—C (10%, 620 mg) in ethyl acetate and methanol (1:1, 400 ml) was placed in a Parr apparatus. After the appropriate amount of hydrogen was taken up, the catalyst was filtered and the filtrate was concentrated in vacuo to give 6.2 g white solid (99% yield). LC-MS: m/e 197 (M−1)

c) Preparation of 6-Fluoro-5-methoxy-indan-1-one

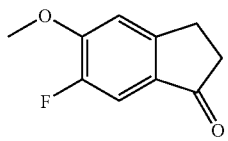

3-(4-Fluoro-3-methoxy-phenyl)-propionic acid (2 g, 10 mmol) and Methanesulfonic acid (15 ml) were sealed in process vial (20 ml) and it was heated at 90° C. for 10 minutes under microwave irradiation. The mixture was poured into ice and neutralized with NaOH. The solid was collected and dried to give 1.7 g of product (93.5% yield). LC-MS: m/e 181 (MH$^+$)

d) Preparation of 6-Fluoro-5-methoxy-indan-1,2-dione 2-oxime

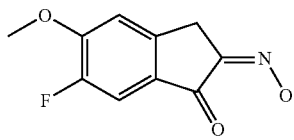

To a solution of 6-Fluoro-5-methoxy-indan-1-one (4.8 g) in 65 ml of MeOH was added 2.7 ml of concentrated HCl, then a solution of n-butylnitrite (3.47 ml) at room temperature. The resulting mixture was stirred for 2 hrs, the precipitate was collected and dried to yield the product as a white solid (3.9 g, 70% yield). LC-MS: m/e 210 (MH$^+$)

e) Preparation of 2-Cyanomethyl-5-fluoro-4-methoxy-benzoic acid

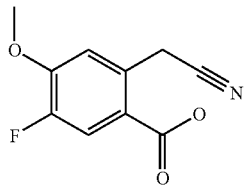

6-Fluoro-5-methoxy-indan-1,2-dione 2-oxime (3.9 g) was added to a solution of 36.4 ml 8% NaOH, and the mixture was heated to 50° C. Then p-Toluenesulfonyl chloride (4.62 g) was added in portions to the mixture, and the mixture was heated at 80° C. for 15 min. After cooled to room temperature, the precipitate was removed from the mixture. The filtrate was acidified with concentrated HCl to PH=3-4 and the precipitate was collected and dried to give product as colorless solid (3.5 g, 90% yield). LC-MS: m/e 208 (M−1)

f) Preparation of 7-Fluoro-6-methoxy-3-(5-methyl-1H-pyrazol-3-ylamino)-isoquinolin-1-ol

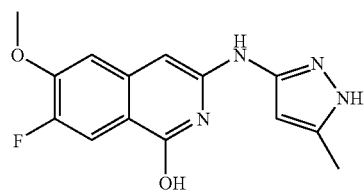

2-Cyanomethyl-5-fluoro-4-methoxy-benzoic acid (1.75 g), 3-amino-5-methylpyrazol (1.63 g), acetic acid (15 ml), were sealed in a process vial. The mixture was heated at 130° C. for 30 minutes under microwave irradiation. The mixture was concentrated, and the residue was dissolved in 5 ml MeOH. The resulting solution was added dropwise to 200 ml water. After stirred for 1 hour, the solid was collected, and dried to give product (1.85 g, 77% yield). LC-MS: m/e 289 (MH$^+$)

g) Preparation of (1-Chloro-7-fluoro-6-methoxy-isoquinolin-3-yl)-(5-methyl-1H-pyrazol-3-yl)-amine

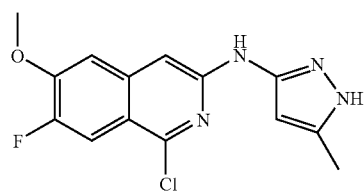

7-Fluoro-6-methoxy-3-(5-methyl-1H-pyrazol-3-ylamino)-isoquinolin-1-ol (1.9 g), POCl$_3$ (15 ml), were sealed in a process vial (20 ml). The mixture was heated at 150° C. for 30 minutes under microwave irradiation. The mixture was concentrated, and the residue was treated with 5 ml MeOH. The mixture was stirred for 2 hours at room temperature, and the solid was collected and dried to give desired product (1.3 g, 64% yield). LC-MS: m/e 307 (MH$^+$)

Example 9C

[1-Chloro-6-methoxy-7-(2-methoxy-ethoxy)-isoquinolin-3-yl]-(5-methyl-1H-pyrazol-3-yl)-amine

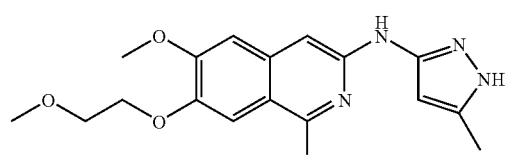

a) Preparation of 5-Methoxy-6-(2-methoxy-ethoxy)-indan-1-one

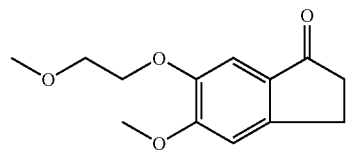

To a mixture of 6-Hydroxy-5-methoxy-indan-1-one (10.5 g, 59 mmol), K₂CO₃ (16 g, 118 mmol), tetrabutyl-ammonium iodide (2 g, 5.9 mmol) suspended in actone (200 ml), 1-Bromo-3-methoxy-propane (8.5 ml, 88.5 mmol) was added, and then the mixture was heated to reflux for 4 hs under N₂. The solid was filtered off and washed by actone (50 ml×3), the filtrate was concentrated to give the crude product which was used directly for next step without purification. LC-MS: m/e 237 (MH⁺)

b) Preparation of 5-Methoxy-6-(2-methoxy-ethoxy)-indan-1,2-dione 2-oxime

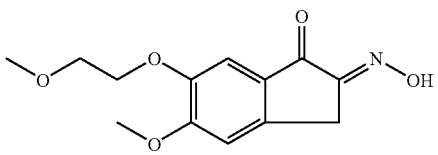

To a solution of 1-indanone (7.5 g, 31.78 mmol) in methanol (100 ml) was added n-butyl-nitrite (4.0 ml, 34.95 mmol) followed by concentrated HCl (2.5 ml). The solution was stirred at room temperature overnight during which time a precipitate was formed. The precipitate was collected and dried to yield product as a yellow solid (8.0 g, 95%). LC-MS: m/e 266 (MH⁺).

c) Preparation of 2-Cyanomethyl-4-methoxy-5-(2-methoxy-ethoxy)-benzoic acid

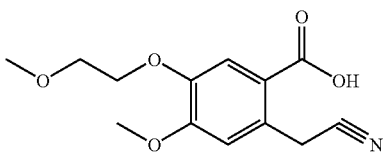

To a solution of NaOH (5.15 g, 129.2 mmol) in H₂O (100 ml) was added 5-Methoxy-6-(2-methoxy-ethoxy)-indan-1,2-dione 2-oxime (9.0 g, 34 mmol), and the mixture was heated to 50° C. Then p-Toluenesulfonyl chloride (8.5 g, 44.2 mmol) was added in portions to the mixture, and the mixture was heated at 80° C. for 15 min. After cooling to room temperature, the precipitate (a little) was filtered. The filtrate was acidified by concentrated HCl to PH=3-4, and the precipitate was collected and dried to give product (4.0 g, 44.1%). LC-MS: m/e 265 (M−1).

d) Preparation of 6-Methoxy-7-(2-methoxy-ethoxy)-3-(5-methyl-1H-pyrazol-3-ylamino)-isoquinolin-1-ol

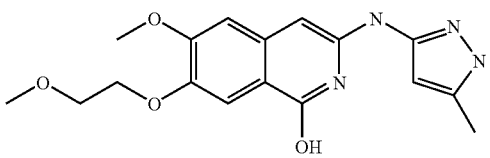

A mixture of 2-Cyanomethyl-4-methoxy-5-(2-methoxy-ethoxy)-benzoic acid (1.0 g, 3.77 mmol), 3-amino-5-methylpyrazol (0.73 g, 7.54 mmol) in acetic acid (10 ml) were sealed in microwave process vial (20 ml). The mixture was heated at 130° C. for 30 minutes under microwave irradiation. After removal of acetic acid, the residue was dissolved in 2 ml MeOH. This solution was added dropwise to 100 ml water, and the solid was collected and dried to give product (0.8 g, 61.6%). LC-MS: m/e 345 (MH⁺).

e) Preparation of [1-Chloro-6-methoxy-7-(2-methoxy-ethoxy)-isoquinolin-3-yl]-(5-methyl-1H-pyrazol-3-yl)-amine

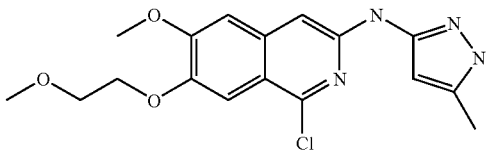

A mixture of 6-Methoxy-7-(2-methoxy-ethoxy)-3-(5-methyl-1H-pyrazol-3-ylamino)-isoquinolin-1-ol (1.0 g, 1.45 mmol) in POCl₃ (20 ml) was sealed in 2 microwave process vial (20 ml). The mixture was heated at 160° C. for 30 minutes under microwave irradiation. After removal of excess solvent, the residue was poured into ice-water, neutralized by 2M NaOH, extracted by EtOAc. The organic layer was concentrated and the residue was purified by flash column chromatography to give product as solid (0.33 g, 62.7%). LC-MS: m/e 363 (MH⁺).

Example 9D

6-Hydroxy-5-methoxy-indan-1-one

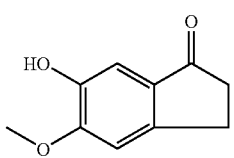

a) Preparation of 3-(4-Hydroxy-3-methoxy-phenyl)-acrylic acid

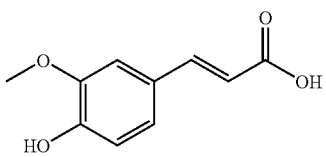

Vanillin (40 g, 263 mmol) was dissolved in pyridine (120 ml), and malonic acid (41 g, 395 mm ol) was added, followed by piperidine (4 ml). The mixture was heated at 90° C. for 6 hs under N₂. After removal of pridine, the residue was poured into water (500 ml), acidified to PH=3 by aq.HCl. The precipitate was collected, washed by water (150 ml×3), and dried to give product (47 g, 91.8%). LC-MS: m/e 193 (M−1)

b) Preparation of 3-(4-Hydroxy-3-methoxy-phenyl)-propionic acid

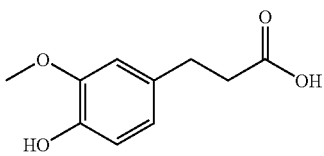

To a solution of 3-(4-Hydroxy-3-methoxy-phenyl)-acrylic acid (20 g, 103 mmol) in EtOAc (100 ml) and MeOH (100 ml) was added carefully 10% Pd/C (2.0 g), the reaction mixture was shaken in Parr apparatus for 5 hs under 30-40 psi of hydrogen, then the solution was passed through a celite pad and the catalyst was washed with methanol, the filtrate was concentrated and dried at 50° C. under reduced pressure to give product (18 g, 89.16%). LC-MS: m/e 195 (M−1).

c) Preparation of 6-Hydroxy-5-methoxy-indan-1-one

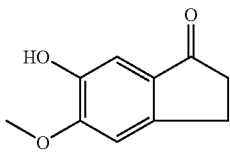

The 3-(4-Hydroxy-3-methoxy-phenyl)-propionic acid (2 g×10) was dissolved in methanesulfonic acid (10 ml×10) in microwave process vial (20 ml×10), the mixture was heated at 90° C. for 10 minutes under microwave irradiation. The mixture was poured into ice (500 g), and then stirred for 20 minutes. The precipitate was collected and dried to give 6-Hydroxy-5-methoxy-indan-1-one (15 g, 82.6%). LC-MS: m/e 179 (MH+)

Example 9E

[1-Chloro-6,7-bis-(2-methoxy-ethoxy)-isoquinolin-3-yl]-(5-methyl-1H-pyrazol-3-yl)-amine

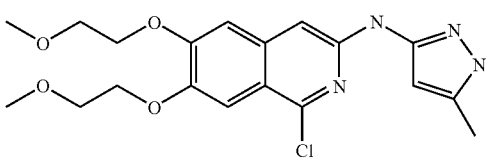

a) Preparation of 3,4-Bis-(2-methoxy-ethoxy)-benzaldehyde

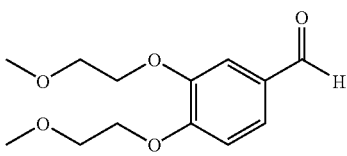

To a mixture of 3,4-Dihydroxy-benzaldehyde (10.0 g, 72.4 mmol), K$_2$CO$_3$ (40 g, 289 mmol), tetrabutyl-ammonium iodide (5.3 g, 14.48 mmol) suspended in actone (200 ml), 1-Bromo-3-methoxy-propane (20 ml, 217.2 mmol) was added, and then heated to reflux for 4 hs under N$_2$. The solid was filtered off, the filtrate was concentrated to give crude product which was used for next step without purification. LC-MS: m/e 255 (MH+)

b) Preparation of 3-[3,4-Bis-(2-methoxy-ethoxy)-phenyl]-acrylic acid

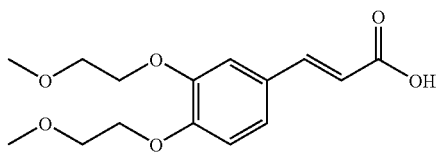

To a solution of 3,4-Bis-(2-methoxy-ethoxy)-benzaldehyde (19 g, 72.4 mmol) in pyridine (60 ml), malonic acid (11.3 g, 108.6 mmol) was added, followed by piperidine (2 ml), the resulting mixture was heated at 110° C. for 6 hs under N$_2$. After removal of most of pyridine, the residue was poured into water (200 ml) and acidified to PH=3 by aq.HCl. The precipitate was collected and dried to give product (20 g, 93.3%). LC-MS: m/e 295 (M−1)

c) Preparation of 3-[3,4-Bis-(2-methoxy-ethoxy)-phenyl]-propionic acid

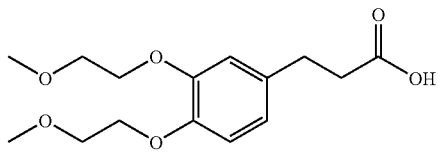

To a solution of 3-[3,4-Bis-(2-methoxy-ethoxy)-phenyl]-acrylic acid (20 g, 67.5 mmol) in EtOAc (100 ml) and MeOH (100 ml) was added carefully 10% Pd/C (1.5 g), then the mixture was shaken in Parr apparatus for 5 hs under 30-40 psi of hydrogen. The solution was passed through a celite pad, and the filtrate was concentrated to give product (15 g, 78.5%). LC-MS: m/e 297 (M−1)

d) Preparation of 5,6-Bis-(2-methoxy-ethoxy)-indan-1-one

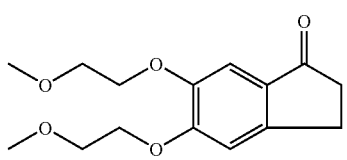

3-[3,4-Bis-(2-methoxy-ethoxy)-phenyl]-propionic acid (2 g×5) was dissolved in methanesulfonic acid (10 ml×5) in microwave process vial (20 ml×5), and the mixture was heated at 100° C. for 10 minutes under microwave irradiation. The reaction mixture was poured into ice (250 g), neutralized by 2M NaOH to PH 8-9, and then extracted by EtOAc/isopropyl alcohol. The organic layer was concentrated to give product (2.68 g, 28.3%). LC-MS: m/e 281 (MH+)

e) Preparation of 5,6-Bis-(2-methoxy-ethoxy)-indan-1,2-dione 2-oxime

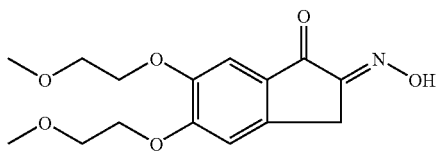

To a solution of 5,6-Bis-(2-methoxy-ethoxy)-indan-1-one (2.6 g, 9.28 mmol) in the methanol (20 ml) was added n-butylnitrite (1.25 ml, 10.2 mmol) followed by concentrated HCl (0.8 ml). The solution was stirred at room temperature overnight during which time a precipitate was formed. The precipitate was collected and dried to yield product as a yellow solid (1.11 g, 38.58%). LC-MS: m/e 310 (MH+).

f) Preparation of 2-Cyanomethyl-4,5-bis-(2-methoxy-ethoxy)-benzoic acid

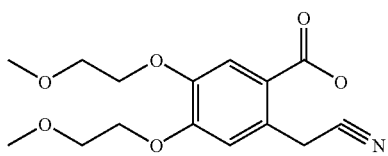

To a solution of NaOH (0.55 g, 13.64 mmol) in H$_2$O (10 ml) was added 5,6-Bis-(2-methoxy-ethoxy)-indan-1,2-dione 2-oxime (1.11 g, 3.59 mmol), and the mixture was heated to 50° C. Then p-Toluenesulfonyl chloride (0.89 g, 4.66 mmol) was added in portions to the mixture, and then the mixture was heated at 80° C. for 15 min. After cooling careful to room temperature, the precipitate (a little) was filtered off, the filtrate was acidified by concentrated HCl to PH=3-4. The precipitate was collected and dried to give product (0.777 mg, yield 70%). LC-MS: m/e 208 (M−1).

g) Preparation of 6,7-Bis-(2-methoxy-ethoxy)-3-(5-methyl-1H-pyrazol-3-ylamino)-isoquinolin-1-ol

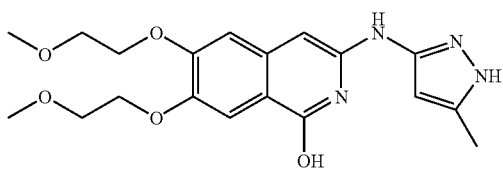

A mixture of 2-Cyanomethyl-4,5-bis-(2-methoxy-ethoxy)-benzoic acid (2 g, 6.47 mmol), 3-amino-5-methylpyrazol (1.26 g, 12.9 mmol) in acetic acid (10 ml) was sealed in microwave process vial (20 ml). The mixture was heated at 130° C. for 30 minutes under microwave irradiation. After removal of acetic acid, the residue was dissolved in 1 ml MeOH, and this solution was added dropwise to 20 ml water. After stirred for half an hour, solid was collected and dried to give product (2 g, 79.7%). LC-MS: m/e 389(MH+).

h) Preparation of [1-Chloro-6,7-bis-(2-methoxy-ethoxy)-isoquinolin-3-yl]-(5-methyl-1H-pyrazol-3-yl)-amine

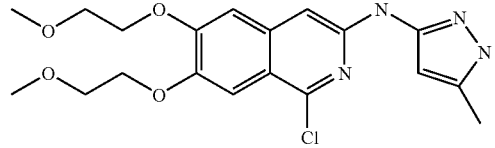

A mixture of 6,7-Bis-(2-methoxy-ethoxy)-3-(5-methyl-1H-pyrazol-3-ylamino)-isoquinolin-1-ol (1.8 g, 4.64 mmol) in POCl$_3$ (15 ml) was sealed in microwave process vial (20 ml). The mixture was heated at 170° C. for 30 minutes under microwave irradiation. After removal of solvent, the ice water was added to the residue, and the mixture was neutralized by 2M NaOH, extracted by EtOAc. The organic layer was concentrated and the residue was purified by flash column chromatography to give product as a solid (0.7 g, 37.6%). LC-MS: m/e 408 (MH+).

Example 9F

Chloro-6,8-dimethoxy-isoquinolin-3-yl)-(5-methyl-1H-pyrazol-3-yl)-amine

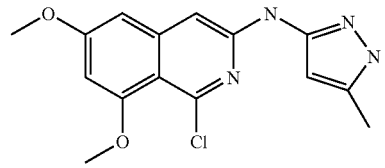

a) Preparation of 3-(3,5-Dimethoxy-phenyl)-acrylic acid

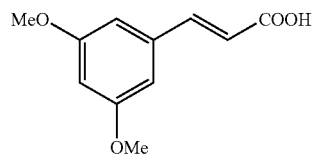

To a solution of 3,5-Dimethoxy-benzaldehyde (9.5 g, 57.17 mmol) in pyridine (60 ml), malonic acid (9 g, 85.725 mmol) was added, and followed by piperidine (2 ml), the mixture was heated to 100° C. and stirred at this temperature for 6 hs under N$_2$. Then most of pridine was removed, and the residue was poured into water (250 ml), acidified to PH=3 by aq.HCl, the precipitate was collected and dried to give product (10.9 g, 91.8%). LC-MS: m/e 207 (M−1)

b) Preparation of 3-(3,5-Dimethoxy-phenyl)-propionic acid

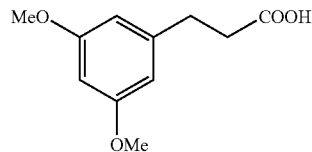

To a solution of 3-(3,5-Dimethoxy-phenyl)-acrylic acid (12 g, 57.7 mmol) in EtOAc (100 ml) and MeOH (100 ml) was added carefully 10% Pd/C (1.3 g), the reaction mixture was shaken in Parr apparatus for 5 hs under 30-40 psi of hydrogen, then the solution was passed through a celite pad, the filtrate was concentrated and dried at 50° C. under reduced pressure to give product (11.7 g, 96.55%). LC-MS: m/e 209 (M−1)

c) Preparation of 5,7-Dimethoxy-indan-1-one

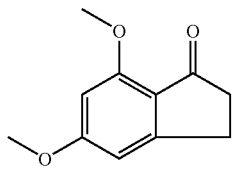

The 3-(3,5-Dimethoxy-phenyl)-propionic acid (2 g×5) was dissolved in methanesulfonic acid (10 ml×5) in microwave process vial (20 ml×5), the mixture was heated at 90° C. for 10 minutes under microwave irradiation. The mixture was poured into ice (250 g), neutralized by 2M NaOH to PH 8-9, and extracted by EtOAc. The organic layer was concentrated to give the product (8.8 g, 96.2%). LC-MS: m/e 193 (MH$^+$)

d) Preparation of 5,7-Dimethoxy-indan-1,2-dione 2-oxime

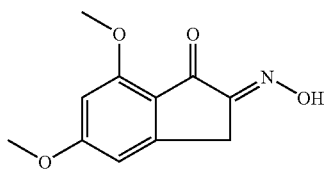

To a solution of 5,7-Dimethoxy-indan-1-one (8.7 g, 45.26 mmol) in the methanol (80 ml) was added n-butylnitrite (6.13 ml, 49.78 mmol) followed by concentrated HCl (4.4 ml). The solution was stirred at 40° C. for one hour during which time a precipitate was formed. The precipitate was collected and dried to yield product as a yellow solid (10 g, 99%). LC-MS: m/e 222 (MH$^+$).

e) Preparation of 2-Cyanomethyl-4,6-dimethoxy-benzoic acid

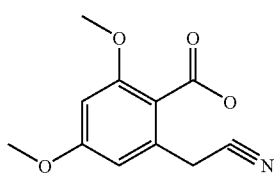

To a solution of NaOH (3.4 g, 85 mmol) in H$_2$O (50 ml) was added of 5,7-Dimethoxy-indan-1,2-dione 2-oxime (5.0 g, 22.6 mmol). The mixture was heated to 50° C. Then p-Toluenesulfonyl chloride (5.7 g, 30 mmol) was added in portions to the mixture. The mixture was heated at 80° C. for 15 min. After cooling carefully to room temperature, the precipitate (a little) was removed from the mixture. Mother liquid was acidified by concentrated HCl to PH=3-4 and precipitate was formed. The precipitate was collected and dried to give product (3.5 g, 70%). LC-MS: m/e 220 (M−1).

f) Preparation of 6,8-Dimethoxy-3-(5-methyl-1H-pyrazol-3-ylamino)-isoquinolin-1-ol

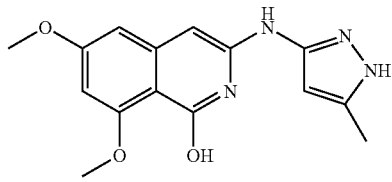

A mixture of 2-Cyanomethyl-4,6-dimethoxy-benzoic acid (1.75 g×3), 3-amino-5-methylpyrazole (1.5 g×3) in acetic acid (10 ml×3) were sealed in microwave process vial (20 ml×3). The mixture was heated at 140° C. for 30 minutes under microwave irradiation. The mixture was evaporated to oil, and the oil was dissolved in 1.5 ml MeOH. This solution was added dropwise to 50 ml water. After stirred for 1 hour, solid was collected and was purified by flash column chromatography to give product (6.07 g, 85%). LC-MS: m/e 301 (MH$^+$).

g) Preparation of (1-Chloro-6,8-dimethoxy-isoquinolin-3-yl)-(5-methyl-1H-pyrazol-3-yl)-amine

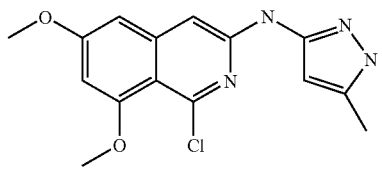

A mixture of 6,8-Dimethoxy-3-(5-methyl-1H-pyrazol-3-ylamino)-isoquinolin-1-ol (0.4 g, 1.33 mmol) in POCl$_3$ (4 ml), were sealed in microwave process vials (5 ml). The mixture was heated at 140° C. for 75 minutes under microwave irradiation. The mixture was concentrated, and the residue was treated with 1 ml MeOH. The solid was collected and dried to give desired product (0.2 g, 47.28%). LC-MS: m/e 319 (MH$^+$).

Example 9G

Chloro-6-methoxy-3-(5-methyl-1H-pyrazol-3-ylamino)-isoquinoline-7-carboxylic acid dimethylamide

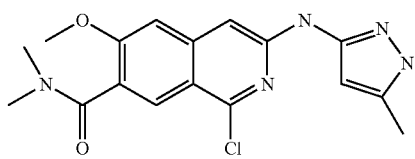

a) Preparation of Trifluoro-methanesulfonic acid 6-methoxy-3-oxo-indan-5-yl ester

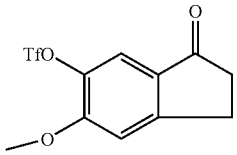

To a solution of 6-Hydroxy-5-methoxy-indan-1-one (6 g, 33.7 mmol), Et₃N (18 ml, 134.8 mmol) in CH₂Cl₂ (180 ml) trifluoro-methanesulfonic anhydride (12 ml, 67.4 mmol) was added at 0° C. Then the mixture was stirred at room temperature for 2 hrs. Another 10 ml CH₂Cl₂ was added, and the organic layer was washed with saturated aqueous sodium bicarbonate, brine and dried over anhydrous sodium sulfate. After removal of solvent, the residue was purified by column chromatography (petroleum ether:ethyl acetate=2:1) to give product as brown solid (7.5 g, 71.8% yield). LC-MS: m/e 311 (MH⁺)

b) Preparation of 6-Methoxy-3-oxo-indan-5-carboxylic acid methyl ester

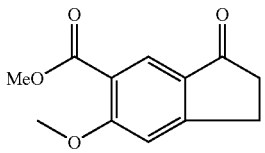

A mixture of Trifluoro-methanesulfonic acid 6-methoxy-3-oxo-indan-5-yl ester (7.5 g, 24.2 mmol), Pd(OAc)₂ (480 mg, 2.14 mmol), Pd(PPh₃)₄ (240 mg), DPPP (990 mg) in methanol and DMF (2:1, 150 ml) was placed in a Parr apparatus. The mixture was stirred under 30 psi of CO at room temperature for 2 h, then it was heated at 50° C. for 2 h, and 90° C. for 15 h. The catalyst was filtered off and the filtrate was concentrated in vacuo. The crude product was purified by column chromatography to give yellow solid (5.8 g, 96% yield). LC-MS: m/e 221 (MH⁺)

c) Preparation of 6-Methoxy-3-oxo-indan-5-carboxylic acid

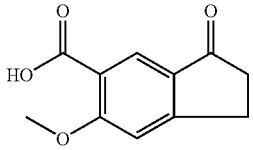

6-Methoxy-3-oxo-indan-5-carboxylic acid methyl ester (4 g, 18.18 mmol) was added to a solution of LiOH.H₂O (2.2 g, 54.5 mmol) in THF (40 ml) and H₂O (40 ml), then the mixture was heated to reflux and stirred for one hour. After removal of THF, the residue was acidified to PH=3, and the precipitate was collected and dried to give a white solid (3.38 g, 89.8%). LC-MS: m/e 207 (MH⁺)

d) Preparation of 6-Methoxy-3-oxo-indan-5-carboxylic acid dimethylamide

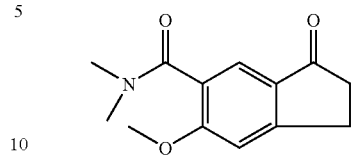

To a solution of Dimethylamine hydrochloride (2.22 g, 27.24 mmol) and triethylamine (7 ml, 54.48 mmol) in CH₂Cl₂ (30 ml) was added 6-Methoxy-3-oxo-indan-5-carboxylic acid (2 g, 9.08 mmol), HOBt (2.45 g, 18.18 mmol), EDCI (3.48 g, 18.18 mmol) at 0° C. in order. The mixture was stirred at room temperature for 3 hrs and washed with 8% NaOH, water and brine. The organic layer was dried over anhydrous sodium sulfate and concentrated to give the product (1.69 g, 80% yield). LC-MS: m/e 234 (MH⁺)

e) Preparation of 2-Hydroxyimino-6-methoxy-3-oxo-indan-5-carboxylic acid dimethylamide

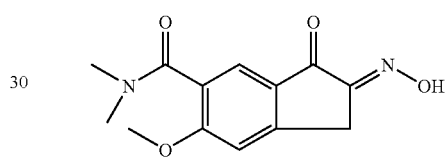

To a solution of 6-Methoxy-3-oxo-indan-5-carboxylic acid dimethylamide (2.56 g, 10.97 mmol) in the methanol (40 ml) and dioxane (40 ml) was added n-butylnitrite (1.48 ml, 12.067 mmol) followed by concentrated HCl (1 ml). The solution was stirred at r.t overnight during which time a precipitate was formed. The precipitate was collected and dried to yield a yellow solid (2.8 g, 97%). LC-MS: m/e 263 (MH⁺).

f) Preparation of 6-Cyanomethyl-4-methoxy-N,N-dimethyl-isophthalamic acid

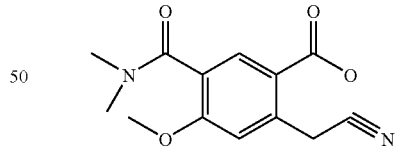

To a solution of NaOH (1.6 g, 40.54 mmol) in H₂O (30 ml) was added of 2-Hydroxyimino-6-methoxy-3-oxo-indan-5-carboxylic acid dimethylamide (2.8 g, 10.67 mmol). The mixture was heated at 50° C. Then p-Toluenesulfonyl chloride (5.7 g, 30 mmol) was added in portions to the mixture. The mixture was heated at 80° C. for 15 min. After cooling carefully to room temperature, the precipitate (a little) was removed from the mixture. Mother liquid was acidified by concentrated HCl to PH=3-4 and the precipitate was collected and dried to give product (2.5 g, 89.28%). LC-MS: m/e 261 (M−1).

g) Preparation of 1-Hydroxy-6-methoxy-3-(5-methyl-1H-pyrazol-3-ylamino)-isoquinoline-7-carboxylic acid dimethylamide

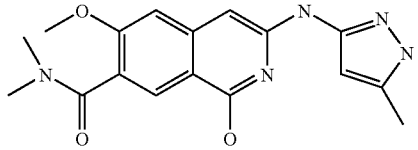

A mixture of 6-Cyanomethyl-4-methoxy-N,N-dimethyl-isophthalamic acid (2.0 g, 7.6 mmol), 3-amino-5-methylpyrazol (1.5 g, 15.44 mmol), acetic acid (10 ml) were sealed in microwave process vial (20 ml). The mixture was heated at 130° C. for 30 minutes under microwave irradiation. After removal of acetic acid, the residue was dissolved in 1.5 ml MeOH, and this solution was added dropwise to 30 ml water. After stirred for 1 hour, the solid was collected and was purified by flash column chromatography to give product (2.2 g, 85%). LC-MS: m/e 342 (MH$^+$).

h) Preparation of 1-Chloro-6-methoxy-3-(5-methyl-1H-pyrazol-3-ylamino)-isoquinoline-7-carboxylic acid dimethylamide

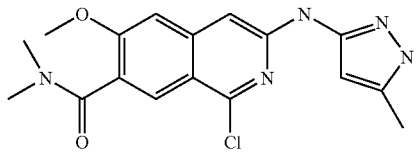

A mixture of 1-Hydroxy-6-methoxy-3-(5-methyl-1H-pyrazol-3-ylamino)-isoquinoline-7-carboxylic acid dimethylamide (0.1 g, 0.29 mmol) in POCl$_3$ (4 ml) was sealed in microwave process vial (5 ml). The mixture was heated at 130° C. for 30 minutes under microwave irradiation. The mixture was concentrated, and the residue was treated with 1 ml MeOH. After stirred for half an hour at room temperature, the solid was collected and dried to give desired product (0.072 g, 70%). LC-MS: m/e 360 (MH$^+$).

Example 9H

1-Chloro-6-methoxy-3-(5-methyl-1H-pyrazol-3-ylamino)-isoquinoline-7-carbonitrile

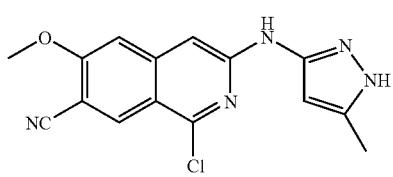

a) Preparation of 6-Methoxy-3-oxo-indan-5-carboxylic acid amide

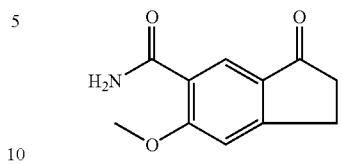

6-Methoxy-3-oxo-indan-5-carboxylic acid methyl ester (7 g, 31.82 mmol) was suspended in NH$_3$.H$_2$O (150 ml), and the mixture was heated to 40° C. and stirred for two hours, during this time the precipitate was formed. The precipitate was collected and dried to give product as white solid (5.2 g, 80% yield). LC-MS: m/e 206(MH$^+$)

b) Preparation of 2-Hydroxyimino-6-methoxy-3-oxo-indan-5-carboxylic acid amide

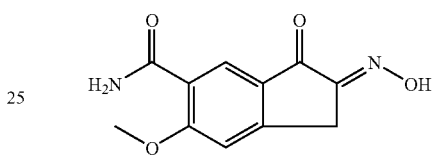

To a solution of 6-Methoxy-3-oxo-indan-5-carboxylic acid amide (3 g, 14.6 mmol) in the methanol (50 ml) was added n-butylnitrite (1.8 ml, 16.06 mmol), followed by concentrated HCl (1.2 ml). The solution was stirred at r.t overnight during which time a precipitate was formed. The precipitate was collected and dried to yield product as a yellow solid (2.78 g, 81.37%). LC-MS: m/e 235(MH$^+$).

c) Preparation of 6-Cyanomethyl-4-methoxy-isophthalamic acid

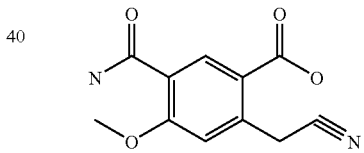

To a solution of NaOH (0.97 g, 19.2 mmol) in H$_2$O (20 ml) was added 2-Hydroxyimino-6-methoxy-3-oxo-indan-5-carboxylic acid amide (1.5 g, 6.4 mmol). The mixture was heated to 50° C. Then p-Toluenesulfonyl chloride (1.6 g, 8.32 mmol) was added in portions to the mixture. The mixture was heated at 80° C. for 15 min. After cooling carefully to room temperature, the precipitate (a little) was removed from the mixture. Mother liquid was acidified by concentrated HCl to PH=3-4 and the precipitate was collected and dried to give product as a solid (1.33 g, 89%). LC-MS: m/e 233 (M−1).

d) Preparation of 1-Hydroxy-6-methoxy-3-(5-methyl-1H-pyrazol-3-ylamino)-isoquinoline-7-carboxylic acid amide

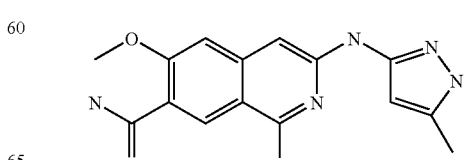

A mixture of 6-Cyanomethyl-4-methoxy-isophthalamic acid (0.5 g, 2.34 mmol), 3-amino-5-methylpyrazol (0.45 g, 4.68 mmol), acetic acid (10 ml) were sealed in microwave process vial (20 ml). The mixture was heated at 130° C. for 30 minutes under microwave irradiation. After removal of acetic acid, the residue was dissolved in 1.5 ml MeOH. This solution was added dropwise to 30 ml water, and the formed solid was collected and purified by flash column chromatography to give product (0.63 g, 86%). LC-MS: m/e 314 (MH$^+$).

e) Preparation of 1-Chloro-6-methoxy-3-(5-methyl-1H-pyrazol-3-ylamino)-isoquinoline-7-carbonitrile

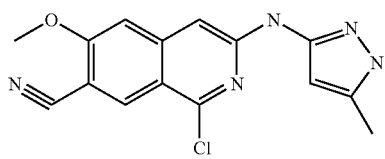

A mixture of 1-Hydroxy-6-methoxy-3-(5-methyl-1H-pyrazol-3-ylamino)-isoquinoline-7-carboxylic acid amide (0.4 g, 1.28 mmol) in POCl$_3$ (10 ml) was sealed in microwave process vial (20 ml). The mixture was heated at 130° C. for 30 minutes under microwave irradiation. The mixture was concentrated, and the residue was poured into ice water, and the precipitate was collected and purified by preparative HPLC to give product (0.28 g, 70%). LC-MS: m/e 314 (MH$^+$).

Synthesis of Final Products

Example 10

[1-(4-Methoxy-phenoxy)-isoquinolin-3-yl]-(5-methyl-1H-pyrazol-3-yl)-amine

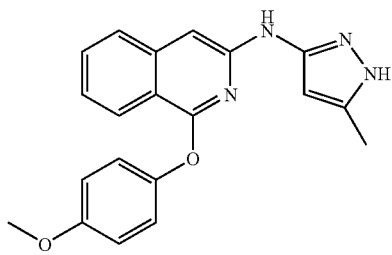

NaH (155 mg) was added to a solution of 4-methoxyphenol (500 mg) in dimethyl ether (DME) (2 ml) and stirred for 1 hour. (1-chloro-isoquinolin-3-yl)-(5-methyl-1H-pyrazol-3-yl)-amine (100 mg) was added to the mixture, and the mixture was heated at 150° C. for 30 minutes under microwave irradiation. The reaction mixture was acidified to pH=7 with acetic acid and purified by preparative LC-MS to give [1-(4-methoxy-phenoxy)-isoquinolin-3-yl]-(5-methyl-1H-pyrazol-3-yl)-amine (30 mg). LC-MS: m/e 347(MH$^+$). $^1$H NMR(CDCl$_3$): δ 2.18(s, 3H), δ 3.85(s, 3H), δ 5.64(s, 1H), δ 6.78(s, 1H), δ 6.87(s, 1H), δ 7.02(m, 2H), δ 7.21(m, 3H), δ 7.31(m, 1H), δ 7.54(d, 2H), δ 8.27(d, 1H).

Example 11

(5-Methyl-1H-pyrazol-3-yl)-(1-phenoxy-isoquinolin-3-yl)-amine

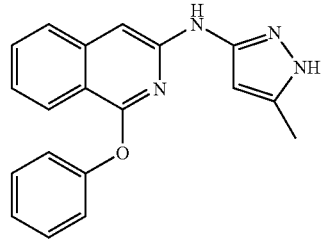

Similar procedure as described in example 10 was used, starting from phenol and (1-chloro-isoquinolin-3-yl)-(5-methyl-1H-pyrazol-3-yl)-amine to give (5-methyl-1H-pyrazol-3-yl)-(1-phenoxy-isoquinolin-3-yl)-amine. LC-MS: m/e 317 (MH$^+$). $^1$H NMR(DMSO): δ 2.12(s, 3H), δ 5.56(s, 1H), δ 7.22(s, 1H), δ 7.32(m, 5H), δ 7.51(m, 2H), δ 7.65(m, 2H), δ 8.15(d, 1H), δ 9.05(s, 1H).

Example 12

(1-Benzyloxy-isoquinolin-3-yl)-(5-methyl-1H-pyrazol-3-yl)-amine

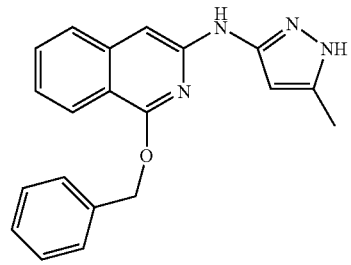

Similar procedure as described in example 10 was used, starting from phenyl-methanol and (1-chloro-isoquinolin-3-yl)-(5-methyl-1H-pyrazol-3-yl)-amine to give (1-benzyloxy-isoquinolin-3-yl)-(5-methyl-1H-pyrazol-3-yl)-amine. LC-MS: m/e 331 (MH$^+$).

Example 13

[1-(4-Fluoro-phenoxy)-isoquinolin-3-yl]-(5-methyl-1H-pyrazol-3-yl)-amine

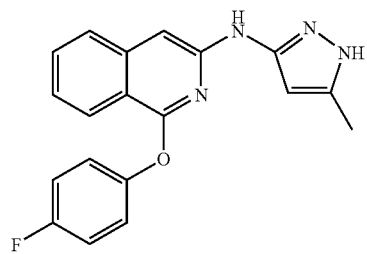

Similar procedure as described in example 10 was used, starting from 4-fluoro-phenol and (1-chloro-isoquinolin-3-yl)-(5-methyl-1H-pyrazol-3-yl)-amine to give [1-(4-fluoro-phenoxy)-isoquinolin-3-yl]-(5-methyl-1H-pyrazol-3-yl)-amine. LC-MS m/e 335(MH+).

Example 14

(5-Methyl-1H-pyrazol-3-yl)-(1-p-tolyloxy-isoquinolin-3-yl)-amine

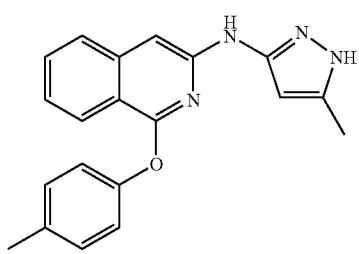

Similar procedure as described in example 10 was used, starting from 4-methyl-phenol and (1-chloro-isoquinolin-3-yl)-(5-methyl-1H-pyrazol-3-yl)-amine to give (5-methyl-1H-pyrazol-3-yl)-(1-p-tolyloxy-isoquinolin-3-yl)-amine. LC-MS m/e 331 (MH+).

Example 15

4-[3-(5-methyl-1H-pyrazol-3-ylamino)-isoquinolin-1-yloxy]-benzonitrile

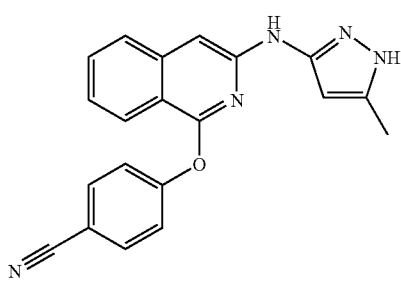

Similar procedure as described in example 10 was used, starting from 4-hydroxy-benzonitrile and (1-chloro-isoquinolin-3-yl)-(5-methyl-1H-pyrazol-3-yl)-amine to give 4-[3-(5-methyl-1H-pyrazol-3-ylamino)-isoquinolin-1-yloxy]-benzonitrile. LC-MS m/e 342(MH+).

Example 16

[1-(4-Chloro-phenoxy)-isoquinolin-3-yl]-(5-methyl-1H-pyrazol-3-yl)-amine

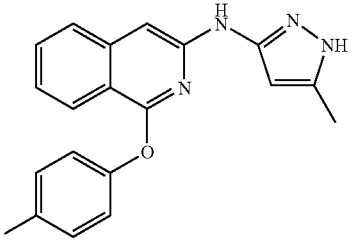

Similar procedure as described in example 10 was used, starting from 4-chloro-phenol and (1-chloro-isoquinolin-3-yl)-(5-methyl-1H-pyrazol-3-yl)-amine to give [1-(4-chloro-phenoxy)-isoquinolin-3-yl]-(5-methyl-1H-pyrazol-3-yl)-amine. LC-MS m/e 352(MH+).

Example 17

(5-Methyl-1H-pyrazol-3-yl)-(1-m-tolyloxy-isoquinolin-3-yl)-amine

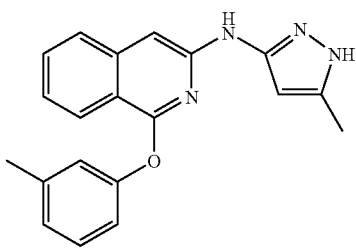

Similar procedure as described in example 10 was used, starting from 3-methyl-phenol and (1-chloro-isoquinolin-3-yl)-(5-methyl-1H-pyrazol-3-yl)-amine to give (5-methyl-1H-pyrazol-3-yl)-(1-m-tolyloxy-isoquinolin-3-yl)-amine. LC-MS m/e 331(MH+).

Example 18

[1-(3-Fluoro-phenoxy)-isoquinolin-3-yl]-(5-methyl-1H-pyrazol-3-yl)-amine

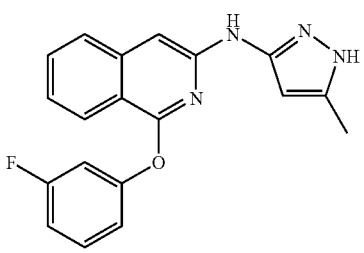

Similar procedure as described in example 10 was used, starting from 3-fluoro-phenol and (1-chloro-isoquinolin-3-yl)-(5-methyl-1H-pyrazol-3-yl)-amine to give [1-(3-fluoro-phenoxy)-isoquinolin-3-yl]-(5-methyl-1H-pyrazol-3-yl)-amine. LC-MS m/e 335(MH$^+$).

Example 19

[1-(3-chloro-phenoxy)-isoquinolin-3-yl]-(5-methyl-1H-pyrazol-3-yl)-amine

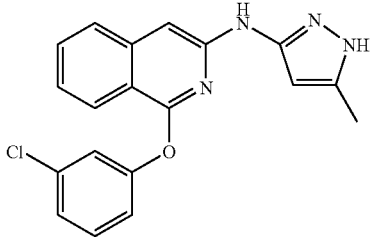

Similar procedure as described in example 10 was used, starting from 3-chloro-phenol and (1-chloro-isoquinolin-3-yl)-(5-methyl-1H-pyrazol-3-yl)-amine to give [1-(3-chloro-phenoxy)-isoquinolin-3-yl]-(5-methyl-1H-pyrazol-3-yl)-amine. LC-MS m/e 352(MH$^+$).

Example 20

[1-(3-Methoxy-phenoxy)-isoquinolin-3-yl]-(5-methyl-1H-pyrazol-3-yl)-amine

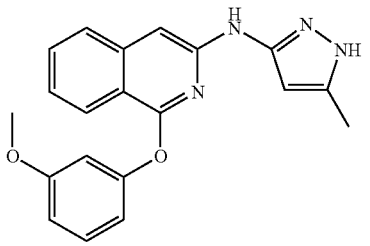

Similar procedure as described in example 10 was used, starting from 3-methoxy-phenol and (1-chloro-isoquinolin-3-yl)-(5-methyl-1H-pyrazol-3-yl)-amine to give [1-(3-methoxy-phenoxy)-isoquinolin-3-yl]-(5-methyl-1H-pyrazol-3-yl)-amine. LC-MS m/e 347(MH$^+$).

Example 21

(5-Methyl-1H-pyrazol-3-yl)-(1-o-tolyloxy-isoquinolin-3-yl)-amine

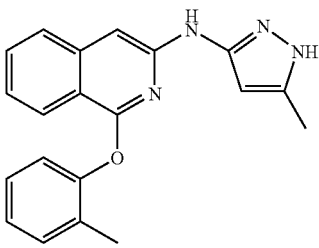

Similar procedure as described in example 10 was used, starting from 2-methyl-phenol and (1-chloro-isoquinolin-3-yl)-(5-methyl-1H-pyrazol-3-yl)-amine to give (5-methyl-1H-pyrazol-3-yl)-(1-o-tolyloxy-isoquinolin-3-yl)-amine. LC-MS m/e 331(MH$^+$).

Example 22

[1-(2-Fluoro-phenoxy)-isoquinolin-3-yl]-(5-methyl-1H-pyrazol-3-yl)-amine

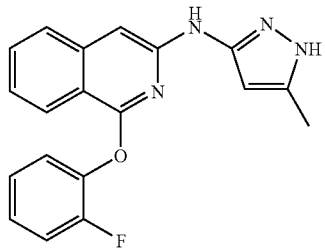

Similar procedure as described in example 10 was used, starting from 2-fluoro-phenol and (1-chloro-isoquinolin-3-yl)-(5-methyl-1H-pyrazol-3-yl)-amine to give [1-(2-fluoro-phenoxy)-isoquinolin-3-yl]-(5-methyl-1H-pyrazol-3-yl)-amine. LC-MS m/e 335(MH$^+$).

Example 23

[1-(2-Chloro-phenoxy)-isoquinolin-3-yl]-(5-methyl-1H-pyrazol-3-yl)-amine

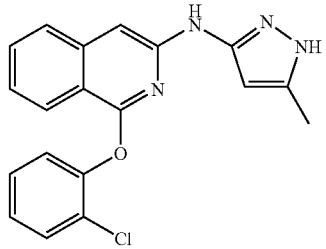

Similar procedure as described in example 10 was used, starting from 2-chloro-phenol and (1-chloro-isoquinolin-3-yl)-(5-methyl-1H-pyrazol-3-yl)-amine to give [1-(2-chloro-phenoxy)-isoquinolin-3-yl]-(5-methyl-1H-pyrazol-3-yl)-amine. LC-MS m/e 352(MH$^+$).

Example 24

[1-(2-Methoxy-phenoxy)-isoquinolin-3-yl]-(5-methyl-1H-pyrazol-3-yl)-amine

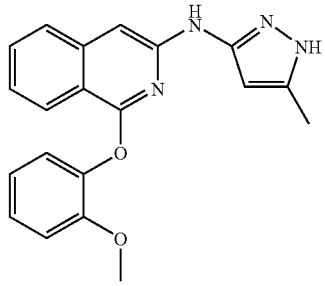

Similar procedure as described in example 10 was used, starting from 2-methoxy-phenol and (1-chloro-isoquinolin- 3-yl)-(5-methyl-1H-pyrazol-3-yl)-amine to give [1-(2-methoxy-phenoxy)-isoquinolin-3-yl]-(5-methyl-1H-pyrazol-3-yl)-amine. LC-MS m/e 347(MH⁺).

Example 25

(1-Methoxy-isoquinolin-3-yl)-(5-methyl-1H-pyrazol-3-yl)-amine

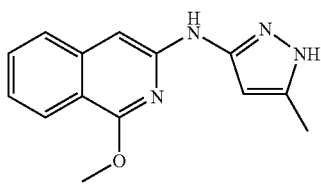

Similar procedure as described in example 10 was used, starting from methanol and (1-chloro-isoquinolin-3-yl)-(5-methyl-1H-pyrazol-3-yl)-amine to give (1-methoxy-isoquinolin-3-yl)-(5-methyl-1H-pyrazol-3-yl)-amine. LC-MS m/e 255 (MH⁺).

Example 26

(1-Isobutoxy-isoquinolin-3-yl)-(5-methyl-1H-pyrazol-3-yl)-amine

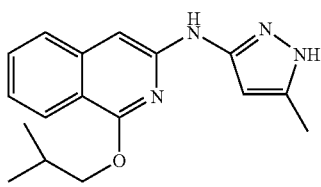

Similar procedure as described in example 10 was used, starting from 3-methyl-butan-1-ol and (1-chloro-isoquinolin-3-yl)-(5-methyl-1H-pyrazol-3-yl)-amine to give (1-Isobutoxy-isoquinolin-3-yl)-(5-methyl-1H-pyrazol-3-yl)-amine. LC-MS m/e 297(MH⁺).

Example 27

{1-[2-(2-Ethoxy-ethoxy)-ethoxy]-isoquinolin-3-yl}-(5-methyl-1H-pyrazol-3-yl)-amine

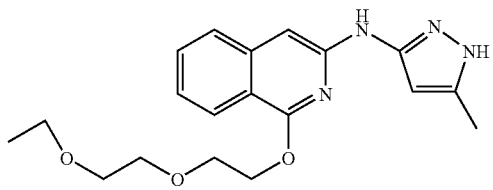

Similar procedure as described in example 10 was used, starting from 2-(2-ethoxy-ethoxy)-ethanol and (1-chloro-isoquinolin-3-yl)-(5-methyl-1H-pyrazol-3-yl)-amine to give {-[2-(2-ethoxy-ethoxy)-ethoxy]-isoquinolin-3-yl}-(5-methyl-1H-pyrazol-3-yl)-amine. LC-MS m/e 357(MH⁺).

Example 28

3-[3-(5-Methyl-1H-pyrazol-3-ylamino)-isoquinolin-1-yloxy]-benzonitrile

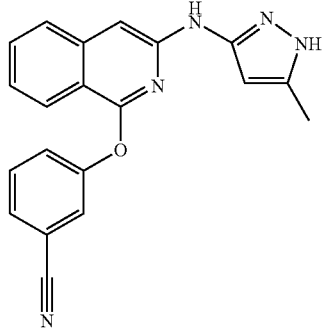

Similar procedure as described in example 10 was used, starting from 3-hydroxy-benzonitrile and (1-chloro-isoquinolin-3-yl)-(5-methyl-1H-pyrazol-3-yl)-amine to give 3-[3-(5-methyl-1H-pyrazol-3-ylamino)-isoquinolin-1-yloxy]-benzonitrile. LC-MS m/e 342(MH⁺).

Example 29

(5-Methyl-1H-pyrazol-3-yl)-[1-(3-trifluoromethyl-phenoxy)-isoquinolin-3-yl]-amine

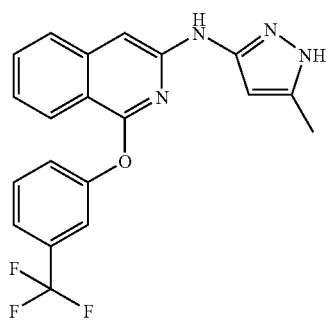

Similar procedure as described in example 10 was used, starting from 3-trifluoromethyl-phenol and (1-chloro-isoquinolin-3-yl)-(5-methyl-1H-pyrazol-3-yl)-amine to give (5-methyl-1H-pyrazol-3-yl)-[1-(3-trifluoromethyl-phenoxy)-isoquinolin-3-yl]-amine. LC-MS m/e 385(MH⁺).

Example 30

(5-Methyl-1H-pyrazol-3-yl)-[1-(2-morpholin-4-yl-ethoxy)-isoquinolin-3-yl]-amine

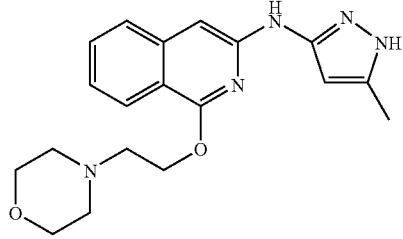

Similar procedure as described in example 10 was used, starting from 2-morpholin-4-yl-ethanol and (1-chloro-isoquinolin-3-yl)-(5-methyl-1H-pyrazol-3-yl)-amine to give (5-methyl-1H-pyrazol-3-yl)-[1-(2-morpholin-4-yl-ethoxy)-isoquinolin-3-yl]-amine. LC-MS m/e 354(MH⁺).

Example 31

(5-Methyl-1H-pyrazol-3-yl)-[1-(2-piperidin-1-yl-ethoxy)-isoquinolin-3-yl]-amine

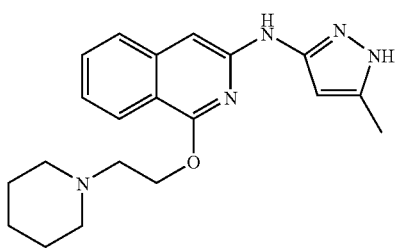

Similar procedure as described in example 10 was used, starting from 2-piperidin-1-yl-ethanol and (1-chloro-isoquinolin-3-yl)-(5-methyl-1H-pyrazol-3-yl)-amine to give (5-methyl-1H-pyrazol-3-yl)-[1-(2-piperidin-1-yl-ethoxy)-isoquinolin-3-yl]-amine. LC-MS m/e 352(MH⁺).

Example 32

(1-Isopropoxy-isoquinolin-3-yl)-(5-methyl-1H-pyrazol-3-yl)-amine

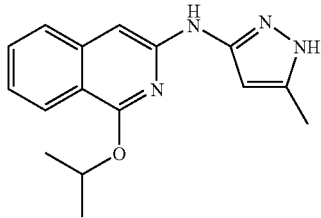

Similar procedure as described in example 10 was used, starting from propan-2-ol, (1-chloro-isoquinolin-3-yl)-(5-methyl-1H-pyrazol-3-yl)-amine to give (1-isopropoxy-isoquinolin-3-yl)-(5-methyl-1H-pyrazol-3-yl)-amine. LC-MS m/e 283 (MH⁺).

Example 33

(1-Cyclohexyloxy-isoquinolin-3-yl)-(5-methyl-1H-pyrazol-3-yl)-amine

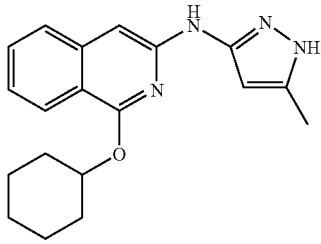

Similar procedure as described in example 10 was used, starting from cyclohexanol and (1-chloro-isoquinolin-3-yl)-(5-methyl-1H-pyrazol-3-yl)-amine to give (1-cyclohexyloxy-isoquinolin-3-yl)-(5-methyl-1H-pyrazol-3-yl)-amine. LC-MS m/e 323(MH⁺).

Example 34

[6-Methoxy-1-(4-methoxy-phenoxy)-isoquinolin-3-yl]-(5-methyl-1H-pyrazol-3-yl)-amine

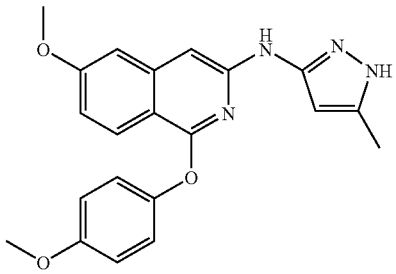

Similar procedure as described in example 10 was used, starting from 4-methoxy-phenol and (1-chloro-6-methoxy-isoquinolin-3-yl)-(5-methyl-1H-pyrazol-3-yl)-amine to give [6-methoxy-1-(4-methoxy-phenoxy)-isoquinolin-3-yl]-(5-methyl-1H-pyrazol-3-yl)-amine. LC-MS m/e 377(MH⁺).

Example 35

(6-Methoxy-1-phenoxy-isoquinolin-3-yl)-(5-methyl-1H-pyrazol-3-yl)-amine

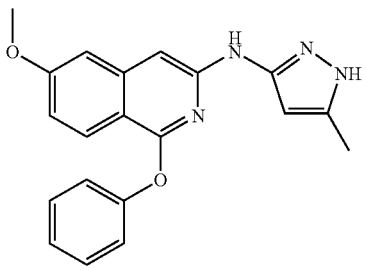

Similar procedure as described in example 10 was used, starting from phenol and (1-chloro-6-methoxy-isoquinolin-3-yl)-(5-methyl-1H-pyrazol-3-yl)-amine to give (6-methoxy-1-phenoxy-isoquinolin-3-yl)-(5-methyl-1H-pyrazol-3-yl)-amine. LC-MS m/e 337(MH⁺).

Example 36

(1-Benzyloxy-6-methoxy-isoquinolin-3-yl)-(5-methyl-1H-pyrazol-3-yl)-amine

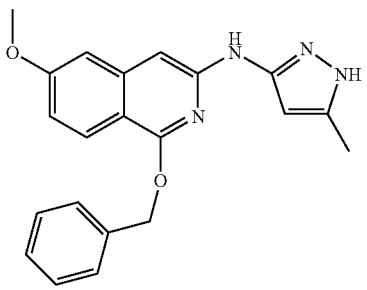

Similar procedure as described in example 10 was used, starting from phenyl-methanol, (1-chloro-6-methoxy-isoquinolin-3-yl)-(5-methyl-1H-pyrazol-3-yl)-amine to give (1-benzyloxy-6-methoxy-isoquinolin-3-yl)-(5-methyl-1H-pyrazol-3-yl)-amine. LC-MS m/e 361(MH+).

Example 37

[1-(4-Fluoro-phenoxy)-6-methoxy-isoquinolin-3-yl]-(5-methyl-1H-pyrazol-3-yl)-amine

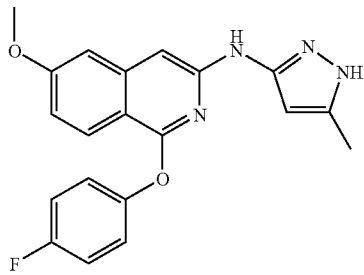

Similar procedure as described in example 10 was used, starting from 4-fluoro-phenol and (1-chloro-6-methoxy-isoquinolin-3-yl)-(5-methyl-1H-pyrazol-3-yl)-amine to give [1-(4-fluoro-phenoxy)-6-methoxy-isoquinolin-3-yl]-(5-methyl-1H-pyrazol-3-yl)-amine. LC-MS m/e 365(MH+).

Example 38

(5-Methyl-1H-pyrazol-3-yl)-(1-p-tolyloxy-6-methoxy-isoquinolin-3-yl)-amine

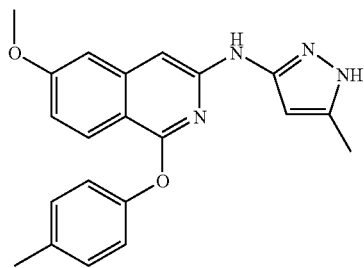

Similar procedure as described in example 10 was used, starting from 4-methyl-phenol and (1-chloro-6-methoxy-isoquinolin-3-yl)-(5-methyl-1H-pyrazol-3-yl)-amine to give (5-methyl-1H-pyrazol-3-yl)-(1-p-tolyloxy-6-methoxy-isoquinolin-3-yl)-amine. LC-MS m/e 361(MH+).

Example 39

4-[3-(5-Methyl-1H-pyrazol-3-ylamino)-6-methoxy-isoquinolin-1-yloxy]-benzonitrile

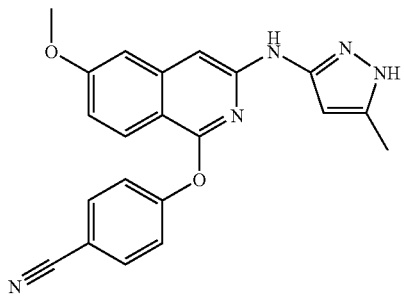

Similar procedure as described in example 10 was used, starting from 4-hydroxy-benzonitrile and (1-chloro-6-methoxy-isoquinolin-3-yl)-(5-methyl-1H-pyrazol-3-yl)-amine to give 4-[3-(5-Methyl-1H-pyrazol-3-ylamino)-6-methoxy-isoquinolin-1-yloxy]-benzonitrile. LC-MS m/e 372(MH+).

Example 40

[1-(4-Chloro-phenoxy)-6-methoxy-isoquinolin-3-yl]-(5-methyl-1H-pyrazol-3-yl)-amine

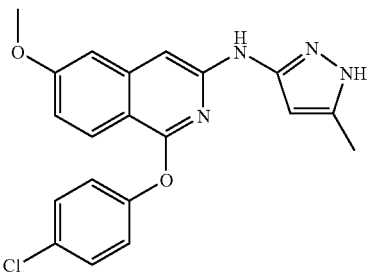

Similar procedure as described in example 10 was used, starting from 4-chloro-phenol and (1-chloro-6-methoxy-isoquinolin-3-yl)-(5-methyl-1H-pyrazol-3-yl)-amine to give [1-(4-Chloro-phenoxy)-6-methoxy-isoquinolin-3-yl]-(5-methyl-1H-pyrazol-3-yl)-amine. LC-MS m/e 382(MH+).

Example 41

(5-Methyl-1H-pyrazol-3-yl)-(1-m-tolyloxy-6-methoxy-isoquinolin-3-yl)-amine

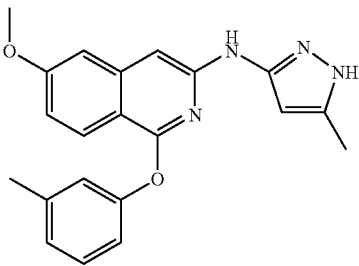

Similar procedure as described in example 10 was used, starting from 3-methyl-phenol and (1-chloro-6-methoxy-isoquinolin-3-yl)-(5-methyl-1H-pyrazol-3-yl)-amine to give (5-methyl-1H-pyrazol-3-yl)-(1-m-tolyloxy-6-methoxy-isoquinolin-3-yl)-amine. LC-MS m/e 361(MH+).

Example 42

[1-(3-Fluoro-phenoxy)-6-methoxy-isoquinolin-3-yl]-(5-methyl-1H-pyrazol-3-yl)-amine

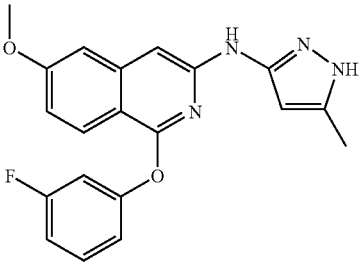

Similar procedure as described in example 10 was used, starting from 3-fluoro-phenol and (1-chloro-6-methoxy-isoquinolin-3-yl)-(5-methyl-1H-pyrazol-3-yl)-amine to give [1-(3-Fluoro-phenoxy)-6-methoxy-isoquinolin-3-yl]-(5-methyl-1H-pyrazol-3-yl)-amine. LC-MS m/e 365(MH+).

Example 43

[1-(3-Chloro-phenoxy)-6-methoxy-isoquinolin-3-yl]-(5-methyl-1H-pyrazol-3-yl)-amine

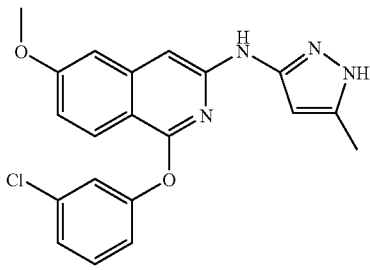

Similar procedure as described in example 10 was used, starting from 3-chloro-phenol and (1-chloro-6-methoxy-isoquinolin-3-yl)-(5-methyl-1H-pyrazol-3-yl)-amine to give [1-(3-Chloro-phenoxy)-6-methoxy-isoquinolin-3-yl]-(5-methyl-1H-pyrazol-3-yl)-amine. LC-MS m/e 382(MH$^+$).

Example 44

[1-(3-Methoxy-phenoxy)-6-methoxy-isoquinolin-3-yl]-(5-methyl-1H-pyrazol-3-yl)-amine

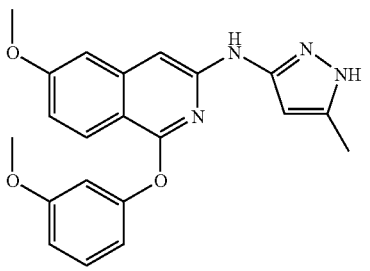

Similar procedure as described in example 10 was used, starting from 3-methoxy-phenol and (1-chloro-6-methoxy-isoquinolin-3-yl)-(5-methyl-1H-pyrazol-3-yl)-amine to give [1-(3-Methoxy-phenoxy)-6-methoxy-isoquinolin-3-yl]-(5-methyl-1H-pyrazol-3-yl)-amine. LC-MS m/e 377(MH$^+$).

Example 45

(5-Methyl-1H-pyrazol-3-yl)-(1-o-tolyloxy-6-methoxy-isoquinolin-3-yl)-amine

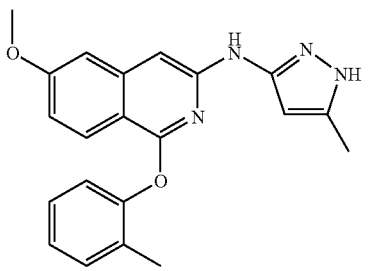

Similar procedure as described in example 10 was used, starting from 2-methyl-phenol and (1-chloro-6-methoxy-isoquinolin-3-yl)-(5-methyl-1H-pyrazol-3-yl)-amine to give (5-methyl-1H-pyrazol-3-yl)-(1-o-tolyloxy-6-methoxy-isoquinolin-3-yl)-amine. LC-MS m/e 361(MH$^+$).

Example 46

[1-(2-Fluoro-phenoxy)-6-methoxy-isoquinolin-3-yl]-(5-methyl-1H-pyrazol-3-yl)-amine

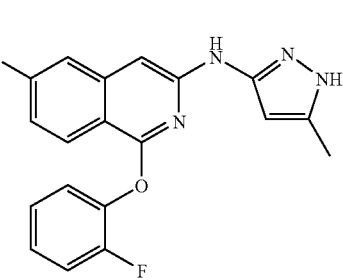

Similar procedure as described in example 10 was used, starting from 2-fluoro-phenol and (1-chloro-6-methoxy-isoquinolin-3-yl)-(5-methyl-1H-pyrazol-3-yl)-amine to give [1-(2-Fluoro-phenoxy)-6-methoxy-isoquinolin-3-yl]-(5-methyl-1H-pyrazol-3-yl)-amine. LC-MS m/e 365(MH$^+$).

Example 47

[1-(2-Chloro-phenoxy)-6-methoxy-isoquinolin-3-yl]-(5-methyl-1H-pyrazol-3-yl)-amine

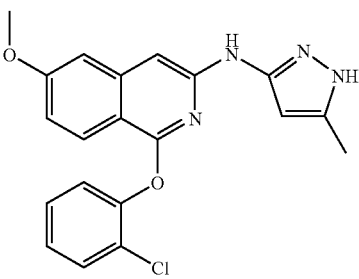

Similar procedure as described in example 10 was used, starting from 2-chloro-phenol and (1-chloro-6-methoxy-isoquinolin-3-yl)-(5-methyl-1H-pyrazol-3-yl)-amine to give [1-(2-chloro-phenoxy)-6-methoxy-isoquinolin-3-yl]-(5-methyl-1H-pyrazol-3-yl)-amine. LC-MS m/e 382(MH$^+$).

Example 48

[6-Methoxy-1-(2-piperidin-1-yl-ethoxy)-isoquinolin-3-yl]-(5-methyl-1H-pyrazol-3-yl)-amine

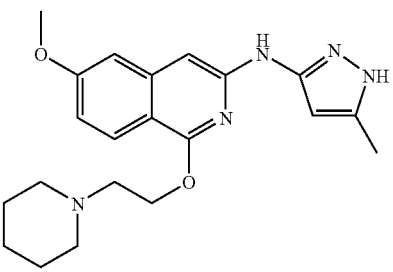

Similar procedure as described in example 10 was used, starting from 2-piperidin-1-yl-ethanol and (1-chloro-6-methoxy-isoquinolin-3-yl)-(5-methyl-1H-pyrazol-3-yl)-amine to give [6-methoxy-1-(2-piperidin-1-yl-ethoxy)-isoquinolin-3-yl]-(5-methyl-1H-pyrazol-3-yl)-amine. LC-MS m/e 382(MH⁺).

Example 49

(1-Methoxy-6-methoxy-isoquinolin-3-yl)-(5-methyl-1H-pyrazol-3-yl)-amine

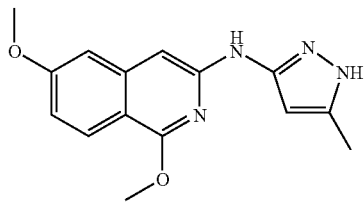

Similar procedure as described in example 10 was used, starting from methanol and (1-chloro-6-methoxy-isoquinolin-3-yl)-(5-methyl-1H-pyrazol-3-yl)-amine to give (1-methoxy-6-methoxy-isoquinolin-3-yl)-(5-methyl-1H-pyrazol-3-yl)-amine. LC-MS m/e 285(MH⁺).

Example 50

(1-Isobutoxy-6-methoxy-isoquinolin-3-yl)-(5-methyl-1H-pyrazol-3-yl)-amine

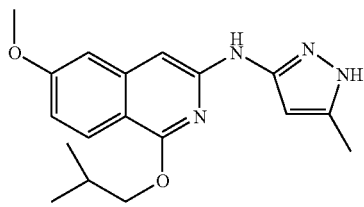

Similar procedure as described in example 10 was used, starting from 3-methyl-butan-1-ol and (1-chloro-6-methoxy-isoquinolin-3-yl)-(5-methyl-1H-pyrazol-3-yl)-amine to give (1-isobutoxy-6-methoxy-isoquinolin-3-yl)-(5-methyl-1H-pyrazol-3-yl)-amine. LC-MS m/e 327(MH⁺).

Example 51

{1-[2-(2-Ethoxy-ethoxy)-ethoxy]-6-methoxy-isoquinolin-3-yl}-(5-methyl-1H-pyrazol-3-yl)-amine

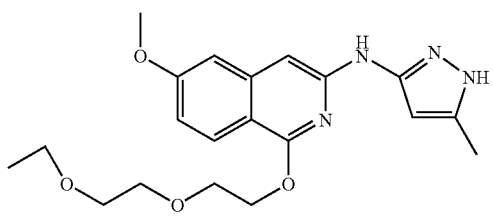

Similar procedure as described in example 10 was used, starting from 2-(2-ethoxy-ethoxy)-ethanol and (1-chloro-6-methoxy-isoquinolin-3-yl)-(5-methyl-1H-pyrazol-3-yl)-amine to give {1-[2-(2-ethoxy-ethoxy)-ethoxy]-6-methoxy-isoquinolin-3-yl}-(5-methyl-1H-pyrazol-3-yl)-amine. LC-MS m/e 387(MH⁺).

Example 52

[1-(4-Methoxy-phenoxy)-isoquinolin-3-yl]-(1H-pyrazol-3-yl)-amine

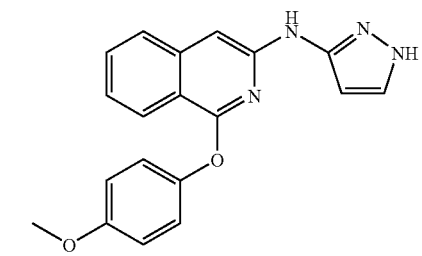

Similar procedure as described in example 10 was used, starting from 4-methoxy-phenol and (1-chloro-isoquinolin-3-yl)-(1H-pyrazol-3-yl)-amine to give [1-(4-methoxy-phenoxy)-isoquinolin-3-yl]-(1H-pyrazol-3-yl)-amine. LC-MS m/e 333(MH⁺).

Example 53

(5-Methyl-1H-pyrazol-3-yl)-[1-(2-morpholin-4-yl-ethoxy)-6-methoxy-isoquinolin-3-yl]-amine

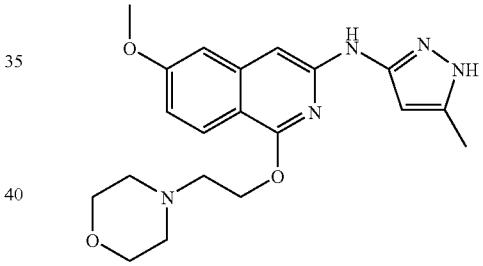

Similar procedure as described in example 10 was used, starting from 2-morpholin-4-yl-ethanol and (1-chloro-6-methoxy-isoquinolin-3-yl)-(5-methyl-1H-pyrazol-3-yl)-amine to give (5-methyl-1H-pyrazol-3-yl)-[1-(2-morpholin-4-yl-ethoxy)-6-methoxy-isoquinolin-3-yl]-amine. LC-MS m/e 384(MH⁺).

Example 54

(1-Isopropoxy-isoquinolin-3-yl)-(1H-pyrazol-3-yl)-amine

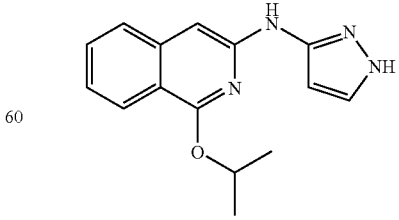

Similar procedure as described in example 10 was used, starting from (1-chloro-isoquinolin-3-yl)-(1H-pyrazol-3-yl)- amine and propan-2-ol to give (1-isopropoxy-isoquinolin-3-yl)-(1H-pyrazol-3-yl)-amine. LC-MS m/e 269(MH⁺).

Example 55

3-[6-Methoxy-3-(1H-pyrazol-3-ylamino)-isoquinolin-1-yloxy]-benzonitrile

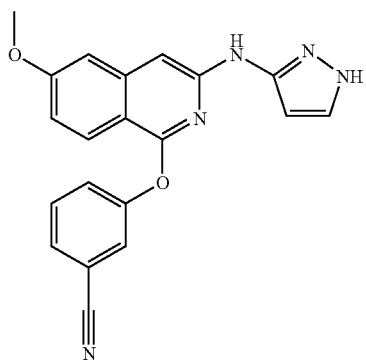

Similar procedure as described in example 10 was used, starting from 3-hydroxy-benzonitrile and (1-chloro-6-methoxy-isoquinolin-3-yl)-(1H-pyrazol-3-yl)-amine to give 3-[6-methoxy-3-(1H-pyrazol-3-ylamino)-isoquinolin-1-yloxy]-benzonitrile. LC-MS m/e 358(MH⁺).

Example 56

(1-Isopropoxy-6-methoxy-isoquinolin-3-yl)-(5-methyl-1H-pyrazol-3-yl)-amine

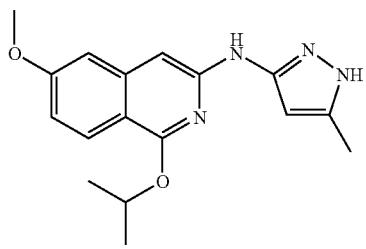

Similar procedure as described in example 10 was used, starting from propan-2-ol and (1-chloro-6-methoxy-isoquinolin-3-yl)-(5-methyl-1H-pyrazol-3-yl)-amine to give (1-isopropoxy-6-methoxy-isoquinolin-3-yl)-(5-methyl-1H-pyrazol-3-yl)-amine. LC-MS m/e 313(MH⁺).

Example 57

(1-Cyclohexyloxy-6-methoxy-isoquinolin-3-yl)-(5-methyl-1H-pyrazol-3-yl)-amine

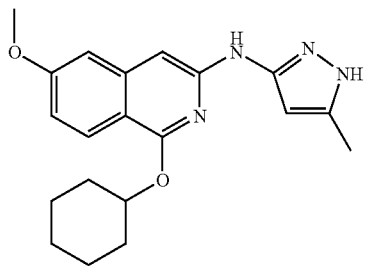

Similar procedure as described in example 10 was used, starting from cyclohexanol and (1-chloro-6-methoxy-isoquinolin-3-yl)-(5-methyl-1H-pyrazol-3-yl)-amine to give (1-cyclohexyloxy-6-methoxy-isoquinolin-3-yl)-(5-methyl-1H-pyrazol-3-yl)-amine. LC-MS m/e 353(MH⁺).

Example 58

N-{4-[6-Methoxy-3-(5-methyl-1H-pyrazol-3-ylamino)-isoquinolin-1-yloxy]-phenyl}-acetamide

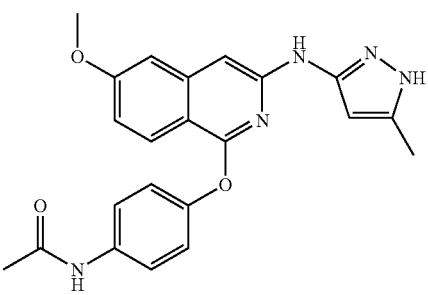

Similar procedure as described in example 10 was used, starting from N-(4-hydroxy-phenyl)-acetamide and (1-chloro-6-methoxy-isoquinolin-3-yl)-(5-methyl-1H-pyrazol-3-yl)-amine to give N-{4-[6-methoxy-3-(5-methyl-1H-pyrazol-3-ylamino)-isoquinolin-1-yloxy]-phenyl}-acetamide. LC-MS m/e 404(MH⁺).

Example 59

N-{4-[-3-(5-Methyl-1H-pyrazol-3-ylamino)-isoquinolin-1-yloxy]-phenyl}-acetamide

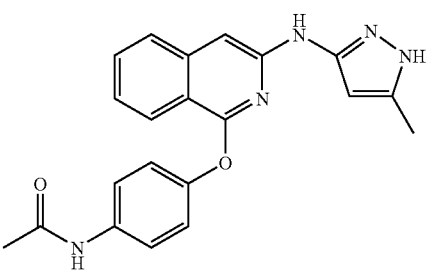

Similar procedure as described in example 10 was used, starting from N-(4-hydroxy-phenyl)-acetamide and (1-chloro-isoquinolin-3-yl)-(5-methyl-1H-pyrazol-3-yl)-amine to give N-{4-[-3-(5-methyl-1H-pyrazol-3-ylamino)-isoquinolin-1-yloxy]-phenyl}-acetamide. LC-MS m/e 374(MH⁺).

Example 60

N-{4-[5-Methoxy-3-(5-methyl-1H-pyrazol-3-ylamino)-isoquinolin-1-yloxy]-phenyl}-acetamide

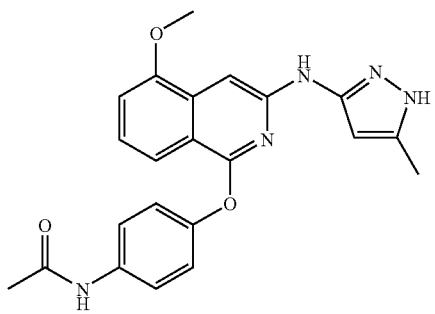

Similar procedure as described in example 10 was used, starting from N-(4-hydroxy-phenyl)-acetamide and (1-chloro-5-methoxy-isoquinolin-3-yl)-(5-methyl-1H-pyrazol-3-yl)-amine to give N-{4-[5-methoxy-3-(5-methyl-1H-pyrazol-3-ylamino)-isoquinolin-1-yloxy]-phenyl}-acetamide. LC-MS m/e 404(MH$^+$).

Example 61

N-{4-[7-Methoxy-3-(5-methyl-1H-pyrazol-3-ylamino)-isoquinolin-1-yloxy]-phenyl}-acetamide

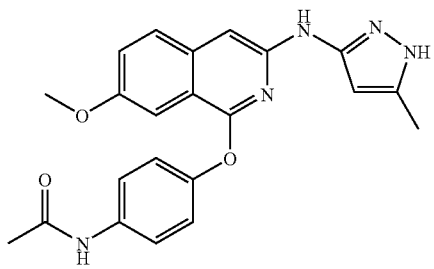

Similar procedure as described in example 10 was used, starting from N-(4-hydroxy-phenyl)-acetamide and (1-chloro-7-methoxy-isoquinolin-3-yl)-(5-methyl-1H-pyrazol-3-yl)-amine to give N-{4-[7-methoxy-3-(5-methyl-1H-pyrazol-3-ylamino)-isoquinolin-1-yloxy]-phenyl}-acetamide. LC-MS m/e 404(MH$^+$).

Example 62

(1-Isopropoxy-5-methoxy-isoquinolin-3-yl)-(5-methyl-1H-pyrazol-3-yl)-amine

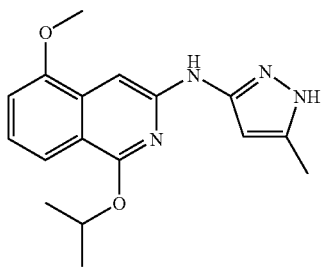

Similar procedure as described in example 10 was used, starting from propan-2-ol and (1-chloro-5-methoxy-isoquinolin-3-yl)-(5-methyl-1H-pyrazol-3-yl)-amine to give (1-isopropoxy-5-methoxy-isoquinolin-3-yl)-(5-methyl-1H-pyrazol-3-yl)-amine. LC-MS m/e 313(MH$^+$).

Example 63

(1-Methoxy-5-methoxy-isoquinolin-3-yl)-(5-methyl-1H-pyrazol-3-yl)-amine

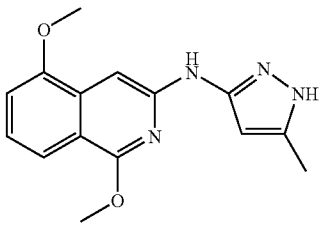

Similar procedure as described in example 10 was used, starting from methanol and (1-chloro-5-methoxy-isoquinolin-3-yl)-(5-methyl-1H-pyrazol-3-yl)-amine to give (1-methoxy-5-methoxy-isoquinolin-3-yl)-(5-methyl-1H-pyrazol-3-yl)-amine. LC-MS m/e 285(MH$^+$).

Example 64

[5-Methoxy-1-(4-methoxy-phenoxy)-isoquinolin-3-yl]-(5-methyl-1H-pyrazol-3-yl)-amine

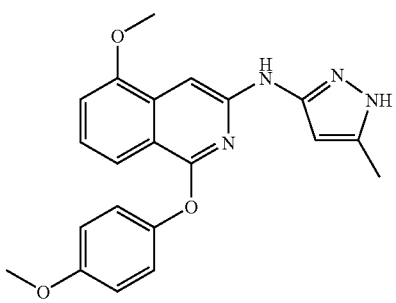

Similar procedure as described in example 10 was used, starting from 4-methoxy-phenol and (1-chloro-5-methoxy-isoquinolin-3-yl)-(5-methyl-1H-pyrazol-3-yl)-amine to give [5-methoxy-1-(4-methoxy-phenoxy)-isoquinolin-3-yl]-(5-methyl-1H-pyrazol-3-yl)-amine. LC-MS m/e 377(MH$^+$).

Example 65

(5-Methoxy-1-phenoxy-isoquinolin-3-yl)-(5-methyl-1H-pyrazol-3-yl)-amine

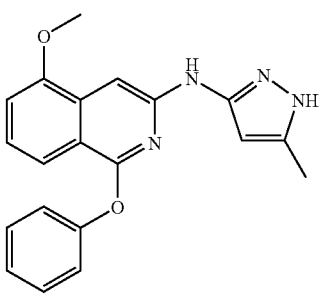

Similar procedure as described in example 10 was used, starting from phenol and (1-chloro-5-methoxy-isoquinolin-3-yl)-(5-methyl-1H-pyrazol-3-yl)-amine to give (5-methoxy-1-phenoxy-isoquinolin-3-yl)-(5-methyl-1H-pyrazol-3-yl)-amine. LC-MS m/e 337(MH⁺).

Example 66

[1-(4-Fluoro-phenoxy)-5-methoxy-isoquinolin-3-yl]-(5-methyl-1H-pyrazol-3-yl)-amine

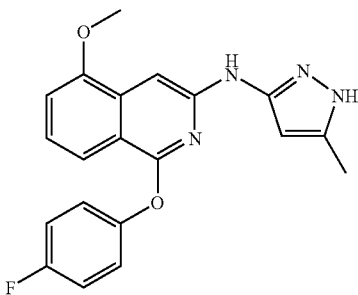

Similar procedure as described in example 10 was used, starting from 4-Fluoro-phenol and (1-chloro-5-methoxy-isoquinolin-3-yl)-(5-methyl-1H-pyrazol-3-yl)-amine to give [1-(4-fluoro-phenoxy)-5-methoxy-isoquinolin-3-yl]-(5-methyl-1H-pyrazol-3-yl)-amine. LC-MS m/e 365(MH⁺).

Example 67

(5-Methyl-1H-pyrazol-3-yl)-(1-p-tolyloxy-5-methoxy-isoquinolin-3-yl)-amine

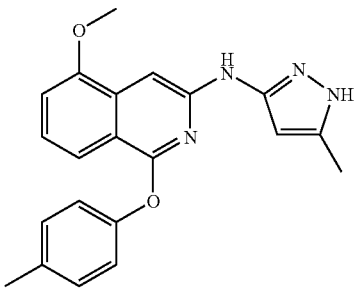

Similar procedure as described in example 10 was used, starting from 4-methyl-phenol and (1-chloro-5-methoxy-isoquinolin-3-yl)-(5-methyl-1H-pyrazol-3-yl)-amine to give (5-methyl-1H-pyrazol-3-yl)-(1-p-tolyloxy-5-methoxy-isoquinolin-3-yl)-amine. LC-MS m/e 361(MH⁺).

Example 68

4-[3-(5-Methyl-1H-pyrazol-3-ylamino)-5-methoxy-isoquinolin-1-yloxy]-benzonitrile

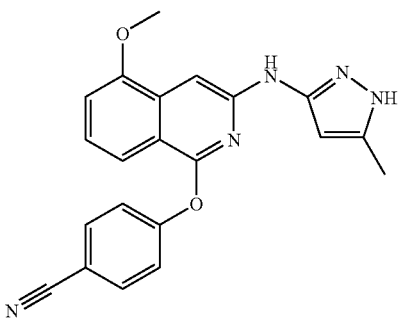

Similar procedure as described in example 10 was used, starting from 4-hydroxy-benzonitrile and (1-chloro-5-methoxy-isoquinolin-3-yl)-(5-methyl-1H-pyrazol-3-yl)-amine to give 4-[3-(5-methyl-1H-pyrazol-3-ylamino)-5-methoxy-isoquinolin-1-yloxy]-benzonitrile. LC-MS m/e 372(MH⁺).

Example 69

[1-(4-Chloro-phenoxy)-5-methoxy-isoquinolin-3-yl]-(5-methyl-1H-pyrazol-3-yl)-amine

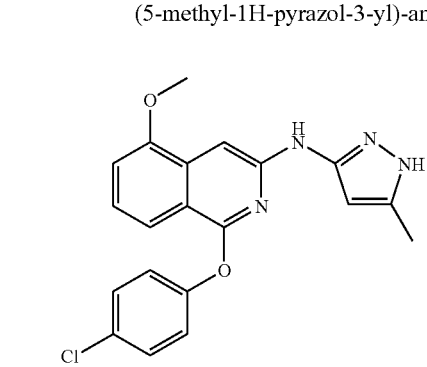

Similar procedure as described in example 10 was used, starting from 4-chloro-phenol and (1-chloro-5-methoxy-isoquinolin-3-yl)-(5-methyl-1H-pyrazol-3-yl)-amine to give [1-(4-Chloro-phenoxy)-5-methoxy-isoquinolin-3-yl]-(5-methyl-1H-pyrazol-3-yl)-amine. LC-MS m/e 382(MH⁺).

Example 70

(1-Isopropoxy-7-methoxy-isoquinolin-3-yl)-(5-methyl-1H-pyrazol-3-yl)-amine

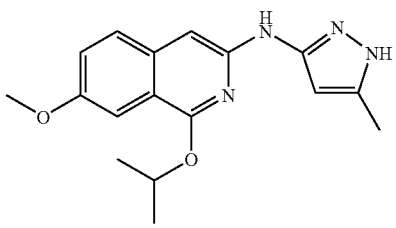

Similar procedure as described in example 10 was used, starting from propan-2-ol and (1-chloro-7-methoxy-isoquinolin-3-yl)-(5-methyl-1H-pyrazol-3-yl)-amine to give (1-isopropoxy-7-methoxy-isoquinolin-3-yl)-(5-methyl-1H-pyrazol-3-yl)-amine. LC-MS m/e 313(MH⁺).

Example 71

(1-Methoxy-7-methoxy-isoquinolin-3-yl)-(5-methyl-1H-pyrazol-3-yl)-amine

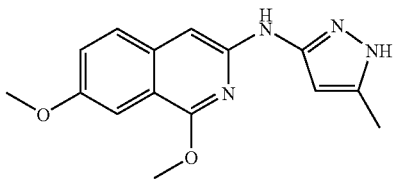

Similar procedure as described in example 10 was used, starting from Methanol, (1-chloro-7-methoxy-isoquinolin-3-yl)-(5-methyl-1H-pyrazol-3-yl)-amine to give (1-Methoxy-7-methoxy-isoquinolin-3-yl)-(5-methyl-1H-pyrazol-3-yl)-amine. LC-MS m/e 285(MH⁺).

Example 72

[7-Methoxy-1-(4methoxy-phenoxy)-isoquinolin-3-yl]-(5-methyl-1H-pyrazol-3-yl)-amine

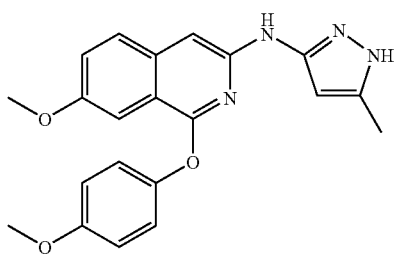

Similar procedure as described in example 10 was used, starting from 4-methoxy-phenol and (1-chloro-7-methoxy-isoquinolin-3-yl)-(5-methyl-1H-pyrazol-3-yl)-amine to give [7-Methoxy-1-(4-methoxy-phenoxy)-isoquinolin-3-yl]-(5-methyl-1H-pyrazol-3-yl)-amine. LC-MS m/e 377(MH+).

Example 73

(7-Methoxy-1-phenoxy-isoquinolin-3-yl)-(5-methyl-1H-pyrazol-3-yl)-amine

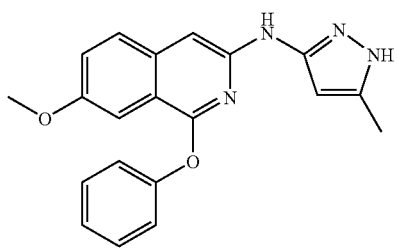

Similar procedure as described in example 10 was used, starting from phenol and (1-chloro-7-methoxy-isoquinolin-3-yl)-(5-methyl-1H-pyrazol-3-yl)-amine to give (7-Methoxy-1-phenoxy-isoquinolin-3-yl)-(5-methyl-1H-pyrazol-3-yl)-amine. LC-MS m/e 337(MH+).

Example 74

[1-(4-Fluoro-phenoxy)-7-methoxy-isoquinolin-3-yl]-(5-methyl-1H-pyrazol-3-yl)-amine

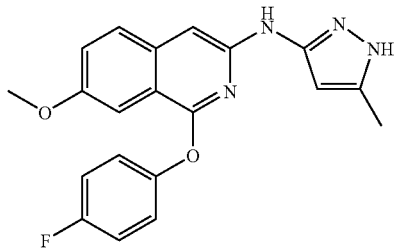

Similar procedure as described in example 10 was used, starting from 4-fluoro-phenol and (1-chloro-7-methoxy-isoquinolin-3-yl)-(5-methyl-1H-pyrazol-3-yl)-amine to give [1-(4-fluoro-phenoxy)-7-methoxy-isoquinolin-3-yl]-(5-methyl-1H-pyrazol-3-yl)-amine. LC-MS m/e 365(MH+).

Example 75

N-{4-[6-Methoxy-3-(1H-pyrazol-3-ylamino)-isoquinolin-1-yloxy]-phenyl}-acetamide

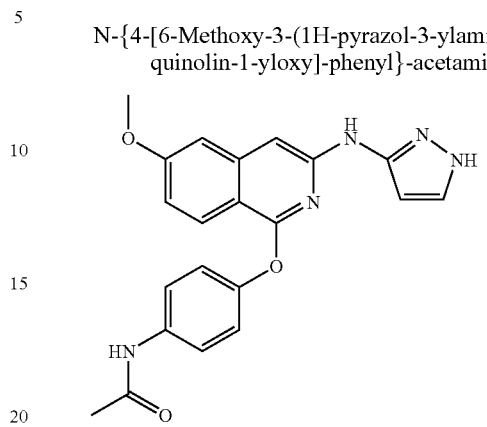

Similar procedure as described in example 10 was used, starting from N-(4-Hydroxy-phenyl)-acetamide and (1-chloro-6-methoxy-isoquinolin-3-yl)-(1H-pyrazol-3-yl)-amine to give N-{4-[6-methoxy-3-(1H-pyrazol-3-ylamino)-isoquinolin-1-yloxy]-phenyl}-acetamide. LC-MS m/e 390(MH+).

Example 76

4-[3-(5-Methyl-1H-pyrazol-3-ylamino)-7-methoxy-isoquinolin-1-yloxy]-benzonitrile

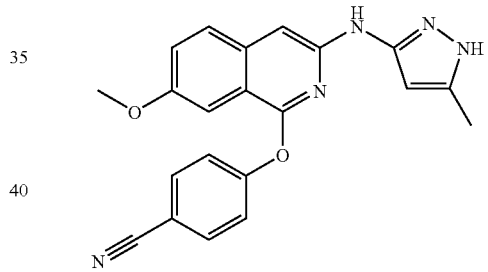

Similar procedure as described in example 10 was used, starting from 4-Hydroxy-benzonitrile and (1-chloro-7-methoxy-isoquinolin-3-yl)-(5-methyl-1H-pyrazol-3-yl)-amine to give 4-[3-(5-methyl-1H-pyrazol-3-ylamino)-7-methoxy-isoquinolin-1-yloxy]-benzonitrile. LC-MS m/e 372(MH+).

Example 77

[1-(4-Chloro-phenoxy)-7-methoxy-isoquinolin-3-yl]-(5-methyl-1H-pyrazol-3-yl)-amine

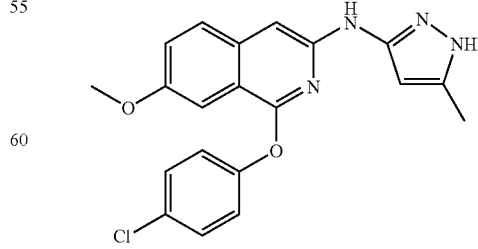

Similar procedure as described in example 10 was used, starting from 4-chloro-phenol and (1-chloro-7-methoxy-isoquinolin-3-yl)-(5-methyl-1H-pyrazol-3-yl)-amine to give [1-(4-chloro-phenoxy)-7-methoxy-isoquinolin-3-yl]-(5-methyl-1H-pyrazol-3-yl)-amine. LC-MS m/e 381(MH⁺).

Example 78

(1-Methoxy-5-methyl-isoquinolin-3-yl)-(5-methyl-1H-pyrazol-3-yl)-amine

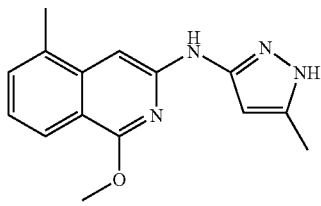

Similar procedure as described in example 10 was used, starting from methanol and (1-chloro-5-methyl-isoquinolin-3-yl)-(5-methyl-1H-pyrazol-3-yl)-amine to give (1-methoxy-5-methyl-isoquinolin-3-yl)-(5-methyl-1H-pyrazol-3-yl)-amine. LC-MS m/e 271(MH⁺).

Example 79

[5-Methyl-1-(4-methoxy-phenoxy)-isoquinolin-3-yl]-(5-methyl-1H-pyrazol-3-yl)-amine

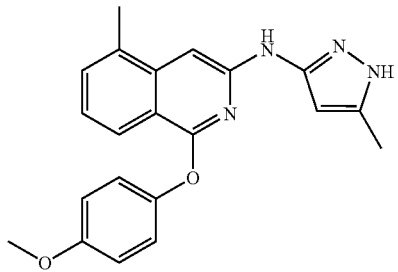

Similar procedure as described in example 10 was used, starting from 4-methoxy-phenol and (1-chloro-5-methyl-isoquinolin-3-yl)-(5-methyl-1H-pyrazol-3-yl)-amine to give [5-methyl-1-(4-methoxy-phenoxy)-isoquinolin-3-yl]-(5-methyl-1H-pyrazol-3-yl)-amine. LC-MS m/e 361(MH⁺).

Example 80

(5-Methyl-1-phenoxy-isoquinolin-3-yl)-(5-methyl-1H-pyrazol-3-yl)-amine

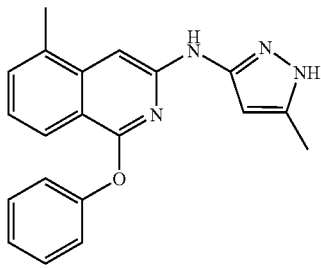

Similar procedure as described in example 10 was used, starting from phenol and (1-chloro-5-methyl-isoquinolin-3-yl)-(5-methyl-1H-pyrazol-3-yl)-amine to give (5-methyl-1-phenoxy-isoquinolin-3-yl)-(5-methyl-1H-pyrazol-3-yl)-amine. LC-MS m/e 321(MH⁺).

Example 81

[1-(4-Fluoro-phenoxy)-5-methyl-isoquinolin-3-yl]-(5-methyl-1H-pyrazol-3-yl)-amine

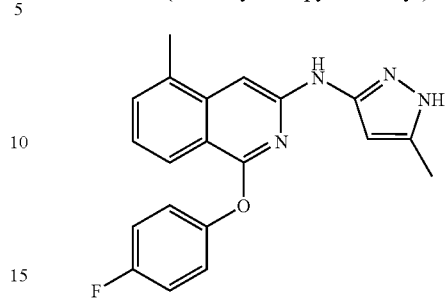

Similar procedure as described in example 10 was used, starting from 4-fluoro-phenol and (1-chloro-5-methyl-isoquinolin-3-yl)-(5-methyl-1H-pyrazol-3-yl)-amine to give [1-(4-fluoro-phenoxy)-5-methyl-isoquinolin-3-yl]-(5-methyl-1H-pyrazol-3-yl)-amine. LC-MS m/e 349(MH⁺).

Example 82

(5-Methyl-1H-pyrazol-3-yl)-(1-p-tolyloxy-5-methyl-isoquinolin-3-yl)-amine

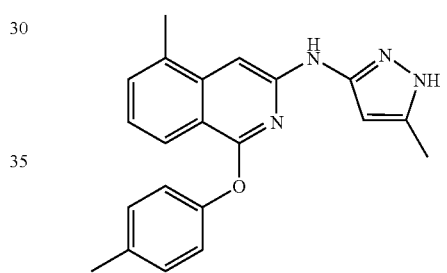

Similar procedure as described in example 10 was used, starting from 4-methyl-phenol and (1-chloro-5-methyl-isoquinolin-3-yl)-(5-methyl-1H-pyrazol-3-yl)-amine to give (5-methyl-1H-pyrazol-3-yl)-(1-p-tolyloxy-5-methyl-isoquinolin-3-yl)-amine. LC-MS m/e 345(MH⁺).

Example 83

[1-(4-Chloro-phenoxy)-5-methyl-isoquinolin-3-yl]-(5-methyl-1H-pyrazol-3-yl)-amine

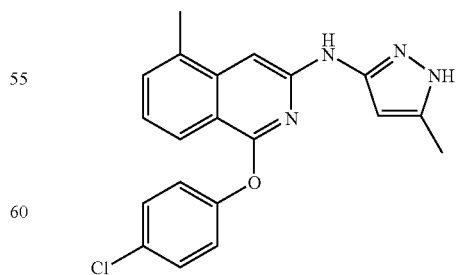

Similar procedure as described in example 10 was used, starting from 4-chloro-phenol and (1-chloro-5-methyl-isoquinolin-3-yl)-(5-methyl-1H-pyrazol-3-yl)-amine to give [1-

(4-chloro-phenoxy)-5-methyl-isoquinolin-3-yl]-(5-methyl-1H-pyrazol-3-yl)-amine. LC-MS m/e 366(MH+).

Example 84

(1-Isopropoxy-6,7-dimethoxy-isoquinolin-3-yl)-(5-methyl-1H-pyrazol-3-yl)-amine

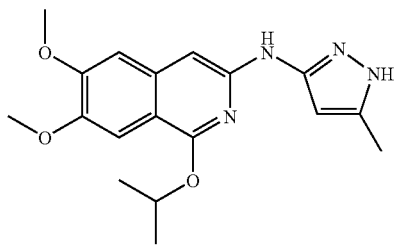

Similar procedure as described in example 10 was used, starting from propan-2-ol and (1-chloro-6,7-dimethoxy-isoquinolin-3-yl)-(5-methyl-1H-pyrazol-3-yl)-amine to give (1-isopropoxy-6,7-dimethoxy-isoquinolin-3-yl)-(5-methyl-1H-pyrazol-3-yl)-amine. LC-MS m/e 343(MH+).

Example 85

(1-Methoxy-6,7-dimethoxy-isoquinolin-3-yl)-(5-methyl-1H-pyrazol-3-yl)-amine

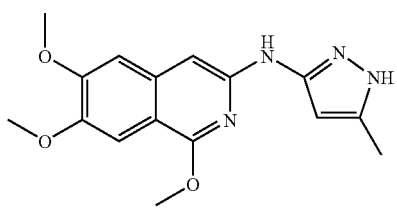

Similar procedure as described in example 10 was used, starting from methanol and (1-chloro-6,7-dimethoxy-isoquinolin-3-yl)-(5-methyl-1H-pyrazol-3-yl)-amine to give (1-methoxy-6,7-dimethoxy-isoquinolin-3-yl)-(5-methyl-1H-pyrazol-3-yl)-amine. LC-MS m/e 315(MH+).

Example 86

(6,7-Dimethoxy-1-phenoxy-isoquinolin-3-yl)-(5-methyl-1H-pyrazol-3-yl)-amine

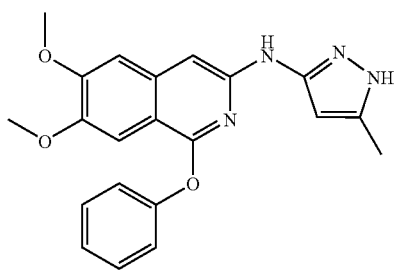

Similar procedure as described in example 10 was used, starting from phenol and (1-chloro-6,7-dimethoxy-isoquinolin-3-yl)-(5-methyl-1H-pyrazol-3-yl)-amine to give (6,7-dimethoxy-1-phenoxy-isoquinolin-3-yl)-(5-methyl-1H-pyrazol-3-yl)-amine. LC-MS m/e 367(MH+).

Example 87

[1-(4-Fluoro-phenoxy)-6,7-dimethoxy-isoquinolin-3-yl]-(5-methyl-1H-pyrazol-3-yl)-amine

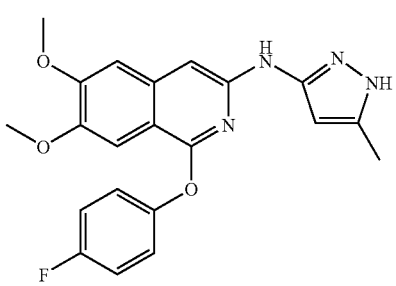

Similar procedure as described in example 10 was used, starting from 4-fluoro-phenol and (1-chloro-6,7-dimethoxy-isoquinolin-3-yl)-(5-methyl-1H-pyrazol-3-yl)-amine to give [1-(4-fluoro-phenoxy)-6,7-dimethoxy-isoquinolin-3-yl]-(5-methyl-1H-pyrazol-3-yl)-amine. LC-MS m/e 395(MH+).

Example 88

N-{4-[3-(1H-Pyrazol-3-ylamino)-isoquinolin-1-yloxy]-phenyl}-acetamide

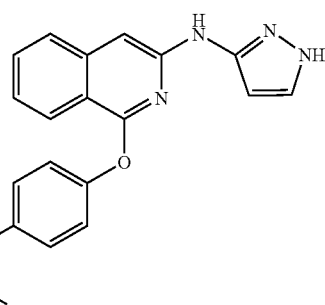

Similar procedure as described in example 10 was used, starting from N-(4-hydroxy-phenyl)-acetamide and (1-chloro-isoquinolin-3-yl)-(1H-pyrazol-3-yl)-amine to give N-{4-[3-(1H-pyrazol-3-ylamino)-isoquinolin-1-yloxy]-phenyl}-acetamide. LC-MS m/e 360(MH+).

Example 89

(1-Ethoxy-6,7-dimethoxy-isoquinolin-3-yl)-(5-methyl-1H-pyrazol-3-yl)-amine

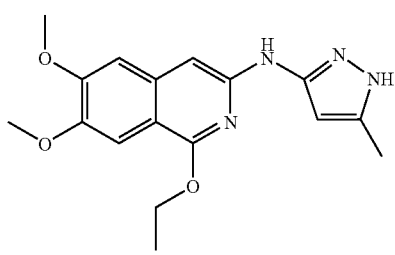

Similar procedure as described in example 10 was used, starting from ethanol and (1-chloro-5,6-dimethoxy-isoquinolin-3-yl)-(5-methyl-1H-pyrazol-3-yl)-amine to give (1-ethoxy-6,7-dimethoxy-isoquinolin-3-yl)-(5-methyl-1H-pyrazol-3-yl)-amine. LC-MS m/e 329(MH$^+$).

Example 90

N-{4-[6,7-Dimethoxy-3-(5-methyl-1H-pyrazol-3-ylamino)-isoquinolin-1-yloxy]-phenyl}-acetamide

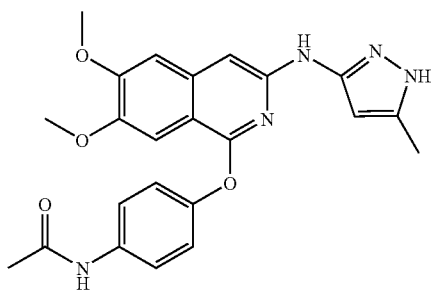

Similar procedure as described in example 10 was used, starting from N-(4-hydroxy-phenyl)-acetamide and (1-chloro-6,7-dimethoxy-isoquinolin-3-yl)-(5-methyl-1H-pyrazol-3-yl)-amine to give N-{4-[6,7-dimethoxy-3-(5-methyl-1H-pyrazol-3-ylamino)-isoquinolin-1-yloxy]-phenyl}-acetamide. LC-MS m/e 434(MH$^+$).

Example 91

(1-Isopropoxy-5,6-dimethoxy-isoquinolin-3-yl)-(5-methyl-1H-pyrazol-3-yl)-amine

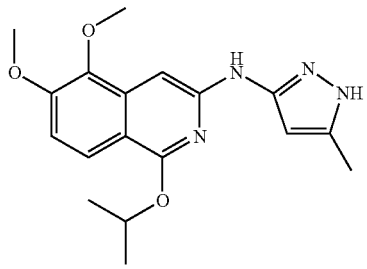

Similar procedure as described in example 10 was used, starting from propan-2-ol and (1-chloro-5,6-dimethoxy-isoquinolin-3-yl)-(5-methyl-1H-pyrazol-3-yl)-amine to give (1-isopropoxy-5,6-dimethoxy-isoquinolin-3-yl)-(5-methyl-1H-pyrazol-3-yl)-amine. LC-MS m/e 343(MH$^+$).

Example 92

(1-Methoxy-5,6-dimethoxy-isoquinolin-3-yl)-(5-methyl-1H-pyrazol-3-yl)-amine

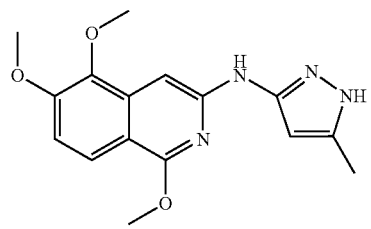

Similar procedure as described in example 10 was used, starting from methanol and (1-chloro-5,6-dimethoxy-isoquinolin-3-yl)-(5-methyl-1H-pyrazol-3-yl)-amine to give (1-methoxy-5,6-dimethoxy-isoquinolin-3-yl)-(5-methyl-1H-pyrazol-3-yl)-amine. LC-MS m/e 315(MH$^+$).

Example 93

(5,6-Dimethoxy-1-phenoxy-isoquinolin-3-yl)-(5-methyl-1H-pyrazol-3-yl)-amine

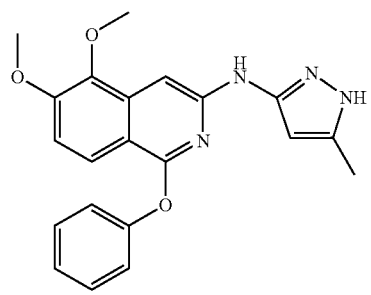

Similar procedure as described in example 10 was used, starting from phenol and (1-chloro-5,6-dimethoxy-isoquinolin-3-yl)-(5-methyl-1H-pyrazol-3-yl)-amine to give (5,6-dimethoxy-1-phenoxy-isoquinolin-3-yl)-(5-methyl-1H-pyrazol-3-yl)-amine. LC-MS m/e 367(MH$^+$).

Example 94

[1-(4-Fluoro-phenoxy)-5,6-dimethoxy-isoquinolin-3-yl]-(5-methyl-1H-pyrazol-3-yl)-amine

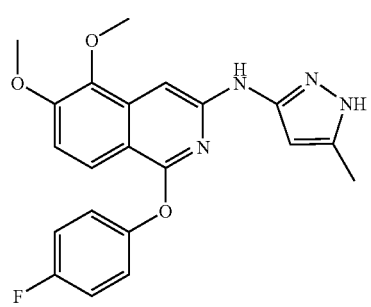

Similar procedure as described in example 10 was used, starting from 4-fluoro-phenol and (1-chloro-5,6-dimethoxy-isoquinolin-3-yl)-(5-methyl-1H-pyrazol-3-yl)-amine to give

[1-(4-fluoro-phenoxy)-5,6-dimethoxy-isoquinolin-3-yl]-(5-methyl-1H-pyrazol-3-yl)-amine. LC-MS m/e 395(MH+).

Example 95

4-[3-(5-Methyl-1H-pyrazol-3-ylamino)-5,6-methoxy-isoquinolin-1-yloxy]-benzonitrile

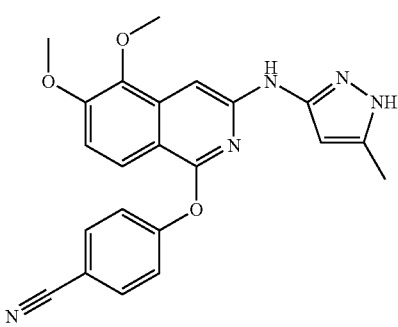

Similar procedure as described in example 10 was used, starting from 4-hydroxy-benzonitrile and (1-chloro-5,6-dimethoxy-isoquinolin-3-yl)-(5-methyl-1H-pyrazol-3-yl)-amine to give 4-[3-(5-methyl-1H-pyrazol-3-ylamino)-5,6-dimethoxy-isoquinolin-1-yloxy]-benzonitrile. LC-MS m/e 402(MH+).

Example 96

[1-(4-Chloro-phenoxy)-5,6-dimethoxy-isoquinolin-3-yl]-(5-methyl-1H-pyrazol-3-yl)-amine

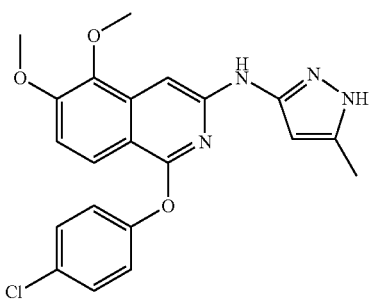

Similar procedure as described in example 10 was used, starting from 4-chloro-phenol and (1-Chloro-5,6-dimethoxy-isoquinolin-3-yl)-(5-methyl-1H-pyrazol-3-yl)-amine to give [1-(4-chloro-phenoxy)-5,6-dimethoxy-isoquinolin-3-yl]-(5-methyl-1H-pyrazol-3-yl)-amine. LC-MS m/e 411 (MH+).

Example 97

N-{4-[5,6-Dimethoxy-3-(5-methyl-1H-pyrazol-3-ylamino)-isoquinolin-1-yloxy]-phenyl}-acetamide

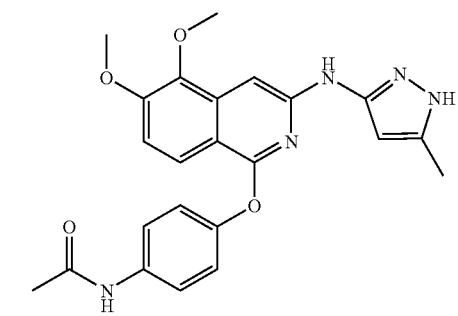

Similar procedure as described in example 10 was used, starting from N-(4-hydroxy-phenyl)-acetamide and (1-chloro-5,6-dimethoxy-isoquinolin-3-yl)-(5-methyl-1H-pyrazol-3-yl)-amine to give N-{4-[5,6-dimethoxy-3-(5-methyl-1H-pyrazol-3-ylamino)-isoquinolin-1-yloxy]-phenyl}-acetamide. LC-MS m/e 434(MH+).

Example 98

(1-Methoxy-isoquinolin-3-yl)-(1H-pyrazol-3-yl)-amine

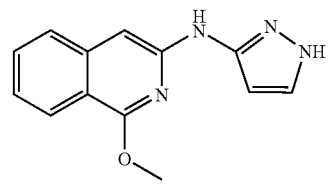

Similar procedure as described in example 10 was used, starting from (1-chloro-isoquinolin-3-yl)-(1H-pyrazol-3-yl)-amine and methanol to give (1-methoxy-isoquinolin-3-yl)-(1H-pyrazol-3-yl)-amine. LC-MS m/e 241(MH+).

Example 99

(1-Isobutoxy-isoquinolin-3-yl)-(1H-pyrazol-3-yl)-amine

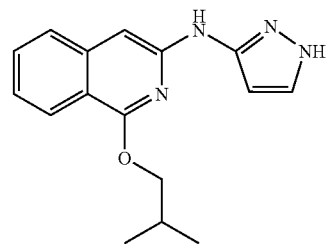

Similar procedure as described in example 10 was used, starting from (1-chloro-isoquinolin-3-yl)-(1H-pyrazol-3-yl)- amine and 2-methyl-propan-1-ol to give (1-isobutoxy-isoquinolin-3-yl)-(1H-pyrazol-3-yl)-amine. LC-MS m/e 283(MH+).

Example 100

(1H-Pyrazol-3-yl)-(1-m-tolyloxy-isoquinolin-3-yl)-amine

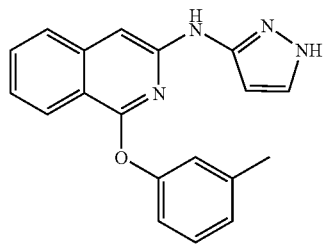

Similar procedure as described in example 10 was used, starting from (1-chloro-isoquinolin-3-yl)-(1H-pyrazol-3-yl)-amine and 3-methyl-phenol to give (1H-pyrazol-3-yl)-(1-m-tolyloxy-isoquinolin-3-yl)-amine. LC-MS m/e 317(MH+).

Example 101

(1H-Pyrazol-3-yl)-(1-p-tolyloxy-isoquinolin-3-yl)-amine

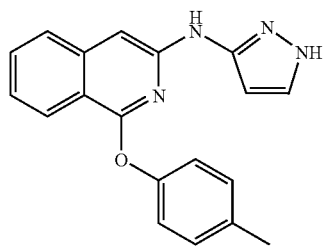

Similar procedure as described in example 10 was used, starting from (1-chloro-isoquinolin-3-yl)-(1H-pyrazol-3-yl)-amine and 4-methyl-phenol to give (1H-pyrazol-3-yl)-(1-p-tolyloxy-isoquinolin-3-yl)-amine. LC-MS m/e 317(MH+).

Example 102

(1H-Pyrazol-3-yl)-(1-o-tolyloxy-isoquinolin-3-yl)-amine

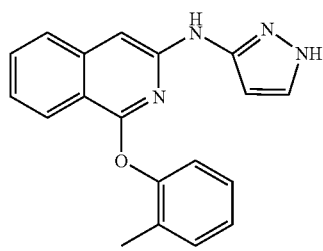

Similar procedure as described in example 10 was used, starting from (1-chloro-isoquinolin-3-yl)-(1H-pyrazol-3-yl)-amine and 2-methyl-phenol to give (1H-pyrazol-3-yl)-(1-o-tolyloxy-isoquinolin-3-yl)-amine. LC-MS m/e 317(MH+).

Example 103

[1-(3-Methoxy-phenoxy)-isoquinolin-3-yl]-(1H-pyrazol-3-yl)-amine

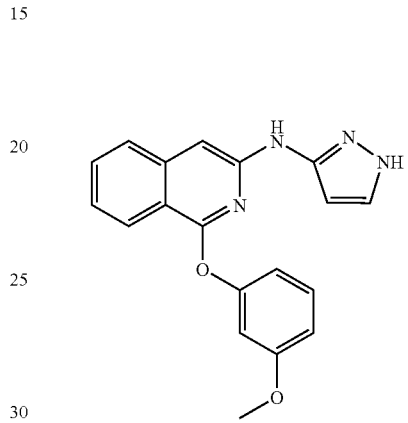

Similar procedure as described in example 10 was used, starting from (1-chloro-isoquinolin-3-yl)-(1H-pyrazol-3-yl)-amine and 3-methoxy-phenol to give [1-(3-methoxy-phenoxy)-isoquinolin-3-yl]-(1H-pyrazol-3-yl)-amine. LC-MS m/e 333(MH+).

Example 104

[1-(2-Methoxy-phenoxy)-isoquinolin-3-yl]-(1H-pyrazol-3-yl)-amine

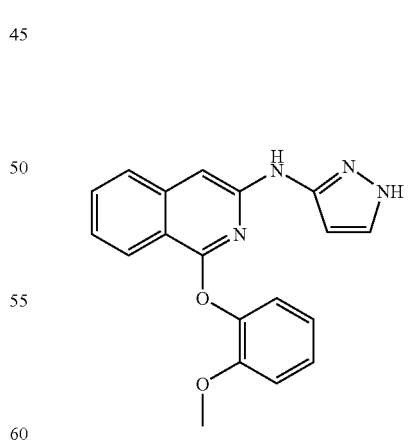

Similar procedure as described in example 10 was used, starting from (1-chloro-isoquinolin-3-yl)-(1H-pyrazol-3-yl)-amine and 2-methoxy-phenol to give [1-(2-methoxy-phenoxy)-isoquinolin-3-yl]-(1H-pyrazol-3-yl)-amine. LC-MS m/e 333(MH+).

Example 105

[1-(2-Fluoro-phenoxy)-isoquinolin-3-yl]-(1H-pyrazol-3-yl)-amine

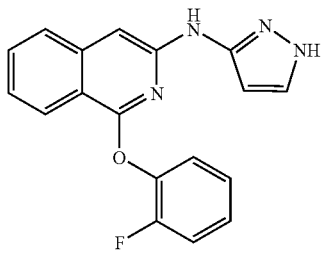

Similar procedure as described in example 10 was used, starting from (1-chloro-isoquinolin-3-yl)-(1H-pyrazol-3-yl)-amine and 2-fluoro-phenol to give [1-(2-fluoro-phenoxy)-isoquinolin-3-yl]-(1H-pyrazol-3-yl)-amine. LC-MS m/e 321 (MH$^+$).

Example 106

[1-(3-Fluoro-phenoxy)-isoquinolin-3-yl]-(1H-pyrazol-3-yl)-amine

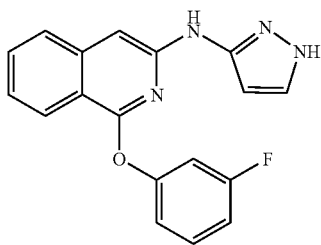

Similar procedure as described in example 10 was used, starting from (1-chloro-isoquinolin-3-yl)-(1H-pyrazol-3-yl)-amine and 3-fluoro-phenol to give [1-(3-fluoro-phenoxy)-isoquinolin-3-yl]-(1H-pyrazol-3-yl)-amine. LC-MS m/e 321 (MH$^+$).

Example 107

3-[3-(1H-Pyrazol-3-ylamino)-isoquinolin-1-yloxy]-benzonitrile

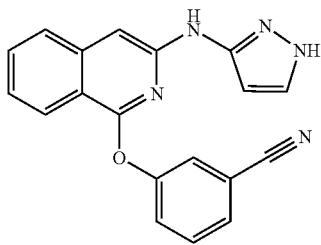

Similar procedure as described in example 10 was used, starting from (1-chloro-isoquinolin-3-yl)-(1H-pyrazol-3-yl)-amine and 3-cyano-phenol to give 3-[3-(1H-pyrazol-3-ylamino)-isoquinolin-1-yloxy]-benzonitrile. LC-MS m/e 328(MH$^+$).

Example 108

4-[3-(1H-Pyrazol-3-ylamino)-isoquinolin-1-yloxy]-benzonitrile

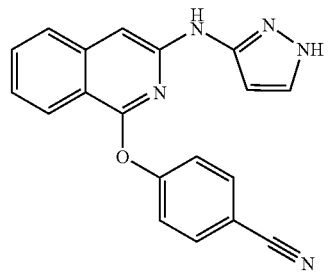

Similar procedure as described in example 10 was used, starting from (1-chloro-isoquinolin-3-yl)-(1H-pyrazol-3-yl)-amine and 4-cyano-phenol to give 4-[3-(1H-pyrazol-3-ylamino)-isoquinolin-1-yloxy]-benzonitrile. LC-MS m/e 328(MH$^+$).

Example 109

(1-Benzyloxy-isoquinolin-3-yl)-(1H-pyrazol-3-yl)-amine

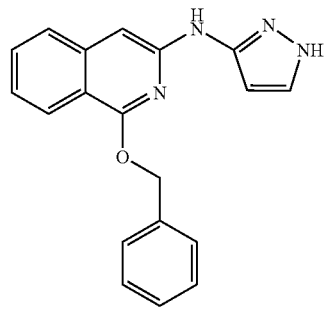

Similar procedure as described in example 10 was used, starting from (1-chloro-isoquinolin-3-yl)-(1H-pyrazol-3-yl)-amine and phenyl methanol to give (1-benzyloxy-isoquinolin-3-yl)-(1H-pyrazol-3-yl)-amine. LC-MS m/e 317(MH$^+$).

Example 110

{1-[2-(2-Ethoxy-ethoxy)-ethoxy]-isoquinolin-3-yl}-(1H-pyrazol-3-yl)-amine

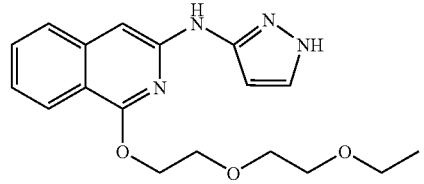

Similar procedure as described in example 10 was used, starting from (1-chloro-isoquinolin-3-yl)-(1H-pyrazol-3-yl)-amine and 2-(2-ethoxy-ethoxy)-ethanol to give {1-[2-(2-ethoxy-ethoxy)-ethoxy]-isoquinolin-3-yl}-(1H-pyrazol-3-yl)-amine. LC-MS m/e 343(MH$^+$).

Example 111

[1-(4-Chloro-phenoxy)-isoquinolin-3-yl]-(1H-pyrazol-3-yl)-amine

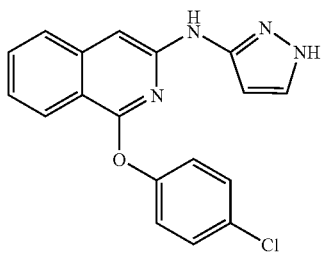

Similar procedure as described in example 10 was used, starting from (1-chloro-isoquinolin-3-yl)-(1H-pyrazol-3-yl)-amine and 4-chloro-phenol to give [1-(4-chloro-phenoxy)-isoquinolin-3-yl]-(1H-pyrazol-3-yl)-amine. LC-MS m/e 337 (MH+).

Example 112

[1-(4-Chloro-phenoxy)-isoquinolin-3-yl]-(1H-pyrazol-3-yl)-amine

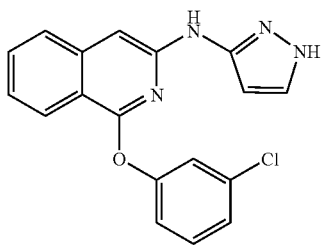

Similar procedure as described in example 10 was used, starting from (1-chloro-isoquinolin-3-yl)-(1H-pyrazol-3-yl)-amine and 3-chloro-phenol to give [1-(3-chloro-phenoxy)-isoquinolin-3-yl]-(1H-pyrazol-3-yl)-amine. LC-MS m/e 337 (MH+).

Example 113

[1-(2-Chloro-phenoxy)-isoquinolin-3-yl]-(1H-pyrazol-3-yl)-amine

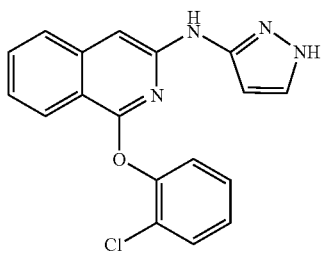

Similar procedure as described in example 10 was used, starting from (1-chloro-isoquinolin-3-yl)-(1H-pyrazol-3-yl)-amine and 2-chloro-phenol to give [1-(2-chloro-phenoxy)-isoquinolin-3-yl]-(1H-pyrazol-3-yl)-amine. LC-MS m/e 337 (MH+).

Example 114

(1-Phenoxy-isoquinolin-3-yl)-(1H-pyrazol-3-yl)-amine

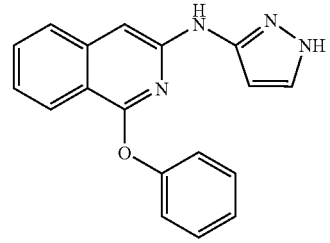

Similar procedure as described in example 10 was used, starting from (1-chloro-isoquinolin-3-yl)-(1H-pyrazol-3-yl)-amine and phenol to give (1-phenoxy-isoquinolin-3-yl)-(1H-pyrazol-3-yl)-amine. LC-MS m/e 303(MH+).

Example 115

[1-(4-Fluoro-phenoxy)-isoquinolin-3-yl]-(1H-pyrazol-3-yl)-amine

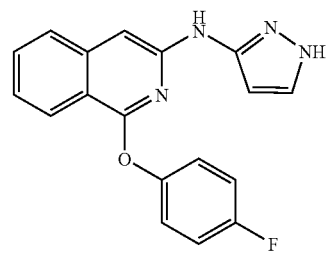

Similar procedure as described in example 10 was used, starting from (1-chloro-isoquinolin-3-yl)-(1H-pyrazol-3-yl)-amine and 4-fluoro-phenol to give [1-(4-fluoro-phenoxy)-isoquinolin-3-yl]-(1H-pyrazol-3-yl)-amine. LC-MS m/e 321 (MH+).

Example 116

(1-Isobutoxy-6-methoxy-isoquinolin-3-yl)-(1H-pyrazol-3-yl)-amine

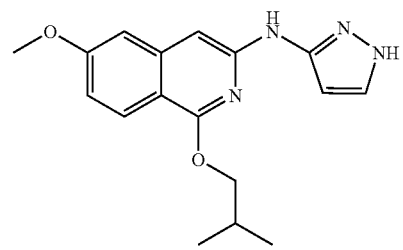

Similar procedure as described in example 10 was used, starting from (1-chloro-6-methoxy-isoquinolin-3-yl)-(1H-pyrazol-3-yl)-amine and 2-methyl-propan-1-ol to give (1-isobutoxy-6-methoxy-isoquinolin-3-yl)-(1H-pyrazol-3-yl)-amine. LC-MS m/e 313 (MH+).

Example 117

(1-Cyclopentyloxy-6,7-dimethoxy-isoquinolin-3-yl)-(5-methyl-1H-pyrazol-3-yl)-amine

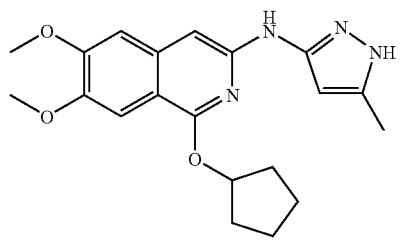

Similar procedure as described in example 10 was used, starting from (1-chloro-6,7-dimethoxy-isoquinolin-3-yl)-(5-methyl-1H-pyrazol-3-yl)-amine and cyclopentanol to give (1-Cyclopentyloxy-6,7-dimethoxy-isoquinolin-3-yl)-(5-methyl-1H-pyrazol-3-yl)-amine. LC-MS m/e 369(MH+).

Example 118

(6-Methoxy-1-phenoxy-isoquinolin-3-yl)-(1H-pyrazol-3-yl)-amine

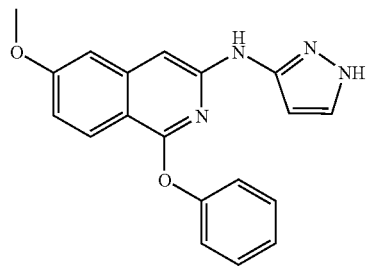

Similar procedure as described in example 10 was used, starting from (1-chloro-6-methoxy-isoquinolin-3-yl)-(1H-pyrazol-3-yl)-amine and phenol to give (6-methoxy-1-phenoxy-isoquinolin-3-yl)-(1H-pyrazol-3-yl)-amine. LC-MS m/e 333(MH+).

Example 119

(1-Benzyloxy-6-methoxy-isoquinolin-3-yl)-(1H-pyrazol-3-yl)-amine

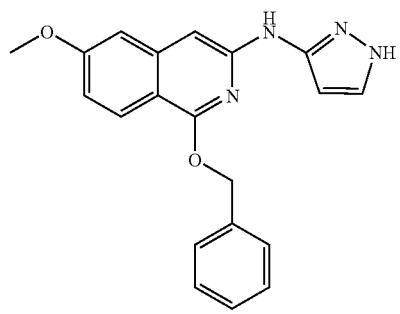

Similar procedure as described in example 10 was used, starting from (1-chloro-6-methoxy-isoquinolin-3-yl)-(1H-pyrazol-3-yl)-amine and phenyl-methanol to give (1-benzyloxy-6-methoxy-isoquinolin-3-yl)-(1H-pyrazol-3-yl)-amine. LC-MS m/e 347(MH+).

Example 120

[1-(4-Fluoro-phenoxy)-6-methoxy-isoquinolin-3-yl]-(1H-pyrazol-3-yl)-amine

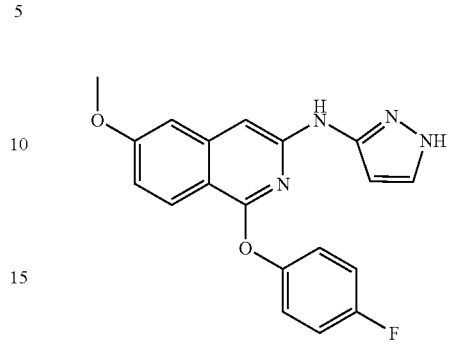

Similar procedure as described in example 10 was used, starting from (1-chloro-6-methoxy-isoquinolin-3-yl)-(1H-pyrazol-3-yl)-amine and 4-fluoro-phenol to give [1-(4-fluoro-phenoxy)-6-methoxy-isoquinolin-3-yl]-(1H-pyrazol-3-yl)-amine. LC-MS m/e 351(MH+).

Example 121

[1-(3-Fluoro-phenoxy)-6-methoxy-isoquinolin-3-yl]-(1H-pyrazol-3-yl)-amine

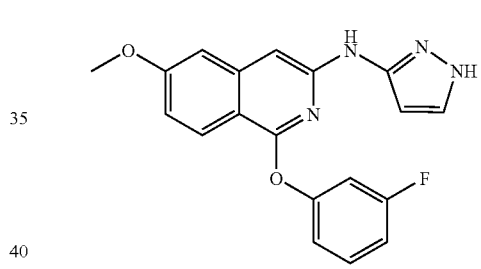

Similar procedure as described in example 10 was used, starting from (1-chloro-6-methoxy-isoquinolin-3-yl)-(1H-pyrazol-3-yl)-amine and 3-fluoro-phenol to give [1-(3-fluoro-phenoxy)-6-methoxy-isoquinolin-3-yl]-(1H-pyrazol-3-yl)-amine. LC-MS m/e 351(MH+).

Example 122

[1-(2-Fluoro-phenoxy)-6-methoxy-isoquinolin-3-yl]-(1H-pyrazol-3-yl)-amine

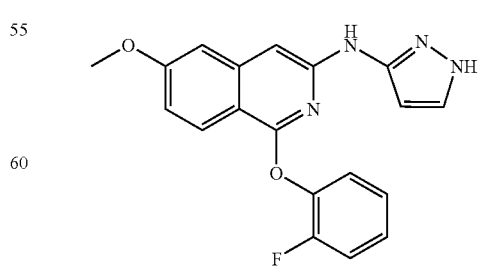

Similar procedure as described in example 10 was used, starting from (1-chloro-6-methoxy-isoquinolin-3-yl)-(1H- pyrazol-3-yl)-amine and 2-fluoro-phenol to give [1-(2-fluoro-phenoxy)-6-methoxy-isoquinolin-3-yl]-(1H-pyrazol-3-yl)-amine. LC-MS m/e 351(MH+).

Example 123

(6-Methoxy-1-p-tolyloxy-isoquinolin-3-yl)-(1H-pyrazol-3-yl)-amine

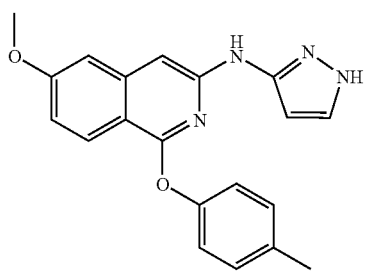

Similar procedure as described in example 10 was used, starting from (1-chloro-6-methoxy-isoquinolin-3-yl)-(1H-pyrazol-3-yl)-amine and 4-methyl-phenol to give (6-methoxy-1-p-tolyloxy-isoquinolin-3-yl)-(1H-pyrazol-3-yl)-amine. LC-MS m/e 347(MH+).

Example 124

(6-Methoxy-1-m-tolyloxy-isoquinolin-3-yl)-(1H-pyrazol-3-yl)-amine

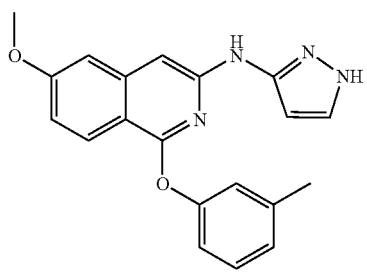

Similar procedure as described in example 10 was used, starting from (1-chloro-6-methoxy-isoquinolin-3-yl)-(1H-pyrazol-3-yl)-amine and 3-methyl-phenol to give (6-methoxy-1-m-tolyloxy-isoquinolin-3-yl)-(1H-pyrazol-3-yl)-amine. LC-MS m/e 347(MH+).

Example 125

(1-Cyclobutoxy-6,7-dimethoxy-isoquinolin-3-yl)-(5-methyl-1H-pyrazol-3-yl)-amine

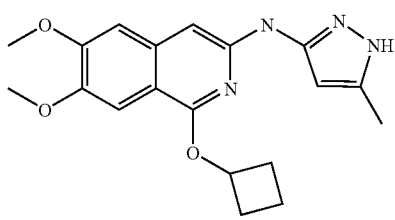

Similar procedure as described in example 10 was used, starting from (1-chloro-6,7-dimethoxy-isoquinolin-3-yl)-(5-methyl-1H-pyrazol-3-yl)-amine and cyclobutanol to give (1-cyclobutoxy-6,7-dimethoxy-isoquinolin-3-yl)-(5-methyl-1H-pyrazol-3-yl)-amine. LC-MS m/e 355(MH+).

Example 126

[6-Methoxy-1-(4-methoxy-phenoxy)-isoquinolin-3-yl]-(1H-pyrazol-3-yl)-amine

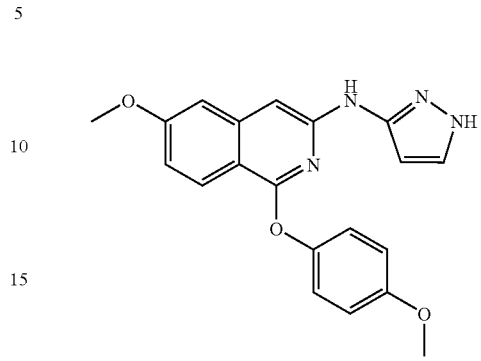

Similar procedure as described in example 10 was used, starting from (1-chloro-6-methoxy-isoquinolin-3-yl)-(1H-pyrazol-3-yl)-amine and 2-methoxy-phenol to give [6-methoxy-1-(4-methoxy-phenoxy)-isoquinolin-3-yl]-(1H-pyrazol-3-yl)-amine. LC-MS m/e 363(MH+).

Example 127

[6-Methoxy-1-(3-methoxy-phenoxy)-isoquinolin-3-yl]-(1H-pyrazol-3-yl)-amine

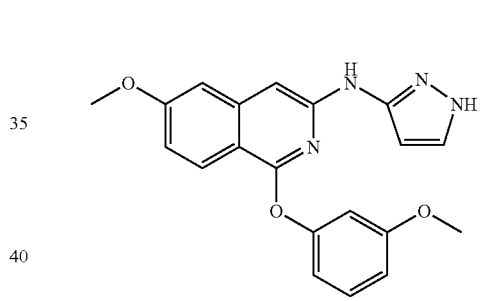

Similar procedure as described in example 10 was used, starting from (1-chloro-6-methoxy-isoquinolin-3-yl)-(1H-pyrazol-3-yl)-amine and 3-methoxy-phenol to give [6-methoxy-1-(3-methoxy-phenoxy)-isoquinolin-3-yl]-(1H-pyrazol-3-yl)-amine. LC-MS m/e 363(MH+).

Example 128

[1-(4-Chloro-phenoxy)-6-methoxy-isoquinolin-3-yl]-(1H-pyrazol-3-yl)-amine

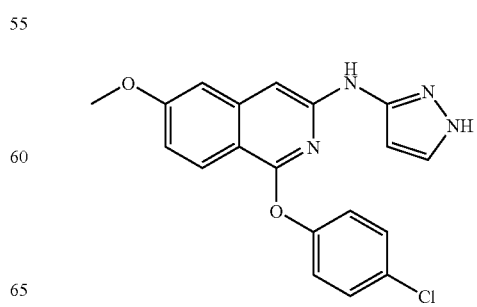

Similar procedure as described in example 10 was used, starting from (1-chloro-6-methoxy-isoquinolin-3-yl)-(1H-pyrazol-3-yl)-amine and 4-chloro-phenol to give [1-(4-chloro-phenoxy)-6-methoxy-isoquinolin-3-yl]-(1H-pyrazol-3-yl)-amine. LC-MS m/e 367(MH+).

Example 129

[1-(3-Chloro-phenoxy)-6-methoxy-isoquinolin-3-yl]-(1H-pyrazol-3-yl)-amine

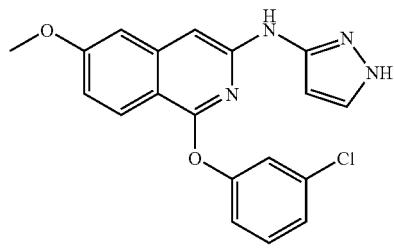

Similar procedure as described in example 10 was used, starting from (1-chloro-6-methoxy-isoquinolin-3-yl)-(1H-pyrazol-3-yl)-amine and 3-chloro-phenol to give [1-(3-chloro-phenoxy)-6-methoxy-isoquinolin-3-yl]-(1H-pyrazol-3-yl)-amine. LC-MS m/e 367(MH+).

Example 130

(1-Isopropoxy-6-methoxy-isoquinolin-3-yl)-(1H-pyrazol-3-yl)-amine

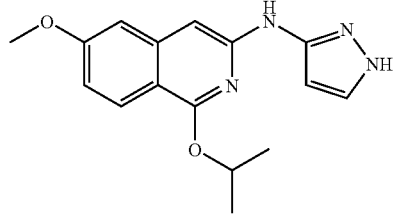

Similar procedure as described in example 10 was used, starting from (1-chloro-6-methoxy-isoquinolin-3-yl)-(1H-pyrazol-3-yl)-amine and propan-2-ol to give (1-isopropoxy-6-methoxy-isoquinolin-3-yl)-(1H-pyrazol-3-yl)-amine. LC-MS m/e 299(MH+).

Example 131

(5-Methyl-1H-pyrazol-3-yl)-(1-phenyl-isoquinolin-3-yl)-amine

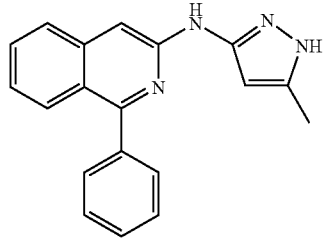

The mixture of (1-chloro-isoquinolin-3-yl)-(5-methyl-1H-pyrazol-3-yl)-amine (100 mg), phenylboronic acid (84 mg), $Na_2CO_3$ (145 mg), Tetrakis(triphenyl-phosphine)palladium (0) (40 mg), N,N-dimethylformamide (DMF) (1 ml) and water (1 ml) was heated at 180° C. for 30 minutes under microwave irradiation. After reaction finished, the reaction mixture was purified by preparative LC-MS to give (5-methyl-1H-pyrazol-3-yl)-(1-phenyl-isoquinolin-3-yl)-amine (40 mg). LC-MS m/e 301(MH+).+.) $^1H$ NMR(CDCl$_3$): δ 2.23 (s, 3H), δ 5.86(s, 1H), δ 7.22(m, 1H), δ 7.40(m, 1H), δ 7.55(m, 5H), δ 7.70(m,4H), δ 7.90(d, 1H).

Example 132

[1-(4-Fluoro-phenyl)-isoquinolin-3-yl]-(5-methyl-1H-pyrazol-3-yl)-amine

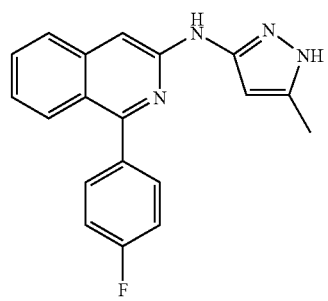

Similar procedure as described in example 131 was used, starting from (1-chloro-isoquinolin-3-yl)-(5-methyl-1H-pyrazol-3-yl)-amine and 4-fluoro-phenylboronic acid to give [1-(4-fluoro-phenyl)-isoquinolin-3-yl]-(5-methyl-1H-pyrazol-3-yl)-amine. LC-MS m/e 319(MH+). $^1H$ NMR(CDCl$_3$): δ 2.26(s, 3H), δ 5.89(s, 1H), δ 7.25(m, 3H), δ 7.32(br, 1H), δ 7.55(m, 1H), δ 7.65(s,1H), δ 7.70(m, 4H), δ 7.87(d,1H).

Example 133

(6-Methoxy-1-pyridin-4-yl-isoquinolin-3-yl)-(1H-pyrazol-3-yl)-amine

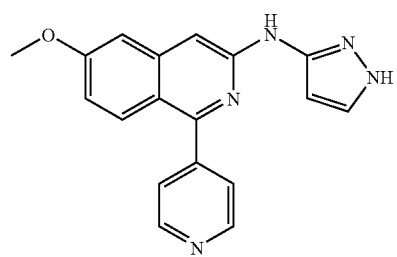

Similar procedure as described in example 131 was used, starting from (1-chloro-6-methoxy-isoquinolin-3-yl)-(1H-pyrazol-3-yl)-amine and 4-pyridinylboronic acid to give (6-methoxy-1-pyridin-4-yl-isoquinolin-3-yl)-(1H-pyrazol-3-yl)-amine. LC-MS m/e 318(MH+).

Example 134

(6-Methoxy-1-pyridin-3-yl-isoquinolin-3-yl)-(1H-pyrazol-3-yl)-amine

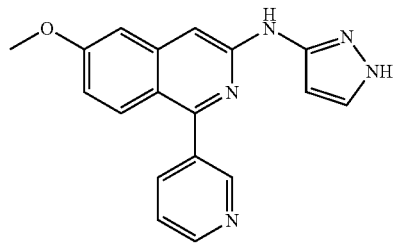

Similar procedure as described in example 131 was used, starting from (1-chloro-6-methoxy-isoquinolin-3-yl)-(1H-pyrazol-3-yl)-amine and 3-pyridinylboronic acid to give (6-methoxy-1-pyridin-3-yl-isoquinolin-3-yl)-(1H-pyrazol-3-yl)-amine. LC-MS m/e 318(MH$^+$).

Example 135

[6-Methoxy-1-(1-methyl-1H-pyrazol-4-yl)-isoquinolin-3-yl]-(1H-pyrazol-3-yl)-amine

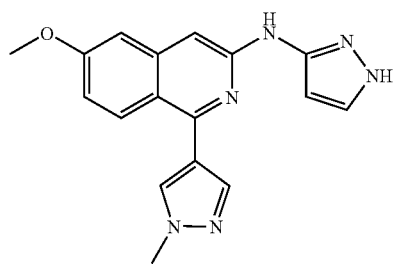

Similar procedure as described in example 131 was used, starting from (1-chloro-6-methoxy-isoquinolin-3-yl)-(1H-pyrazol-3-yl)-amine and 1-methyl-4-(4,4,5,5-tetramethyl-[1,3,2]dioxaborolan-2-yl)-1H-pyrazole to give [6-methoxy-1-(1-methyl-1H-pyrazol-4-yl)-isoquinolin-3-yl]-(1H-pyrazol-3-yl)-amine. LC-MS m/e 321(MH$^+$).

Example 136

4-[3-(5-Methyl-1H-pyrazol-3-ylamino)-isoquinolin-1-yl]-benzonitrile

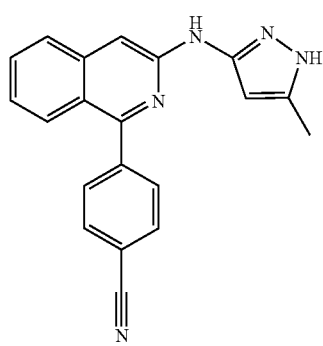

Similar procedure as described in example 131 was used, starting from (1-chloro-isoquinolin-3-yl)-(5-methyl-1H-pyrazol-3-yl)-amine and 4-cyano-phenylboronic acid to give 4-[3-(5-methyl-1H-pyrazol-3-ylamino)-isoquinolin-1-yl]-benzonitrile. LC-MS m/e 326(MH$^+$).

Example 137

[1-(4-Methoxy-phenyl)-isoquinolin-3-yl]-(5-methyl-1H-pyrazol-3-yl)-amine

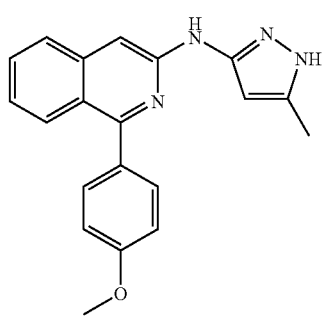

Similar procedure as described in example 131 was used, starting from (1-chloro-isoquinolin-3-yl)-(5-methyl-1H-pyrazol-3-yl)-amine and 4-methoxy-phenylboronic acid to give [1-(4-methoxy-phenyl)-isoquinolin-3-yl]-(5-methyl-1H-pyrazol-3-yl)-amine. LC-MS m/e 331 (MH$^+$).

Example 138

(5-Methyl-1H-pyrazol-3-yl)-[1-(4-trifluoromethyl-phenyl)-isoquinolin-3-yl]-amine

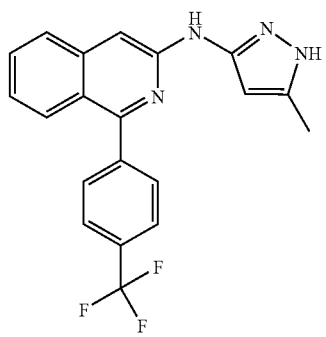

Similar procedure as described in example 131 was used, starting from (1-chloro-isoquinolin-3-yl)-(5-methyl-1H-pyrazol-3-yl)-amine and 4-trifluoromethyl-phenylboronic acid to give (5-methyl-1H-pyrazol-3-yl)-[1-(4-trifluoromethyl-phenyl)-isoquinolin-3-yl]-amine. LC-MS m/e 369(MH$^+$).

Example 139

[1-(4-Methyl-phenyl)-isoquinolin-3-yl]-(5-methyl-1H-pyrazol-3-yl)-amine

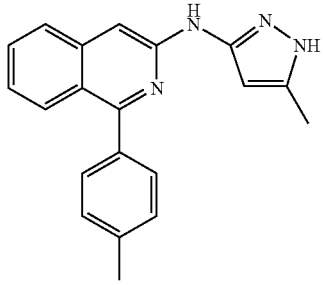

Similar procedure as described in example 131 was used, starting from (1-chloro-isoquinolin-3-yl)-(5-methyl-1H-pyrazol-3-yl)-amine and 4-fluoro-phenylboronic acid to give [1-(4-fluoro-phenyl)-isoquinolin-3-yl]-(5-methyl-1H-pyrazol-3-yl)-amine. LC-MS m/e 315(MH+).

Example 140

[1-(4-Chloro-phenyl)-isoquinolin-3-yl]-(5-methyl-1H-pyrazol-3-yl)-amine

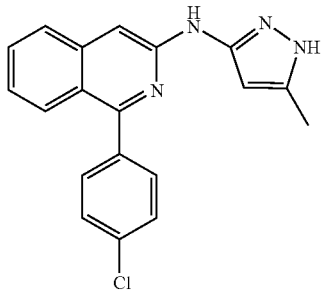

Similar procedure as described in example 131 was used, starting from (1-chloro-isoquinolin-3-yl)-(5-methyl-1H-pyrazol-3-yl)-amine and 4-chloro-Phenylboronic acid to give [1-(4-chloro-phenyl)-isoquinolin-3-yl]-(5-methyl-1H-pyrazol-3-yl)-amine. LC-MS m/e 335(MH+).

Example 141

[1-(3-Chloro-phenyl)-isoquinolin-3-yl]-(5-methyl-1H-pyrazol-3-yl)-amine

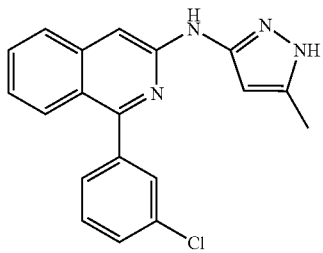

Similar procedure as described in example 131 was used, starting from (1-chloro-isoquinolin-3-yl)-(5-methyl-1H-pyrazol-3-yl)-amine and 3-chloro-phenylboronic acid to give [1-(3-chloro-phenyl)-isoquinolin-3-yl]-(5-methyl-1H-pyrazol-3-yl)-amine. LC-MS m/e 335(MH+).

Example 142

[1-(3-Fluoro-phenyl)-isoquinolin-3-yl]-(5-methyl-1H-pyrazol-3-yl)-amine

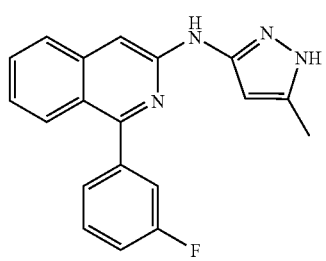

Similar procedure as described in example 131 was used, starting from (1-chloro-isoquinolin-3-yl)-(5-methyl-1H-pyrazol-3-yl)-amine and 3-fluoro-phenylboronic acid to give [1-(3-fluoro-phenyl)-isoquinolin-3-yl]-(5-methyl-1H-pyrazol-3-yl)-amine. LC-MS m/e 319(MH+).

Example 143

3-[3-(5-Methyl-1H-pyrazol-3-ylamino)-isoquinolin-1-yl]-benzonitrile

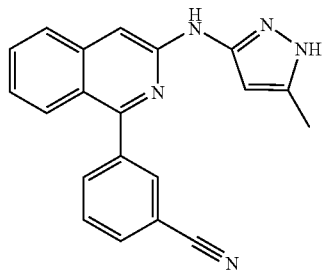

Similar procedure as described in example 131 was used, starting from (1-chloro-isoquinolin-3-yl)-(5-methyl-1H-pyrazol-3-yl)-amine and 3-cyano-phenylboronic acid to give 3-[3-(5-methyl-1H-pyrazol-3-ylamino)-isoquinolin-1-yl]-benzonitrile LC-MS m/e 326(MH+).

Example 144

[1-(3-Methoxy-phenyl)-isoquinolin-3-yl]-(5-methyl-1H-pyrazol-3-yl)-amine

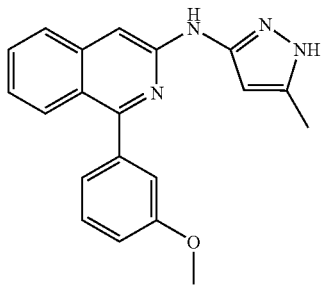

Similar procedure as described in example 131 was used, starting from (1-chloro-isoquinolin-3-yl)-(5-methyl-1H-pyrazol-3-yl)-amine and 3-methoxy-phenylboronic acid to give [1-(3-methoxy-phenyl)-isoquinolin-3-yl]-(5-methyl-1H-pyrazol-3-yl)-amine. LC-MS m/e 331 (MH$^+$).

Example 145

[1-(3-trifluoromethyl-phenyl)-isoquinolin-3-yl]-(5-methyl-1H-pyrazol-3-yl)-amine

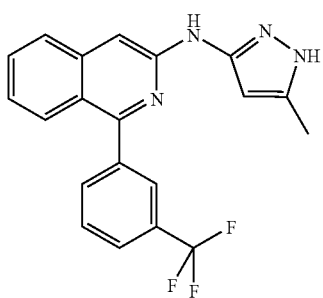

Similar procedure as described in example 131 was used, starting from (1-chloro-isoquinolin-3-yl)-(5-methyl-1H-pyrazol-3-yl)-amine and 3-trifluoromethyl-phenylboronic acid to give [1-(3-trifluoromethyl-phenyl)-isoquinolin-3-yl]-(5-methyl-1H-pyrazol-3-yl)-amine. LC-MS m/e 369(MH$^+$).

Example 146

[1-(3-Methyl-phenyl)-isoquinolin-3-yl]-(5-methyl-1H-pyrazol-3-yl)-amine

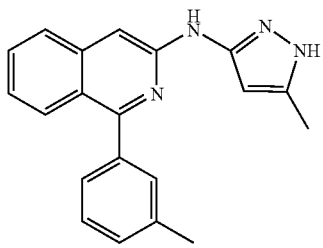

Similar procedure as described in example 131 was used, starting from (1-chloro-isoquinolin-3-yl)-(5-methyl-1H-pyrazol-3-yl)-amine and 3-methyl-phenylboronic acid to give [1-(3-methyl-phenyl)-isoquinolin-3-yl]-(5-methyl-1H-pyrazol-3-yl)-amine. LC-MS m/e 315(MH$^+$).

Example 147

1-{3-[3-(5-Methyl-1H-pyrazol-3-ylamino)-isoquinolin-1-yl]-phenyl}-ethanone

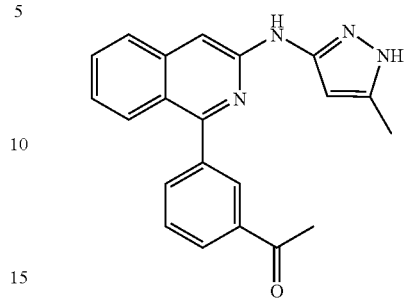

Similar procedure as described in example 131 was used, starting from (1-chloro-isoquinolin-3-yl)-(5-methyl-1H-pyrazol-3-yl)-amine and 3-acetyl-phenylboronic acid to give 1-{3-[3-(5-methyl-1H-pyrazol-3-ylamino)-isoquinolin-1-yl]-phenyl}-ethanone. LC-MS m/e 343(MH$^+$).

Example 148

1-{4-[3-(5-Methyl-1H-pyrazol-3-ylamino)-isoquinolin-1-yl]-phenyl}-ethanone

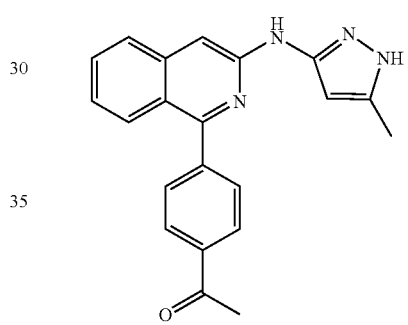

Similar procedure as described in example 131 was used, starting from (1-chloro-isoquinolin-3-yl)-(5-methyl-1H-pyrazol-3-yl)-amine and 4-acetyl-phenylboronic acid to give 1-{4-[3-(5-methyl-1H-pyrazol-3-ylamino)-isoquinolin-1-yl]-phenyl}-ethanone. LC-MS m/e 343(MH$^+$).

Example 149

[1-(2-Fluoro-phenyl)-isoquinolin-3-yl]-(5-methyl-1H-pyrazol-3-yl)-amine

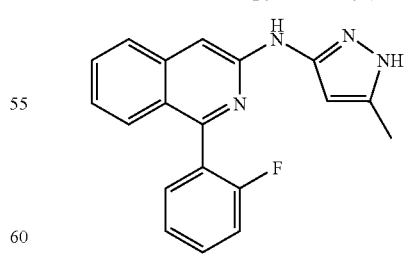

Similar procedure as described in example 131 was used, starting from (1-chloro-isoquinolin-3-yl)-(5-methyl-1H-pyrazol-3-yl)-amine and 2-fluoro-phenylboronic acid to give [1-(2-fluoro-phenyl)-isoquinolin-3-yl]-(5-methyl-1H-pyrazol-3-yl)-amine. LC-MS m/e 319(MH$^+$).

Example 150

[1-(2-Methoxy-phenyl)-isoquinolin-3-yl]-(5-methyl-1H-pyrazol-3-yl)-amine

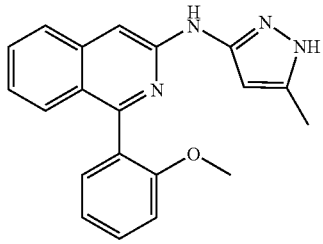

Similar procedure as described in example 131 was used, starting from (1-chloro-isoquinolin-3-yl)-(5-methyl-1H-pyrazol-3-yl)-amine and 2-methoxy-phenylboronic acid to give [1-(2-methoxy-phenyl)-isoquinolin-3-yl]-(5-methyl-1H-pyrazol-3-yl)-amine. LC-MS m/e 331(MH$^+$).

Example 151

[1-(2,4-Difluoro-phenyl)-6,7-dimethoxy-isoquinolin-3-yl]-(5-methyl-1H-pyrazol-3-yl)-amine

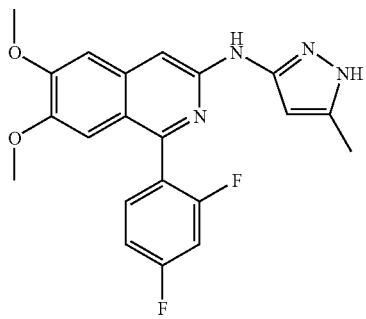

Similar procedure as described in example 131 was used, starting from (1-chloro-6,7-dimethoxy-isoquinolin-3-yl)-(5-methyl-1H-pyrazol-3-yl)-amine and 2,4-difluoro-phenylboronic acid to give [1-(2,4-difluoro-phenyl)-6,7-dimethoxy-isoquinolin-3-yl]-(5-methyl-1H-pyrazol-3-yl)-amine. LC-MS m/e 397(MH$^+$).

Example 152

(5-Methyl-1H-pyrazol-3-yl)-(1-naphthalen-2-yl-isoquinolin-3-yl)-amine

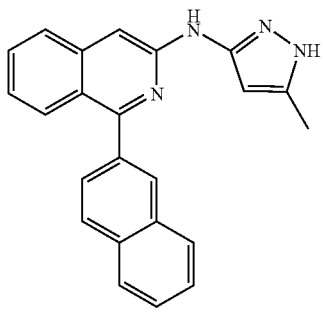

Similar procedure as described in example 131 was used, starting from (1-chloro-isoquinolin-3-yl)-(5-methyl-1H-pyrazol-3-yl)-amine and naphthalene-2-boronic acid to give (5-methyl-1H-pyrazol-3-yl)-(1-naphthalen-2-yl-isoquinolin-3-yl)-amine. LC-MS m/e 351 (MH$^+$).

Example 153

[1-(4-tert-Butyl-phenyl)-isoquinolin-3-yl]-(5-methyl-1H-pyrazol-3-yl)-amine

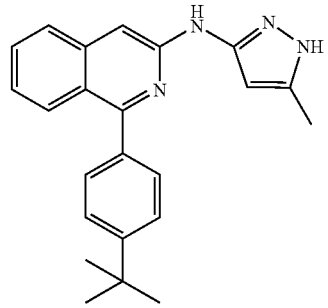

Similar procedure as described in example 131 was used, starting from (1-chloro-isoquinolin-3-yl)-(5-methyl-1H-pyrazol-3-yl)-amine and 4-tert-butyl-phenylboronic acid to give [1-(4-tert-butyl-phenyl)-isoquinolin-3-yl]-(5-methyl-1H-pyrazol-3-yl)-amine. LC-MS m/e 357(MH$^+$).

Example 154

[1-(2,4-Difluoro-phenyl)-isoquinolin-3-yl]-(5-methyl-1H-pyrazol-3-yl)-amine

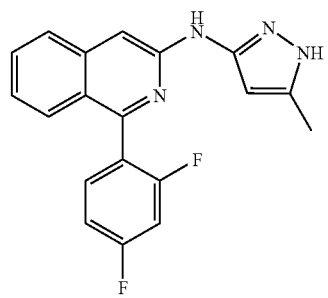

Similar procedure as described in example 131 was used, starting from (1-chloro-isoquinolin-3-yl)-(5-methyl-1H-pyrazol-3-yl)-amine and 2,4-difluoro-phenylboronic acid to give [1-(2,4-difluoro-phenyl)-isoquinolin-3-yl]-(5-methyl-1H-pyrazol-3-yl)-amine. LC-MS m/e 337(MH$^+$).

Example 155

[1-(3,4-Difluoro-phenyl)-isoquinolin-3-yl]-(5-methyl-1H-pyrazol-3-yl)-amine

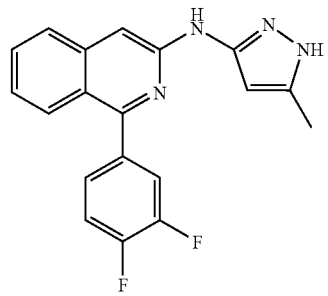

Similar procedure as described in example 131 was used, starting from (1-chloro-isoquinolin-3-yl)-(5-methyl-1H- pyrazol-3-yl)-amine and 3,4-difluoro-phenylboronic acid to give [1-(3,4-difluoro-phenyl)-isoquinolin-3-yl]-(5-methyl-1H-pyrazol-3-yl)-amine. LC-MS m/e 337(MH$^+$).

Example 156

[1-(3,4-Dimethoxy-phenyl)-isoquinolin-3-yl]-(5-methyl-1H-pyrazol-3-yl)-amine

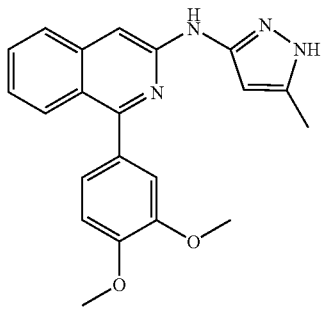

Similar procedure as described in example 131 was used, starting from (1-chloro-isoquinolin-3-yl)-(5-methyl-1H-pyrazol-3-yl)-amine and 3,4-dimethoxy-phenylboronic acid to give [1-(3,4-dimethoxy-phenyl)-isoquinolin-3-yl]-(5-methyl-1H-pyrazol-3-yl)-amine. LC-MS m/e 361(MH$^+$).

Example 157

(5-Methyl-1H-pyrazol-3-yl)-[1-(4-methyl-thiophen-3-yl)-isoquinolin-3-yl]-amine

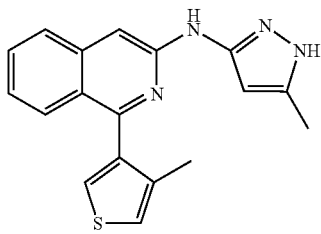

Similar procedure as described in example 131 was used, starting from (1-chloro-isoquinolin-3-yl)-(5-methyl-1H-pyrazol-3-yl)-amine and 4-methyl-thiophene-3-boronic acid to give (5-methyl-1H-pyrazol-3-yl)-[1-(4-methyl-thiophen-3-yl)-isoquinolin-3-yl]-amine. LC-MS m/e 321(MH$^+$).

Example 158

(5-Methyl-1H-pyrazol-3-yl)-(1-thiophen-3-yl-isoquinolin-3-yl)-amine

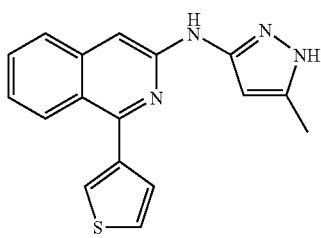

Similar procedure as described in example 131 was used, starting from (1-chloro-isoquinolin-3-yl)-(5-methyl-1H-pyrazol-3-yl)-amine and thiophene-3-boronic acid to give (5-methyl-1H-pyrazol-3-yl)-(1-thiophen-3-yl-isoquinolin-3-yl)-amine. LC-MS m/e 307(MH$^+$).

Example 159

(1-Benzo[b]thiophen-3-yl-isoquinolin-3-yl)-(5-methyl-1H-pyrazol-3-yl)-amine

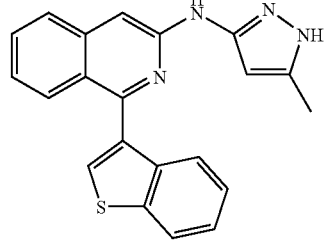

Similar procedure as described in example 131 was used, starting from (1-chloro-isoquinolin-3-yl)-(5-methyl-1H-pyrazol-3-yl)-amine and benzo[b]thiophene-3-boronic acid to give (1-benzo[b]thiophen-3-yl-isoquinolin-3-yl)-(5-methyl-1H-pyrazol-3-yl)-amine. LC-MS m/e 357(MH$^+$).

Example 160

N-{4-[3-(5-Methyl-1H-pyrazol-3-ylamino)-isoquinolin-1-yl]-phenyl}-acetamide

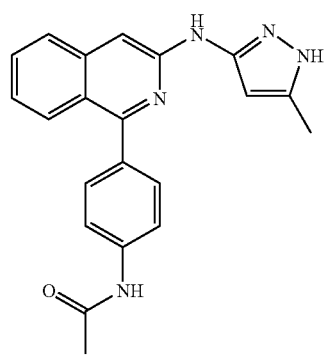

Similar procedure as described in example 131 was used, starting from (1-chloro-isoquinolin-3-yl)-(5-methyl-1H-pyrazol-3-yl)-amine and 4-acetylamino-phenylboronic acid to give N-{4-[3-(5-methyl-1H-pyrazol-3-ylamino)-isoquinolin-1-yl]-phenyl}-acetamide. LC-MS m/e 358(MH$^+$).

Example 161

(5-Methyl-1H-pyrazol-3-yl)-(1-pyridin-3-yl-isoquinolin-3-yl)-amine

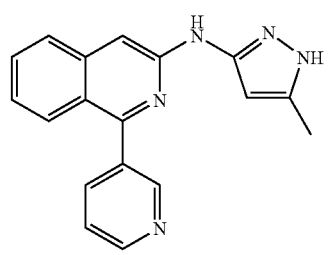

Similar procedure as described in example 131 was used, starting from (1-chloro-isoquinolin-3-yl)-(5-methyl-1H-pyrazol-3-yl)-amine and 3-pyridine-boronic acid to give (5-methyl-1H-pyrazol-3-yl)-(1-pyridin-3-yl-isoquinolin-3-yl)-amine. LC-MS m/e 302(MH$^+$).

Example 162

(5-Methyl-1H-pyrazol-3-yl)-(1-pyridin-4-yl-isoquinolin-3-yl)-amine

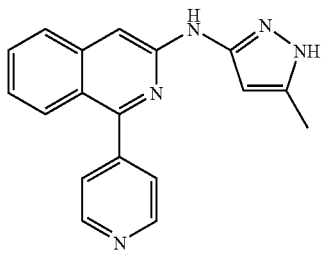

Similar procedure as described in example 131 was used, starting from (1-chloro-isoquinolin-3-yl)-(5-methyl-1H-pyrazol-3-yl)-amine and 4-pyridine-boronic acid to give (5-methyl-1H-pyrazol-3-yl)-(1-pyridin-4-yl-isoquinolin-3-yl)-amine. LC-MS m/e 302(MH$^+$).

Example 163

(5-Methyl-1H-pyrazol-3-yl)-[1-(1H-pyrazol-4-yl)-isoquinolin-3-yl]-amine

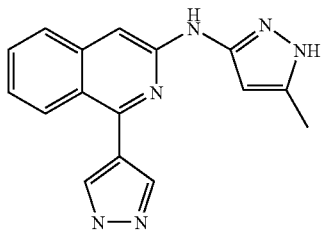

Similar procedure as described in example 131 was used, starting from (1-chloro-isoquinolin-3-yl)-(5-methyl-1H-pyrazol-3-yl)-amine and 1H-pyrazole-4-boronic acid to give (5-methyl-1H-pyrazol-3-yl)-[1-(1H-pyrazol-4-yl)-isoquinolin-3-yl]-amine. LC-MS m/e 291 (MH$^+$).

Example 164

(5-Methyl-1H-pyrazol-3-yl)-[1-(1-methyl-1H-pyrazol-4-yl)-isoquinolin-3-yl]-amine

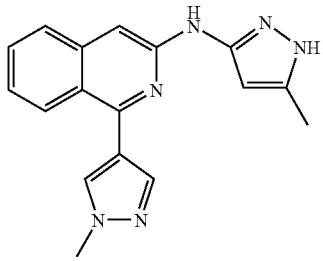

Similar procedure as described in example 131 was used, starting from (1-chloro-isoquinolin-3-yl)-(5-methyl-1H-pyrazol-3-yl)-amine and N-methyl-pyrazole-4-boronic acid to give (5-methyl-1H-pyrazol-3-yl)-[1-(1H-pyrazol-4-yl)-isoquinolin-3-yl]-amine. LC-MS m/e 305(MH$^+$).

Example 165

(6-Methoxy-1-phenyl-isoquinolin-3-yl)-(5-methyl-1H-pyrazol-3-yl)-amine

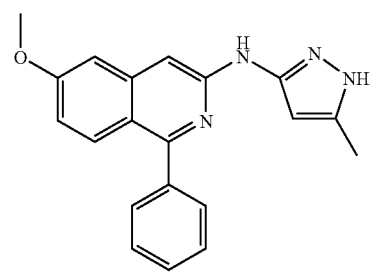

Similar procedure as described in example 131 was used, starting from (1-chloro-6-methoxy-isoquinolin-3-yl)-(5-methyl-1H-pyrazol-3-yl)-amine and phenylboronic acid to give (6-methoxy-1-phenyl-isoquinolin-3-yl)-(5-methyl-1H-pyrazol-3-yl)-amine. LC-MS m/e 331 (MH$^+$).

Example 166

[1-(4-Fluoro-phenyl)-6-methoxy-isoquinolin-3-yl]-(5-methyl-1H-pyrazol-3-yl)-amine

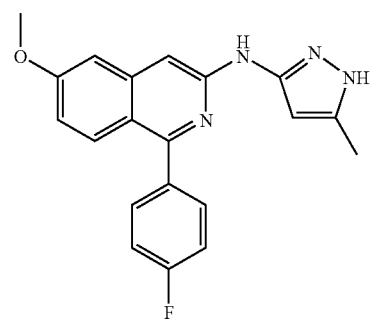

Similar procedure as described in example 131 was used, starting from (1-chloro-6-methoxy-isoquinolin-3-yl)-(5-methyl-1H-pyrazol-3-yl)-amine and 4-fluoro-phenylboronic acid to give [1-(4-fluoro-phenyl)-6-methoxy-isoquinolin-3-yl]-(5-methyl-1H-pyrazol-3-yl)-amine.). LC-MS m/e 349(MH$^+$).

Example 167

4-[6-Methoxy-3-(5-methyl-1H-pyrazol-3-ylamino)-isoquinolin-1-yl]-benzonitrile

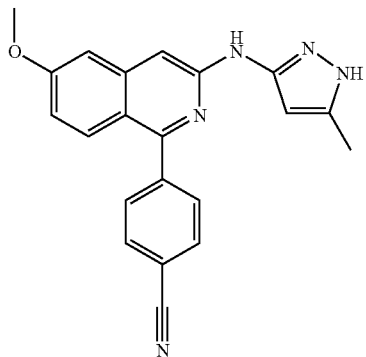

Similar procedure as described in example 131 was used, starting from (1-chloro-6-methoxy-isoquinolin-3-yl)-(5-methyl-1H-pyrazol-3-yl)-amine and 4-cyano-phenylboronic acid to give 4-[6-methoxy-3-(5-methyl-1H-pyrazol-3-ylamino)-isoquinolin-1-yl]-benzonitrile. LC-MS m/e 356(MH$^+$).

Example 168

[1-(4-ethoxy-phenyl)-6-methoxy-isoquinolin-3-yl]-(5-methyl-1H-pyrazol-3-yl)-amine

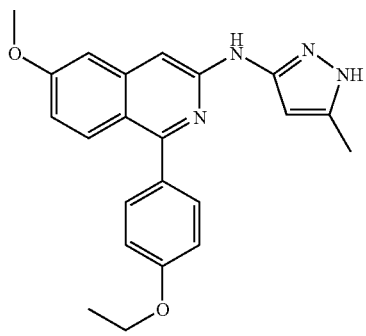

Similar procedure as described in example 131 was used, starting from (1-chloro-6-methoxy-isoquinolin-3-yl)-(5-methyl-1H-pyrazol-3-yl)-amine and 4-ethoxy-phenylboronic acid to give [1-(4-ethoxy-phenyl)-6-methoxy-isoquinolin-3-yl]-(5-methyl-1H-pyrazol-3-yl)-amine. LC-MS m/e 375(MH$^+$).

Example 169

(5-Methyl-1H-pyrazol-3-yl)-[1-(4-trifluoromethyl-phenyl)-6-methoxy-isoquinolin-3-yl]-amine

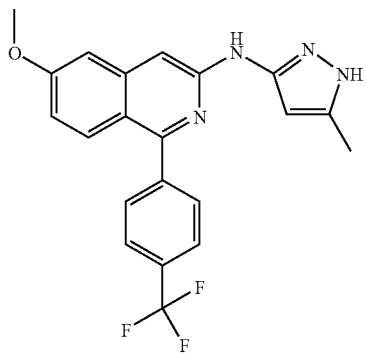

Similar procedure as described in example 131 was used, starting from (1-chloro-6-methoxy-isoquinolin-3-yl)-(5-methyl-1H-pyrazol-3-yl)-amine and 4-trifluoromethyl-phenylboronic acid to give (5-methyl-1H-pyrazol-3-yl)-[1-(4-trifluoromethyl-phenyl)-6-methoxy-isoquinolin-3-yl]-amine. LC-MS m/e 399(MH$^+$).

Example 170

[1-(4-Methyl-phenyl)-6-methoxy-isoquinolin-3-yl]-(5-methyl-1H-pyrazol-3-yl)-amine

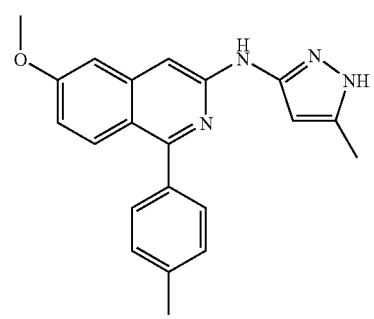

Similar procedure as described in example 131 was used, starting from (1-chloro-6-methoxy-isoquinolin-3-yl)-(5-methyl-1H-pyrazol-3-yl)-amine and 4-fluoro-phenylboronic acid to give [1-(4-fluoro-phenyl)-6-methoxy-isoquinolin-3-yl]-(5-methyl-1H-pyrazol-3-yl)-amine. LC-MS m/e 345(MH$^+$).

Example 171

[1-(4-Chloro-phenyl)-6-methoxy-isoquinolin-3-yl]-(5-methyl-1H-pyrazol-3-yl)-amine

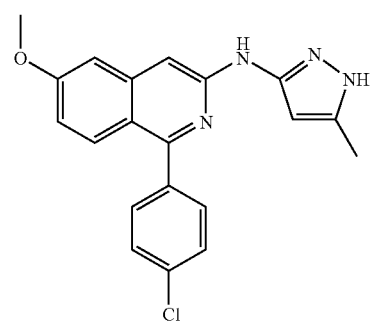

Similar procedure as described in example 131 was used, starting from (1-chloro-6-methoxy-isoquinolin-3-yl)-(5-methyl-1H-pyrazol-3-yl)-amine and 4-chloro-phenylboronic acid to give [1-(4-chloro-phenyl)-6-methoxy-isoquinolin-3-yl]-(5-methyl-1H-pyrazol-3-yl)-amine. LC-MS m/e 365(MH$^+$).

Example 172

[1-(3-Chloro-phenyl)-6-methoxy-isoquinolin-3-yl]-(5-methyl-1H-pyrazol-3-yl)-amine

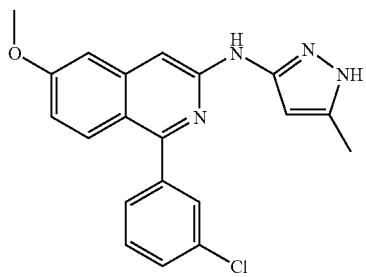

Similar procedure as described in example 131 was used, starting (1-chloro-6-methoxy-isoquinolin-3-yl)-(5-methyl-1H-pyrazol-3-yl)-amine and 3-chloro-phenylboronic acid to give [1-(3-chloro-phenyl)-6-methoxy-isoquinolin-3-yl]-(5-methyl-1H-pyrazol-3-yl)-amine. LC-MS m/e 365(MH$^+$).

Example 173

[1-(3-Fluoro-phenyl)-6-methoxy-isoquinolin-3-yl]-(5-methyl-1H-pyrazol-3-yl)-amine

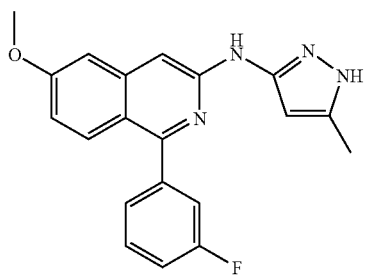

Similar procedure as described in example 131 was used, starting from (1-chloro-6-methoxy-isoquinolin-3-yl)-(5-methyl-1H-pyrazol-3-yl)-amine and 3-fluoro-phenylboronic acid to give [1-(3-Fluoro-phenyl)-6-methoxy-isoquinolin-3-yl]-(5-methyl-1H-pyrazol-3-yl)-amine. LC-MS m/e 349(MH$^+$).

Example 174

3-[3-(5-Methyl-1H-pyrazol-3-ylamino)-6-methoxy-isoquinolin-1-yl]-benzonitrile

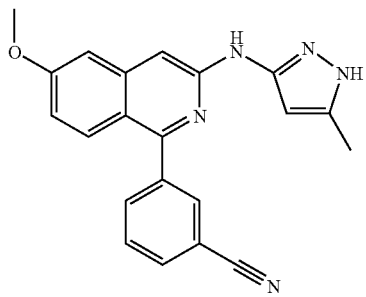

Similar procedure as described in example 131 was used, starting from (1-chloro-6-methoxy-isoquinolin-3-yl)-(5-methyl-1H-pyrazol-3-yl)-amine and 3-cyano-phenylboronic acid to give 3-[3-(5-methyl-1H-pyrazol-3-ylamino)-6-methoxy-isoquinolin-1-yl]-benzonitrile LC-MS m/e 356(MH$^+$).

Example 175

[1-(3-Methoxy-phenyl)-6-methoxy-isoquinolin-3-yl]-(5-methyl-1H-pyrazol-3-yl)-amine

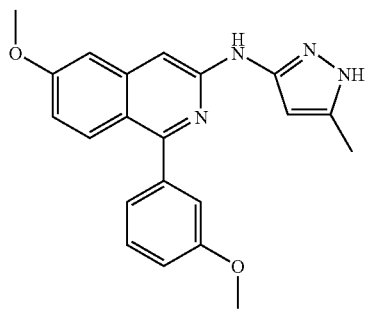

Similar procedure as described in example 131 was used, starting from (1-chloro-6-methoxy-isoquinolin-3-yl)-(5-methyl-1H-pyrazol-3-yl)-amine and 3-methoxy-phenylboronic acid to give [1-(3-methoxy-phenyl)-6-methoxy-isoquinolin-3-yl]-(5-methyl-1H-pyrazol-3-yl)-amine. LC-MS m/e 361(MH$^+$).

Example 176

[1-(3-trifluoromethyl-phenyl)-6-methoxy-isoquinolin-3-yl]-(5-methyl-1H-pyrazol-3-yl)-amine

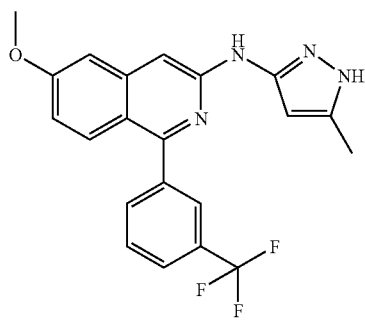

Similar procedure as described in example 131 was used, starting from (1-chloro-6-methoxy-isoquinolin-3-yl)-(5-methyl-1H-pyrazol-3-yl)-amine and 3-trifluoromethyl-phenylboronic acid to give [1-(3-trifluoromethyl-phenyl)-6-methoxy-isoquinolin-3-yl]-(5-methyl-1H-pyrazol-3-yl)-amine. LC-MS m/e 399(MH$^+$).

Example 177

[1-(3-Methyl-phenyl)-6-methoxy-isoquinolin-3-yl]-(5-methyl-1H-pyrazol-3-yl)-amine

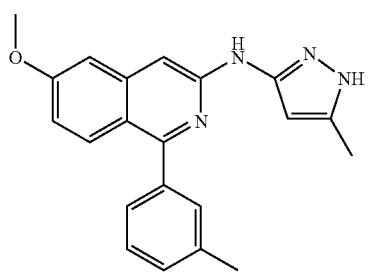

Similar procedure as described in example 131 was used, starting from (1-chloro-6-methoxy-isoquinolin-3-yl)-(5-methyl-1H-pyrazol-3-yl)-amine and 3-methyl-phenylboronic acid to give [1-(3-methyl-phenyl)-6-methoxy-isoquinolin-3-yl]-(5-methyl-1H-pyrazol-3-yl)-amine. LC-MS m/e 345(MH⁺).

Example 178

1-{3-[3-(5-Methyl-1H-pyrazol-3-ylamino)-6-methoxy-isoquinolin-1-yl]-phenyl}-ethanone

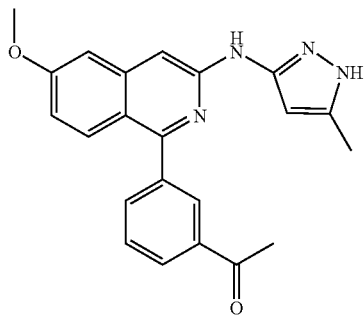

Similar procedure as described in example 131 was used, starting from (1-chloro-6-methoxy-isoquinolin-3-yl)-(5-methyl-1H-pyrazol-3-yl)-amine and 3-acetyl-phenylboronic acid to give 1-{3-[3-(5-methyl-1H-pyrazol-3-ylamino)-6-methoxy-isoquinolin-1-yl]-phenyl}-ethanone. LC-MS m/e 373(MH⁺).

Example 179

1-{4-[3-(5-Methyl-1H-pyrazol-3-ylamino)-6-methoxy-isoquinolin-1-yl]-phenyl}-ethanone

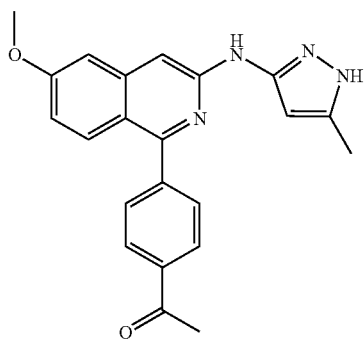

Similar procedure as described in example 131 was used, starting from (1-chloro-6-methoxy-isoquinolin-3-yl)-(5-methyl-1H-pyrazol-3-yl)-amine and 4-acetyl-phenylboronic acid to give 1-{4-[3-(5-methyl-1H-pyrazol-3-ylamino)-6-methoxy-isoquinolin-1-yl]-phenyl}-ethanone. LC-MS m/e 373(MH⁺).

Example 180

[1-(2-Fluoro-phenyl)-6-methoxy-isoquinolin-3-yl]-(5-methyl-1H-pyrazol-3-yl)-amine

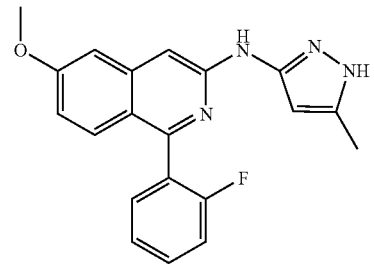

Similar procedure as described in example 131 was used, starting from (1-chloro-6-methoxy-isoquinolin-3-yl)-(5-methyl-1H-pyrazol-3-yl)-amine and 2-fluoro-phenylboronic acid to give [1-(2-fluoro-phenyl)-6-methoxy-isoquinolin-3-yl]-(5-methyl-1H-pyrazol-3-yl)-amine. LC-MS m/e 349(MH⁺).

Example 181

[1-(2-Methoxy-phenyl)-6-methoxy-isoquinolin-3-yl]-(5-methyl-1H-pyrazol-3-yl)-amine

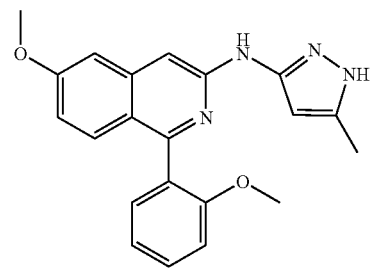

Similar procedure as described in example 131 was used, starting from (1-chloro-6-methoxy-isoquinolin-3-yl)-(5-methyl-1H-pyrazol-3-yl)-amine and 2-methoxy-phenylboronic acid to give [1-(2-methoxy-phenyl)-6-methoxy-isoquinolin-3-yl]-(5-methyl-1H-pyrazol-3-yl)-amine. LC-MS m/e 361(MH⁺).

Example 182

[6-Methoxy-1-(1H-pyrazol-4-yl)-isoquinolin-3-yl]-(1H-pyrazol-3-yl)-amine

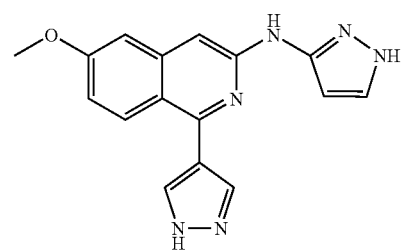

Similar procedure as described in example 131 was used, starting from (1-chloro-6-methoxy-isoquinolin-3-yl)-(1H-pyrazol-3-yl)-amine and 4-(4,4,5,5-tetramethyl-[1,3,2]dioxaborolan-2-yl)-1H-pyrazole to give [6-methoxy-1-(1H-pyrazol-4-yl)-isoquinolin-3-yl]-(1H-pyrazol-3-yl)-amine. LC-MS m/e 307(MH$^+$).

Example 183

(5-Methyl-1H-pyrazol-3-yl)-(1-naphthalen-2-yl-6-methoxy-isoquinolin-3-yl)-amine

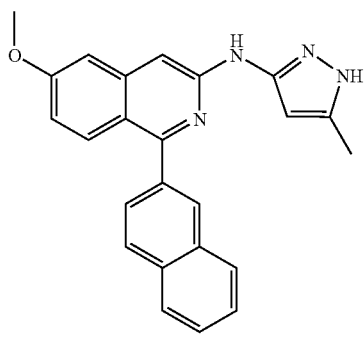

Similar procedure as described in example 131 was used, starting (1-chloro-6-methoxy-isoquinolin-3-yl)-(5-methyl-1H-pyrazol-3-yl)-amine and naphthalene-2-boronic acid to give (5-methyl-1H-pyrazol-3-yl)-(1-naphthalen-2-yl-6-methoxy-isoquinolin-3-yl)-amine. LC-MS m/e 381(MH$^+$).

Example 184

[1-(4-tert-Butyl-phenyl)-6-methoxy-isoquinolin-3-yl]-(5-methyl-1H-pyrazol-3-yl)-amine

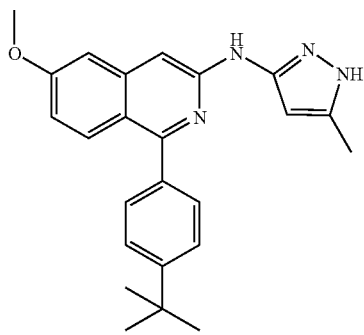

Similar procedure as described in example 131 was used, starting from (1-chloro-6-methoxy-isoquinolin-3-yl)-(5-methyl-1H-pyrazol-3-yl)-amine and 4-tert-butyl-phenylboronic acid to give [1-(4-tert-butyl-phenyl)-6-methoxy-isoquinolin-3-yl]-(5-methyl-1H-pyrazol-3-yl)-amine. LC-MS m/e 387(MH$^+$).

Example 185

[1-(2,4-Difluoro-phenyl)-6-methoxy-isoquinolin-3-yl]-(5-methyl-1H-pyrazol-3-yl)-amine

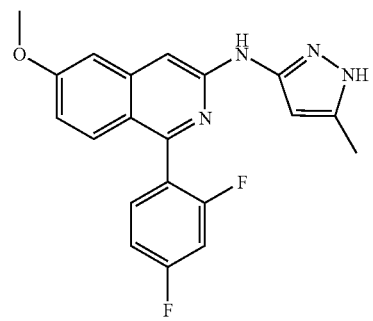

Similar procedure as described in example 131 was used, starting from (1-chloro-6-methoxy-isoquinolin-3-yl)-(5-methyl-1H-pyrazol-3-yl)-amine and 2,4-difluoro-phenylboronic acid to give [1-(2,4-difluoro-phenyl)-6-methoxy-isoquinolin-3-yl]-(5-methyl-1H-pyrazol-3-yl)-amine. LC-MS m/e 367(MH$^+$).

Example 186

[1-(3,4-Difluoro-phenyl)-6-methoxy-isoquinolin-3-yl]-(5-methyl-1H-pyrazol-3-yl)-amine

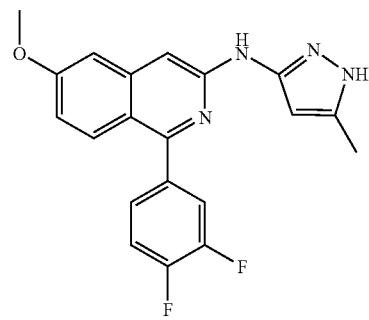

Similar procedure as described in example 131 was used, starting from (1-chloro-6-methoxy-isoquinolin-3-yl)-(5-methyl-1H-pyrazol-3-yl)-amine and 3,4-difluoro-phenylboronic acid to give [1-(3,4-difluoro-phenyl)-6-methoxy-isoquinolin-3-yl]-(5-methyl-1H-pyrazol-3-yl)-amine. LC-MS m/e 367(MH$^+$).

Example 187

[1-(3,4-Dimethoxy-phenyl)-6-methoxy-isoquinolin-3-yl]-(5-methyl-1H-pyrazol-3-yl)-amine

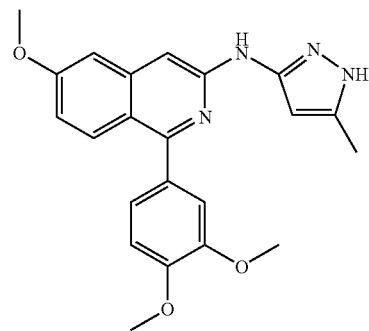

Similar procedure as described in example 131 was used, starting from (1-chloro-6-methoxy-isoquinolin-3-yl)-(5-methyl-1H-pyrazol-3-yl)-amine and 3,4-dimethoxy-phenylboronic acid to give [1-(3,4-dimethoxy-phenyl)-6-methoxy-isoquinolin-3-yl]-(5-methyl-1H-pyrazol-3-yl)-amine. LC-MS m/e 391(MH$^+$).

Example 188

(5-Methyl-1H-pyrazol-3-yl)-[1-(4-methyl-thiophen-3-yl)-6-methoxy-isoquinolin-3-yl]-amine

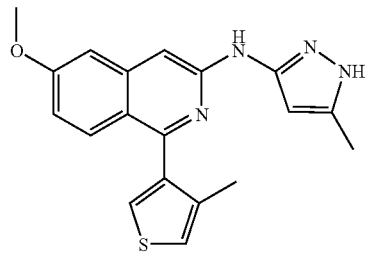

Similar procedure as described in example 131 was used, starting from (1-chloro-6-methoxy-isoquinolin-3-yl)-(5-methyl-1H-pyrazol-3-yl)-amine and 4-methyl-thiophene-3-boronic acid to give (5-methyl-1H-pyrazol-3-yl)-[1-(4-methyl-thiophen-3-yl)-6-methoxy-isoquinolin-3-yl]-amine. LC-MS m/e 351(MH$^+$).

Example 189

(5-Methyl-1H-pyrazol-3-yl)-(1-thiophen-3-yl-6-methoxy-isoquinolin-3-yl)-amine

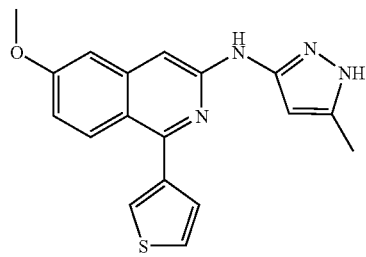

Similar procedure as described in example 131 was used, starting from (1-chloro-6-methoxy-isoquinolin-3-yl)-(5-methyl-1H-pyrazol-3-yl)-amine and thiophene-3-boronic acid to give (5-methyl-1H-pyrazol-3-yl)-(1-thiophen-3-yl-6-methoxy-isoquinolin-3-yl)-amine. LC-MS m/e 337(MH$^+$).

Example 190

(1-Benzo[b]thiophen-3-yl-6-methoxy-isoquinolin-3-yl)-(5-methyl-1H-pyrazol-3-yl)-amine

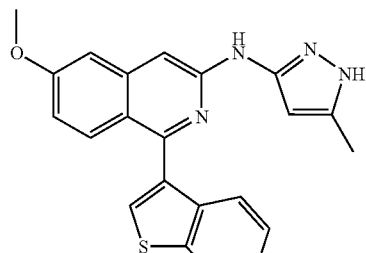

Similar procedure as described in example 131 was used, starting from (1-chloro-6-methoxy-isoquinolin-3-yl)-(5-methyl-1H-pyrazol-3-yl)-amine and benzo[b]thiophene-3-boronic acid to give (1-benzo[b]thiophen-3-yl-6-methoxy-isoquinolin-3-yl)-(5-methyl-1H-pyrazol-3-yl)-amine. LC-MS m/e 387(MH$^+$).

Example 191

N-{4-[3-(5-Methyl-1H-pyrazol-3-ylamino)-6-methoxy-isoquinolin-1-yl]-phenyl}-acetamide

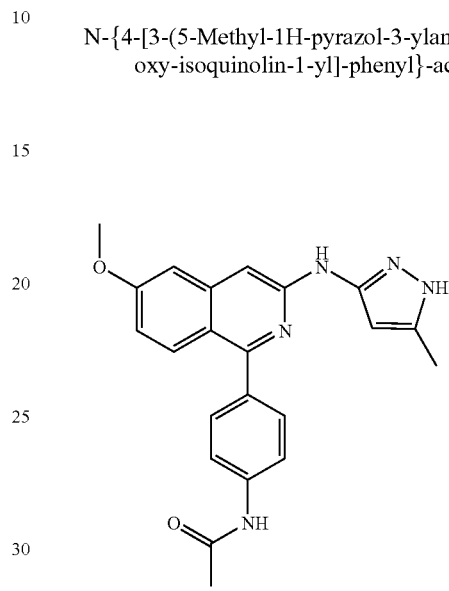

Similar procedure as described in example 131 was used, starting from (1-chloro-6-methoxy-isoquinolin-3-yl)-(5-methyl-1H-pyrazol-3-yl)-amine and 4-acetylamino-phenylboronic acid to give N-{4-[3-(5-methyl-1H-pyrazol-3-ylamino)-6-methoxy-isoquinolin-1-yl]-phenyl}-acetamide. LC-MS m/e 388(MH$^+$).

Example 192

(5-Methyl-1H-pyrazol-3-yl)-(1-pyridin-3-yl-6-methoxy-isoquinolin-3-yl)-amine

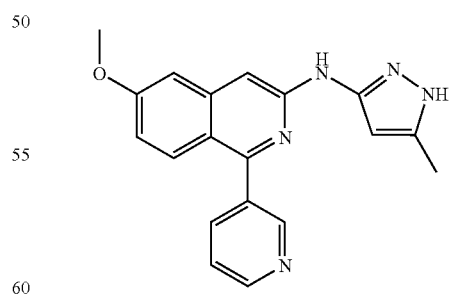

Similar procedure as described in example 131 was used, starting from (1-chloro-6-methoxy-isoquinolin-3-yl)-(5-methyl-1H-pyrazol-3-yl)-amine and 3-pyridine-boronic acid to give (5-methyl-1H-pyrazol-3-yl)-(1-pyridin-3-yl-6-methoxy-isoquinolin-3-yl)-amine. LC-MS m/e 332(MH$^+$).

Example 193

(5-Methyl-1H-pyrazol-3-yl)-(1-pyridin-4-yl-6-methoxy-isoquinolin-3-yl)-amine

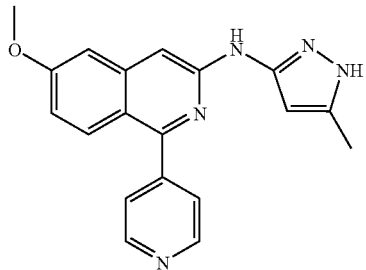

Similar procedure as described in example 131 was used, starting from (1-chloro-6-methoxy-isoquinolin-3-yl)-(5-methyl-1H-pyrazol-3-yl)-amine and 4-pyridine-boronic acid to give (5-methyl-1H-pyrazol-3-yl)-(1-pyridin-4-yl-6-methoxy-isoquinolin-3-yl)-amine. LC-MS m/e 332(MH+).

Example 194

(5-Methyl-1H-pyrazol-3-yl)-[1-(1H-pyrazol-4-yl)-6-methoxy-isoquinolin-3-yl]-amine

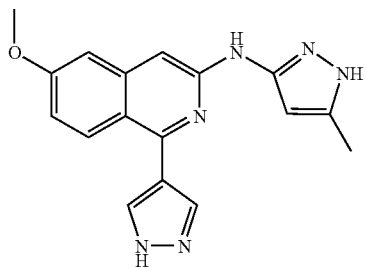

Similar procedure as described in example 131 was used, starting from (1-chloro-6-methoxy-isoquinolin-3-yl)-(5-methyl-1H-pyrazol-3-yl)-amine and 1H-pyrazole-4-boronic acid to give (5-methyl-1H-pyrazol-3-yl)-[1-(1H-pyrazol-4-yl)-6-methoxy-isoquinolin-3-yl]-amine. LC-MS m/e 221(MH+).

Example 195

(5-Methyl-1H-pyrazol-3-yl)-[1-(1-methyl-1H-pyrazol-4-yl)-6-methoxy-isoquinolin-3-yl]-amine

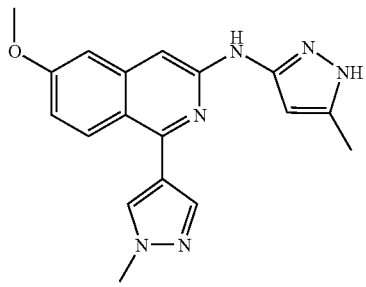

Similar procedure as described in example 131 was used, starting from (1-chloro-6-methoxy-isoquinolin-3-yl)-(5-methyl-1H-pyrazol-3-yl)-amine and N-methyl-pyrazole-4-boronic acid to give (5-methyl-1H-pyrazol-3-yl)-[1-(1H-pyrazol-4-yl)-6-methoxy-isoquinolin-3-yl]-amine. LC-MS m/e 335(MH+).

Example 196

(5-Methyl-1H-pyrazol-3-yl)-[1-(1-methyl-1H-pyrazol-4-yl)-5-methoxy-isoquinolin-3-yl]-amine

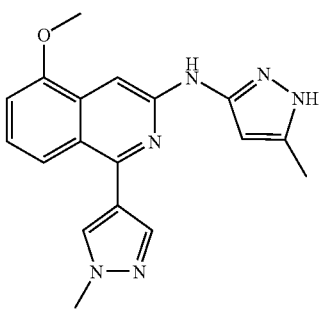

Similar procedure as described in example 131 was used, starting from (1-chloro-5-methoxy-isoquinolin-3-yl)-(5-methyl-1H-pyrazol-3-yl)-amine and N-methyl-pyrazole-4-boronic acid to give (5-methyl-1H-pyrazol-3-yl)-[1-(1H-pyrazol-4-yl)-5-methoxy-isoquinolin-3-yl]-amine. LC-MS m/e 335(MH+).

Example 197

(5-Methyl-1H-pyrazol-3-yl)-(1-pyridin-3-yl-5-methoxy-isoquinolin-3-yl)-amine

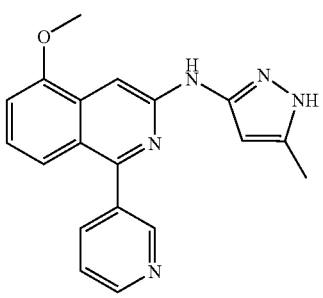

Similar procedure as described in example 131 was used, starting from (1-chloro-5-methoxy-isoquinolin-3-yl)-(5-methyl-1H-pyrazol-3-yl)-amine and 3-pyridine-boronic acid to give (5-methyl-1H-pyrazol-3-yl)-(1-pyridin-3-yl-5-methoxy-isoquinolin-3-yl)-amine. LC-MS m/e 332(MH+).

Example 198

(5-Methyl-1H-pyrazol-3-yl)-(1-thiophen-3-yl-5-methoxy-isoquinolin-3-yl)-amine

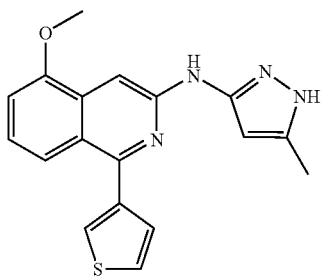

Similar procedure as described in example 131 was used, starting from (1-chloro-5-methoxy-isoquinolin-3-yl)-(5-methyl-1H-pyrazol-3-yl)-amine and thiophene-3-boronic acid to give (5-methyl-1H-pyrazol-3-yl)-(1-thiophen-3-yl-5-methoxy-isoquinolin-3-yl)-amine. LC-MS m/e 337(MH$^+$).

Example 199

[1-(2-Fluoro-phenyl)-5-methoxy-isoquinolin-3-yl]-(5-methyl-1H-pyrazol-3-yl)-amine

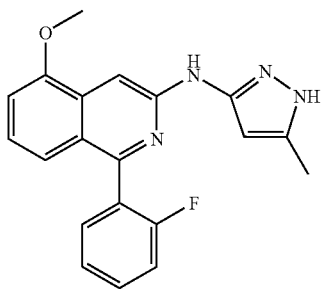

Similar procedure as described in example 131 was used, starting from (1-chloro-5-methoxy-isoquinolin-3-yl)-(5-methyl-1H-pyrazol-3-yl)-amine and 2-fluoro-phenylboronic acid to give [1-(2-Fluoro-phenyl)-5-methoxy-isoquinolin-3-yl]-(5-methyl-1H-pyrazol-3-yl)-amine. LC-MS m/e 349(MH$^+$).

Example 200

[1-(3-Methoxy-phenyl)-5-methoxy-isoquinolin-3-yl]-(5-methyl-1H-pyrazol-3-yl)-amine

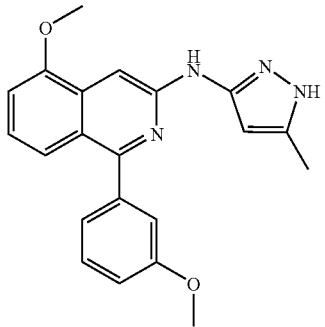

Similar procedure as described in example 131 was used, starting from (1-chloro-5-methoxy-isoquinolin-3-yl)-(5-methyl-1H-pyrazol-3-yl)-amine and 3-methoxy-phenylboronic acid to give [1-(3-methoxy-phenyl)-5-methoxy-isoquinolin-3-yl]-(5-methyl-1H-pyrazol-3-yl)-amine. LC-MS m/e 361(MH$^+$).

Example 201

3-[3-(5-Methyl-1H-pyrazol-3-ylamino)-5-methoxy-isoquinolin-1-yl]-benzonitrile

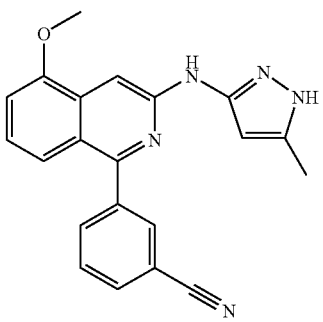

Similar procedure as described in example 131 was used, starting from (1-chloro-5-methoxy-isoquinolin-3-yl)-(5-methyl-1H-pyrazol-3-yl)-amine and 3-cyano-phenylboronic acid to give 3-[3-(5-methyl-1H-pyrazol-3-ylamino)-5-methoxy-isoquinolin-1-yl]-benzonitrile LC-MS m/e 356(MH$^+$).

Example 202

(5-Methoxy-1-phenyl-isoquinolin-3-yl)-(5-methyl-1H-pyrazol-3-yl)-amine

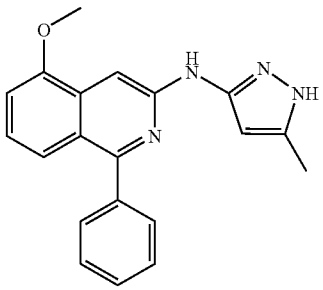

Similar procedure as described in example 131 was used, starting from (1-chloro-5-methoxy-isoquinolin-3-yl)-(5-methyl-1H-pyrazol-3-yl)-amine and phenylboronic acid to give (5-Methoxy-1-phenyl-isoquinolin-3-yl)-(5-methyl-1H-pyrazol-3-yl)-amine. LC-MS m/e 331(MH$^+$).

Example 203

(5-Methyl-1H-pyrazol-3-yl)-[1-(1-methyl-1H-pyrazol-4-yl)-7-methoxy-isoquinolin-3-yl]-amine

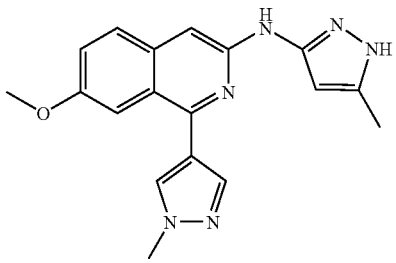

Similar procedure as described in example 131 was used, starting from (1-chloro-7-methoxy-isoquinolin-3-yl)-(5-methyl-1H-pyrazol-3-yl)-amine and N-methyl-pyrazole-4-boronic acid to give (5-methyl-1H-pyrazol-3-yl)-[1-(1H-pyrazol-4-yl)-7-methoxy-isoquinolin-3-yl]-amine. LC-MS m/e 335(MH+).

Example 204

(5-Methyl-1H-pyrazol-3-yl)-(1-pyridin-3-yl-7-methoxy-isoquinolin-3-yl)-amine

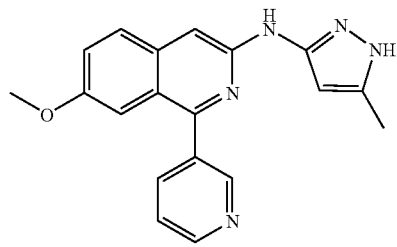

Similar procedure as described in example 131 was used, starting from (1-chloro-7-methoxy-isoquinolin-3-yl)-(5-methyl-1H-pyrazol-3-yl)-amine and 3-pyridine-boronic acid to give (5-methyl-1H-pyrazol-3-yl)-(1-pyridin-3-yl-7-methoxy-isoquinolin-3-yl)-amine. LC-MS m/e 332(MH+).

Example 205

(5-Methyl-1H-pyrazol-3-yl)-(1-thiophen-3-yl-7-methoxy-isoquinolin-3-yl)-amine

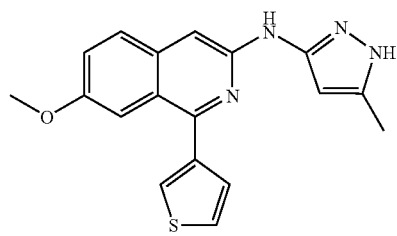

Similar procedure as described in example 131 was used, starting from (1-chloro-7-methoxy-isoquinolin-3-yl)-(5-methyl-1H-pyrazol-3-yl)-amine and thiophene-3-boronic acid to give (5-methyl-1H-pyrazol-3-yl)-(1-thiophen-3-yl-7-methoxy-isoquinolin-3-yl)-amine. LC-MS m/e 337(MH+).

Example 206

[1-(2-Fluoro-phenyl)-7-methoxy-isoquinolin-3-yl]-(5-methyl-1H-pyrazol-3-yl)-amine

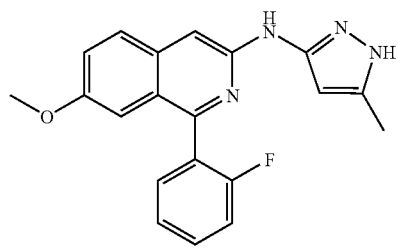

Similar procedure as described in example 131 was used, starting from (1-chloro-7-methoxy-isoquinolin-3-yl)-(5-methyl-1H-pyrazol-3-yl)-amine and 2-fluoro-phenylboronic acid to give [1-(2-fluoro-phenyl)-7-methoxy-isoquinolin-3-yl]-(5-methyl-1H-pyrazol-3-yl)-amine. LC-MS m/e 349(MH+).

Example 207

[1-(3-Methoxy-phenyl)-7-methoxy-isoquinolin-3-yl]-(5-methyl-1H-pyrazol-3-yl)-amine

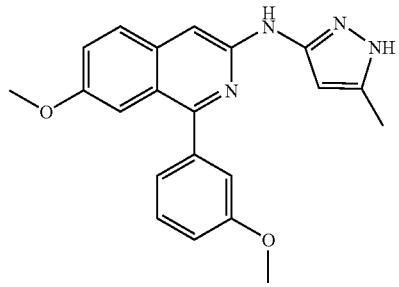

Similar procedure as described in example 131 was used, starting from (1-chloro-7-methoxy-isoquinolin-3-yl)-(5-methyl-1H-pyrazol-3-yl)-amine and 3-methoxy-phenylboronic acid to give [1-(3-methoxy-phenyl)-7-methoxy-isoquinolin-3-yl]-(5-methyl-1H-pyrazol-3-yl)-amine. LC-MS m/e 361(MH+).

Example 208

3-[3-(5-Methyl-1H-pyrazol-3-ylamino)-7-methoxy-isoquinolin-1-yl]-benzonitrile

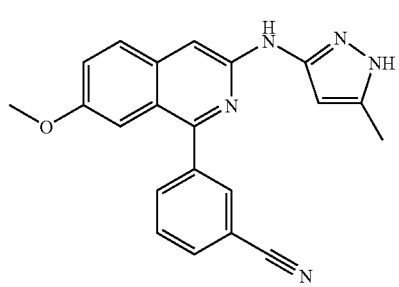

Similar procedure as described in example 131 was used, starting from (1-chloro-7-methoxy-isoquinolin-3-yl)-(5-methyl-1H-pyrazol-3-yl)-amine and 3-cyano-phenylboronic acid to give 3-[3-(5-methyl-1H-pyrazol-3-ylamino)-7-methoxy-isoquinolin-1-yl]-benzonitrile LC-MS m/e 356(MH+).

Example 209

(7-Methoxy-1-phenyl-isoquinolin-3-yl)-(5-methyl-1H-pyrazol-3-yl)-amine

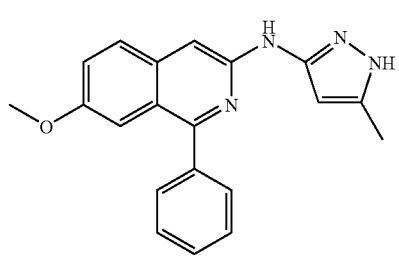

Similar procedure as described in example 131 was used, starting from (1-chloro-7-methoxy-isoquinolin-3-yl)-(5-methyl-1H-pyrazol-3-yl)-amine and phenylboronic acid to give (7-methoxy-1-phenyl-isoquinolin-3-yl)-(5-methyl-1H-pyrazol-3-yl)-amine. LC-MS m/e 331(MH+).

Example 210

[1-(2,4-Difluoro-phenyl)-5-methoxy-isoquinolin-3-yl]-(5-methyl-1H-pyrazol-3-yl)-amine

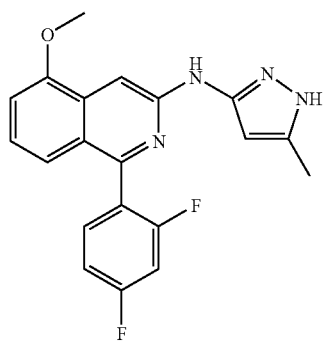

Similar procedure as described in example 131 was used, starting from (1-chloro-5-methoxy-isoquinolin-3-yl)-(5-methyl-1H-pyrazol-3-yl)-amine and 2,4-difluoro-phenylboronic acid to give [1-(2,4-difluoro-phenyl)-5-methoxy-isoquinolin-3-yl]-(5-methyl-1H-pyrazol-3-yl)-amine. LC-MS m/e 367(MH+).

Example 211

[1-(2,4-Difluoro-phenyl)-7-methoxy-isoquinolin-3-yl]-(5-methyl-1H-pyrazol-3-yl)-amine

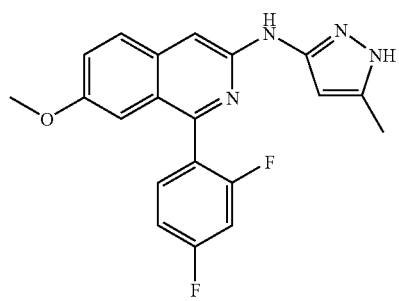

Similar procedure as described in example 131 was used, starting from (1-chloro-7-methoxy-isoquinolin-3-yl)-(5-methyl-1H-pyrazol-3-yl)-amine and 2,4-difluoro-phenylboronic acid to give [1-(2,4-difluoro-phenyl)-7-methoxy-isoquinolin-3-yl]-(5-methyl-1H-pyrazol-3-yl)-amine. LC-MS m/e 367(MH+).

Example 212

[1-(2-Fluoro-phenyl)-6,7-dimethoxy-isoquinolin-3-yl]-(5-methyl-1H-pyrazol-3-yl)-amine

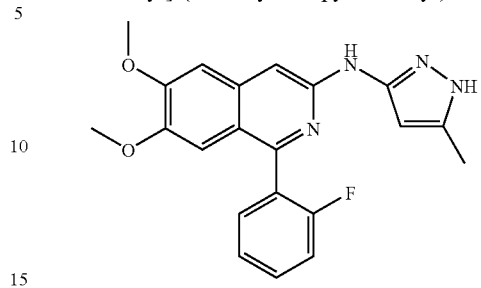

Similar procedure as described in example 131 was used, starting from (1-chloro-6,7-dimethoxy-isoquinolin-3-yl)-(5-methyl-1H-pyrazol-3-yl)-amine and 2-fluoro-phenylboronic acid to give [1-(2-fluoro-phenyl)-6,7-dimethoxy-isoquinolin-3-yl]-(5-methyl-1H-pyrazol-3-yl)-amine. LC-MS m/e 379(MH+).

Example 213

[1-(3-Methoxy-phenyl)-6,7-dimethoxy-isoquinolin-3-yl]-(5-methyl-1H-pyrazol-3-yl)-amine

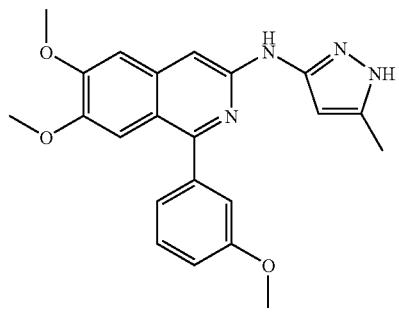

Similar procedure as described in example 131 was used, starting from (1-chloro-6,7-dimethoxy-isoquinolin-3-yl)-(5-methyl-1H-pyrazol-3-yl)-amine and 3-methoxy-phenylboronic acid to give [1-(3-Methoxy-phenyl)-6,7-dimethoxy-isoquinolin-3-yl]-(5-methyl-1H-pyrazol-3-yl)-amine. LC-MS m/e 391(MH+).

Example 214

(6,7-Dimethoxy-1-phenyl-isoquinolin-3-yl)-(5-methyl-1H-pyrazol-3-yl)-amine

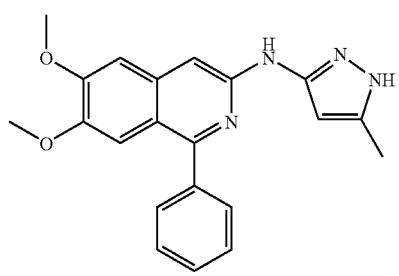

Similar procedure as described in example 131 was used, starting from (1-Chloro-6,7-dimethoxy-isoquinolin-3-yl)-(5-methyl-1H-pyrazol-3-yl)-amine and Phenylboronic acid to give (6,7-dimethoxy-1-phenyl-isoquinolin-3-yl)-(5-methyl-1H-pyrazol-3-yl)-amine. LC-MS m/e 361(MH⁺).

Example 215

[1-(2-Fluoro-phenyl)-5,6-dimethoxy-isoquinolin-3-yl]-(5-methyl-1H-pyrazol-3-yl)-amine

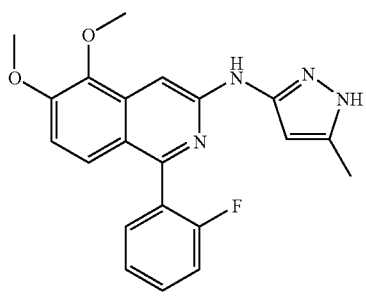

Similar procedure as described in example 131 was used, starting from (1-chloro-5,6-dimethoxy-isoquinolin-3-yl)-(5-methyl-1H-pyrazol-3-yl)-amine and 2-fluoro-phenylboronic acid to give [1-(2-fluoro-phenyl)-5,6-dimethoxy-isoquinolin-3-yl]-(5-methyl-1H-pyrazol-3-yl)-amine. LC-MS m/e 379(MH⁺).

Example 216

[1-(3-Methoxy-phenyl)-5,6-dimethoxy-isoquinolin-3-yl]-(5-methyl-1H-pyrazol-3-yl)-amine

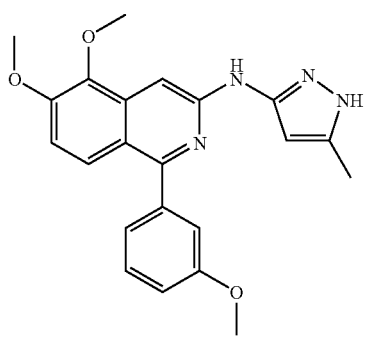

Similar procedure as described in example 131 was used, starting from (1-chloro-5,6-dimethoxy-isoquinolin-3-yl)-(5-methyl-1H-pyrazol-3-yl)-amine and 3-methoxy-phenylboronic acid to give [1-(3-methoxy-phenyl)-5,6-dimethoxy-isoquinolin-3-yl]-(5-methyl-1H-pyrazol-3-yl)-amine. LC-MS m/e 391(MH⁺).

Example 217

(5,6-Dimethoxy-1-phenyl-isoquinolin-3-yl)-(5-methyl-1H-pyrazol-3-yl)-amine

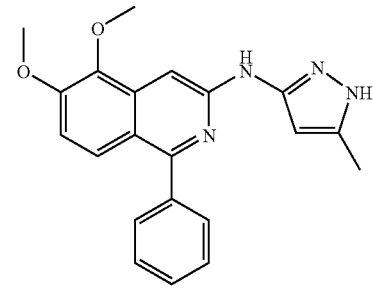

Similar procedure as described in example 131 was used, starting from (1-chloro-5,6-dimethoxy-isoquinolin-3-yl)-(5-methyl-1H-pyrazol-3-yl)-amine and phenylboronic acid to give (5,6-dimethoxy-1-phenyl-isoquinolin-3-yl)-(5-methyl-1H-pyrazol-3-yl)-amine. LC-MS m/e 361(MH⁺).

Example 218

(1-Phenyl-isoquinolin-3-yl)-(1H-pyrazol-3-yl)-amine

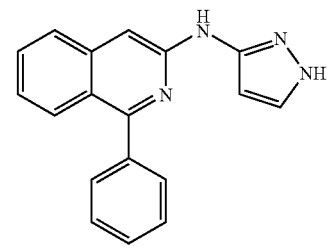

Similar procedure as described in example 131 was used, starting from (1-chloro-isoquinolin-3-yl)-(1H-pyrazol-3-yl)-amine and phenylboronic acid to give (1-phenyl-isoquinolin-3-yl)-(1H-pyrazol-3-yl)-amine. LC-MS m/e 287(MH⁺).

Example 219

[1-(2-Methoxy-phenyl)-isoquinolin-3-yl]-(1H-pyrazol-3-yl)-amine

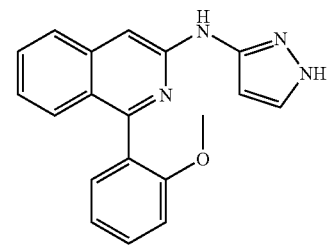

Similar procedure as described in example 131 was used, starting from (1-chloro-isoquinolin-3-yl)-(1H-pyrazol-3-yl)-amine and 2-methoxy-phenylboronic acid to give [1-(2-Methoxy-phenyl)-isoquinolin-3-yl]-(1H-pyrazol-3-yl)-amine. LC-MS m/e 317(MH⁺).

Example 220

(1H-Pyrazol-3-yl)-[1-(4-trifluoromethyl-phenyl)-isoquinolin-3-yl]-amine

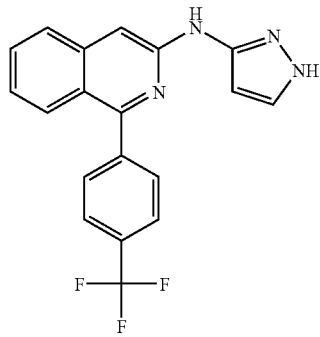

Similar procedure as described in example 131 was used, starting from (1-chloro-isoquinolin-3-yl)-(1H-pyrazol-3-yl)-amine and 4-trifluoromethyl-phenylboronic acid to give (1H-pyrazol-3-yl)-[1-(4-trifluoromethyl-phenyl)-isoquinolin-3-yl]-amine. LC-MS m/e 355(MH⁺).

Example 221

[1-(3-Fluoro-phenyl)-isoquinolin-3-yl]-(1H-pyrazol-3-yl)-amine

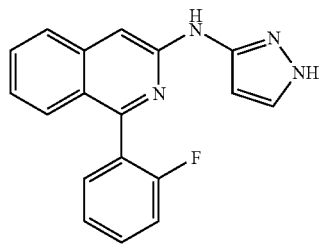

Similar procedure as described in example 131 was used, starting from (1-chloro-isoquinolin-3-yl)-(1H-pyrazol-3-yl)-amine and 3-fluoro-phenylboronic acid to give [1-(3-fluoro-phenyl)-isoquinolin-3-yl]-(1H-pyrazol-3-yl)-amine. LC-MS m/e 305(MH⁺).

Example 222

3-[3-(1H-Pyrazol-3-ylamino)-isoquinolin-1-yl]-benzoic acid ethyl ester

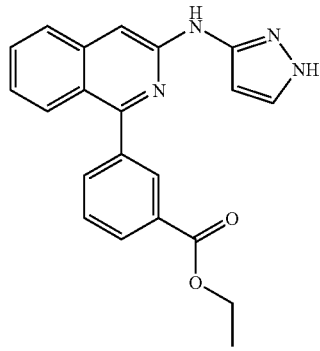

Similar procedure as described in example 131 was used, starting from (1-chloro-isoquinolin-3-yl)-(1H-pyrazol-3-yl)-amine and 3-ethoxycarbonyl-phenylboronic acid to give 3-[3-(1H-pyrazol-3-ylamino)-isoquinolin-1-yl]-benzoic acid ethyl ester. LC-MS m/e 359(MH⁺).

Example 223

[1-(4-Fluoro-phenyl)-isoquinolin-3-yl]-(1H-pyrazol-3-yl)-amine

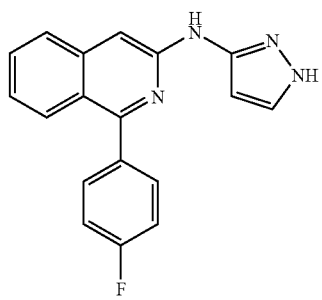

Similar procedure as described in example 131 was used, starting from (1-chloro-isoquinolin-3-yl)-(1H-pyrazol-3-yl)-amine and 4-fluoro-phenylboronic acid to give [1-(4-fluoro-phenyl)-isoquinolin-3-yl]-(1H-pyrazol-3-yl)-amine. LC-MS m/e 305(MH⁺).

Example 224

[1-(3-Methoxy-phenyl)-isoquinolin-3-yl]-(1H-pyrazol-3-yl)-amine

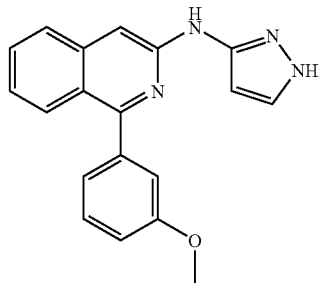

Similar procedure as described in example 131 was used, starting from (1-chloro-isoquinolin-3-yl)-(1H-pyrazol-3-yl)-amine and 3-methoxy-phenylboronic acid to give [1-(3-methoxy-phenyl)-soquinolin-3-yl]-(1H-pyrazol-3-yl)-amine. LC-MS m/e 317(MH⁺).

Example 225

4-[3-(1H-Pyrazol-3-ylamino)-isoquinolin-1-yl]-benzoic acid

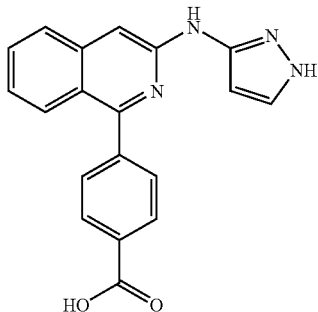

Similar procedure as described in example 131 was used, starting from (1-chloro-isoquinolin-3-yl)-(1H-pyrazol-3-yl)-amine and 4-ethoxycarbonyl-phenylboronic acid to give 4-[3-(1H-pyrazol-3-ylamino)-isoquinolin-1-yl]-benzoic acid. LC-MS m/e 331(MH$^+$).

Example 226

[1-(2-Fluoro-phenyl)-isoquinolin-3-yl]-(1H-pyrazol-3-yl)-amine

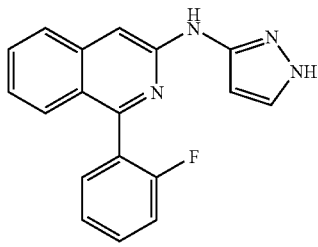

Similar procedure as described in example 131 was used, starting from (1-chloro-isoquinolin-3-yl)-(1H-pyrazol-3-yl)-amine and 2-fluoro-phenylboronic acid to give [1-(2-fluoro-phenyl)-isoquinolin-3-yl]-(1H-pyrazol-3-yl)-amine. LC-MS m/e 305(MH$^+$).

Example 227

[1-(3,4-Difluoro-phenyl)-isoquinolin-3-yl]-(1H-pyrazol-3-yl)-amine

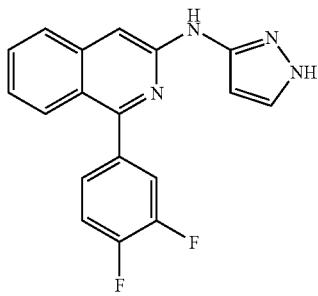

Similar procedure as described in example 131 was used, starting from (1-chloro-isoquinolin-3-yl)-(1H-pyrazol-3-yl)-amine and 3,4-difluoro-phenylboronic acid to give [1-(3,4-difluoro-phenyl)-isoquinolin-3-yl]-(1H-pyrazol-3-yl)-amine. LC-MS m/e 323(MH$^+$).

Example 228

[1-(2,4-Difluoro-phenyl)-isoquinolin-3-yl]-(1H-pyrazol-3-yl)-amine

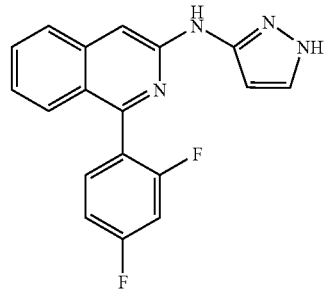

Similar procedure as described in example 131 was used, starting from (1-chloro-isoquinolin-3-yl)-(1H-pyrazol-3-yl)-amine and 2,4-difluoro-phenylboronic acid to give [1-(2,4-difluoro-phenyl)-isoquinolin-3-yl]-(1H-pyrazol-3-yl)-amine. LC-MS m/e 323(MH$^+$).

Example 229

(1H-Pyrazol-3-yl)-[1-(3-trifluoromethyl-phenyl)-isoquinolin-3-yl]-amine

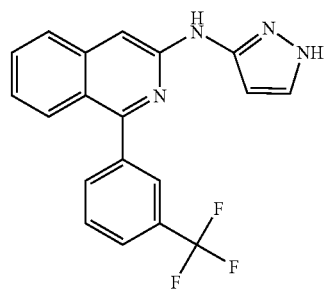

Similar procedure as described in example 131 was used, starting from (1-chloro-isoquinolin-3-yl)-(1H-pyrazol-3-yl)-amine and 4-trifluoromethyl-phenylboronic acid to give (1H-pyrazol-3-yl)-[1-(3-trifluoromethyl-phenyl)-isoquinolin-3-yl]-amine. LC-MS m/e 355(MH$^+$).

Example 230

(1-Naphthalen-2-yl-isoquinolin-3-yl)-(1H-pyrazol-3-yl)-amine

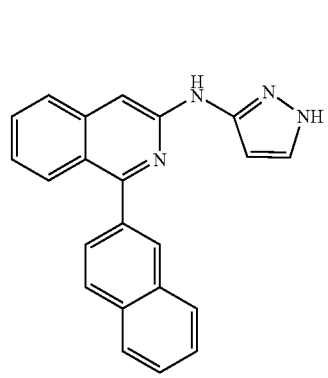

Similar procedure as described in example 131 was used, starting from (1-chloro-isoquinolin-3-yl)-(1H-pyrazol-3-yl)- amine and 2-naphthaleneboronic acid to give (1-naphthalen-2-yl-isoquinolin-3-yl)-(1H-pyrazol-3-yl)-amine. LC-MS m/e 337(MH+).

Example 231

3-[3-(1H-Pyrazol-3-ylamino)-isoquinolin-1-yl]-benzonitrile

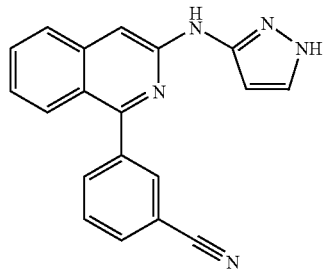

Similar procedure as described in example 131 was used, starting from (1-chloro-isoquinolin-3-yl)-(1H-pyrazol-3-yl)-amine and 3-cyano-phenylboronic acid to give 3-[3-(1H-pyrazol-3-ylamino)-isoquinolin-1-yl]-benzonitrile. LC-MS m/e 312(MH+).

Example 232

(1H-Pyrazol-3-yl)-(1-p-tolyl-isoquinolin-3-yl)-amine

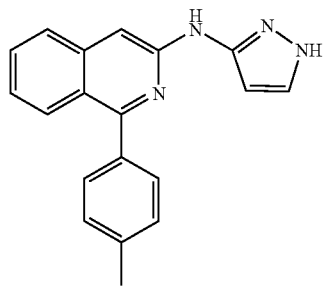

Similar procedure as described in example 131 was used, starting from (1-chloro-isoquinolin-3-yl)-(1H-pyrazol-3-yl)-amine and p-tolylboronic acid to give (1H-pyrazol-3-yl)-(1-p-tolyl-isoquinolin-3-yl)-amine. LC-MS m/e 301(MH+).

Example 233

(1H-Pyrazol-3-yl)-(1-m-tolyl-isoquinolin-3-yl)-amine

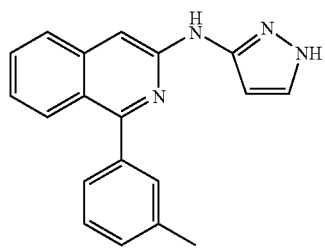

Similar procedure as described in example 131 was used, starting from (1-chloro-isoquinolin-3-yl)-(1H-pyrazol-3-yl)-amine and m-tolylboronic acid to give (1H-pyrazol-3-yl)-(1-m-tolyl-isoquinolin-3-yl)-amine. LC-MS m/e 301(MH+).

Example 234

[1-(4-tert-Butyl-phenyl)-isoquinolin-3-yl]-(1H-pyrazol-3-yl)-amine

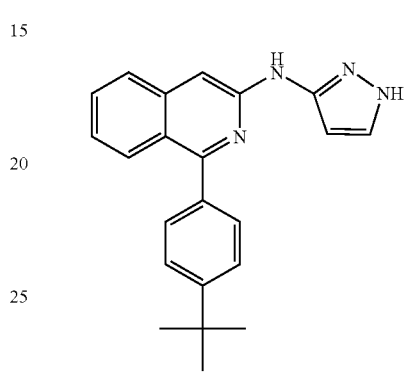

Similar procedure as described in example 131 was used, starting from (1-chloro-isoquinolin-3-yl)-(1H-pyrazol-3-yl)-amine and 4-tert-butylphenylboronic acid to give [1-(4-tert-butyl-phenyl)-isoquinolin-3-yl]-(1H-pyrazol-3-yl)-amine. LC-MS m/e 343(MH+).

Example 235

1-{4-[3-(1H-Pyrazol-3-ylamino)-isoquinolin-1-yl]-phenyl}-ethanone

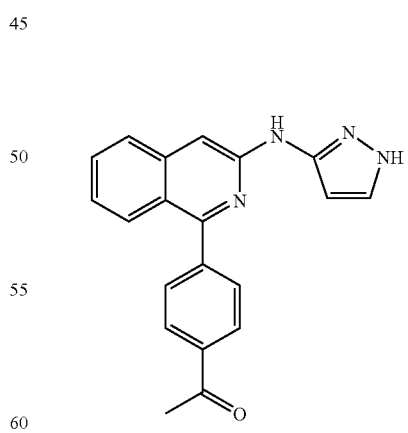

Similar procedure as described in example 131 was used, starting from (1-chloro-isoquinolin-3-yl)-(1H-pyrazol-3-yl)-amine and 4-acetyl-phenylboronic acid to give 1-{4-[3-(1H-pyrazol-3-ylamino)-isoquinolin-1-yl]-phenyl}-ethanone. LC-MS m/e 329(MH+).

Example 236

1-{3-[3-(1H-Pyrazol-3-ylamino)-isoquinolin-1-yl]-phenyl}-ethanone

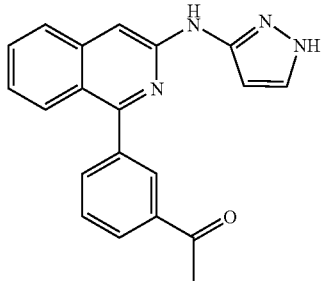

Similar procedure as described in example 131 was used, starting from (1-chloro-isoquinolin-3-yl)-(1H-pyrazol-3-yl)-amine and 3-acetyl-phenylboronic acid to give 1-{3-[3-(1H-Pyrazol-3-ylamino)-isoquinolin-1-yl]-phenyl}-ethanone. LC-MS m/e 329(MH$^+$).

Example 237

[1-(4-Methyl-thiophen-3-yl)-isoquinolin-3-yl]-(1H-pyrazol-3-yl)-amine

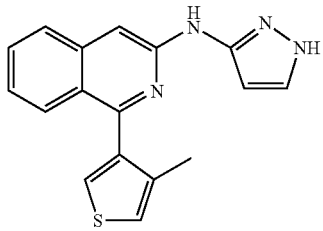

Similar procedure as described in example 131 was used, starting from (1-chloro-isoquinolin-3-yl)-(1H-pyrazol-3-yl)-amine and 4-methyl-3-thiopheneboronic acid to give [1-(4-methyl-thiophen-3-yl)-isoquinolin-3-yl]-(1H-pyrazol-3-yl)-amine. LC-MS m/e 307(MH$^+$).

Example 238

[1-(4-Chloro-phenyl)-isoquinolin-3-yl]-(1H-pyrazol-3-yl)-amine

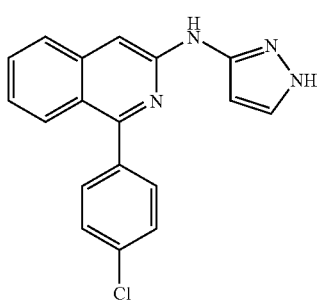

Similar procedure as described in example 131 was used, starting from (1-chloro-isoquinolin-3-yl)-(1H-pyrazol-3-yl)-amine and 4-chloro-phenylboronic acid to give [1-(4-chloro-phenyl)-isoquinolin-3-yl]-(1H-pyrazol-3-yl)-amine. LC-MS m/e 321(MH$^+$).

Example 239

[1-(3,4-Dimethoxy-phenyl)-isoquinolin-3-yl]-(1H-pyrazol-3-yl)-amine

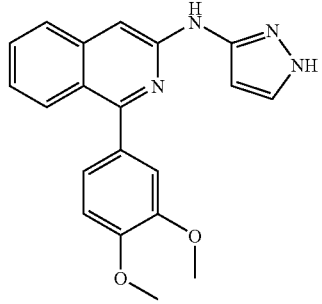

Similar procedure as described in example 131 was used, starting from (1-chloro-isoquinolin-3-yl)-(1H-pyrazol-3-yl)-amine and 3,4-dimethoxy-phenylboronic acid to give [1-(3,4-dimethoxy-phenyl)-isoquinolin-3-yl]-(1H-pyrazol-3-yl)-amine. LC-MS m/e 347(MH$^+$).

Example 240

(1-Benzo[b]thiophen-3-yl-isoquinolin-3-yl)-(1H-pyrazol-3-yl)-amine

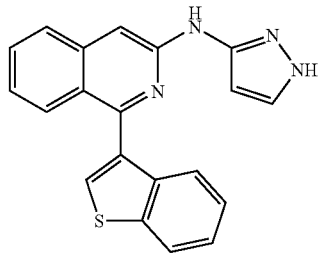

Similar procedure as described in example 131 was used, starting from (1-chloro-isoquinolin-3-yl)-(1H-pyrazol-3-yl)-amine and thianaphthene-3-boronic acid to give (1-benzo[b]thiophen-3-yl-isoquinolin-3-yl)-(1H-pyrazol-3-yl)-amine. LC-MS m/e 343(MH$^+$).

Example 241

(1H-Pyrazol-3-yl)-(1-thiophen-3-yl-isoquinolin-3-yl)-amine

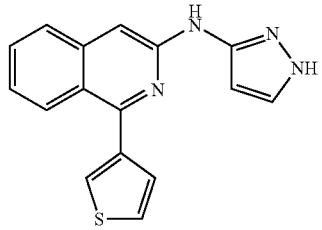

Similar procedure as described in example 131 was used, starting from (1-chloro-isoquinolin-3-yl)-(1H-pyrazol-3-yl)-amine and 3-thiophene boronic acid to give (1H-pyrazol-3-yl)-(1-thiophen-3-yl-isoquinolin-3-yl)-amine. LC-MS m/e 293(MH$^+$).

Example 242

[1-(4-Ethoxy-phenyl)-isoquinolin-3-yl]-(1H-pyrazol-3-yl)-amine

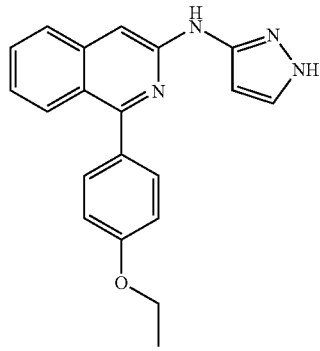

Similar procedure as described in example 131 was used, starting from (1-chloro-isoquinolin-3-yl)-(1H-pyrazol-3-yl)-amine and 4-ethoxy-phenylboronic acid to give [1-(4-ethoxy-phenyl)-isoquinolin-3-yl]-(1H-pyrazol-3-yl)-amine. LC-MS m/e 331(MH$^+$).

Example 243

4-[3-(1H-Pyrazol-3-ylamino)-isoquinolin-1-yl]-benzonitrile

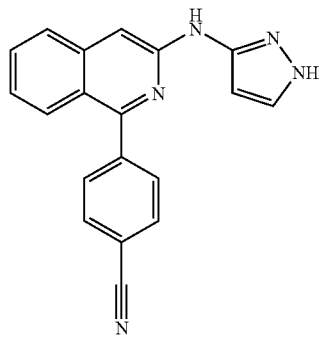

Similar procedure as described in example 131 was used, starting from (1-chloro-isoquinolin-3-yl)-(1H-pyrazol-3-yl)-amine and 4-cyano-phenylboronic acid to give 4-[3-(1H-pyrazol-3-ylamino)-isoquinolin-1-yl]-benzonitrile. LC-MS m/e 312(MH$^+$).

Example 244

N-{4-[3-(1H-Pyrazol-3-ylamino)-isoquinolin-1-yl]-phenyl}-acetamide

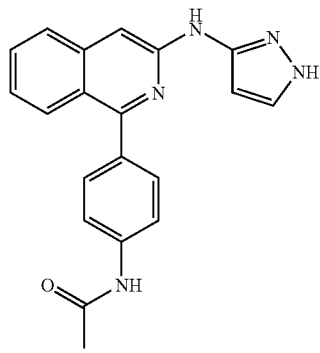

Similar procedure as described in example 131 was used, starting from (1-chloro-isoquinolin-3-yl)-(1H-pyrazol-3-yl)-amine and 4-acetamide-phenylboronic acid to give N-{4-[3-(1H-pyrazol-3-ylamino)-isoquinolin-1-yl]-phenyl}-acetamide. LC-MS m/e 344(MH$^+$).

Example 245

(1H-Pyrazol-3-yl)-[1-(1H-pyrazol-4-yl)-isoquinolin-3-yl]-amine

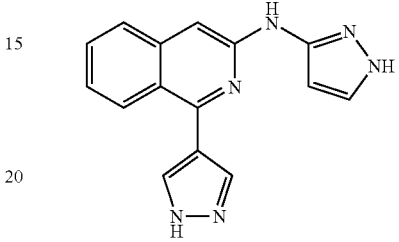

Similar procedure as described in example 131 was used, starting from (1-chloro-isoquinolin-3-yl)-(1H-pyrazol-3-yl)-amine and 4-(4,4,5,5-tetramethyl-[1,3,2]dioxaborolan-2-yl)-1H-pyrazole to give (1H-pyrazol-3-yl)-[1-(1H-pyrazol-4-yl)-isoquinolin-3-yl]-amine. LC-MS m/e 277(MH$^+$).

Example 246

[1-(1-Methyl-1H-pyrazol-4-yl)-isoquinolin-3-yl]-(1H-pyrazol-3-yl)-amine

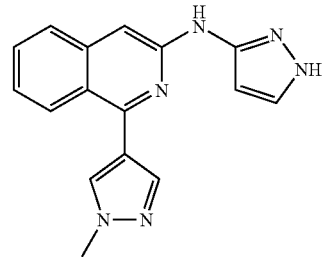

Similar procedure as described in example 131 was used, starting from (1-chloro-isoquinolin-3-yl)-(1H-pyrazol-3-yl)-amine and 1-methyl-4-(4,4,5,5-tetramethyl-[1,3,2]dioxaborolan-2-yl)-1H-pyrazole to give [1-(1-methyl-1H-pyrazol-4-yl)-isoquinolin-3-yl]-(1H-pyrazol-3-yl)-amine. LC-MS m/e 291(MH$^+$).

Example 247

(1H-Pyrazol-3-yl)-(1-pyridin-3-yl-isoquinolin-3-yl)-amine

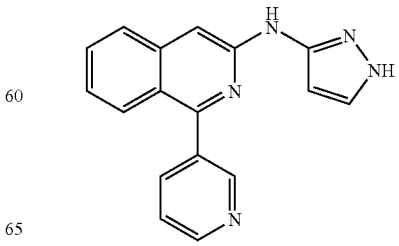

Similar procedure as described in example 131 was used, starting from (1-chloro-isoquinolin-3-yl)-(1H-pyrazol-3-yl)-amine and 3-pyridinylboronic acid to give (1H-pyrazol-3-yl)-(1-pyridin-3-yl-isoquinolin-3-yl)-amine. LC-MS m/e 288(MH+).

Example 248

(1H-Pyrazol-3-yl)-(1-pyridin-4-yl-isoquinolin-3-yl)-amine

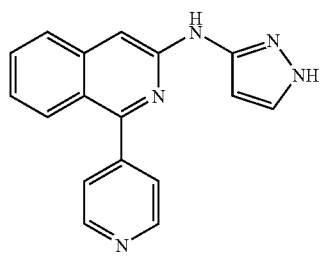

Similar procedure as described in example 131 was used, starting from (1-chloro-isoquinolin-3-yl)-(1H-pyrazol-3-yl)-amine and 4-pyridinylboronic acid to give ((1H-pyrazol-3-yl)-(1-pyridin-4-yl-isoquinolin-3-yl)-amine. LC-MS m/e 288(MH+).

Example 249

(6-Methoxy-1-phenyl-isoquinolin-3-yl)-(1H-pyrazol-3-yl)-amine

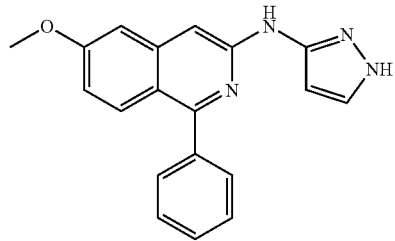

Similar procedure as described in example 131 was used, starting from (1-chloro-6-methoxy-isoquinolin-3-yl)-(1H-pyrazol-3-yl)-amine and phenylboronic acid to give (6-methoxy-1-phenyl-isoquinolin-3-yl)-(1H-pyrazol-3-yl)-amine. LC-MS m/e 317(MH+).

Example 250

[1-(4-Fluoro-phenyl)-6-methoxy-isoquinolin-3-yl]-(1H-pyrazol-3-yl)-amine

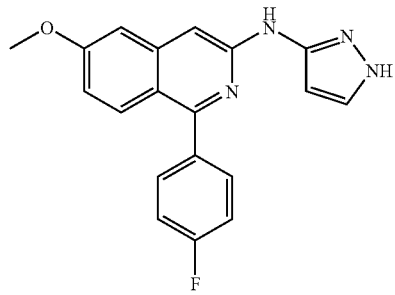

Similar procedure as described in example 131 was used, starting from (1-chloro-6-methoxy-isoquinolin-3-yl)-(1H-pyrazol-3-yl)-amine and 4-fluoro-phenylboronic acid to give [1-(4-fluoro-phenyl)-6-methoxy-isoquinolin-3-yl]-(1H-pyrazol-3-yl)-amine. LC-MS m/e 335(MH+).

Example 251

1-{3-[6-Methoxy-3-(1H-pyrazol-3-ylamino)-isoquinolin-1-yl]-phenyl}-ethanone

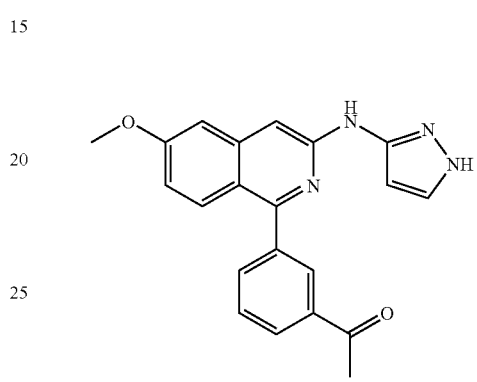

Similar procedure as described in example 131 was used, starting from (1-chloro-6-methoxy-isoquinolin-3-yl)-(1H-pyrazol-3-yl)-amine and 3-acetyl-phenylboronic acid to give 1-{3-[6-methoxy-3-(1H-pyrazol-3-ylamino)-isoquinolin-1-yl]-phenyl}-ethanone. LC-MS m/e 359(MH+).

Example 252

1-{4-[6-Methoxy-3-(1H-pyrazol-3-ylamino)-isoquinolin-1-yl]-phenyl}-ethanone

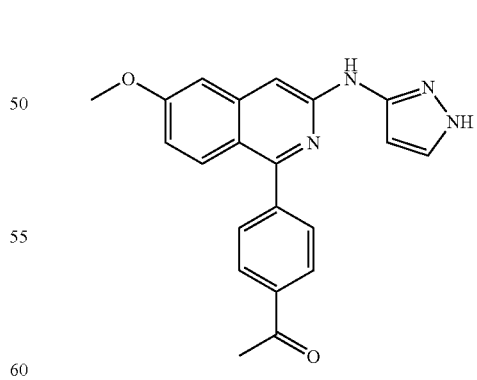

Similar procedure as described in example 131 was used, starting from (1-chloro-6-methoxy-isoquinolin-3-yl)-(1H-pyrazol-3-yl)-amine and 4-acetyl-phenylboronic acid to give 1-{4-[6-methoxy-3-(1H-pyrazol-3-ylamino)-isoquinolin-1-yl]-phenyl}-ethanone. LC-MS m/e 359(MH+).

Example 253

[1-(2-Fluoro-phenyl)-6-methoxy-isoquinolin-3-yl]-(1H-pyrazol-3-yl)-amine

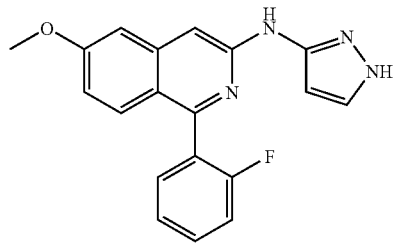

Similar procedure as described in example 131 was used, starting from (1-chloro-6-methoxy-isoquinolin-3-yl)-(1H-pyrazol-3-yl)-amine and 2-fluoro-phenylboronic acid to give [1-(2-fluoro-phenyl)-6-methoxy-isoquinolin-3-yl]-(1H-pyrazol-3-yl)-amine. LC-MS m/e 335(MH+).

Example 254

[6-Methoxy-1-(3-methoxy-phenyl)-isoquinolin-3-yl]-(1H-pyrazol-3-yl)-amine

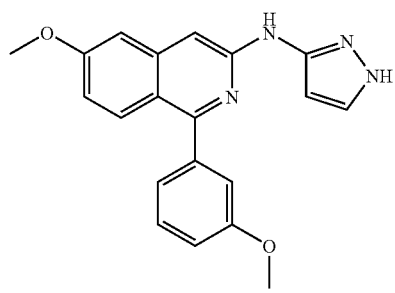

Similar procedure as described in example 131 was used, starting from (1-chloro-6-methoxy-isoquinolin-3-yl)-(1H-pyrazol-3-yl)-amine and 3-methoxy-phenylboronic acid to give [6-methoxy-1-(3-methoxy-phenyl)-isoquinolin-3-yl]-(1H-pyrazol-3-yl)-amine. LC-MS m/e 347(MH+).

Example 255

[6-Methoxy-1-(4-trifluoromethyl-phenyl)-isoquinolin-3-yl]-(1H-pyrazol-3-yl)-amine

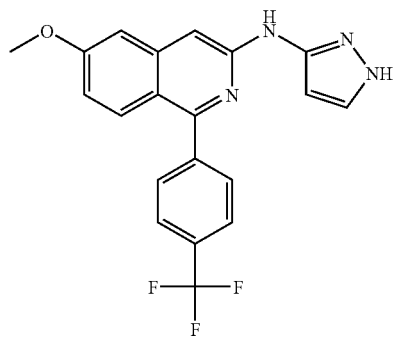

Similar procedure as described in example 131 was used, starting from (1-chloro-6-methoxy-isoquinolin-3-yl)-(1H-pyrazol-3-yl)-amine and 4-trifluoromethyl-phenylboronic acid to give [6-methoxy-1-(4-trifluoromethyl-phenyl)-isoquinolin-3-yl]-(1H-pyrazol-3-yl)-amine. LC-MS m/e 385(MH+).

Example 256

[1-(4-Chloro-phenyl)-6-methoxy-isoquinolin-3-yl]-(1H-pyrazol-3-yl)-amine

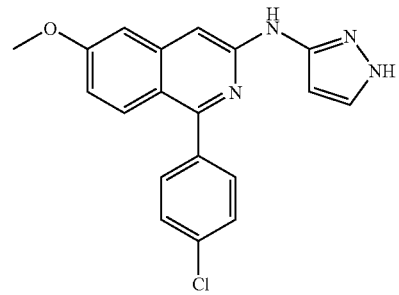

Similar procedure as described in example 131 was used, starting from (1-chloro-6-methoxy-isoquinolin-3-yl)-(1H-pyrazol-3-yl)-amine and 4-chloro-phenylboronic acid to give [1-(4-Chloro-phenyl)-6-methoxy-isoquinolin-3-yl]-(1H-pyrazol-3-yl)-amine. LC-MS m/e 351(MH+).

Example 257

4-[6-Methoxy-3-(1H-pyrazol-3-ylamino)-isoquinolin-1-yl]-benzonitrile

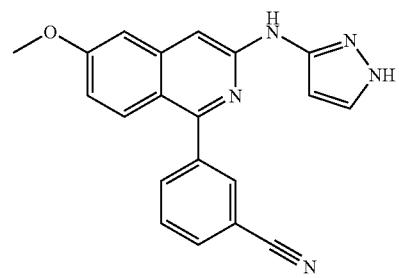

Similar procedure as described in example 131 was used, starting from (1-chloro-6-methoxy-isoquinolin-3-yl)-(1H-pyrazol-3-yl)-amine and 3-cyano phenylboronic acid to give 3-[6-methoxy-3-(1H-pyrazol-3-ylamino)-isoquinolin-1-yl]-benzonitrile. LC-MS m/e 342(MH+).

Example 258

[6-Methoxy-1-(3-trifluoromethyl-phenyl)-isoquinolin-3-yl]-(1H-pyrazol-3-yl)-amine

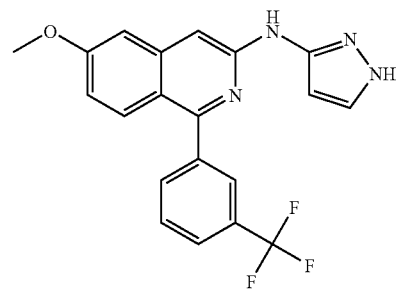

Similar procedure as described in example 131 was used, starting from (1-chloro-6-methoxy-isoquinolin-3-yl)-(1H-pyrazol-3-yl)-amine and 3-trifluoromethyl-phenylboronic acid to give [6-methoxy-1-(3-trifluoromethyl-phenyl)-isoquinolin-3-yl]-(1H-pyrazol-3-yl)-amine. LC-MS m/e 385(MH+).

Example 259

[1-(2,4-Difluoro-phenyl)-6-methoxy-isoquinolin-3-yl]-(1H-pyrazol-3-yl)-amine

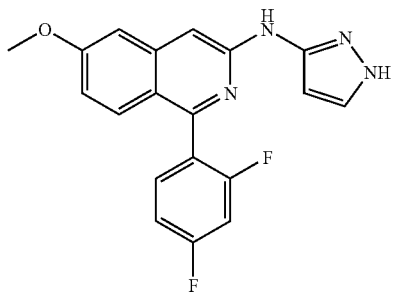

Similar procedure as described in example 131 was used, starting from (1-chloro-6-methoxy-isoquinolin-3-yl)-(1H-pyrazol-3-yl)-amine and 2,4-difluoro-phenylboronic acid to give [1-(2,4-difluoro-phenyl)-6-methoxy-isoquinolin-3-yl]-(1H-pyrazol-3-yl)-amine. LC-MS m/e 353(MH$^+$).

Example 260

[1-(3,4-Difluoro-phenyl)-6-methoxy-isoquinolin-3-yl]-(1H-pyrazol-3-yl)-amine

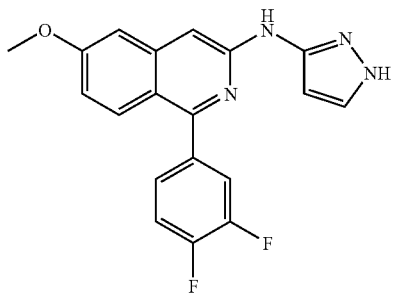

Similar procedure as described in example 131 was used, starting from (1-chloro-6-methoxy-isoquinolin-3-yl)-(1H-pyrazol-3-yl)-amine and 3,4-difluoro-phenylboronic acid to give [1-(3,4-difluoro-phenyl)-6-methoxy-isoquinolin-3-yl]-(1H-pyrazol-3-yl)-amine. LC-MS m/e 353(MH$^+$).

Example 261

[1-(3,5-Difluoro-phenyl)-6-methoxy-isoquinolin-3-yl]-(1H-pyrazol-3-yl)-amine

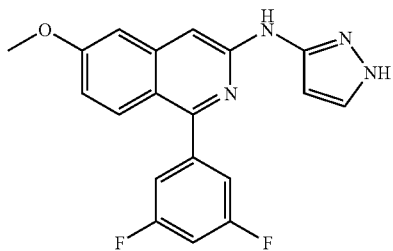

Similar procedure as described in example 131 was used, starting from (1-chloro-6-methoxy-isoquinolin-3-yl)-(1H-pyrazol-3-yl)-amine and 3,5-difluoro-phenylboronic acid to give [1-(3,5-difluoro-phenyl)-6-methoxy-isoquinolin-3-yl]-(1H-pyrazol-3-yl)-amine. LC-MS m/e 353(MH$^+$).

Example 262

[6-Methoxy-1-(2-methoxy-phenyl)-isoquinolin-3-yl]-(1H-pyrazol-3-yl)-amine

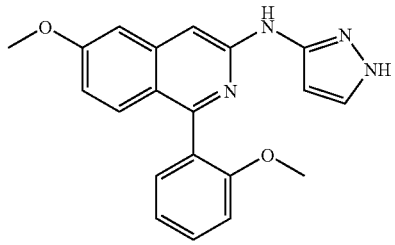

Similar procedure as described in example 131 was used, starting from (1-chloro-6-methoxy-isoquinolin-3-yl)-(1H-pyrazol-3-yl)-amine and 2-methoxy-phenylboronic acid to give [6-methoxy-1-(2-methoxy-phenyl)-isoquinolin-3-yl]-(1H-pyrazol-3-yl)-amine. LC-MS m/e 347(MH$^+$).

Example 263

(6-Methoxy-1-p-tolyl-isoquinolin-3-yl)-(1H-pyrazol-3-yl)-amine

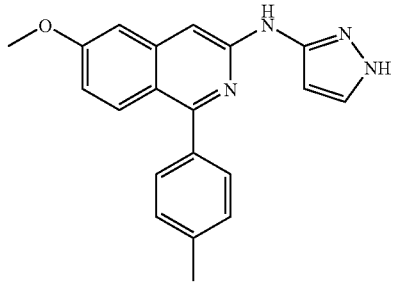

Similar procedure as described in example 131 was used, starting from (1-chloro-6-methoxy-isoquinolin-3-yl)-(1H-pyrazol-3-yl)-amine and p-tolylboronic acid to give (6-methoxy-1-p-tolyl-isoquinolin-3-yl)-(1H-pyrazol-3-yl)-amine. LC-MS m/e 331 (MH$^+$).

Example 264

[1-(3-Fluoro-phenyl)-6-methoxy-isoquinolin-3-yl]-(1H-pyrazol-3-yl)-amine

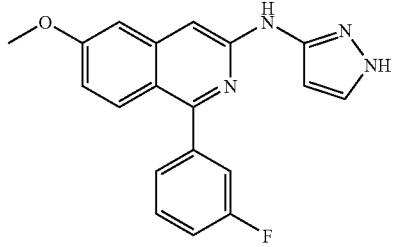

Similar procedure as described in example 131 was used, starting from (1-chloro-6-methoxy-isoquinolin-3-yl)-(1H-pyrazol-3-yl)-amine and 3-fluoro-phenylboronic acid to give [1-(3-fluoro-phenyl)-6-methoxy-isoquinolin-3-yl]-(1H-pyrazol-3-yl)-amine. LC-MS m/e 335(MH$^+$).

Example 265

(6-Methoxy-1-naphthalen-2-yl-isoquinolin-3-yl)-(1H-pyrazol-3-yl)-amine

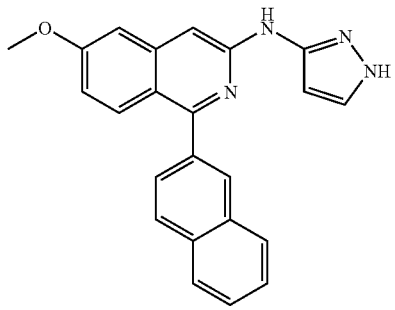

Similar procedure as described in example 131 was used, starting from (1-chloro-6-methoxy-isoquinolin-3-yl)-(1H-pyrazol-3-yl)-amine and 2-naphthaleneboronic acid to give (6-methoxy-1-naphthalen-2-yl-isoquinolin-3-yl)-(1H-pyrazol-3-yl)-amine. LC-MS m/e 367(MH$^+$).

Example 266

[1-(4-Ethoxy-phenyl)-6-methoxy-isoquinolin-3-yl]-(1H-pyrazol-3-yl)-amine

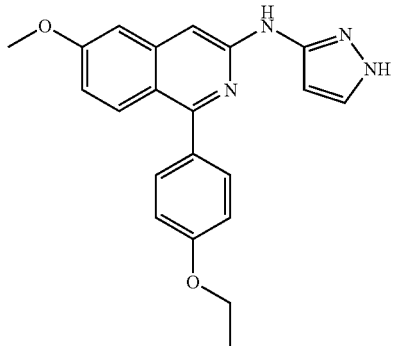

Similar procedure as described in example 131 was used, starting from (1-chloro-6-methoxy-isoquinolin-3-yl)-(1H-pyrazol-3-yl)-amine and 4-ethoxy-phenylboronic acid to give [1-(4-ethoxy-phenyl)-6-methoxy-isoquinolin-3-yl]-(1H-pyrazol-3-yl)-amine. LC-MS m/e 361(MH$^+$).

Example 267

(6-Methoxy-1-m-tolyl-isoquinolin-3-yl)-(1H-pyrazol-3-yl)-amine

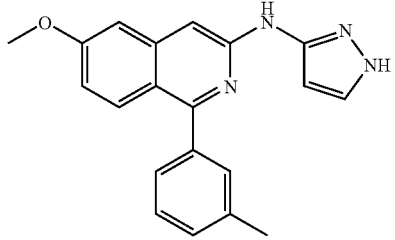

Similar procedure as described in example 131 was used, starting from (1-chloro-6-methoxy-isoquinolin-3-yl)-(1H-pyrazol-3-yl)-amine and m-tolylboronic acid to give (6-methoxy-1-m-tolyl-isoquinolin-3-yl)-(1H-pyrazol-3-yl)-amine. LC-MS m/e 331 (MH$^+$).

Example 268

[1-(3,4-Dimethoxy-phenyl)-6-methoxy-isoquinolin-3-yl]-(1H-pyrazol-3-yl)-amine

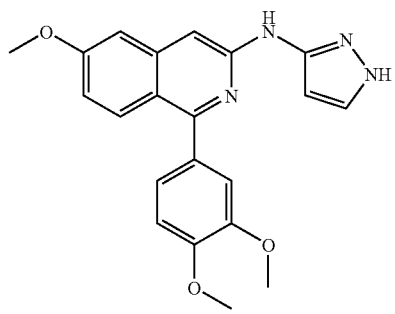

Similar procedure as described in example 131 was used, starting from (1-chloro-6-methoxy-isoquinolin-3-yl)-(1H-pyrazol-3-yl)-amine and 3,4-dimethoxy-phenylboronic acid to give [1-(3,4-dimethoxy-phenyl)-6-methoxy-isoquinolin-3-yl]-(1H-pyrazol-3-yl)-amine. LC-MS m/e 377(MH$^+$).

Example 269

N-{4-[6-Methoxy-3-(1H-pyrazol-3-ylamino)-isoquinolin-1-yl]-phenyl}-acetamide

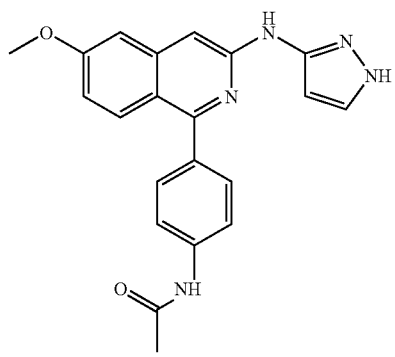

Similar procedure as described in example 131 was used, starting from (1-chloro-6-methoxy-isoquinolin-3-yl)-(1H-pyrazol-3-yl)-amine and 4-acetamide-phenylboronic acid to give N-{4-[6-methoxy-3-(1H-pyrazol-3-ylamino)-isoquinolin-1-yl]-phenyl}-acetamide. LC-MS m/e 373(MH$^+$).

Example 270

(6-Methoxy-1-thiophen-3-yl-isoquinolin-3-yl)-(1H-pyrazol-3-yl)-amine

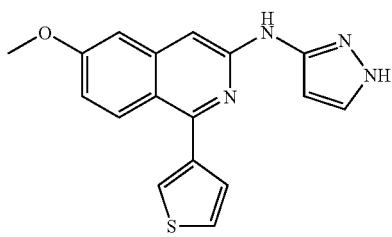

Similar procedure as described in example 131 was used, starting from (1-chloro-6-methoxy-isoquinolin-3-yl)-(1H-pyrazol-3-yl)-amine and 3-thiophene boronic acid to give (6-methoxy-1-thiophen-3-yl-isoquinolin-3-yl)-(1H-pyrazol-3-yl)-amine. LC-MS m/e 323(MH$^+$).

Example 271

[6-Methoxy-1-(4-methyl-thiophen-3-yl)-isoquinolin-3-yl]-(1H-pyrazol-3-yl)-amine

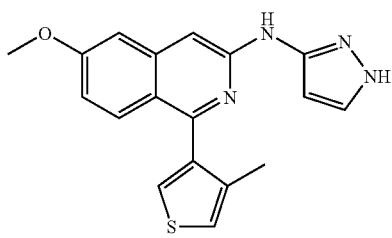

Similar procedure as described in example 131 was used, starting from (1-chloro-6-methoxy-isoquinolin-3-yl)-(1H-pyrazol-3-yl)-amine and 4-methyl-3-thiopheneboronic acid to give [6-methoxy-1-(4-methyl-thiophen-3-yl)-isoquinolin-3-yl]-(1H-pyrazol-3-yl)-amine. LC-MS m/e 337(MH$^+$).

Example 272

(1-Benzo[b]thiophen-3-yl-6-methoxy-isoquinolin-3-yl)-(1H-pyrazol-3-yl)-amine

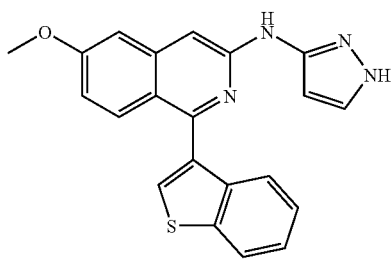

Similar procedure as described in example 131 was used, starting from (1-chloro-6-methoxy-isoquinolin-3-yl)-(1H-pyrazol-3-yl)-amine and thianaphthene-3-boronic acid to give (1-benzo[b]thiophen-3-yl-6-methoxy-isoquinolin-3-yl)-(1H-pyrazol-3-yl)-amine. LC-MS m/e 373(MH$^+$).

Example 273

4-[6-Methoxy-3-(5-methyl-1H-pyrazol-3-ylamino)-isoquinolin-1-ylamino]-benzonitrile

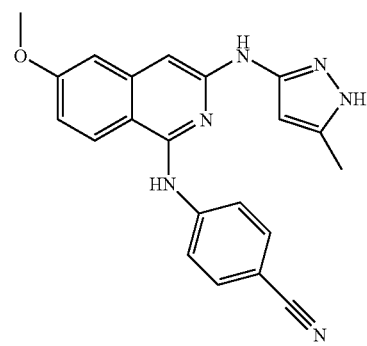

(1-chloro-6-methoxy-isoquinolin-3-yl)-(5-methyl-1H-pyrazol-3-yl)-amine (100 mg), 4-amino-benzonitrile (85 mg), Cs$_2$CO$_3$ (376 mg), 2,2'-Bis(diphenylphosphino)-1'1-binaphthyl (BINAP) (44 mg), Pd(OAc)$_2$ (8 mg), 1,4-dioxane (2 ml), N-methyl-pyrrolidone (NMP) (0.2 ml), were placed in a microwave bottle. The mixture was heated at 150° C. for 30 minutes under microwave irradiation and purified by preparative LC-MS to give 4-[6-methoxy-3-(5-methyl-1H-pyrazol-3-ylamino)-isoquinolin-1-ylamino]-benzonitrile. LC-MS m/e 371 (MH$^+$). $^1$H NMR(DMSO): δ 2.26(s, 3H), δ 3.86(s, 3H), δ 5.75(s, 1H), δ 6.52(m, 1H), δ 6.79(d, 1H), δ 7.12(s, 1H), δ 7.65(d, 2H), δ 8.20(m, 3H), δ 8.65(s,1H), δ 9.30(s, 1H), δ 11.75(s,1H).

Example 274

4-[3-(5-Methyl-1H-pyrazol-3-ylamino)-isoquinolin-1-ylamino]-benzonitrile

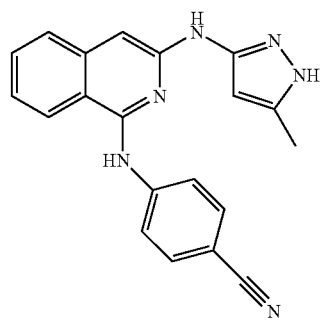

Similar procedure as described in example 273 was used, starting from (1-chloro-isoquinolin-3-yl)-(5-methyl-1H-pyrazol-3-yl)-amine and 4-amino-benzonitrile to give 4-[3-(5-methyl-1H-pyrazol-3-ylamino)-isoquinolin-1-ylamino]-benzonitrile. LC-MS m/e 341(MH$^+$). $^1$H NMR(DMSO): δ 2.26(s, 3H), δ 5.82(s, 1H), δ 6.52(m, 1H), δ 7.25(t, 1H), δ 7.35(br, 1H), δ 7.55(m, 2H), δ 7.71(d, 2H), δ 8.22(d,2H), δ 8.32(d, 1H), δ 8.79(s, 1H), δ 9.47(s,1H), δ 11.75(s, 1H).

Example 275

N¹-(4-Bromo-phenyl)-6-methoxy-N³-(5-methyl-1H-pyrazol-3-yl)-isoquinoline-1,3-diamine

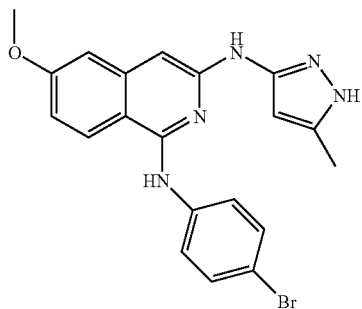

Similar procedure as described in example 273 was used, starting from (1-chloro-6-methoxy-isoquinolin-3-yl)-(5-methyl-1H-pyrazol-3-yl)-amine and 4-bromo-phenylamine to give N¹-(4-bromo-phenyl)-6-methoxy-N³-(5-methyl-1H-pyrazol-3-yl)-isoquinoline-1,3-diamine. LC-MS m/e 424(MH⁺).

Example 276

N¹-(4-Chloro-phenyl)-6-methoxy-N³-(5-methyl-1H-pyrazol-3-yl)-isoquinoline-1,3-diamine

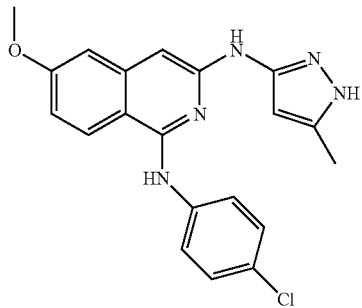

Similar procedure as described in example 273 was used, starting from (1-chloro-6-methoxy-isoquinolin-3-yl)-(5-methyl-1H-pyrazol-3-yl)-amine and 4-chloro-phenylamine to give N¹-(4-chloro-phenyl)-6-methoxy-N³-(5-methyl-1H-pyrazol-3-yl)-isoquinoline-1,3-diamine. LC-MS m/e 381(MH⁺).

Example 277

N¹-(4-Fluoro-phenyl)-6-methoxy-N³-(5-methyl-1H-pyrazol-3-yl)-isoquinoline-1,3-diamine

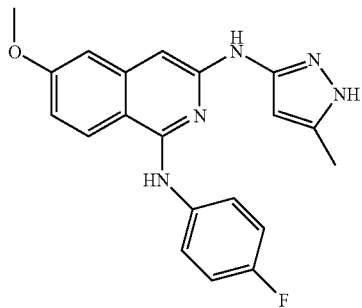

Similar procedure as described in example 273 was used, starting from (1-chloro-6-methoxy-isoquinolin-3-yl)-(5-methyl-1H-pyrazol-3-yl)-amine and 4-fluoro-phenylamine to give N¹-(4-fluoro-phenyl)-6-methoxy-N³-(5-methyl-1H-pyrazol-3-yl)-isoquinoline-1,3-diamine. LC-MS m/e 364(MH⁺).

Example 278

4-[6,7-Dimethoxy-3-(5-methyl-1H-pyrazol-3-ylamino)-isoquinolin-1-ylamino]-benzonitrile

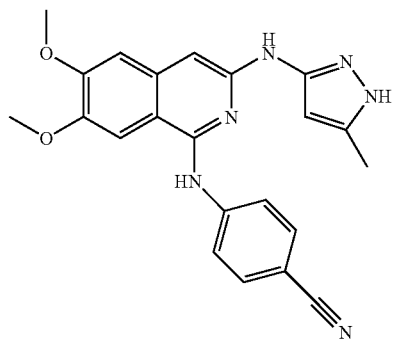

Similar procedure as described in example 273 was used, starting from (1-chloro-6,7-dimethoxy-isoquinolin-3-yl)-(5-methyl-1H-pyrazol-3-yl)-amine and 4-amino-benzonitrile to give 4-[3-(5-methyl-1H-pyrazol-3-ylamino)-6,7-dimethoxy-isoquinolin-1-ylamino]-benzonitrile. LC-MS m/e 401(MH⁺).

Example 279

4-[5,6-Dimethoxy-3-(5-methyl-1H-pyrazol-3-ylamino)-isoquinolin-1-ylamino]-benzonitrile

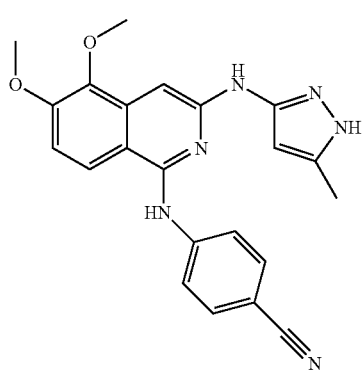

Similar procedure as described in example 273 was used, starting from (1-chloro-5,6-dimethoxy-isoquinolin-3-yl)-(5-methyl-1H-pyrazol-3-yl)-amine and 4-amino-benzonitrile to give 4-[3-(5-methyl-1H-pyrazol-3-ylamino)-5,6-dimethoxy-isoquinolin-1-ylamino]-benzonitrile. LC-MS m/e 401(MH⁺).

Example 280

N$^1$-(4-Butoxy-phenyl)-N$^3$-(5-methyl-1H-pyrazol-3-yl)-isoquinoline-1,3-diamine

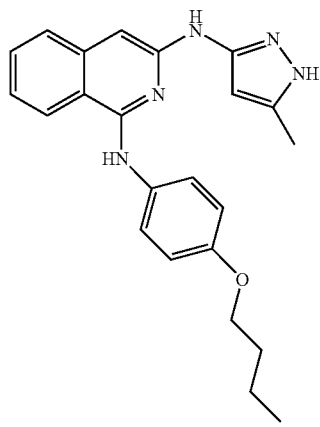

Similar procedure as described in example 273 was used, starting from (1-chloro-isoquinolin-3-yl)-(5-methyl-1H-pyrazol-3-yl)-amine and 4-butoxy-phenylamine to give N$^1$-(4-butoxy-phenyl)-N$^3$-(5-methyl-1H-pyrazol-3-yl)-isoquinoline-1,3-diamine. LC-MS m/e 388(MH$^+$).

Example 281

N$^1$-(4-Butoxy-phenyl)-6-methoxy-N$^3$-(5-methyl-1H-pyrazol-3-yl)-isoquinoline-1,3-diamine

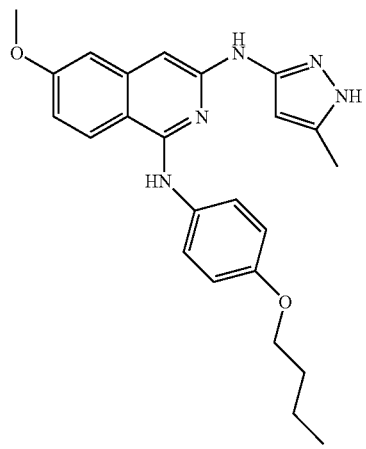

Similar procedure as described in example 273 was used, starting (1-chloro-isoquinolin-3-yl)-(5-methyl-1H-pyrazol-3-yl)-amine and 4-butoxy-phenylamine to give N$^1$-(4-butoxy-phenyl)-6-methoxy-N$^3$-(5-methyl-1H-pyrazol-3-yl)-isoquinoline-1,3-diamine. LC-MS m/e 418 (MH$^+$).

Example 282

N$^1$-(4-Butoxy-phenyl)-N$^3$-(1H-pyrazol-3-yl)-isoquinoline-1,3-diamine

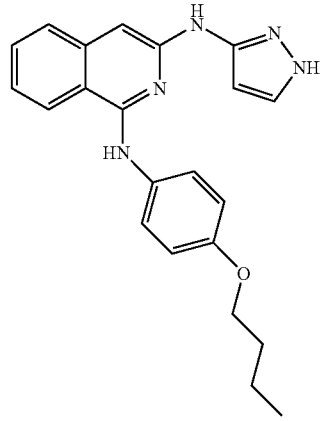

Similar procedure as described in example 273 was used, starting (1-chloro-isoquinolin-3-yl)-(5-methyl-1H-pyrazol-3-yl)-amine and 4-butoxy-phenylamine to give N$^1$-(4-butoxy-phenyl)-N$^3$-(1H-pyrazol-3-yl)-isoquinoline-1,3-diamine. LC-MS m/e 374(MH$^+$).

Example 283

N$^3$-(5-Methyl-1H-pyrazol-3-yl)-N$^1$-pyridin-4-yl-isoquinoline-1,3-diamine

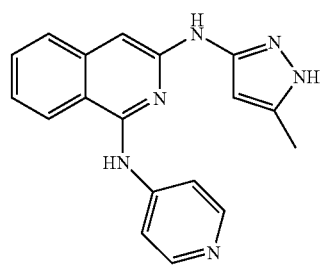

Similar procedure as described in example 273 was used, starting (1-chloro-isoquinolin-3-yl)-(5-methyl-1H-pyrazol-3-yl)-amine and pyridin-4-ylamine to give N$^3$-(5-methyl-1H-pyrazol-3-yl)-N$^1$-pyridin-4-yl-isoquinoline-1,3-diamine. LC-MS m/e 317(MH$^+$).

Example 284

N$^1$-(3,4-Dimethoxy-phenyl)-N$^3$-(1H-pyrazol-3-yl)-isoquinoline-1,3-diamine

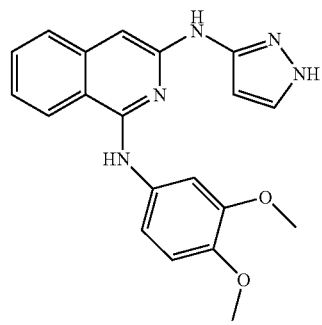

Similar procedure as described in example 273 was used, starting (1-chloro-isoquinolin-3-yl)-(1H-pyrazol-3-yl)-amine and 3,4-dimethoxy-phenylamine to give N¹-(3,4-dimethoxy-phenyl)-N³-(1H-pyrazol-3-yl)-isoquinoline-1,3-diamine. LC-MS m/e 362(MH⁺).

Example 285

N¹-(3,5-Dimethoxy-phenyl)-N³-(1H-pyrazol-3-yl)-isoquinoline-1,3-diamine

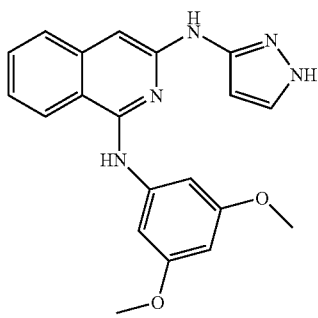

Similar procedure as described in example 273 was used, starting from (1-chloro-isoquinolin-3-yl)-(1H-pyrazol-3-yl)-amine and 3,5-dimethoxy-phenylamine to give N¹-(3,5-dimethoxy-phenyl)-N³-(1H-pyrazol-3-yl)-isoquinoline-1,3-diamine. LC-MS m/e 362(MH⁺).

Example 286

N¹-(3-Ethyl-phenyl)-N³-(5-methyl-1H-pyrazol-3-yl)-isoquinoline-1,3-diamine

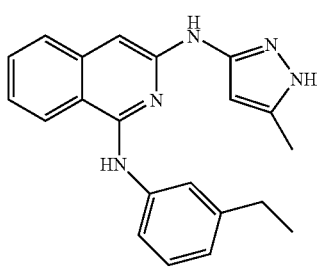

Similar procedure as described in example 273 was used, starting from (1-chloro-isoquinolin-3-yl)-(5-methyl-1H-pyrazol-3-yl)-amine and 3-ethyl-phenylamine give N¹-(3-ethyl-phenyl)-N³-(5-methyl-1H-pyrazol-3-yl)-isoquinoline-1,3-diamine. LC-MS m/e 344(MH⁺).

Example 287

N¹-(3-Ethyl-phenyl)-6-methoxy-N³-(5-methyl-1H-pyrazol-3-yl)-isoquinoline-1,3-diamine

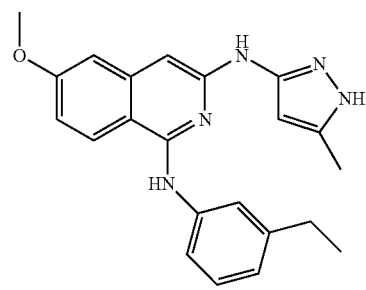

Similar procedure as described in example 273 was used, starting from (1-chloro-6-methoxy-isoquinolin-3-yl)-(5-methyl-1H-pyrazol-3-yl)-amine and 3-ethyl-phenylamine give N¹-(3-ethyl-phenyl)-6-methoxy-N³-(5-methyl-1H-pyrazol-3-yl)-isoquinoline-1,3-diamine. LC-MS m/e 374(MH⁺).

Example 288

6-Methoxy-N³-(5-methyl-1H-pyrazol-3-yl)-N¹-pyridin-4-yl-isoquinoline-1,3-diamine

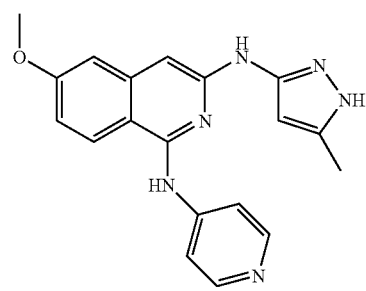

Similar procedure as described in example 273 was used, starting from (1-chloro-6-methoxy-isoquinolin-3-yl)-(5-methyl-1H-pyrazol-3-yl)-amine and pyridin-4-ylamine to give 6-methoxy-N³-(5-methyl-1H-pyrazol-3-yl)-N¹-pyridin-4-yl-isoquinoline-1,3-diamine. LC-MS m/e 347(MH⁺).

Example 289

N³-(1H-pyrazol-3-yl)-N¹-pyridin-4-yl-isoquinoline-1,3-diamine

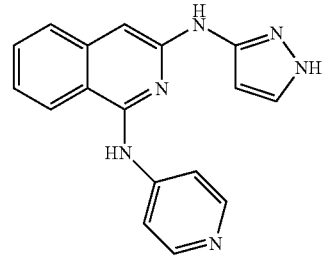

Similar procedure as described in example 273 was used, starting from (1-chloro-isoquinolin-3-yl)-(1H-pyrazol-3-yl)-amine and pyridin-4-ylamine to give $N^3$-(1H-pyrazol-3-yl)-$N^1$-pyridin-4-yl-isoquinoline-1,3-diamine. LC-MS m/e 303 (MH$^+$).

Example 290

6-Methoxy-$N^3$-(5-methyl-1H-pyrazol-3-yl)-$N^1$-pyridin-2-yl-isoquinoline-1,3-diamine

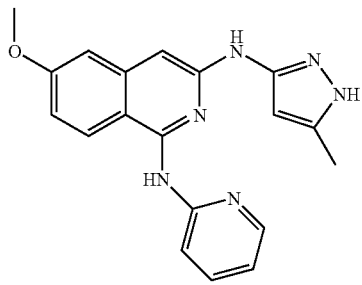

Similar procedure as described in example 273 was used, starting from (1-chloro-6-methoxy-isoquinolin-3-yl)-(5-methyl-1H-pyrazol-3-yl)-amine and pyridin-2-ylamine to give 6-Methoxy-$N^3$-(5-methyl-1H-pyrazol-3-yl)-$N^1$-pyridin-2-yl-isoquinoline-1,3-diamine. LC-MS m/e 347(MH$^+$).

Example 291

$N^3$-(1H-pyrazol-3-yl)-$N^1$-pyridin-2-yl-isoquinoline-1,3-diamine

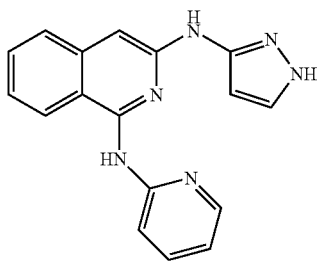

Similar procedure as described in example 273 was used, starting from (1-Chloroioquinolin-3-yl)-(1H-pyrazol-3-yl)-amine and pyridin-2-ylamine to give $N^3$-(1H-pyrazol-3-yl)-$N^1$-pyridin-2-yl-isoquinoline-1,3-diamine. LC-MS m/e 303 (MH$^+$).

Example 292

$N^3$-(5-methyl-1H-pyrazol-3-yl)-$N^1$-pyridin-3-yl-isoquinoline-1,3-diamine

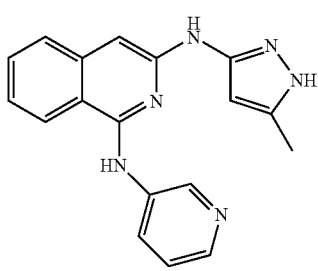

Similar procedure as described in example 273 was used, starting from (1-chloro-isoquinolin-3-yl)-(5-methyl-1H-pyrazol-3-yl)-amine and pyridin-3-ylamine to give $N^3$-(5-methyl-1H-pyrazol-3-yl)-$N^1$-pyridin-3-yl-isoquinoline-1,3-diamine. LC-MS m/e 317(MH$^+$).

Example 293

6-Methoxy-$N^3$-(5-methyl-1H-pyrazol-3-yl)-$N^1$-pyridin-3-yl-isoquinoline-1,3-diamine

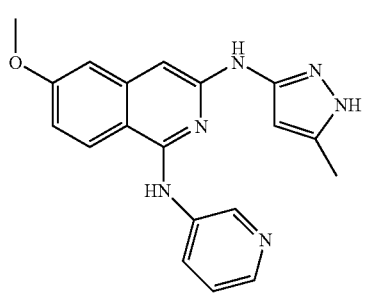

Similar procedure as described in example 273 was used, starting from (1-chloro-6-methoxy-isoquinolin-3-yl)-(5-methyl-1H-pyrazol-3-yl)-amine and pyridin-3-ylamine to give 6-Methoxy-$N^3$-(5-methyl-1H-pyrazol-3-yl)-$N^1$-pyridin-3-yl-isoquinoline-1,3-diamine. LC-MS m/e 347(MH$^+$).

Example 294

$N^1$-(3-Chloro-phenyl)-$N^3$-(5-methyl-1H-pyrazol-3-yl)-isoquinoline-1,3-diamine

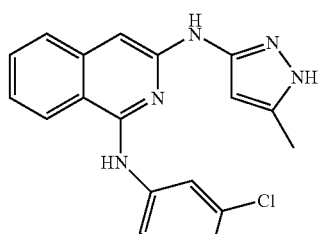

Similar procedure as described in example 273 was used, starting from (1-chloro-isoquinolin-3-yl)-(5-methyl-1H-pyrazol-3-yl)-amine and 3-chloro-phenylamine to give $N^1$-(3-chloro-phenyl)-$N^3$-(5-methyl-1H-pyrazol-3-yl)-isoquinoline-1,3-diamine. LC-MS m/e 350(MH$^+$).

Example 295

N[1]-(3-Chloro-phenyl)-6-methoxy-N[3]-(5-methyl-1H-pyrazol-3-yl)-isoquinoline-1,3-diamine

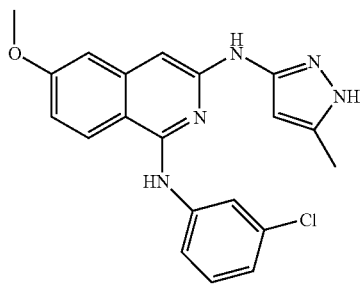

Similar procedure as described in example 273 was used, starting from (1-chloro-6-methoxy-isoquinolin-3-yl)-(5-methyl-1H-pyrazol-3-yl)-amine and 3-chloro-phenylamine to give N[1]-(3-chloro-phenyl)-6-methoxy-N[3]-(5-methyl-1H-pyrazol-3-yl)-isoquinoline-1,3-diamine. LC-MS m/e 380(MH+).

Example 296

N[1]-(3-Ethyl-phenyl)-6-methoxy-N[3]-(1H-pyrazol-3-yl)-isoquinoline-1,3-diamine

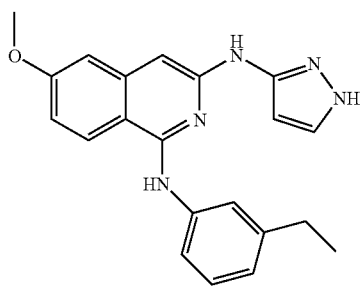

Similar procedure as described in example 273 was used, starting from (1-chloro-6-methoxy-isoquinolin-3-yl)-(1H-pyrazol-3-yl)-amine and 3-ethyl-phenylamine give N[1]-(3-ethyl-phenyl)-6-methoxy-N[3]-(1H-pyrazol-3-yl)-isoquinoline-1,3-diamine. LC-MS m/e 360(MH+).

Example 297

4-[5-Methoxy-3-(5-methyl-1H-pyrazol-3-ylamino)-isoquinolin-1-ylamino]-benzonitrile

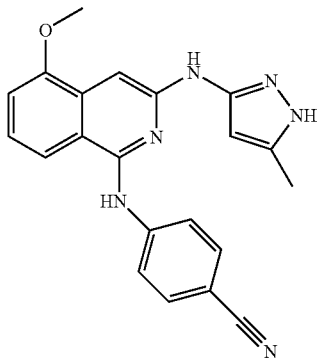

Similar procedure as described in example 273 was used, starting from (1-chloro-5-methoxy-isoquinolin-3-yl)-(5-methyl-1H-pyrazol-3-yl)-amine and 4-amino-benzonitrile to give 4-[3-(5-methyl-1H-pyrazol-3-ylamino)-5-methoxy-isoquinolin-1-ylamino]-benzonitrile. LC-MS m/e 371(MH+).

Example 298

4-[7-Methoxy-3-(5-methyl-1H-pyrazol-3-ylamino)-isoquinolin-1-ylamino]-benzonitrile

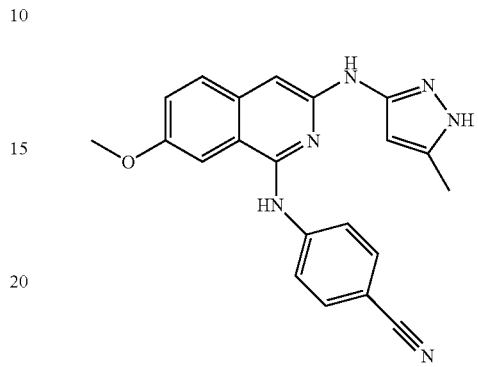

Similar procedure as described in example 273 was used, starting from (1-chloro-7-methoxy-isoquinolin-3-yl)-(5-methyl-1H-pyrazol-3-yl)-amine and 4-amino-benzonitrile to give 4-[3-(5-methyl-1H-pyrazol-3-ylamino)-7-methoxy-isoquinolin-1-ylamino]-benzonitrile. LC-MS m/e 371(MH+).

Example 299

(5-Methyl-1H-pyrazol-3-yl)-[6-(2-morpholin-4-yl-ethoxy)-1-phenyl-isoquinolin-3-yl]-amine

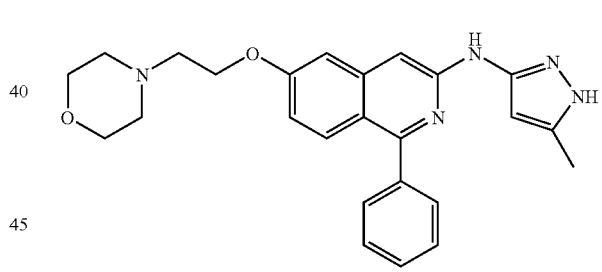

a) Preparation of 3-(5-Methyl-1H-pyrazol-3-ylamino)-1-phenyl-isoquinolin-6-ol

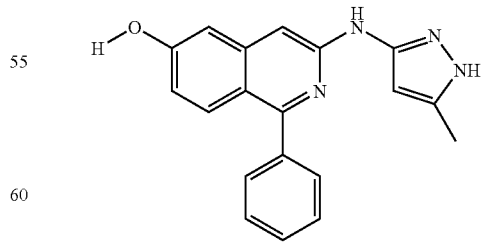

The mixture of (6-methoxy-1-phenyl-isoquinolin-3-yl)-(5-methyl-1H-pyrazol-3-yl)-amine (100 mg), 40% aq. HBr (1 ml), acetic acid (2 ml) was heated at 180° C. for 30 minutes under microwave irradiation. After reaction finished, the mixture was evaporated to oil by reduced pressure and was dissolved in 50 ml ethyl acetate. The organic layer was washed with aq. NaHCO₃ and evaporated to give 70 mg of crude 3-(5-methyl-1H-pyrazol-3-ylamino)-1-phenyl-isoquinolin-6-ol. LC-MS m/e 317(MH⁺).

b) Preparation of (5-methyl-1H-pyrazol-3-yl)-[6-(2-morpholin-4-yl-ethoxy)-1-phenyl-isoquinolin-3-yl]-amine

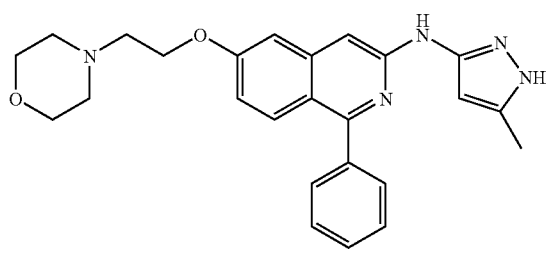

NaH (9 mg) was added to the above crude product 3-(5-methyl-1H-pyrazol-3-ylamino)-1-phenyl-isoquinolin-6-ol (70 mg) in 1 ml of dimethyl ether (DME) to give solution A. NaH (9 mg) was added to N-(2-Chlorethyl)-morpholine hydrochloride (41 mg) in 1 ml of DME to give solution B. After stirred for 1 hour at room temperature, these two solutions were mixed and heated at 150° C. for 30 minutes under microwave irradiation. The mixture was sent to preparative LC-MS and 10 mg of (5-methyl-1H-pyrazol-3-yl)-[6-(2-morpholin-4-yl-ethoxy)-1-phenyl-isoquinolin-3-yl]-amine was produced as a solid. LC-MS m/e 430(MH⁺). ¹H NMR (DMSO): δ 2.20(s, 3H), δ 2.520(m, 4H), δ 2.76(t, 2H), δ 3.63(m, 4H), δ 4.20(t, 2H), δ 5.85(s, 1H), δ 6.78(d, 1H), δ 7.00(d, 1H), δ 7.47(m, 5H), δ 7.60(m, 4H).

Example 300

[1-(3-Methoxy-phenyl)-6-(2-morpholin-4-yl-ethoxy)-isoquinolin-3-yl]-(5-methyl-1H-pyrazol-3-yl)-amine

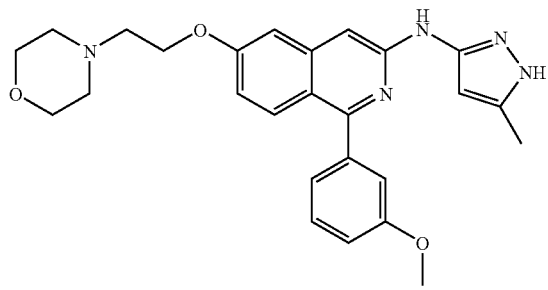

a) Preparation of 1-Bromo-3-(5-methyl-1H-pyrazol-3-ylamino)-isoquinolin-6-ol

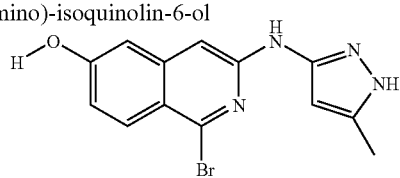

The mixture of (1-chloro-6-methoxy-isoquinolin-3-yl)-(5-methyl-1H-pyrazol-3-yl)-amine (1 g), 40% aq. HBr (15 ml), acetic acid (50 ml) was heated at 120° C. for 8 hours. After reaction finished, the mixture was evaporated to oil and diluted with 20 ml of ethyl acetate. The organic layer was washed with aq. NaHCO₃ and was evaporated to give 450 mg of crude 1-Bromo-3-(5-methyl-1H-pyrazol-3-ylamino)-isoquinolin-6-ol by reduced pressure. LC-MS m/e 319(MH⁺).

b) Preparation of 1-(3-Methoxy-phenyl)-3-(5-methyl-1H-pyrazol-3-ylamino)-isoquinolin-6-ol

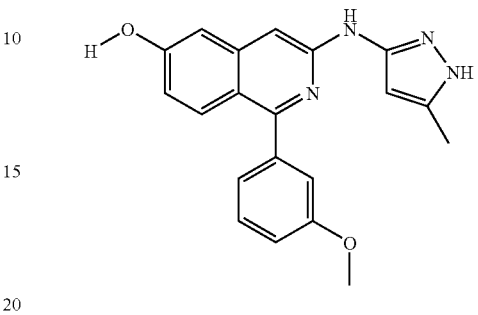

The mixture of 1-Bromo-3-(5-methyl-1H-pyrazol-3-ylamino)-isoquinolin-6-ol (300 mg), 3-methoxy-phenylboronic acid (318 mg), Na₂CO₃ (400 mg), Tetrakis(triphenylphosphine)palladium(0) (100 mg), N,N-dimethylformamide (DMF) (2 ml) and water (2 ml) was heated at 180° C. for 30 minutes under microwave irradiation. After reaction finished, the mixture was sent to preparative LC-MS and 1-(3-methoxy-phenyl)-3-(5-methyl-1H-pyrazol-3-ylamino)-isoquinolin-6-ol (180 mg) was produced as a solid. LC-MS m/e 347(MH⁺).

c) Preparation of [1-(3-Methoxy-phenyl)-6-(2-morpholin-4-yl-ethoxy)-isoquinolin-3-yl]-(5-methyl-1H-pyrazol-3-yl)-amine

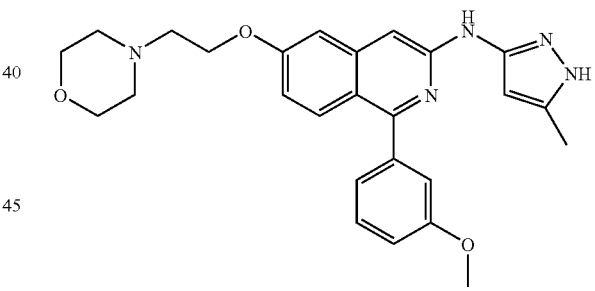

NaH (20 mg) was added to 1-(3-methoxy-phenyl)-3-(5-methyl-1H-pyrazol-3-ylamino)-isoquinolin-6-ol (180 mg) in DME (2 ml) stirred at room temperature to give solution A. NaH (20 mg) was added to N-(2-chlorethyl)-morpholine hydrochloride (96 mg) in DME (1 ml) stirred at room temperature to give solution B. These two solutions were stirred for 1 hour at room temperature and mixed. The mixture was heated at 150° C. for 30 minutes under microwave irradiation and then the mixture was sent to preparative LC-MS and 18 mg of [1-(3-Methoxy-phenyl)-6-(2-morpholin-4-yl-ethoxy)-isoquinolin-3-yl]-(5-methyl-1H-pyrazol-3-yl)-amine was produced. LC-MS m/e 460(MH⁺). ¹H NMR(DMSO): δ 2.26 (s, 3H), δ 2.70(m, 4H), δ 3.05(t, 2H), δ 3.75(m, 4H), δ 3.90(s, 3H), δ 4.30(t, 2H), δ 6.00(s, 1H), δ 6.90(d, 1H), δ 7.15(m, 2H), δ 7.20(m, 2H), δ 7.35(s, 1H), δ 7.45(t, 3H), δ 7.80(d, 2H), δ 8.32(br, 1H).

Example 301

[1-(2,4-Difluoro-phenyl)-3-(5-methyl-1H-pyrazol-3-ylamino)-isoquinolin-6-yl]-morpholin-4-yl-methanone

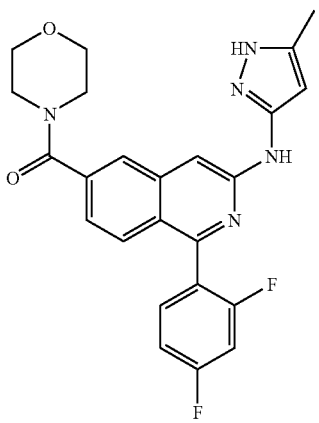

a) Preparation of 1-(2,4-difluoro-phenyl)-3-(5-methyl-1H-pyrazol-3-ylamino)-isoquinolin-6-ol

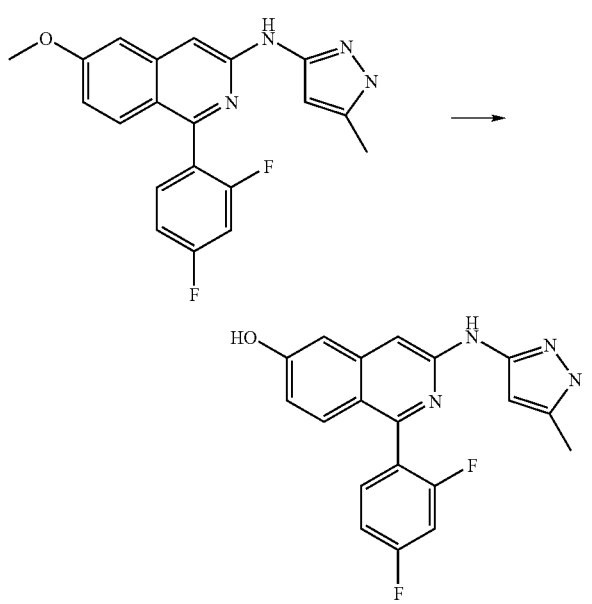

To a solution of [1-(2,4-difluoro-phenyl)-6-methoxy-isoquinolin-3-yl]-(5-methyl-1H-pyrazol-3-yl)-amine (11.0 g) in 10 mL acetic acid was added hydrobromic acid (1 mL, 40%). The mixture was heated at 180° C. for 30 min under microwave irradiation. After cooling, most of the solvent was removed under reduced pressure, the residue was dissolved in 100 mL of ethyl acetate and washed with saturated sodium bicarbonate. The organic phase was dried with anhydrous sodium sulfate and concentrated to give an oil (0.92 g), which was used for the next reaction without further purification. (LC-MS m/e 353 MH$^+$).

b) Preparation of 1-(2,4-Difluoro-phenyl)-3-(5-methyl-1H-pyrazol-3-ylamino)-isoquinolin-6-ol trifluoromethanesulfonate

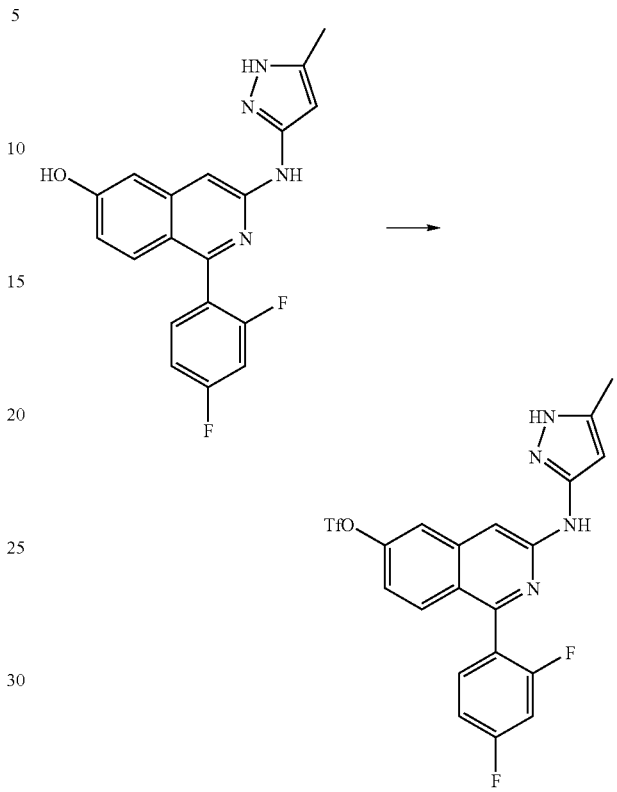

Trifluoromethanesulfonic anhydride (204.4 mg) in 5 mL of dichloromethane was added to the mixture of 1-(2,4-difluoro-phenyl)-3-(5-methyl-1H-pyrazol-3-ylamino)-isoquinolin-6-ol (170 mg, 0.48 mmol) and triethylamine (145.4 mg) in 20 mL of dichloromethane by syringe at 0° C. The solution was stirred at room temperature overnight, and was diluted with dichloromethane (20 mL). The organic layer was washed with 10% hydrochloric acid, sodium bicarbonate, saturated sodium chloride, and evaporated to give an oil which was used for the next reaction without further purification.

c) Preparation of [1-(2,4-Difluoro-phenyl)-3-(5-methyl-1H-pyrazol-3-ylamino)-isoquinolin-6-yl]-morpholin-4-yl-methanone

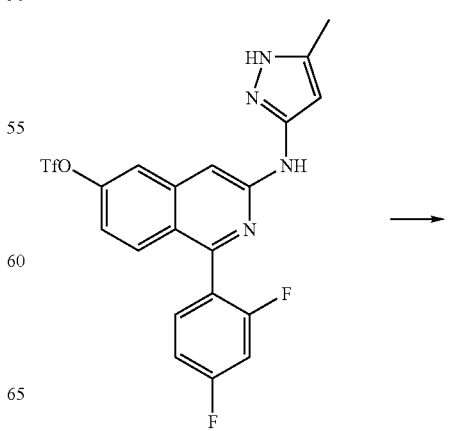

-continued

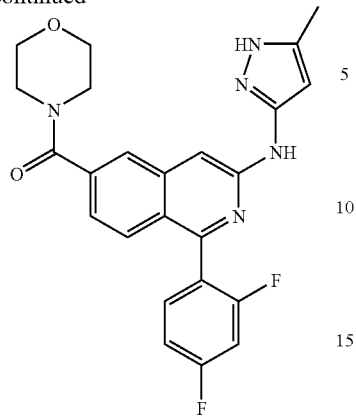

A 0.5-2.0 mL process vial was charged with 1-(2,4-difluoro-phenyl)-3-(5-methyl-1H-pyrazol-3-ylamino)-isoquinolin-6-yl trifluoromethanesulfonate (24.3 mg), Pd(OAc)$_2$ (2 mg), Mo(CO)$_6$ (13.2 mg), morpholine (13.0 mg), 1,8-Diazabicyclo[5.4.0]undecen (DBU) (22.9 mg), and dry tetrahydrofuran (THF) (1 mL). The vial was immediately capped under air and heated at 150° C. for 15 min under microwave irradiation. After cooling, the reaction mixture was filtered through a short silica gel column, and the solvent was removed under reduced pressure. The residue was sent to prep-HPLC to get 5 mg of [1-(2,4-difluoro-phenyl)-3-(5-methyl-1H-pyrazol-3-ylamino)-isoquinolin-6-yl]-morpholin-4-yl-methanone as a yellow solid. LC-MS m/e 450 MH$^+$. $^1$H NMR (400 MHz, CDCl$_3$) 7.74(s, 1H), 7.70(s, 1H), 7.66(m, 1H), 7.54(m, 1H), 7.24(m, 1H), 7.10(t, 1H), 7.02(t, 1H), 6.00(s, 1H), 3.83~3.48(m, 8H), 2.33(s, 3H).

Example 302

1-(2,4-Difluoro-phenyl)-3-(5-methyl-1H-pyrazol-3-ylamino)-isoquinoline-6-carboxylic acid (3-methoxy-propyl)-amide

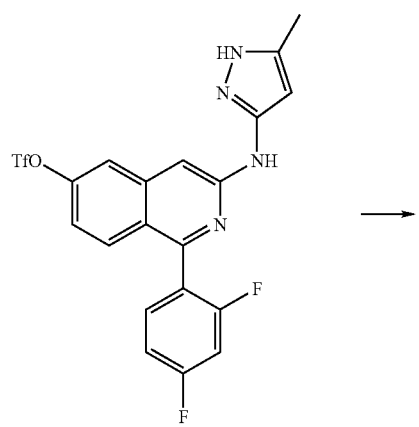

-continued

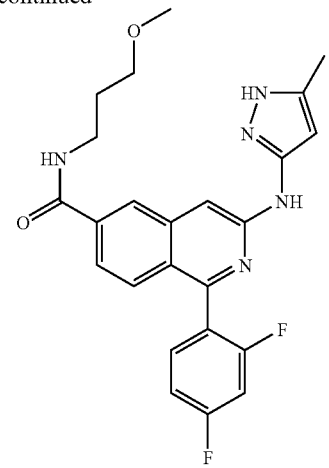

Similar procedure as described in the example 306c was used, starting from 1-(2,4-difluoro-phenyl)-3-(5-methyl-1H-pyrazol-3-ylamino)-isoquinolin-6-yl trifluoromethanesulfonate and 3-methoxy-propylamine to give 4.5 mg of 1-(2,4-Difluoro-phenyl)-3-(5-methyl-1H-pyrazol-3-ylamino)-isoquinoline-6-carboxylic acid (3-methoxy-propyl)-amide as a yellow solid. LC-MS m/e 452(MH$^+$). $^1$H NMR (400 MHz, CDCl$_3$) 8.11(s, 1H), 7.62(m, 2H), 7.54(m, 2H), 7.08(t, 1H), 7.01(t, 1H), 6.09(s, 1H), 3.67~3.60(m, 6H), 3.42(s, 3H), 2.31 (s, 3H).

Example 303

[1-(4-Fluoro-phenoxy)-3-(5-methyl-1H-pyrazol-3-ylamino)-isoquinolin-6-yl]-morpholin-4-yl-methanone

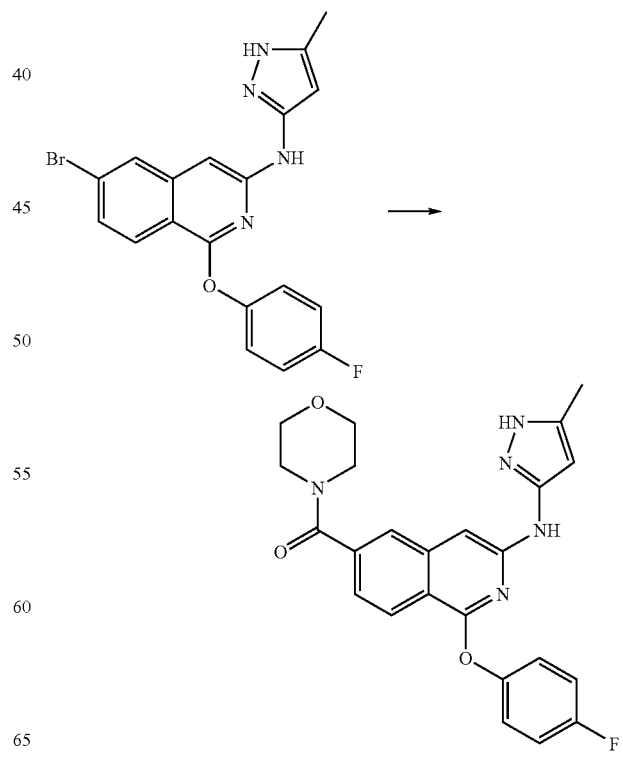

Similar procedure as described in the example 301c was used, starting from [6-Bromo-1-(4-fluoro-phenoxy)-isoquinolin-3-yl]-(5-methyl-1H-pyrazol-3-yl)-amine and morpholine to give 4.2 mg of [1-(4-Fluoro-phenoxy)-3-(5-methyl-1H-pyrazol-3-ylamino)-isoquinolin-6-yl]-morpholin-4-yl-methanone as a yellow solid. LC-MS m/e 448(MH⁺). ¹H NMR (400 MHz, CD₃OD) 8.27(d, 2H), 7.63(s, 1H), 7.27~7.25(m, 6H), 5.60(s, 1H), 3.79~3.66(m, 4H), 3.65~3.49 (m, 4H), 2.15(s, 1H).

Example 304

[1-(2,4-Difluoro-phenyl)-6-(2-methoxy-ethoxy)-isoquinolin-3-yl]-(5-methyl-1H-pyrazol-3-yl)-amine

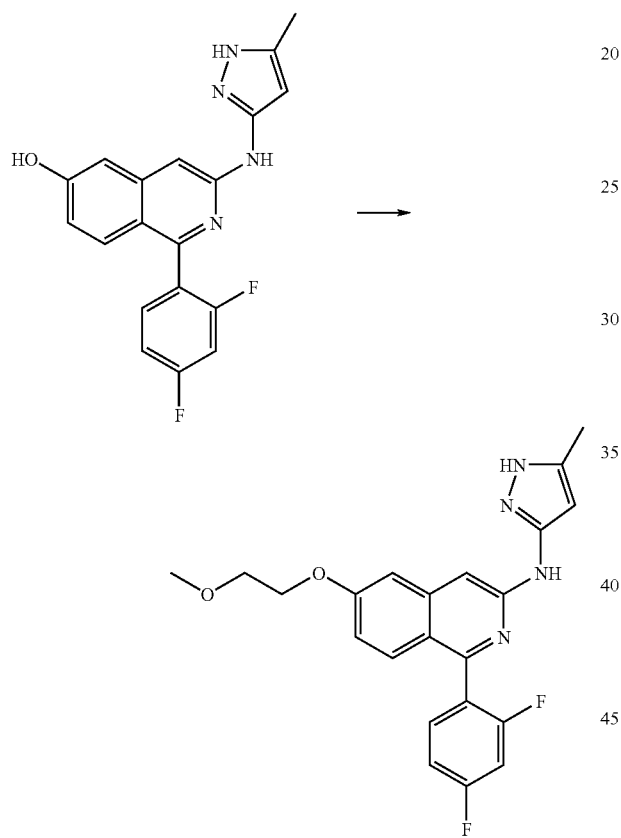

Sodium hydride (17 mg, 60%) was added slowly to an ice-cooled solution of 1-(2,4-difluoro-phenyl)-3-(5-methyl-1H-pyrazol-3-ylamino)-isoquinolin-6-ol (150 mg) in 2 mL N,N-dimethylformamide (DMF). After stirred for 30 min, 1-Bromo-2-methoxy-ethane (59 mg) in 1 mL DMF was added cautiously by syringe. The mixture was warmed to room temperature and stirred overnight, then diluted with 1 mL methanol and directly sent to prep-HPLC. The product [1-(2,4-difluoro-phenyl)-6-(2-methoxy-ethoxy)-isoquinolin-3-yl]-(5-methyl-1H-pyrazol-3-yl)-amine (40 mg) was obtained as a yellow solid. LC-MS m/e 411(MH⁺). ¹H NMR (400 MHz, DMSO) 9.12(s, 1H), 7.81(s, 1H), 7.61(m, 1H), 7.43(t, 1H), 7.34(d, 1H), 7.25(t, 1H), 7.10(d, 1H), 6.85(d, 1H), 5.81(s, 1H), 4.23(m, 2H), 3.71(m, 2H), 3.32(s, 3H), 2.20(s, 3H).

Example 305

(5-Methyl-1H-pyrazol-3-yl)-(1-phenylsulfanyl-isoquinolin-3-yl)-amine

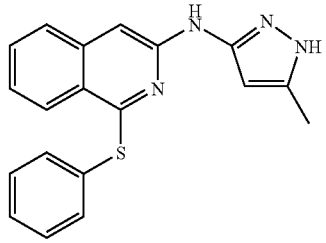

NaH (155 mg) was added to a solution of benzenethiol (500 mg) in DME (2 ml) and the mixture was stirred for 1 hour at room temperature. (1-chloro-isoquinolin-3-yl)-(5-methyl-1H-pyrazol-3-yl)-amine (100 mg) was then added, and the resulting mixture was heated at 150° C. for 30 minutes under microwave irradiation. The reaction mixture was acidified to pH=7 with acetic acid and purified by preparative LC-MS to give 20 mg of (5-methyl-1H-pyrazol-3-yl)-(1-phenylsulfanyl-isoquinolin-3-yl)-amine as a yellow solid. LC-MS: m/e 333(MH⁺).

Example 306

[1-(3-Methoxy-phenylsulfanyl)-isoquinolin-3-yl]-(5-methyl-1H-pyrazol-3-yl)-amine

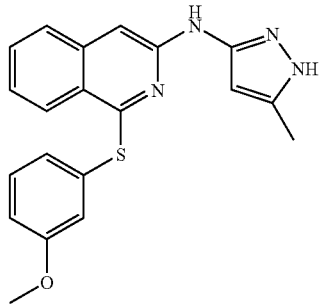

Similar procedure as described in example 305 was used, starting from 3-methoxy-benzenethiol and (1-chloro-isoquinolin-3-yl)-(5-methyl-1H-pyrazol-3-yl)-amine to give [1-(3-methoxy-phenylsulfanyl)-isoquinolin-3-yl]-(5-methyl-1H-pyrazol-3-yl)-amine. LC-MS: m/e 363 (MH⁺).

Example 307

[1-(3-Methoxy-phenylsulfanyl)-6-methoxy-isoquinolin-3-yl]-(5-methyl-1H-pyrazol-3-yl)-amine

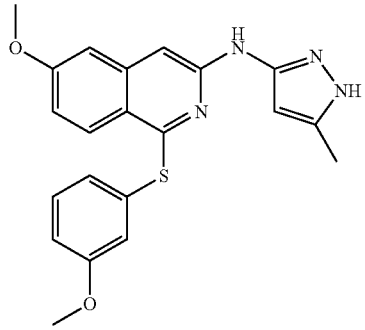

Similar procedure as described in example 305 was used, starting from 3-methoxy-benzenethiol and (1-chloro-6-methoxy-isoquinolin-3-yl)-(5-methyl-1H-pyrazol-3-yl)-amine to give [1-(3-methoxy-phenylsulfanyl)-6-methoxy-isoquinolin-3-yl]-(5-methyl-1H-pyrazol-3-yl)-amine. LC-MS: m/e 393 (MH+).

Example 308

[1-(4-Chloro-phenylsulfanyl)-isoquinolin-3-yl]-(5-methyl-1H-pyrazol-3-yl)-amine

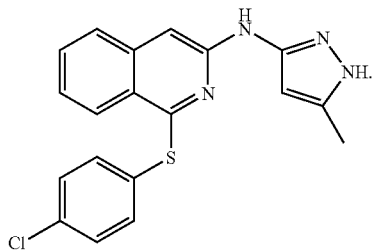

Similar procedure as described in example 305 was used, starting from 4-chloro-benzenethiol and (1-chloro-isoquinolin-3-yl)-(5-methyl-1H-pyrazol-3-yl)-amine to give [1-(4-chloro-phenylsulfanyl)-isoquinolin-3-yl]-(5-methyl-1H-pyrazol-3-yl)-amine. LC-MS: m/e 367 (MH+).

Example 309

[1-(4-Chloro-phenylsulfanyl)-6-methoxy-isoquinolin-3-yl]-(5-methyl-1H-pyrazol-3-yl)-amine

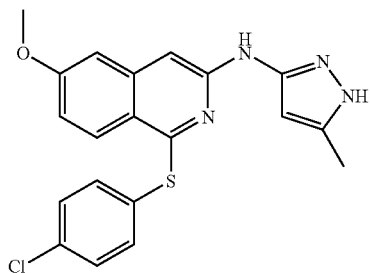

Similar procedure as described in example 305 was used, starting from 4-chloro-benzenethiol and (1-chloro-6-methoxy-isoquinolin-3-yl)-(5-methyl-1H-pyrazol-3-yl)-amine to give [1-(4-chloro-phenylsulfanyl)-6-methoxy-isoquinolin-3-yl]-(5-methyl-1H-pyrazol-3-yl)-amine. LC-MS: m/e 397 (MH+).

Example 310

[1-(3-Fluoro-phenylsulfanyl)-isoquinolin-3-yl]-(5-methyl-1H-pyrazol-3-yl)-amine

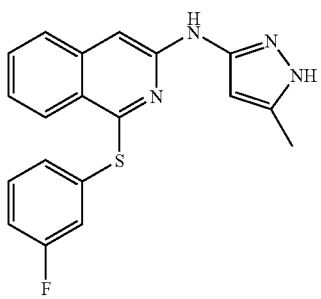

Similar procedure as described in example 305 was used, starting from 3-fluoro-benzenethiol and (1-chloro-isoquinolin-3-yl)-(5-methyl-1H-pyrazol-3-yl)-amine to give [1-(3-fluoro-phenylsulfanyl)-isoquinolin-3-yl]-(5-methyl-1H-pyrazol-3-yl)-amine. LC-MS: m/e 351 (MH+).

Example 311

[1-(3-Fluoro-phenylsulfanyl)-6-methoxy-isoquinolin-3-yl]-(5-methyl-1H-pyrazol-3-yl)-amine

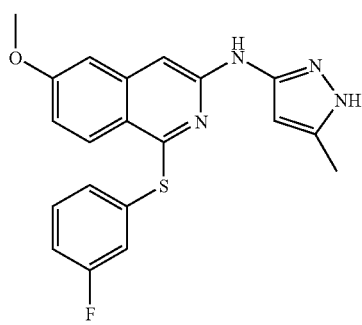

Similar procedure as described in example 305 was used, starting from 3-fluoro-benzenethiol and (1-chloro-6-methoxy-isoquinolin-3-yl)-(5-methyl-1H-pyrazol-3-yl)-amine to give [1-(3-fluoro-phenylsulfanyl)-6-methoxy-isoquinolin-3-yl]-(5-methyl-1H-pyrazol-3-yl)-amine. LC-MS: m/e 381 (MH+).

Example 312

[1-(4-Fluoro-phenylsulfanyl)-isoquinolin-3-yl]-(5-methyl-1H-pyrazol-3-yl)-amine

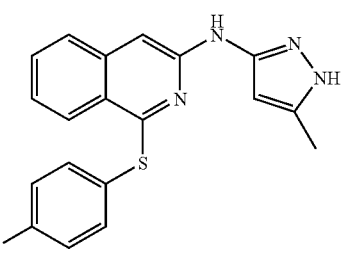

Similar procedure as described in example 305 was used, starting from 4-fluoro-benzenethiol and (1-chloro-isoquinolin-3-yl)-(5-methyl-1H-pyrazol-3-yl)-amine to give [1-(4-fluoro-phenylsulfanyl)-isoquinolin-3-yl]-(5-methyl-1H-pyrazol-3-yl)-amine. LC-MS: m/e 351 (MH+).

Example 313

[1-(4-Fluoro-phenylsulfanyl)-6-methoxy-isoquinolin-3-yl]-(5-methyl-1H-pyrazol-3-yl)-amine

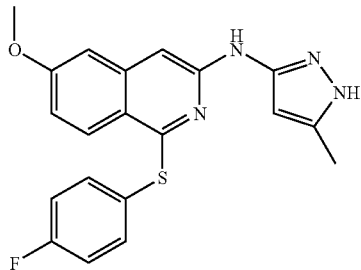

Similar procedure as described in example 305 was used, starting from 4-fluoro-benzenethiol and (1-chloro-6-methoxy-isoquinolin-3-yl)-(5-methyl-1H-pyrazol-3-yl)-amine to give [1-(4-fluoro-phenylsulfanyl)-6-methoxy-isoquinolin-3-yl]-(5-methyl-1H-pyrazol-3-yl)-amine. LC-MS: m/e 381 (MH$^+$).

Example 314

[1-(2-Fluoro-phenylsulfanyl)-isoquinolin-3-yl]-(5-methyl-1H-pyrazol-3-yl)-amine

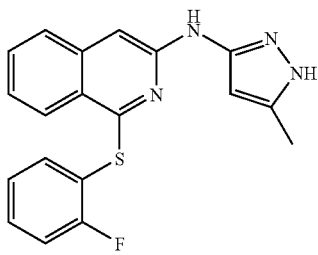

Similar procedure as described in example 305 was used, starting from 2-fluoro-benzenethiol and (1-chloro-isoquinolin-3-yl)-(5-methyl-1H-pyrazol-3-yl)-amine to give [1-(2-fluoro-phenylsulfanyl)-isoquinolin-3-yl]-(5-methyl-1H-pyrazol-3-yl)-amine. LC-MS: m/e 351 (MH$^+$).

Example 315

[1-(2-Fluoro-phenylsulfanyl)-6-methoxy-isoquinolin-3-yl]-(5-methyl-1H-pyrazol-3-yl)-amine

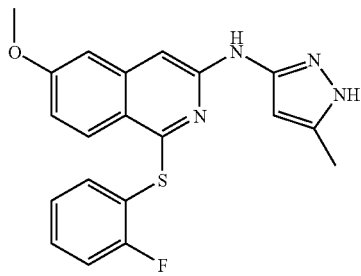

Similar procedure as described in example 305 was used, starting from 2-fluoro-benzenethiol and (1-chloro-6-methoxy-isoquinolin-3-yl)-(5-methyl-1H-pyrazol-3-yl)-amine to give [1-(2-fluoro-phenylsulfanyl)-6-methoxy-isoquinolin-3-yl]-(5-methyl-1H-pyrazol-3-yl)-amine. LC-MS: m/e 381 (MH$^+$).

Example 316

(6-Methoxy-3-(5-methyl-1H-pyrazol-3-ylamino)-isoquinoline-1-carboxylic acid

For this compound please see example 9A, supra.

Example 317

[6-Methoxy-3-(5-methyl-1H-pyrazol-3-ylamino)-isoquinolin-1-yl]-morpholin-4-yl-methanone

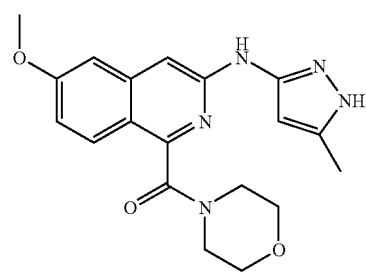

A mixture of 6-methoxy-3-(5-methyl-1H-pyrazol-3-ylamino)-isoquinoline-1-carboxylic acid (100 mg) (example 9A), morpholine (70 mg), 1-hydroxybenzotriazole (HOBt) (130 mg), NMP (100 mg), N,N-dimethylformamide (DMF) (2 ml), 1-ethyl-3-[3-dimethylaminopropyl]carbodiimide hydrochloride (EDCI) (180 mg) was stirred at room temperature overnight. The reaction mixture was purified by preparative LC-MS to give 20 mg of [6-methoxy-3-(5-methyl-1H-pyrazol-3-ylamino)-isoquinolin-1-yl]-morpholin-4-yl-methanone. LC-MS: m/e 368(MH$^+$).

Example 318

6-Methoxy-3-(5-methyl-1H-pyrazol-3-ylamino)-isoquinoline-1-carboxylic acid cyclopropylmethyl-amide

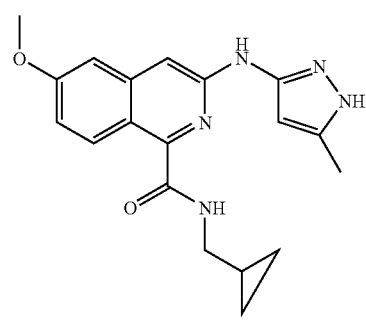

Similar procedure as described in example 317 was used, starting from cyclopropyl-methylamine and 6-methoxy-3-(5-methyl-1H-pyrazol-3-ylamino)-isoquinoline-1-carboxylic acid to give 6-methoxy-3-(5-methyl-1H-pyrazol-3-ylamino)-isoquinoline-1-carboxylic acid cyclopropylmethyl-amide. LC-MS: m/e 352 (MH$^+$).

Example 319

1-{4-[6-Methoxy-3-(5-methyl-1H-pyrazol-3-ylamino)-isoquinoline-1-carbonyl]-piperazin-1-yl}-ethanone

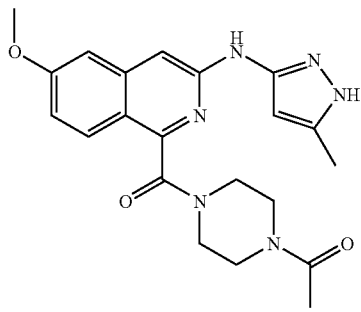

Similar procedure as described in example 317 was used, starting from 1-piperazin-1-yl-ethanone and 6-methoxy-3-(5-methyl-1H-pyrazol-3-ylamino)-isoquinoline-1-carboxylic acid to give 6-methoxy-3-(5-methyl-1H-pyrazol-3-ylamino)-isoquinoline-1-carboxylic acid cyclopropylmethyl-amide. LC-MS: m/e 409 (MH$^+$).

Example 320

6-Methoxy-3-(5-methyl-1H-pyrazol-3-ylamino)-isoquinoline-1-carboxylic acid dimethylamide

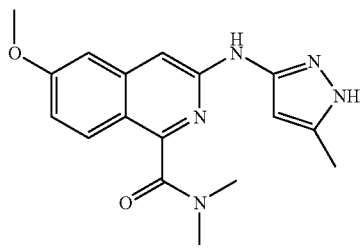

Similar procedure as described in example 317 was used, starting from dimethyl-amine hydrochloride and 6-methoxy-3-(5-methyl-1H-pyrazol-3-ylamino)-isoquinoline-1-carboxylic acid to give 6-methoxy-3-(5-methyl-1H-pyrazol-3-ylamino)-isoquinoline-1-carboxylic acid dimethylamide. LC-MS: m/e 326 (MH$^+$).

Example 321

(1-Isopropyl-6-methoxy-isoquinolin-3-yl)-(5-methyl-1H-pyrazol-3-yl)-amine

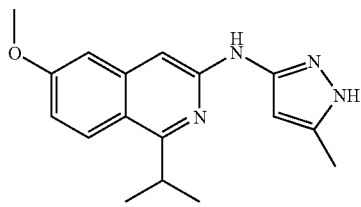

a) Preparation of 2-[6-methoxy-3-(5-methyl-1H-pyrazol-3-ylamino)-isoquinolin-1-yl]-propan-2-ol

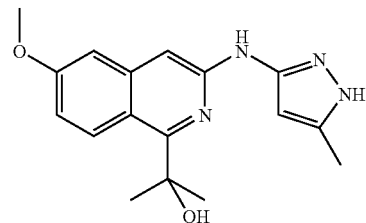

To a solution of 6-methoxy-3-(5-methyl-1H-pyrazol-3-ylamino)-isoquinoline-1-carboxylic acid isopropyl ester (1.5 g, 4.4 mmol) in CH$_2$Cl$_2$ (100 ml) at –78° C. was added MeMgI (20 ml solution in ether, 158 mmol), and the resulting mixture was stirred at –78° C. for 2 hours and then was stirred at room temperature for 2 hours.

40 ml of saturated NH$_4$Cl solution was added, and the aqueous layer was extracted twice with ethyl acetate. The combined organic layer was concentrated to give 600 mg of crude 2-[6-methoxy-3-(5-methyl-1H-pyrazol-3-ylamino)-isoquinolin-1-yl]-propan-2-ol. LC-MS: 313 (MH$^+$).

b) Preparation of (1-Isopropyl-6-methoxy-isoquinolin-3-yl)-(5-methyl-1H-pyrazol-3-yl)-amine

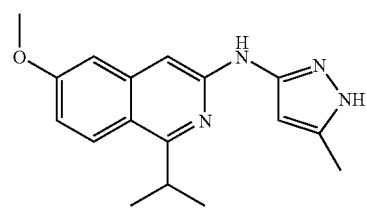

A mixture of 2-[6-methoxy-3-(5-methyl-1H-pyrazol-3-ylamino)-isoquinolin-1-yl]-propan-2-ol (135 mg), 45% HI (1 ml), red phosphorus (54 mg) and acetic acid (3 ml) was heated at 150° C. for 30 minutes under microwave irradiation.

After cooled to room temperature, the reaction mixture was poured into ice-water and was neutralized to pH=7 with 1M NaOH solution. The resulting mixture was extracted with ethyl acetate, and the organic layer was concentrated to dryness under reduced pressure. The solid residue was purified by preparative LC-MS to give 20 mg of (1-isopropyl-6-methoxy-isoquinolin-3-yl)-(5-methyl-1H-pyrazol-3-yl)-amine. LC-MS: m/e 297(MH$^+$).

Example 322

(1-Chloro-6,7-dimethoxy-isoquinolin-3-yl)-(5-cyclopropyl-1H-pyrazol-3-yl)amine

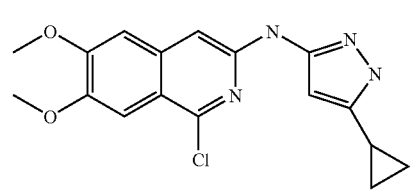

a) Preparation of 3-(5-Cyclopropyl-1H-pyrazol-3-ylamino)-6,7-dimethoxy-2H-isoquinolin-1-one

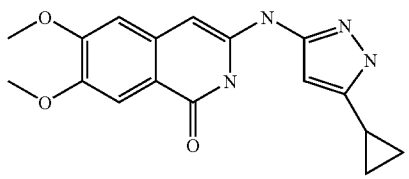

Similar procedure as described in example 2c was used, starting from 2-cyanomethyl-4,5-dimethoxy-benzoic acid and 3-amino-5-cyclopropylpyrazol to give 3-(5-Cyclopropyl-1H-pyrazol-3-ylamino)-6,7-dimethoxy-2H-isoquinolin-1-one. LC-MS: m/e 327 (MH$^+$).

b) Preparation of (1-Chloro-6,7-dimethoxy-isoquinolin-3-yl)-(5-cyclopropyl-1H-pyrazol-3-yl)-amine

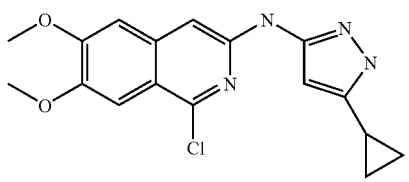

Similar procedure as described in example 2d was used, starting from 3-(5-Cyclopropyl-1H-pyrazol-3-ylamino)-6,7-dimethoxy-2H-isoquinolin-1-one to give (1-Chloro-6,7-dimethoxy-isoquinolin-3-yl)-(5-cyclopropyl-1H-pyrazol-3-yl)-amine. LC-MS: m/e 345 (MH$^+$).

Example 323

(1-Cyclobutoxy-6,7-dimethoxy-isoquinolin-3-yl)-(5-cyclopropyl-1H-pyrazol-3-yl)-amine

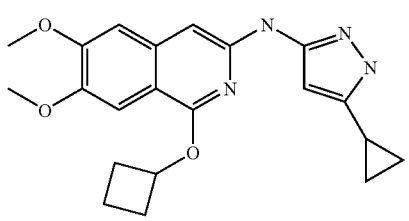

Similar procedure as described in example 10 was used, starting from (1-Chloro-6,7-dimethoxy-isoquinolin-3-yl)-(5-cyclopropyl-1H-pyrazol-3-yl)-amine and cyclobutanol to give (1-Cyclobutoxy-6,7-dimethoxy-isoquinolin-3-yl)-(5-cyclopropyl-1H-pyrazol-3-yl)-amine. LC-MS m/e 381(MH$^+$).

Example 324

(5-Cyclopropyl-1H-pyrazol-3-yl)-(1-ethoxy-6,7-dimethoxy-isoquinolin-3-yl)amine

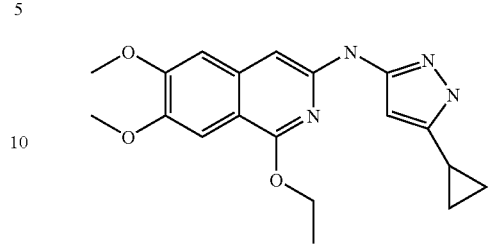

Similar procedure as described in example 10 was used, starting from (1-Chloro-6,7-dimethoxy-isoquinolin-3-yl)-(5-cyclopropyl-1H-pyrazol-3-yl)-amine and ethanol to give (5-Cyclopropyl-1H-pyrazol-3-yl)-(1-ethoxy-6,7-dimethoxy-isoquinolin-3-yl)-amine LC-MS m/e 355(MH$^+$).

Example 325

(5-Cyclopropyl-1H-pyrazol-3-yl)-(1-isopropoxy-6,7-dimethoxy-isoquinolin-3-yl)-amine

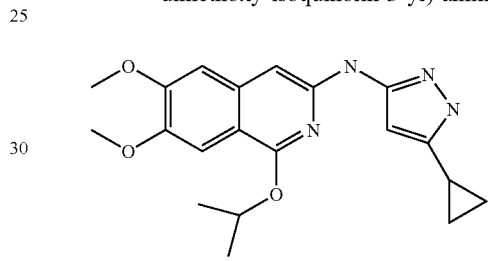

Similar procedure as described in example 10 was used, starting from (1-Chloro-6,7-dimethoxy-isoquinolin-3-yl)-(5-cyclopropyl-1H-pyrazol-3-yl)-amine and propan-2-ol to give (5-Cyclopropyl-1H-pyrazol-3-yl)-(1-isopropoxy-6,7-dimethoxy-isoquinolin-3-yl)-amine. LC-MS m/e 369(MH$^+$).

Example 326

(5-Cyclopropyl-1H-pyrazol-3-yl)-(1-isopropyl-6,7-dimethoxy-isoquinolin-3-yl)-amine

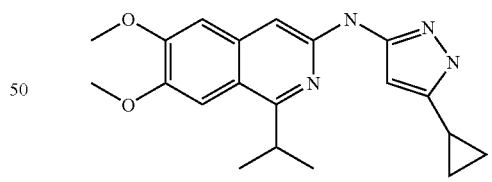

a) Preparation of (5-Cyclopropyl-1H-pyrazol-3-yl)-(1-isopropenyl-6,7-dimethoxy-isoquinolin-3-yl)-amine

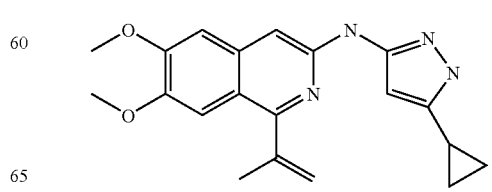

Similar procedure as described in example 131 was used, starting from (1-Chloro-6,7-dimethoxy-isoquinolin-3-yl)-(5-cyclopropyl-1H-pyrazol-3-yl)-amine and isopropenylboronic acid pinacol ester to give (5-Cyclopropyl-1H-pyrazol-3-yl)-(1-isopropenyl-6,7-dimethoxy-isoquinolin-3-yl)-amine. LC-MS m/e 351(MH$^+$).

b) Preparation of (5-Cyclopropyl-1H-pyrazol-3-yl)-(1-isopropyl-6,7-dimethoxy-isoquinolin-3-yl)-amine

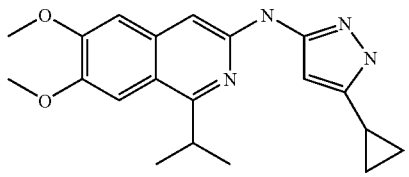

The mixture of (5-Cyclopropyl-1H-pyrazol-3-yl)-(1-isopropenyl-6,7-dimethoxy-isoquinolin-3-yl)-amine (100 mg) and 10% Pd/C (15 mg) was sealed in high-pressure bottle under 40 psi H$_2$ pressure and stirred at room temperature overnight. Then the mixture was filtered, and the filtrate was concentrated to give (5-Cyclopropyl-1H-pyrazol-3-yl)-(1-isopropyl-6,7-dimethoxy-isoquinolin-3-yl)-amine as oil (30 mg). LC-MS: m/e 353 (MH$^+$).

Example 327

1-Isopropoxy-3-(5-methyl-1H-pyrazol-3-ylamino)-isoquinolin-6-ol

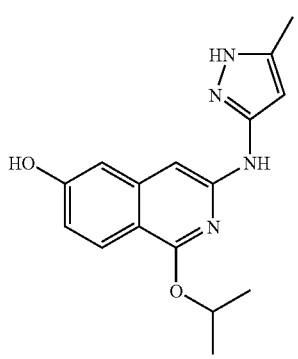

a) Preparation of 1-Bromo-3-(5-methyl-1H-pyrazol-3-ylamino)-isoquinolin-6-ol

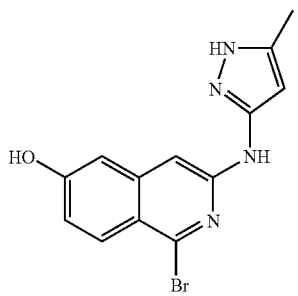

A solution of (1-Chloro-6-methoxy-isoquinolin-3-yl)-(5-methyl-1H-pyrazol-3-yl)-amine (100 mg), 40% HBr (2 ml) and acetic acid (5 ml) was heated at 120° C. overnight. After cooled to room temperature, the reaction mixture was concentrated to oil, and the residue was treated with 50 ml water. The mixture was extracted by ethyl acetate (50 ml×3), and the organic layer was evaporated to give 1-Bromo-3-(5-methyl-1H-pyrazol-3-ylamino)-isoquinolin-6-ol as solid (80 mg). LC-MS: m/e 319 (MH$^+$).

b) Preparation of 1-Isopropoxy-3-(5-methyl-1H-pyrazol-3-ylamino)-isoquinolin-6-ol

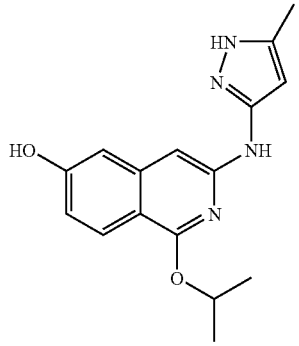

NaH (155 mg) was added to a solution of Propan-2-ol (2 ml) and the resulting mixture was stirred for 1 hour. 1-Bromo-3-(5-methyl-1H-pyrazol-3-ylamino)-isoquinolin-6-ol (100 mg) was added to the mixture, and the mixture was heated at 170° C. for 30 minutes under microwave irradiation. The reaction mixture was acidified to PH=3 with acetic acid and evaporated to oil. The residue was treated with water (50 ml) and the resulting solid was collected to give 1-Isopropoxy-3-(5-methyl-1H-pyrazol-3-ylamino)-isoquinolin-6-ol (50 mg). LC-MS: m/e 299 (MH$^+$).

Example 328

[1-Isopropoxy-6-(2-methoxy-ethoxy)-isoquinolin-3-yl]-(5-methyl-1H-pyrazol-3-yl)-amine

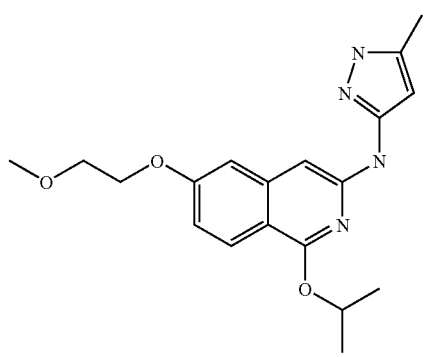

NaH (6 mg) was added to 1-Isopropoxy-3-(5-methyl-1H-pyrazol-3-ylamino)-isoquinolin-6-ol (50 mg) in DMF (2 ml) and stirred at room temperature for 30 minutes. Then 2-bromoethyl methyl ether (23 mg) was added and stirred at room temperature overnight. The mixture was sent to preparative LC-MS and 5 mg of [1-Isopropoxy-6-(2-methoxy-ethoxy)- isoquinolin-3-yl]-(5-methyl-1H-pyrazol-3-yl)-amine was produced. LC-MS m/e 357(MH+).

Example 329

[1-Isopropoxy-6-(2-morpholin-4-yl-ethoxy)-isoquinolin-3-yl]-(5-methyl-1H-pyrazol-3-yl) amine

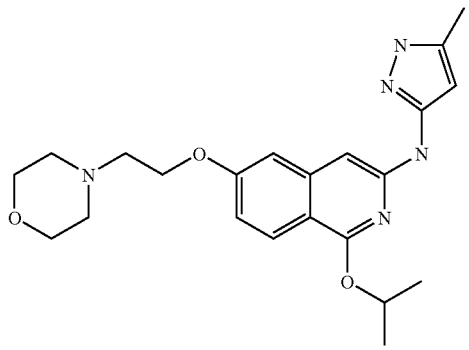

NaH (10 mg) was added to 1-Isopropoxy-3-(5-methyl-1H-pyrazol-3-ylamino)-isoquinolin-6-ol (70 mg) in DMF (1 ml) and stirred at room temperature to give solution A. NaH (10 mg) was added to N-(2-Chloroethyl)-morpholine Hydrochloride (46 mg) in DMF (1 ml) and stirred at room temperature to give solution B. The mixture of A and B was heated at 150° C. for 30 minutes under microwave irradiation and then sent to preparative LC-MS. 3 mg of [1-Isopropoxy-6-(2-morpholin-4-yl-ethoxy)-isoquinolin-3-yl]-(5-methyl-1H-pyrazol-3-yl)-amine was produced. LC-MS m/e 412(MH+).

Example 330

1-Isopropyl-3-(5-methyl-1H-pyrazol-3-ylamino)-isoquinolin-6-ol

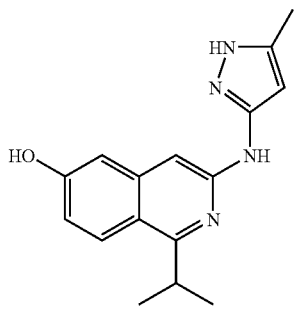

a) Preparation of 1-Isopropenyl-3-(5-methyl-1H-pyrazol-3-ylamino)-isoquinolin-6-ol

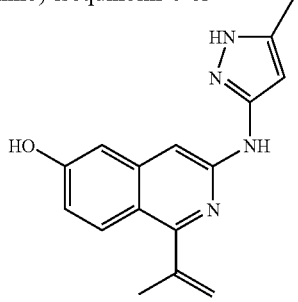

Similar procedure as described in example 131 was used, starting from 1-Bromo-3-(5-methyl-1H-pyrazol-3-ylamino)-isoquinolin-6-ol and isopropenylboronic acid pinacol ester to give 1-Isopropenyl-3-(5-methyl-1H-pyrazol-3-ylamino)-isoquinolin-6-ol. LC-MS m/e 281(MH+).

b) Preparation of 1-Isopropyl-3-(5-methyl-1H-pyrazol-3-ylamino)-isoquinolin-6-ol

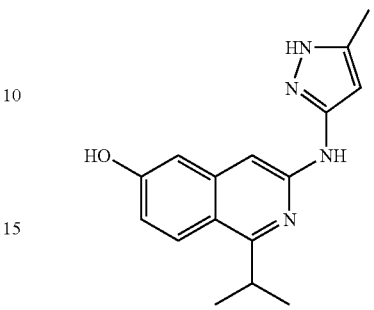

The mixture of 1-Isopropenyl-3-(5-methyl-1H-pyrazol-3-ylamino)-isoquinolin-6-ol (100 mg) and 10% Pd/C (15 mg) was sealed in high-pressure bottle under 40 psi $H_2$ pressure and stirred overnight at room temperature. Then the mixture was filtered, and the filtrate was evaporated to give 1-Isopropyl-3-(5-methyl-1H-pyrazol-3-ylamino)-isoquinolin-6-ol (80 mg) as oil. LC-MS: m/e 283 (MH+).

Example 331

[1-Isopropyl-6-(2-methoxy-ethoxy)-isoquinolin-3-yl]-(5-methyl-1H-pyrazol-3-yl)-amine

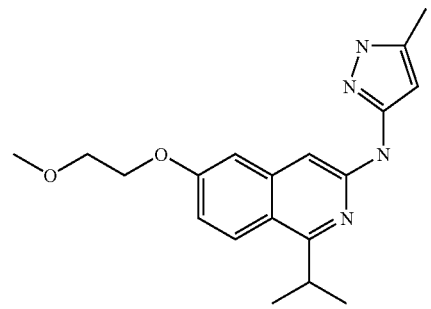

Similar procedure as described in example 328 was used, starting from 1-Isopropyl-3-(5-methyl-1H-pyrazol-3-ylamino)-isoquinolin-6-ol and 2-bromoethyl methyl ether to give [1-Isopropyl-6-(2-methoxy-ethoxy)-isoquinolin-3-yl]-(5-methyl-1H-pyrazol-3-yl)-amine. LC-MS m/e 341(MH+).

Example 332

[1-Isopropyl-6-(2-morpholin-4-yl-ethoxy)-isoquinolin-3-yl]-(5-methyl-1H-pyrazol-3-yl)-amine

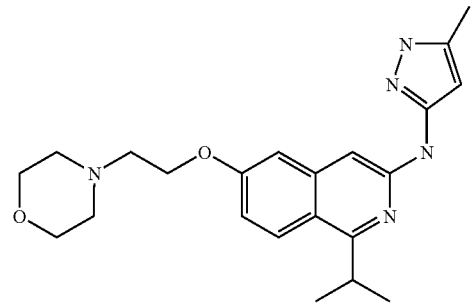

Similar procedure as described in example 329 was used, starting from 1-Isopropyl-3-(5-methyl-1H-pyrazol-3-ylamino)-isoquinolin-6-ol and N-(2-chloroethyl)-morpholine to give [1-Isopropyl-6-(2-morpholin-4-yl-ethoxy)-isoquinolin-3-yl]-(5-methyl-1H-pyrazol-3-yl)-amine. LC-MS m/e 396(MH+).

Example 333

1-Isopropyl-3-(5-methyl-1H-pyrazol-3-ylamino)-isoquinoline-6-carboxylic acid (3-methoxy propyl)-amide

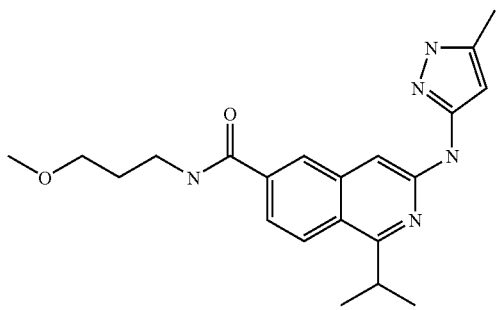

Similar procedure as described in example 301c was used, starting from trifluoro-methanesulfonic acid 1-Isopropyl-3-(5-methyl-1H-pyrazol-3-ylamino)-isoquinolin-6-yl ester and 3-methoxy-propylamine to give 1-Isopropyl-3-(5-methyl-1H-pyrazol-3-ylamino)-isoquinoline-6-carboxylic acid (3-methoxy-propyl)-amide. LC-MS m/e 382(MH+).

Example 334

1-{4-[1-Isopropyl-3-(5-methyl-1H-pyrazol-3-ylamino)-isoquinoline-6-carbonyl]-piperazin-1-yl}-ethanone

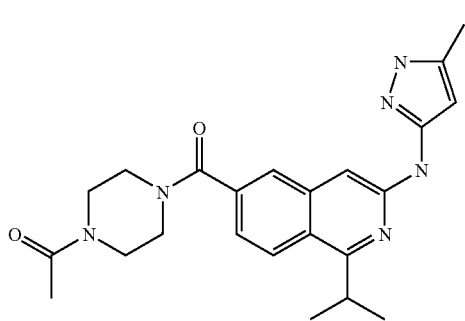

Similar procedure as described in example 301c was used, starting from trifluoromethanesulfonic acid 1-Isopropyl-3-(5-methyl-1H-pyrazol-3-ylamino)-isoquinolin-6-yl ester and 1-acetylpiperazine to give 1-{4-[1-Isopropyl-3-(5-methyl-1H-pyrazol-3-ylamino)-isoquinoline-6-carbonyl]-piperazin-1-yl}-ethanone. LC-MS m/e 421 (MH+).

Example 335

(1-Isopropyl-6,7-dimethoxy-isoquinolin-3-yl)-(5-methyl-1H-pyrazol-3-yl)-amine

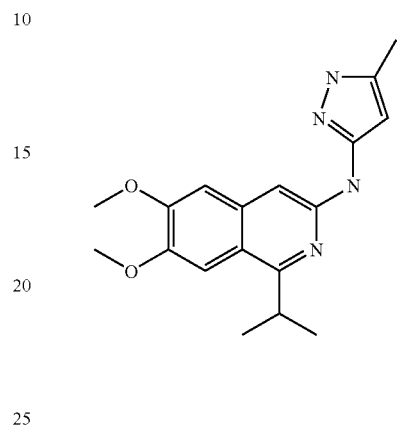

Similar procedure as described in example 330 was used, starting from (1-Chloro-6,7-dimethoxy-isoquinolin-3-yl)-(5-methyl-1H-pyrazol-3-yl)-amine and isopropenylboronic acid pinacol ester to give (1-Isopropyl-6,7-dimethoxy-isoquinolin-3-yl)-(5-methyl-1H-pyrazol-3-yl)-amine. LC-MS m/e 327(MH+).

Example 336

(1-Cyclopropylmethoxy-6,7-dimethoxy-isoquinolin-3-yl)-(5-methyl-1H-pyrazol-3-yl)-amine

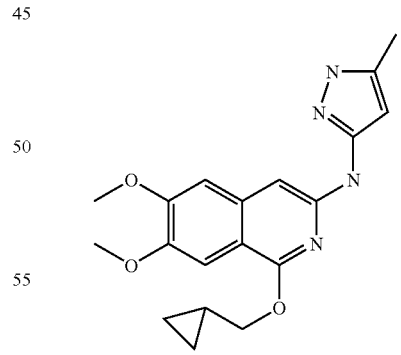

Similar procedure as described in example 10 was used, starting from (1-Chloro-6,7-dimethoxy-isoquinolin-3-yl)-(5-methyl-1H-pyrazol-3-yl)-amine and Cyclopropyl-methanol to give 1-Cyclopropylmethoxy-6,7-dimethoxy-isoquinolin-3-yl)-(5-methyl-1H-pyrazol-3-yl)-amine. LC-MS m/e 355(MH+).

Example 337

(1-Isopropoxy-5-methyl-isoquinolin-3-yl)-(5-methyl-1H-pyrazol-3-yl)-amine

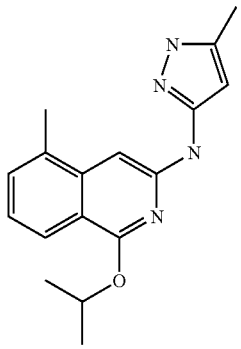

Similar procedure as described in example 10 was used, starting from (1-Chloro-5-methyl-isoquinolin-3-yl)-(5-methyl-1H-pyrazol-3-yl)-amine and 2-propanol to give (1-Isopropoxy-5-methyl-isoquinolin-3-yl)-(5-methyl-1H-pyrazol-3-yl)-amine. LC-MS m/e 297(MH$^+$).

Example 338

[6,7-Dimethoxy-1-(R-tetrahydro-furan-3-yloxy)-isoquinolin-3-yl]-(5-methyl-1H-pyrazol-3-yl)-amine

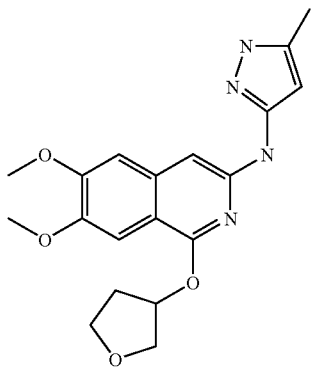

Similar procedure as described in example 10 was used, starting from (1-Chloro-6,7-dimethoxy-isoquinolin-3-yl)-(5-methyl-1H-pyrazol-3-yl)-amine and (R)-tetrahydro-furan-3-ol to give [6,7-Dimethoxy-1-(R-tetrahydro-furan-3-yloxy)-isoquinolin-3-yl]-(5-methyl-1H-pyrazol-3-yl)-amine. LC-MS m/e 371(MH$^+$).

Example 339

[6,7-Dimethoxy-1-(S-tetrahydro-furan-3-yloxy)-isoquinolin-3-yl]-(5-methyl-1H-pyrazol-3-yl)-amine

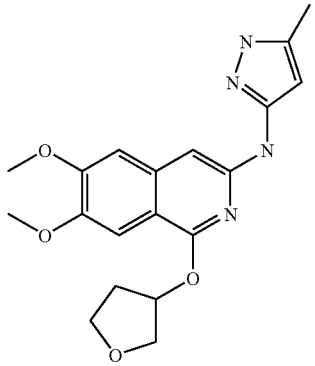

Similar procedure as described in example 10 was used, starting from (1-Chloro-6,7-dimethoxy-isoquinolin-3-yl)-(5-methyl-1H-pyrazol-3-yl)-amine and (S)-tetrahydro-furan-3-ol to give [6,7-Dimethoxy-1-(S-tetrahydro-furan-3-yloxy)-isoquinolin-3-yl]-(5-methyl-1H-pyrazol-3-yl)-amine. LC-MS m/e 371(MH$^+$).

Example 340

[6,7-Dimethoxy-1-(tetrahydro-furan-3-yloxy)-isoquinolin-3-yl]-(5-methyl-1H-pyrazol-3-yl)-amine

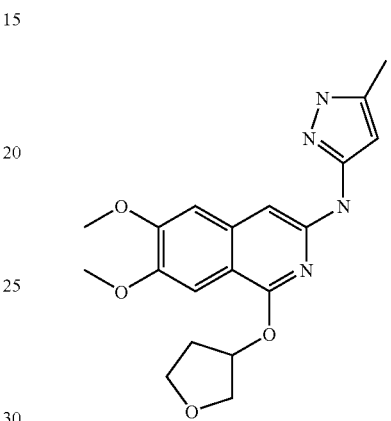

Similar procedure as described in example 10 was used, starting from (1-Chloro-6,7-dimethoxy-isoquinolin-3-yl)-(5-methyl-1H-pyrazol-3-yl)-amine and tetrahydro-furan-3-ol to give [6,7-Dimethoxy-1-(tetrahydro-furan-3-yloxy)-isoquinolin-3-yl]-(5-methyl-1H-pyrazol-3-yl)-amine. LC-MS m/e 371(MH$^+$).

Example 341

(1-Isopropyl-5-methoxy-isoquinolin-3-yl)-(5-methyl-1H-pyrazol-3-yl)-amine

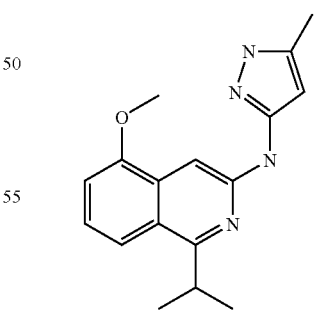

Similar procedure as described in example 330 was used, starting from (1-Chloro-5-methoxy-isoquinolin-3-yl)-(5-methyl-1H-pyrazol-3-yl)-amine and isopropenylboronic acid pinacol ester to give (1-Isopropyl-5-methoxy-isoquinolin-3-yl)-(5-methyl-1H-pyrazol-3-yl)-amine. LC-MS m/e 297(MH$^+$).

Example 342

(1-Ethyl-6-methoxy-isoquinolin-3-yl)-(5-methyl-1H-pyrazol-3-yl)-amine

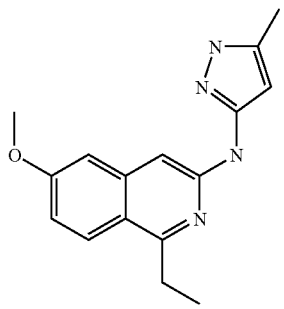

Similar procedure as described in example 330 was used, starting (1-Chloro-6-methoxy-isoquinolin-3-yl)-(5-methyl-1H-pyrazol-3-yl)-amine and ethenylboronic acid pinacol ester to give (1-Ethyl-6-methoxy-isoquinolin-3-yl)-(5-methyl-1H-pyrazol-3-yl)-amine. LC-MS m/e 283(MH$^+$).

Example 343

1-Isopropoxy-7-methoxy-3-(5-methyl-1H-pyrazol-3-ylamino)-isoquinolin-6-ol

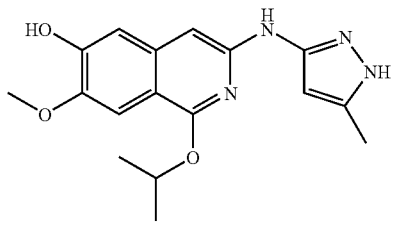

a) Preparation of 3-(3-Hydroxy-4-methoxy-phenyl)-acrylic acid

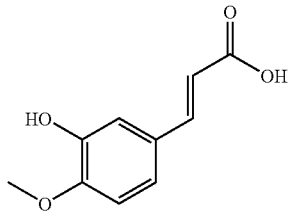

The mixture of 3-hydroxy-4-methoxy-benzaldehyde (30 g) and malonic acid (42 g) in pyridine (80 ml) and piperidine (4 ml) was heated at 120° C. for 6 hours. The solution was cooled to room temperature and concentrated to 20 ml. The residue was dissolved in 500 ml of water and the solution was acidified with concentrated HCl until PH=3. The solid was collected to give 3-(3-Hydroxy-4-methoxy-phenyl)-acrylic acid (40 g). LC-MS: m/e 195 (MH$^+$).

b) Preparation of 3-(3-Hydroxy-4-methoxy-phenyl)-propionic acid

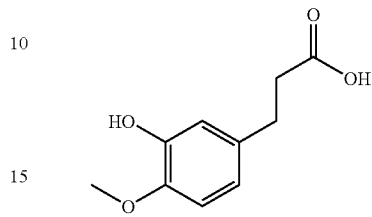

The mixture of 3-(3-Hydroxy-4-methoxy-phenyl)-acrylic acid (3 g), 10% Pd/C (0.5 g), EtOAc (50 ml) and MeOH (50 ml) was shaken in Parr apparatus for 5 hs under 30-40 psi of hydrogen. Then the solution was passed through a celite pad and was concentrated to give 3-(3-Hydroxy-4-methoxy-phenyl)-propionic acid (3 g). LC-MS: m/e 197 (MH$^+$).

c) Preparation of 5-Hydroxy-6-methoxy-indan-1-one

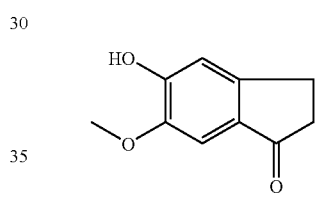

A solution of 3-(3-Hydroxy-4-methoxy-phenyl)-propionic acid in methanesulfonic acid (10 ml) was heated at 90° C. for 10 minutes under microwave irradiation. The mixture was poured into ice (300 g) and stirred for 1 hour. The precipitate was collected and dried to give 5-Hydroxy-6-methoxy-indan-1-one (2 g). LC-MS: m/e 179 (MH$^+$).

d) Preparation of 5-Benzyloxy-6-methoxy-indan-1-one

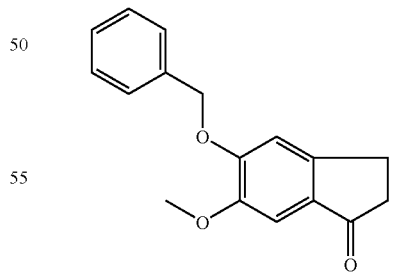

The mixture of 5-Hydroxy-6-methoxy-indan-1-one (2.1 g), K$_2$CO$_3$ (3.3 g), acetone (30 ml) and benzyl bromide was heated to reflux for 5 hours. The mixture was filtered and the filtrate was evaporated to oil. The oil was treated with diethyl ether (50 ml) and the solid was collected to give 5-Benzyloxy-6-methoxy-indan-1-one (3 g). LC-MS: m/e 269 (MH$^+$).

e) Preparation of 5-Benzyloxy-6-methoxy-indan-1,2-dione 2-oxime

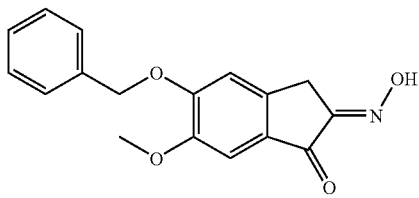

Similar procedure as described in example 2a was used, starting from 5-Benzyloxy-6-methoxy-indan-1-one and n-butylnitrite to give 5-Benzyloxy-6-methoxy-indan-1,2-dione 2-oxime. LC-MS: m/e 298 (MH$^+$).

f) Preparation of 4-Benzyloxy-2-cyanomethyl-5-methoxy-benzoic acid

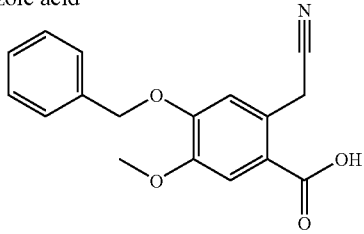

Similar procedure as described in example 2b was used, starting from 5-Benzyloxy-6-methoxy-indan-1,2-dione 2-oxime to give 4-Benzyloxy-2-cyanomethyl-5-methoxy-benzoic acid. LC-MS: m/e 298 (MH$^+$).

g) Preparation of 6-Benzyloxy-7-methoxy-3-(5-methyl-1H-pyrazol-3-ylamino)-2H-isoquinolin-1-one

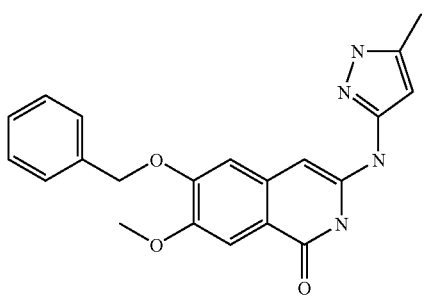

Similar procedure as described in example 2c was used, starting from 4-Benzyloxy-2-cyanomethyl-5-methoxy-benzoic acid and 3-amino-5-methyl-1H-pyrazole to give 6-Benzyloxy-7-methoxy-3-(5-methyl-1H-pyrazol-3-ylamino)-2H-isoquinolin-1-one. LC-MS: m/e 377 (MH$^+$).

h) Preparation of (6-Benzyloxy-1-chloro-7-methoxy-isoquinolin-3-yl)-(5-methyl-1H-pyrazol-3-yl)-amine

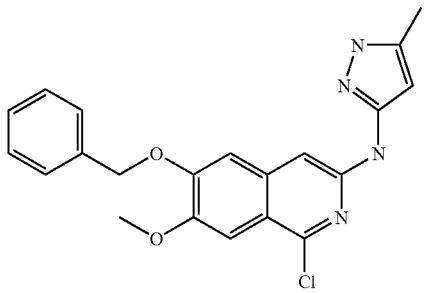

Similar procedure as described in example 2d was used, starting from 6-Benzyloxy-7-methoxy-3-(5-methyl-1H-pyrazol-3-ylamino)-2H-isoquinolin-1-one to give (6-Benzyloxy-1-chloro-7-methoxy-isoquinolin-3-yl)-(5-methyl-1H-pyrazol-3-yl)-amine. LC-MS: m/e 395 (MH$^+$).

i) Preparation of (6-Benzyloxy-1-isopropoxy-7-methoxy-isoquinolin-3-yl)-(5-methyl-1H-pyrazol-3-yl)-amine

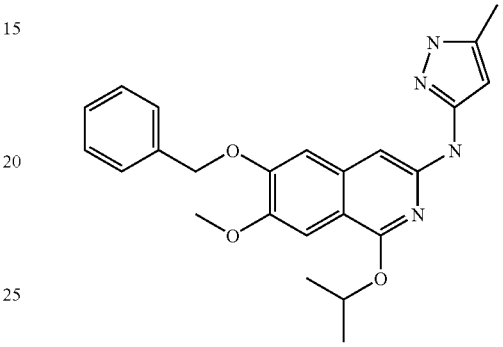

Similar procedure as described in example 10 was used, starting from (6-Benzyloxy-1-chloro-7-methoxy-isoquinolin-3-yl)-(5-methyl-1H-pyrazol-3-yl)-amine and 2-propanol to give (6-benzyloxy-1-isopropoxy-7-methoxy-isoquinolin-3-yl)-(5-methyl-1H-pyrazol-3-yl)-amine. LC-MS m/e 419(MH$^+$).

j) Preparation of 1-Isopropoxy-7-methoxy-3-(5-methyl-1H-pyrazol-3-ylamino)-isoquinolin-6-ol

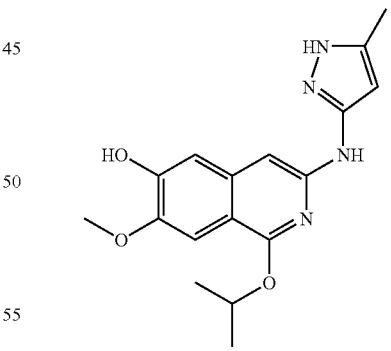

A mixture of (6-benzyloxy-1-isopropoxy-7-methoxy-isoquinolin-3-yl)-(5-methyl-1H-pyrazol-3-yl)-amine (300 mg), 10% Pd/C (50 mg) and MeOH (80 ml) was shaken in Parr apparatus for 5 hs under 30-40 psi of hydrogen at room temperature. Then the mixture was passed through a celite pad and the filtrate was concentrated and dried to give 1-Isopropoxy-7-methoxy-3-(5-methyl-1H-pyrazol-3-ylamino)-isoquinolin-6-ol (250 mg). LC-MS: m/e 329 (MH$^+$).

Example 344

[1-Isopropoxy-7-methoxy-6-(2-methoxy-ethoxy)-isoquinolin-3-yl]-(5-methyl-1H-pyrazol-3-yl)-amine

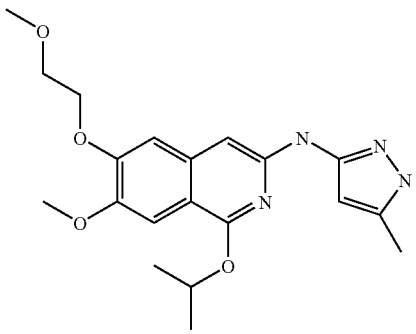

Similar procedure as described in example 328 was used, starting from 1-Isopropoxy-7-methoxy-3-(5-methyl-1H-pyrazol-3-ylamino)-isoquinolin-6-ol and 2-bromoethyl methyl ether to give [1-Isopropoxy-7-methoxy-6-(2-methoxy-ethoxy)-isoquinolin-3-yl]-(5-methyl-1H-pyrazol-3-yl)-amine. LC-MS m/e 387(MH⁺).

Example 345

[1-Isopropoxy-7-methoxy-6-(2-morpholin-4-yl-ethoxy)-isoquinolin-3-yl]-(5-methyl-1H-pyrazol-3-yl)-amine

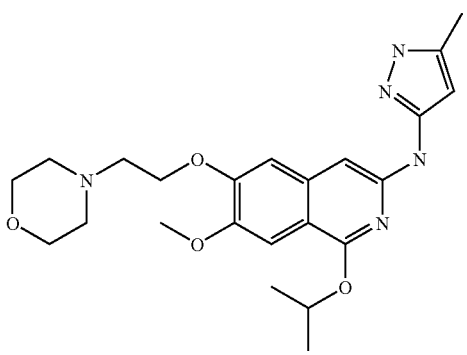

Similar procedure as described in example 329 was used, starting from 1-Isopropoxy-7-methoxy-3-(5-methyl-1H-pyrazol-3-ylamino)-isoquinolin-6-ol and N-(2-chloroethyl)-morpholine to give [1-Isopropoxy-7-methoxy-6-(2-morpholin-4-yl-ethoxy)-isoquinolin-3-yl]-(5-methyl-1H-pyrazol-3-yl)-amine. LC-MS m/e 442(MH⁺).

Example 346

[1-Isopropoxy-7-methoxy-6-(tetrahydro-pyran-4-yloxy)-isoquinolin-3-yl]-(5-methyl-1H-pyrazol-3-yl)-amine

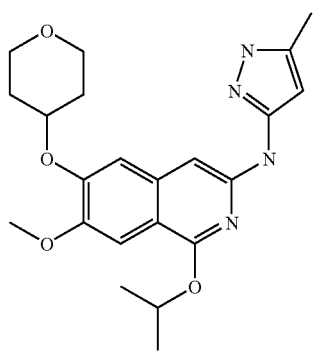

Similar procedure as described in example 328 was used, starting from 1-Isopropoxy-7-methoxy-3-(5-methyl-1H-pyrazol-3-ylamino)-isoquinolin-6-ol and 4-chloro-tetrahydropyran to give [1-Isopropoxy-7-methoxy-6-(tetrahydro-pyran-4-yloxy)-isoquinolin-3-yl]-(5-methyl-1H-pyrazol-3-yl)-amine. LC-MS m/e 413(MH⁺).

Example 347

1-Isopropoxy-7-methoxy-3-(5-methyl-1H-pyrazol-3-ylamino)-isoquinoline-6-carboxylic acid (3-methoxy-propyl)-amide

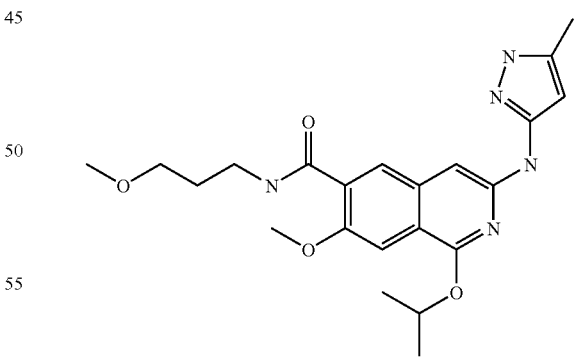

Similar procedure as described in example 301c was used, starting from trifluoromethanesulfonic acid 1-Isopropoxy-7-methoxy-3-(5-methyl-1H-pyrazol-3-ylamino)-isoquinolin-6-yl ester and 3-methoxy-propylamine to give 1-Isopropoxy-7-methoxy-3-(5-methyl-1H-pyrazol-3-ylamino)-isoquinoline-6-carboxylic acid (3-methoxy-propyl)-amide. LC-MS m/e 428(MH⁺).

Example 348

[1-Isopropoxy-7-methoxy-3-(5-methyl-1H-pyrazol-3-ylamino)-isoquinolin-6-yl]-morpholin-4-yl-methanone

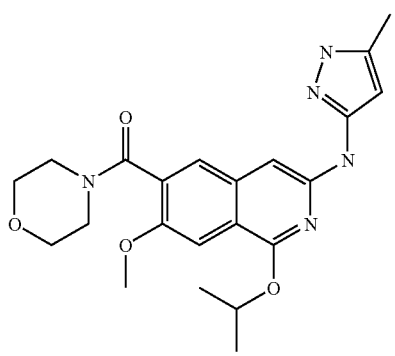

Similar procedure as described in example 301c was used, starting from trifluoromethanesulfonic acid 1-Isopropoxy-7-methoxy-3-(5-methyl-1H-pyrazol-3-ylamino)-isoquinolin-6-yl ester and morpholine to give [1-Isopropoxy-7-methoxy-3-(5-methyl-1H-pyrazol-3-ylamino)-isoquinolin-6-yl]-morpholin-4-yl-methanone. LC-MS m/e 426(MH$^+$).

Example 349

1-Isopropoxy-7-methoxy-3-(5-methyl-1H-pyrazol-3-ylamino)-isoquinoline-6-carboxylic acid dimethylamide

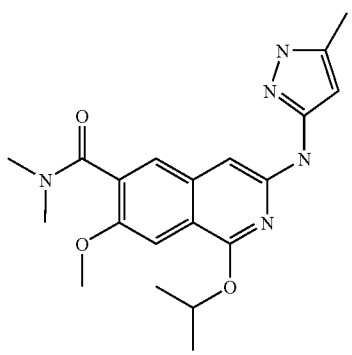

Similar procedure as described in example 301c was used, starting from trifluoromethanesulfonic acid 1-Isopropoxy-7-methoxy-3-(5-methyl-1H-pyrazol-3-ylamino)-isoquinolin-6-yl ester and dimethylamine to give 1-Isopropoxy-7-methoxy-3-(5-methyl-1H-pyrazol-3-ylamino)-isoquinoline-6-carboxylic acid dimethylamide. LC-MS m/e 384(MH$^+$).

Example 350

(8-Chloro-2,3-dihydro-1,4-dioxa-7-aza-phenanthren-6-yl)-(5-methyl-1H-pyrazol-3-yl)-amine

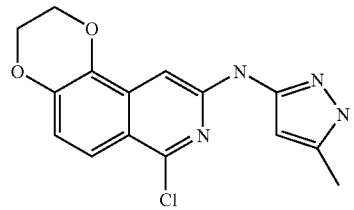

a) Preparation of 2,3-Dihydro-benzo[1,4]dioxine-5-carbaldehyde

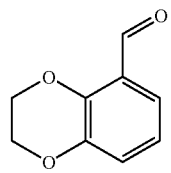

The mixture of 2,3-Dihydroxy-benzaldehyde (10.5 g), K$_2$CO$_3$ (21 g), DMF (150 ml), and CH$_2$Br$_2$ (7.8 ml) was heated at 85° C. for 5 hours. Then 300 ml of water was added and the solution was stirred for 1 hour. The solid was formed and collected to give 2,3-Dihydrobenzo[1,4]dioxine-5-carbaldehyde (11 g). LC-MS: m/e 165 (MH$^+$).

b) Preparation of 3-(2,3-Dihydro-benzo[1,4]dioxin-5-yl)-acrylic acid

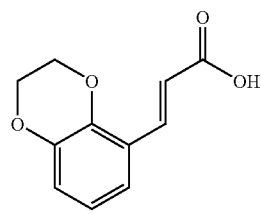

Similar procedure as described in example 343a was used, starting from 2,3-Dihydro-benzo[1,4]dioxine-5-carbaldehyde and malonic acid to give 3-(2,3-Dihydro-benzo[1,4]dioxin-5-yl)-acrylic acid. LC-MS: m/e 207 (MH$^+$).

c) Preparation of 3-(2,3-Dihydro-benzo[1,4]dioxin-5-yl)-propionic acid

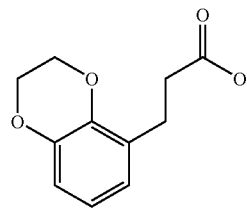

Similar procedure as described in example 343b was used, starting from 3-(2,3-Dihydro-benzo[1,4]dioxin-5-yl)-acrylic acid to give 3-(2,3-Dihydro-benzo[1,4]dioxin-5-yl)-propionic acid. LC-MS: m/e 209 (MH⁺).

d) Preparation of 1,2,7,8-Tetrahydro-6,9-dioxa-cyclopenta[a]naphthalen-3-one

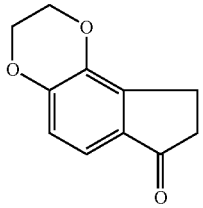

Similar procedure as described in example 343c was used, starting from 3-(2,3-Dihydro-benzo[1,4]dioxin-5-yl)-propionic acid to give 1,2,7,8-Tetrahydro-6,9-dioxa-cyclopenta[a]-naphthalen-3-one. LC-MS: m/e 191 (MH⁺).

e) Preparation of 7,8-Dihydro-1H-6,9-dioxa-cyclopenta[a]naphthalene-2,3-dione 2-oxime

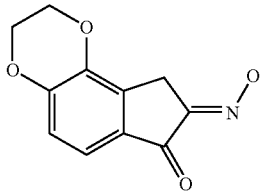

Similar procedure as described in example 2a was used, starting from 2,7,8-Tetrahydro-6,9-dioxa-cyclopenta[a]naphthalen-3-one to give 7,8-Dihydro-1H-6,9-dioxa-cyclopenta [a]-naphthalene-2,3-dione 2-oxime. LC-MS: m/e 220 (MH⁺).

f) Preparation of 5-Cyanomethyl-2,3-dihydro-benzo[1,4]dioxine-6-carboxylic acid

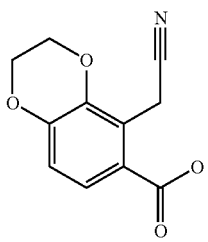

Similar procedure as described in example 2b was used, starting from 7,8-Dihydro-1H-6,9-dioxa-cyclopenta[a]naphthalene-2,3-dione 2-oxime to give 5-Cyanomethyl-2,3-dihydro-benzo[1,4]dioxine-6-carboxylic acid. LC-MS: m/e 220 (MH⁺).

g) Preparation of 6-(5-Methyl-1H-pyrazol-3-ylamino)-2,3-dihydro-7H-1,4-dioxa-7-aza-phenanthren-8-one

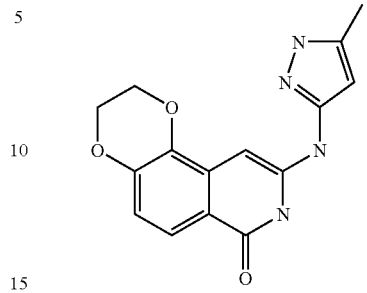

Similar procedure as described in example 2c was used, starting from 5-Cyanomethyl-2,3-dihydro-benzo[1,4]dioxine-6-carboxylic acid and 3-amino-5-methylpyrazole to give 6-(5-Methyl-1H-pyrazol-3-ylamino)-2,3-dihydro-7H-1,4-dioxa-7-aza-phenanthren-8-one. LC-MS: m/e 299 (MH⁺).

h) Preparation of (8-Chloro-2,3-dihydro-1,4-dioxa-7-aza-phenanthren-6-yl)-(5-methyl-1H-pyrazol-3-yl)-amine

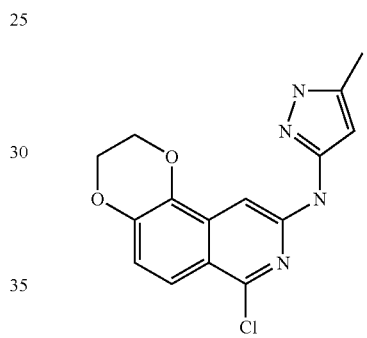

Similar procedure as described in example 2d was used, starting from 6-(5-Methyl-1H-pyrazol-3-ylamino)-2,3-dihydro-7H-1,4-dioxa-7-aza-phenanthren-8-one to give (8-Chloro-2,3-dihydro-1,4-dioxa-7-aza-phenanthren-6-yl)-(5-methyl-1H-pyrazol-3-yl)-amine. LC-MS: m/e 317 (MH⁺).

Example 351

(8-Isopropoxy-2,3-dihydro-1,4-dioxa-7-aza-phenanthren-6-yl)-(5-methyl-1H-pyrazol-3-yl)-amine

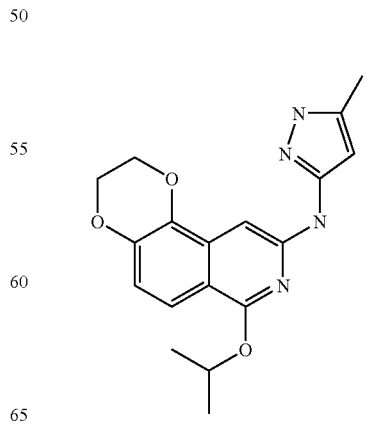

Similar procedure as described in example 10 was used, starting from (8-Chloro-2,3-dihydro-1,4-dioxa-7-aza-phenanthren-6-yl)-(5-methyl-1H-pyrazol-3-yl)-amine and 2-propanol to give (8-Isopropoxy-2,3-dihydro-1,4-dioxa-7-aza-phenanthren-6-yl)-(5-methyl-1H-pyrazol-3-yl)-amine. LC-MS m/e 341(MH+).

Example 352

(8-Isopropyl-2,3-dihydro-1,4-dioxa-7-aza-phenanthren-6-yl)-(5-methyl-1H-pyrazol-3-yl)-amine

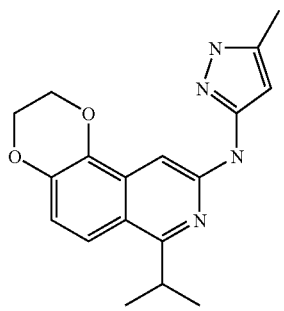

Similar procedure as described in example 330 was used, starting from (8-Chloro-2,3-dihydro-1,4-dioxa-7-aza-phenanthren-6-yl)-(5-methyl-1H-pyrazol-3-yl)-amine and isopropenylboronic acid pinacol ester to give (8-Isopropyl-2,3-dihydro-1,4-dioxa-7-aza-phenanthren-6-yl)-(5-methyl-1H-pyrazol-3-yl)-amine. LC-MS m/e 325(MH+).

Example 353

[1-Chloro-6-fluoro-7-(2-methoxy-ethoxy)-isoquinolin-3-yl]-(5-methyl-1H-pyrazol-3-yl)-amine

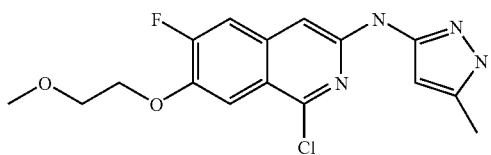

a) Preparation of 3-Fluoro-4-(2-methoxy-ethoxy)-benzaldehyde

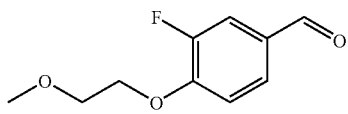

NaH (7.3 g) was carefully added to a solution of 2-Methoxy-ethanol (15 ml) in DMF (200 ml) and the solution was stirred for 4 hours. 3,4-difluoro-benzaldehyde (14 g) was added to the mixture under $N_2$ at 0° C., and the resulting mixture was slowly warmed to room temperature and stirred for another 6 hours. Saturated aqueous $NH_4Cl$ (200 ml) was added to the solution, and the mixture was extracted by ethyl acetate (500 ml×3). The organic layer was evaporated to give 3-Fluoro-4-(2-methoxy-ethoxy)-benzaldehyde as oil (15 g). LC-MS: m/e 199 (MH+).

b) Preparation of 3-[3-Fluoro-4-(2-methoxy-ethoxy)-phenyl]-acrylic acid

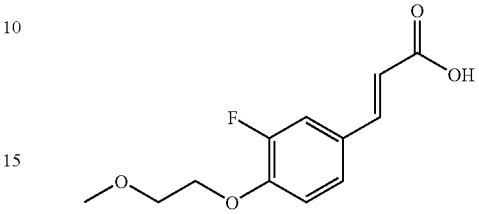

Similar procedure as described in example 343a was used, starting from 3-Fluoro-4-(2-methoxy-ethoxy)-benzaldehyde and malonic acid to give 3-[3-Fluoro-4-(2-methoxy-ethoxy)-phenyl]-acrylic acid. LC-MS: m/e 241 (MH+).

c) Preparation of 3-[3-Fluoro-4-(2-methoxy-ethoxy)-phenyl]-propionic acid

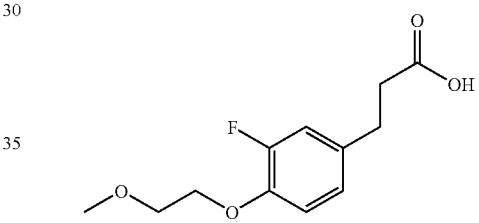

Similar procedure as described in example 343b was used, starting from 3-[3-Fluoro-4-(2-methoxy-ethoxy)-phenyl]-acrylic acid to give 3-[3-Fluoro-4-(2-methoxy-ethoxy)-phenyl]-propionic acid. LC-MS: m/e 243 (MH+).

d) Preparation of 5-Fluoro-6-(2-methoxy-ethoxy)-indan-1-one

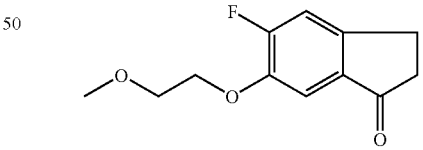

The mixture of 3-[3-Fluoro-4-(2-methoxy-ethoxy)-phenyl]-propionic acid (16 g) in $SOCl_2$ (50 ml) was refluxed for 4 hours. The mixture was evaporated, the residue was dissolved in $CS_2$ (100 ml), and then $AlCl_3$ (20 g) was added. The mixture was heated at 45° C. for 4 hours. 200 ml of ice-water was added to the cooled mixture and the mixture was stirred for another 1 hour. The mixture was extracted by ethyl acetate (300 ml×3). The product was purified by flash column chromatography using ethyl acetate:PE=5:1 as eluent. LC-MS: m/e 225 (MH+).

e) Preparation of 5-Fluoro-6-(2-methoxy-ethoxy)-indan-1,2-dione 2-oxime

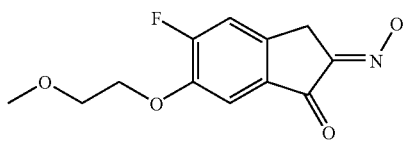

Similar procedure as described in example 2a was used, starting from 5-Fluoro-6-(2-methoxy-ethoxy)-indan-1-one to give 5-Fluoro-6-(2-methoxy-ethoxy)-indan-1,2-dione 2-oxime. LC-MS: m/e 254 (MH$^+$).

f) Preparation of 2-Cyanomethyl-4-fluoro-5-(2-methoxy-ethoxy)-benzoic acid

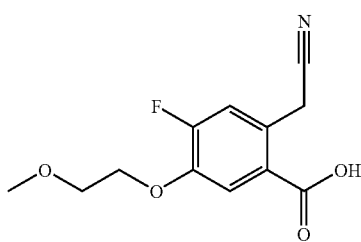

Similar procedure as described in example 2b was used, starting from 5-Fluoro-6-(2-methoxy-ethoxy)-indan-1,2-dione 2-oxime to give 2-Cyanomethyl-4-fluoro-5-(2-methoxy-ethoxy)-benzoic acid. LC-MS: m/e 254(MH$^+$).

g) Preparation of 6-Fluoro-7-(2-methoxy-ethoxy)-3-(5-methyl-1H-pyrazol-3-ylamino)-2H-isoquinolin-1-one

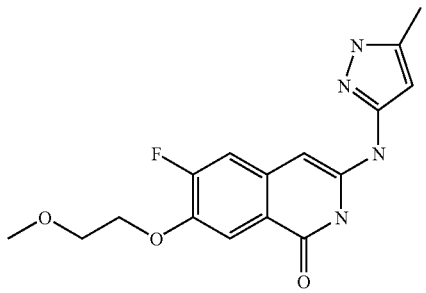

Similar procedure as described in example 2c was used, starting from 2-Cyanomethyl-4-fluoro-5-(2-methoxy-ethoxy)-benzoic acid and 3-amino-5-methylpyrazole to give 6-Fluoro-7-(2-methoxy-ethoxy)-3-(5-methyl-1H-pyrazol-3-ylamino)-2H-isoquinolin-1-one. LC-MS: m/e 333 (MH$^+$).

h) Preparation of [1-Chloro-6-fluoro-7-(2-methoxy-ethoxy)-isoquinolin-3-yl]-(5-methyl-1H-pyrazol-3-yl)-amine

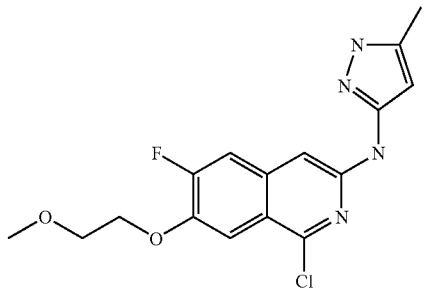

Similar procedure as described in example 2d was used, starting from 6-Fluoro-7-(2-methoxy-ethoxy)-3-(5-methyl-1H-pyrazol-3-ylamino)-2H-isoquinolin-1-one to give [1-Chloro-6-fluoro-7-(2-methoxy-ethoxy)-isoquinolin-3-yl]-(5-methyl-1H-pyrazol-3-yl)-amine. LC-MS: m/e 351(MH$^+$).

Example 354

[1,6-Diethoxy-7-(2-methoxy-ethoxy)-isoquinolin-3-yl]-(5-methyl-1H-pyrazol-3-yl)-amine

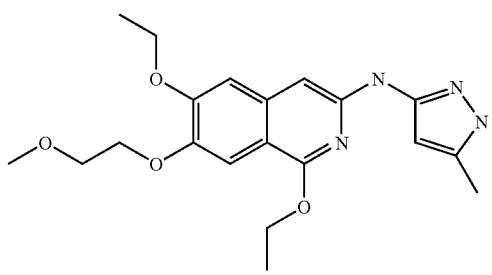

Similar procedure as described in example 10 was used, starting from [1-Chloro-6-fluoro-7-(2-methoxy-ethoxy)-isoquinolin-3-yl]-(5-methyl-1H-pyrazol-3-yl)-amine and ethanol to give [1,6-Diethoxy-7-(2-methoxy-ethoxy)-isoquinolin-3-yl]-(5-methyl-1H-pyrazol-3-yl)-amine. LC-MS m/e 387(MH$^+$).

Example 355

[1,6-Diisopropoxy-7-(2-methoxy-ethoxy)-isoquinolin-3-yl]-(5-methyl-1H-pyrazol-3-yl)-amine

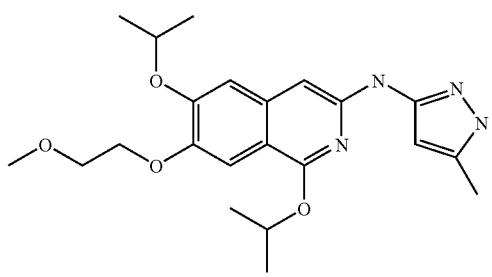

Similar procedure as described in example 10 was used, starting from [1-Chloro-6-fluoro-7-(2-methoxy-ethoxy)-isoquinolin-3-yl]-(5-methyl-1H-pyrazol-3-yl)-amine and 2-propanol to give [1,6-Diisopropoxy-7-(2-methoxy-ethoxy)-isoquinolin-3-yl]-(5-methyl-1H-pyrazol-3-yl)-amine. LC-MS m/e 415(MH$^+$).

Example 356

[1-Isopropoxy-7-(2-methoxy-ethoxy)-6-(tetrahydro-furan-3-yloxy)-isoquinolin-3-yl]-(5-methyl-1H-pyrazol-3-yl)-amine

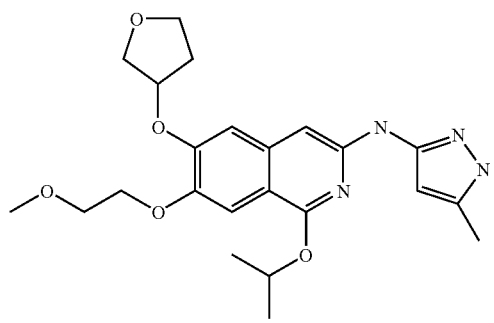

a) Preparation of [1-Chloro-7-(2-methoxy-ethoxy)-6-(tetrahydro-furan-3-yloxy)-isoquinolin-3-yl]-(5-methyl-1H-pyrazol-3-yl)-amine

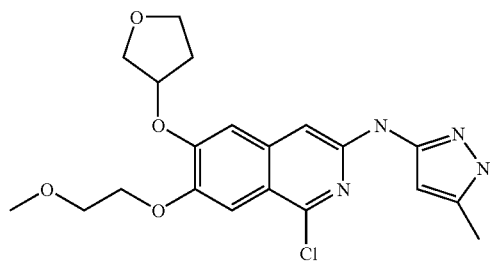

NaH (70 mg) was carefully added to a solution of tetrahydro-furan-3-ol (0.2 ml) in DMF (3 ml) and the mixture was stirred for 1 hour. [1-Chloro-6-fluoro-7-(2-methoxy-ethoxy)-isoquinolin-3-yl]-(5-methyl-1H-pyrazol-3-yl)-amine (100 mg) was added under N$_2$, and the mixture was heated at 90° C. overnight. The mixture was poured to 50 ml of water. The mixture was extracted by ethyl acetate (50 ml×3). The organic layer was evaporated to give [1-Chloro-7-(2-methoxy-ethoxy)-6-(tetrahydro-furan-3-yloxy)-isoquinolin-3-yl]-(5-methyl-1H-pyrazol-3-yl)-amine as oil (100 mg). LC-MS: m/e 419(MH+).

b) Preparation of [1-Isopropoxy-7-(2-methoxy-ethoxy)-6-(tetrahydro-furan-3-yloxy)-isoquinolin-3-yl]-(5-methyl-1H-pyrazol-3-yl)-amine

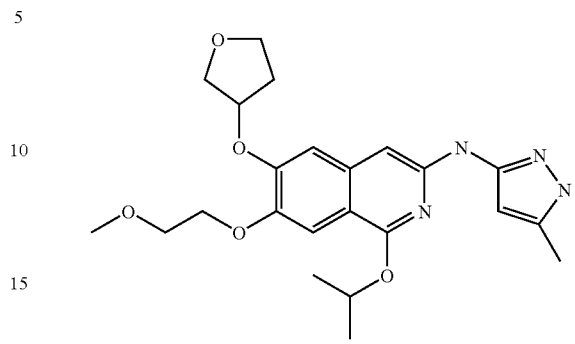

Similar procedure as described in example 10 was used, starting from [1-Chloro-6-fluoro-7-(2-methoxy-ethoxy)-isoquinolin-3-yl]-(5-methyl-1H-pyrazol-3-yl)-amine and 2-propanol to give [1-Isopropoxy-7-(2-methoxy-ethoxy)-6-(tetrahydro-furan-3-yloxy)-isoquinolin-3-yl]-(5-methyl-1H-pyrazol-3-yl)-amine. LC-MS m/e 443(MH$^+$).

Example 357

3-[1-Isopropoxy-7-(2-methoxy-ethoxy)-3-(5-methyl-1H-pyrazol-3-ylamino)-isoquinolin-6-yloxy]-propane-1,2-diol

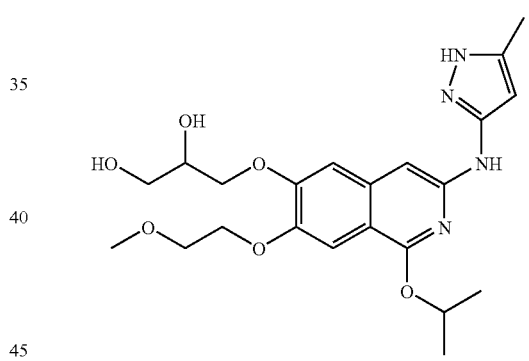

a) Preparation of [1-Chloro-6-(2,2-dimethyl-[1,3]dioxolan-4-ylmethoxy)-7-(2-methoxy-ethoxy)-isoquinolin-3-yl]-(5-methyl-1H-pyrazol-3-yl)-amine

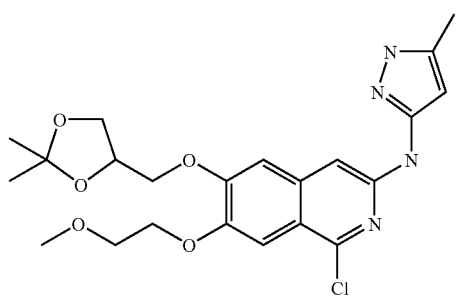

NaH (150 mg) was carefully added to the solution of (2,2-Dimethyl-[1,3]dioxolan-4-yl)-methanol (0.3 ml) in DMF (2 ml) and the mixture was stirred for 1 hour. [1-Chloro-6-fluoro-7-(2-methoxy-ethoxy)-isoquinolin-3-yl]-(5-methyl- 1H-pyrazol-3-yl)-amine (100 mg) was added under N$_2$, and the mixture was heated at 90° C. for 1 hour. The mixture was poured into 50 ml of water. The mixture was extracted by ethyl acetate (50 ml×3). The organic layer was evaporated to give [1-Chloro-6-(2,2-dimethyl-[1,3]dioxolan-4-yl-methoxy)-7-(2-methoxy-ethoxy)-isoquinolin-3-yl]-(5-methyl-1H-pyrazol-3-yl)-amine as oil (100 mg). LC-MS: m/e 463(MH+).

b) Preparation of [6-(2,2-dimethyl-[1,3]dioxolan-4-yl-methoxy)-1-isopropoxy-7-(2-methoxy-ethoxy)-isoquinolin-3-yl]-(5-methyl-1H-pyrazol-3-yl)-amine

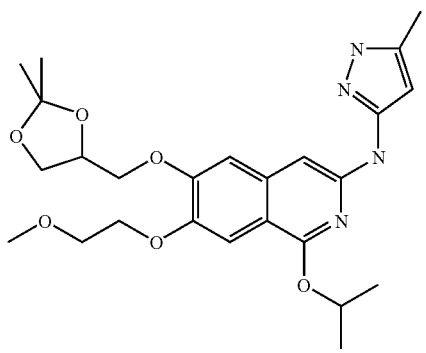

Similar procedure as described in example 10 was used, starting from [1-Chloro-6-(2,2-dimethyl-[1,3]dioxolan-4-yl-methoxy)-7-(2-methoxy-ethoxy)-isoquinolin-3-yl]-(5-methyl-1H-pyrazol-3-yl)-amine and 2-propanol to give [6-(2,2-dimethyl-[1,3]dioxolan-4-ylmethoxy)-1-isopropoxy-7-(2-methoxy-ethoxy)-isoquinolin-3-yl]-(5-methyl-1H-pyrazol-3-yl)-amine. LC-MS m/e 501(MH$^+$).

d) Preparation of 3-[1-Isopropoxy-7-(2-methoxy-ethoxy)-3-(5-methyl-1H-pyrazol-3-ylamino)-isoquinolin-6-yloxy]-propane-1,2-diol

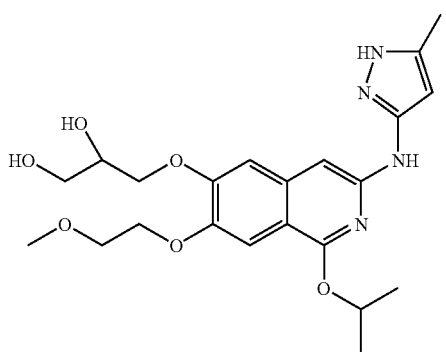

A solution of 30 mg of [6-(2,2-dimethyl-[1,3]dioxolan-4-ylmethoxy)-1-isopropoxy-7-(2-methoxy-ethoxy)-isoquinolin-3-yl]-(5-methyl-1H-pyrazol-3-yl)-amine in 5 ml THF and 1 ml 1NHCl was stirred at room temperature for 3 h, and sent to Prep. LC-MS after neutralized with NaHCO$_3$. 5 mg of 3-[1-Isopropoxy-7-(2-methoxy-ethoxy)-3-(5-methyl-1H-pyrazol-3-ylamino)-isoquinolin-6-yloxy]-propane-1,2-diol was produce as solid. LC-MS: m/e 447 (MH$^+$).

Example 358

[1-Isopropoxy-3-(5-methyl-1H-pyrazol-3-ylamino)-isoquinolin-6-yl]-morpholin-4-yl-methanone

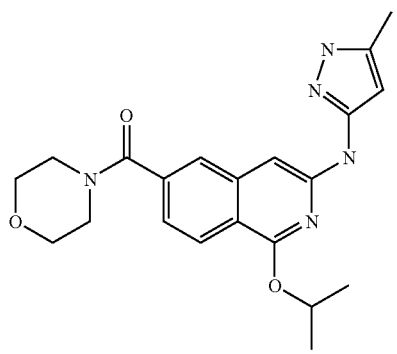

A 2.0~5.0 mL process vial was charged with trifluoro-methanesulfonic acid 1-isopropoxy-3-(5-methyl-1H-pyrazol-3-ylamino)-isoquinolin-6-yl ester (56.2 mg, 1 mmol), Pd(OAc)$_2$ (4 mg), Mo(CO)$_6$ (26.4 mg), morpholine (26.0 mg), DBU (45 mg), and dry THF (2 mL). The vial was immediately capped under air and heated at 150° C. for 15 min under microwave irradiation. After cooling, the reaction mixture was filtered through a short silica gel column, and the solvent was removed under reduced pressure. The residue was sent to prep-HPLC to give 5 mg of [1-Isopropoxy-3-(5-methyl-1H-pyrazol-3-ylamino)-isoquinolin-6-yl]-morpholin-4-yl-methanone as a yellow solid. LC-MS m/e 396 (MH$^+$).

Example 359

1-Isopropoxy-3-(5-methyl-1H-pyrazol-3-ylamino)-isoquinoline-6-carboxylic acid dimethyl-amide

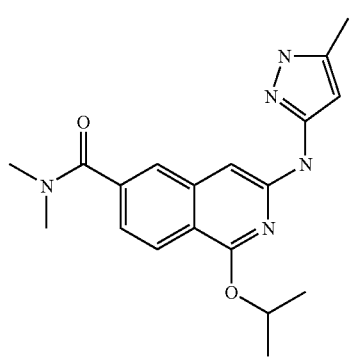

Similar procedure as described in example 358 was used, starting from Trifluoro-methanesulfonic acid 1-isopropoxy-3-(5-methyl-1H-pyrazol-3-ylamino)-isoquinolin-6-yl ester and Dimethylamine hydrochloride to give 5 mg of 1-Isopropoxy-3-(5-methyl-1H-pyrazol-3-ylamino)-isoquinoline-6-carboxylic acid dimethylamide as a yellow solid. LC-MS m/e 354 (MH$^+$).

Example 360

1-Isopropoxy-3-(5-methyl-1H-pyrazol-3-ylamino)-isoquinoline-6-carboxylic acid (3-methoxy-propyl)-amide

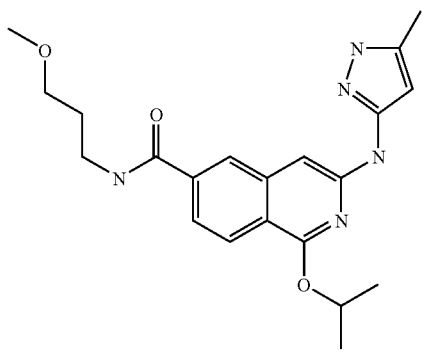

Similar procedure as described in example 358 was used, starting from Trifluoro-methanesulfonic acid 1-isopropoxy-3-(5-methyl-1H-pyrazol-3-ylamino)-isoquinolin-6-yl ester and 3-Methoxy-propylamine to give 5 mg of 1-Isopropoxy-3-(5-methyl-1H-pyrazol-3-ylamino)-isoquinoline-6-carboxylic acid (3-methoxy-propyl)-amide as a yellow solid. LC-MS m/e 398 (MH+).

Example 361

1-Isopropoxy-3-(5-methyl-1H-pyrazol-3-ylamino)-isoquinoline-6-carboxylic acid (3-dimethylamino-propyl)-amide

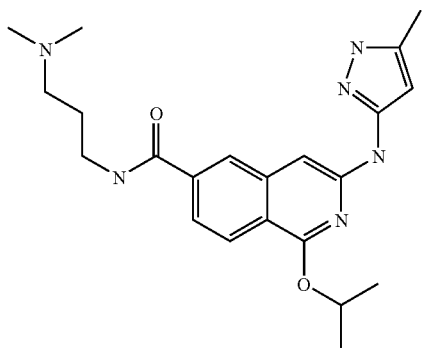

Similar procedure as described in example 358 was used, starting from Trifluoro-methanesulfonic acid 1-isopropoxy-3-(5-methyl-1H-pyrazol-3-ylamino)-isoquinolin-6-yl ester and N,N-Dimethyl-propane-1,3-diamine to give 5 mg of 1-Isopropoxy-3-(5-methyl-1H-pyrazol-3-ylamino)-isoquinoline-6-carboxylic acid (3-dimethylamino-propyl)-amide as a yellow solid. LC-MS m/e 411 (MH+).

Example 362

[1-Isopropoxy-3-(5-methyl-1H-pyrazol-3-ylamino)-isoquinolin-6-yl]-piperidin-1-yl-methanone

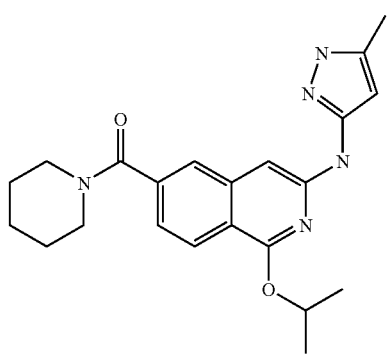

Similar procedure as described in example 358 was used, starting from Trifluoro-methanesulfonic acid 1-isopropoxy-3-(5-methyl-1H-pyrazol-3-ylamino)-isoquinolin-6-yl ester and piperidine to give 5 mg of [1-Isopropoxy-3-(5-methyl-1H-pyrazol-3-ylamino)-isoquinolin-6-yl]-piperidin-1-yl-methanone as a yellow solid. LC-MS m/e 394 (MH+).

Example 363

[1-Isopropoxy-6-(4-methyl-piperazin-1-yl)-isoquinolin-3-yl]-(5-methyl-1H-pyrazol-3-yl)-amine

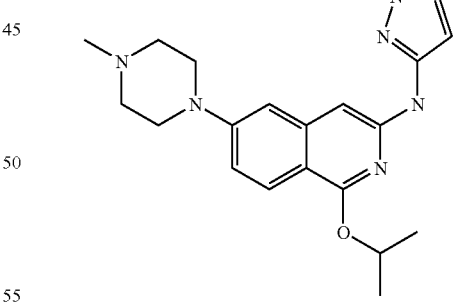

A 2.0~5.0 mL process vial was charged with Trifluoro-methanesulfonic acid 1-isopropoxy-3-(5-methyl-1H-pyrazol-3-ylamino)-isoquinolin-6-yl ester (100 mg) in 2 mL NMP. Excess 1-Methyl-piperazine was added to the mixture. The vial was heated at 200° C. for 2 h under microwave irradiation. After cooling, the reaction mixture was sent to prep-HPLC to give 5 mg of [1-Isopropoxy-6-(4-methyl-piperazin-1-yl)-isoquinolin-3-yl]-(5-methyl-1H-pyrazol-3-yl)-amine as a yellow solid. LC-MS m/e 381 (MH+).

Example 364

(1-Isopropoxy-6-morpholin-4-yl-isoquinolin-3-yl)-(5-methyl-1H-pyrazol-3-yl)-amine

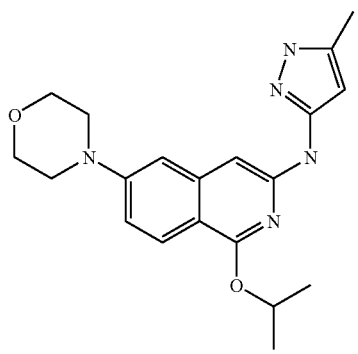

Similar procedure as described in the example 363 was used, starting from Trifluoro-methanesulfonic acid 1-isopropoxy-3-(5-methyl-1H-pyrazol-3-ylamino)-isoquinolin-6-yl ester and Morpholine to give 5 mg of (1-Isopropoxy-6-morpholin-4-yl-isoquinolin-3-yl)-(5-methyl-1H-pyrazol-3-yl)-amine as a yellow solid. LC-MS m/e 368 (MH$^+$).

Example 365

(1-Isopropoxy-6-piperidin-1-yl-isoquinolin-3-yl)-(5-methyl-1H-pyrazol-3-yl)-amine

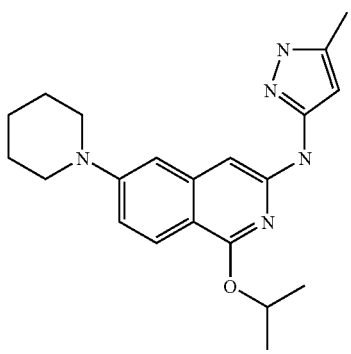

Similar procedure as described in the example 363 was used, starting from Trifluoro-methanesulfonic acid 1-isopropoxy-3-(5-methyl-1H-pyrazol-3-ylamino)-isoquinolin-6-yl ester and piperidine to give 5 mg of (1-Isopropoxy-6-piperidin-1-yl-isoquinolin-3-yl)-(5-methyl-1H-pyrazol-3-yl)-amine as a yellow solid. LC-MS m/e 366 (MH$^+$).

Example 366

(1-Isopropoxy-6-pyrrolidin-1-yl-isoquinolin-3-yl)-(5-methyl-1H-pyrazol-3-yl)-amine

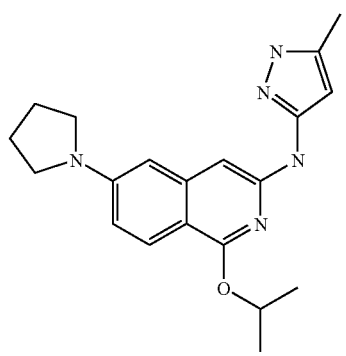

Similar procedure as described in the example 363 was used, starting from Trifluoro-methanesulfonic acid 1-isopropoxy-3-(5-methyl-1H-pyrazol-3-ylamino)-isoquinolin-6-yl ester and Pyrrolidine to give 5 mg of (1-Isopropoxy-6-pyrrolidin-1-yl-isoquinolin-3-yl)-(5-methyl-1H-pyrazol-3-yl)-amine as a yellow solid. LC-MS m/e 352 (MH$^+$).

Example 367

(1-Isopropyl-6-morpholin-4-yl-isoquinolin-3-yl)-(5-methyl-1H-pyrazol-3-yl)-amine

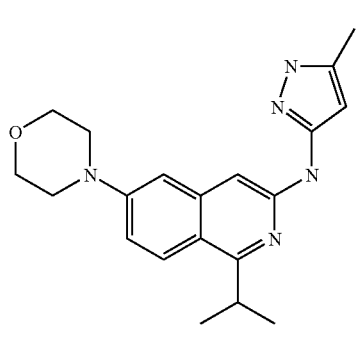

Similar procedure as described in the example 363 was used, starting from Trifluoro-methanesulfonic acid 1-isopropyl-3-(5-methyl-1H-pyrazol-3-ylamino)-isoquinolin-6-yl ester and morpholine to give 5 mg of (1-Isopropyl-6-morpholin-4-yl-isoquinolin-3-yl)-(5-methyl-1H-pyrazol-3-yl)-amine as a yellow solid. LC-MS m/e 352 (MH$^+$).

Example 368

[1-Isopropyl-6-(4-methyl-piperazin-1-yl)-isoquinolin-3-yl]-(5-methyl-1H-pyrazol-3-yl)-amine

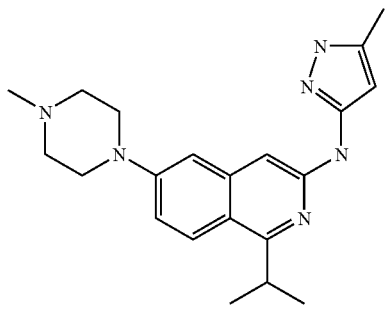

Similar procedure as described in the example 363 was used, starting from Trifluoro-methanesulfonic acid 1-isopropyl-3-(5-methyl-1H-pyrazol-3-ylamino)-isoquinolin-6-yl ester and 1-Methyl-piperazine to give 5 mg of [1-Isopropyl-6-(4-methyl-piperazin-1-yl)-isoquinolin-3-yl]-(5-methyl-1H-pyrazol-3-yl)-amine as a yellow solid. LC-MS m/e 365 (MH$^+$).

Example 369

(6-Methoxy-1-piperidin-1-ylmethyl-isoquinolin-3-yl)-(5-methyl-1H-pyrazol-3-yl)-amine a) Preparation of 6-Methoxy-3-(5-methyl-1H-pyrazol-3-ylamino)-isoquinoline-1-carboxylic acid isopropyl ester

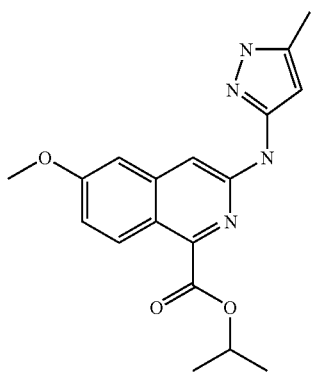

An oven-dried flask was charged with 8.64 g (1-Chloro-6-methoxy-isoquinolin-3-yl)-(5-methyl-1H-pyrazol-3-yl)-amine, 0.54 g Pd(OAc)$_2$, 1.2 g dppp, 0.3 g Pd(PPh$_3$)$_4$, 24 g Cs$_2$CO$_3$ in the solution of 200 mL i-PrOH and 200 mL DMF, then evacuated and filled with CO (4 bar) three cycles. The mixture was shaken at r.t 2 h, at 50° C. 2 h, then 90° C. overnight. After reaction completed, the solvent was removed, and the residue was dissolved in ethyl acetate, washed with water, dried with Na$_2$SO$_4$. After removal of solvent, the residue was purified by the column chromatography on solica gel to give 8.2 g of 6-Methoxy-3-(5-methyl-1H-pyrazol-3-ylamino)-isoquinoline-1-carboxylic acid isopropyl ester.

b) Preparation of [6-Methoxy-3-(5-methyl-1H-pyrazol-3-ylamino)-isoquinolin-1-yl]-methanol

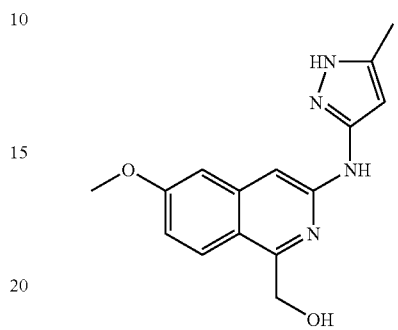

LiAlH$_4$ (0.67 g) was added in portions to a solution of 6-Methoxy-3-(5-methyl-1H-pyrazol-3-ylamino)-isoquinoline-1-carboxylic acid isopropyl ester (1.5 g) in 50 mL THF at 0° C. The mixture was stirred at r.t. overnight. Ice-water was added carefully to the mixture until no gas produced. The pH of the solution was adjusted to 7~8, and then extracted with ethyl acetate three times. The organic layer was washed with saturated NaCl(aq), dried over NaSO$_4$, and concentrated to give the crude product for the next step reaction without further purification.

c) Preparation of Methanesulfonic acid 3-(1-methanesulfonyl-5-methyl-1H-pyrazol-3-ylamino)-6-methoxy-isoquinolin-1-ylmethyl ester

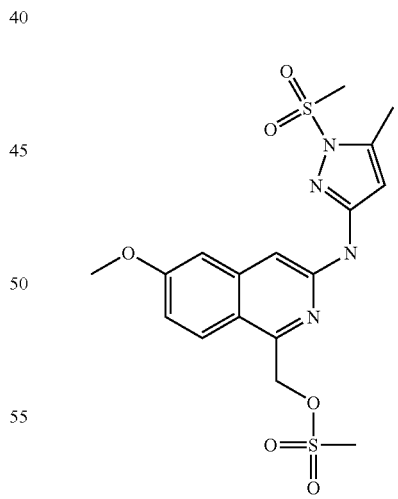

MsCl (1.0 g) in 20 mL CH$_2$Cl$_2$ was added slowly to a mixture of [6-Methoxy-3-(5-methyl-1H-pyrazol-3-ylamino)-isoquinolin-1-yl]-methanol (11.0 g) and Et$_3$N (1.42 g) in 50 mL CH$_2$Cl$_2$ at 0° C. The reaction mixture was stirred at r.t. for 3 h, and then washed with saturated NaHCO$_3$ (aq) and NaCl(aq). The organic layer was dried over Na$_2$SO$_4$, and concentrated to give the crude product.

d) Preparation of (6-Methoxy-1-piperidin-1-ylmethyl-isoquinolin-3-yl)-(5-methyl-1H-pyrazol-3-yl)-amine

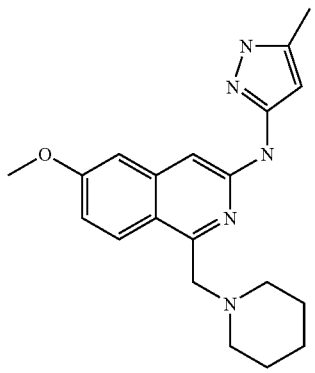

A 2.0~5.0 mL process vial was charged with 50 mg methanesulfonic acid 3-(1-methanesulfonyl-5-methyl-1H-pyrazol-3-ylamino)-6-methoxy-isoquinolin-1-ylmethyl ester, 50 mg piperidine, 75 mg $K_2CO_3$ in 3 mL THF/EtOH(1:1). The vial was heated at 120° C. for 30 min under microwave irradiation. After cooling, the reaction mixture was filtered through a short silica gel column, and the solvent was removed under reduced pressure. The residue in MeOH was sent to prep-HPLC to get 5 mg of (6-Methoxy-1-piperidin-1-ylmethyl-isoquinolin-3-yl)-(5-methyl-1H-pyrazol-3-yl)-amine as a yellow solid. LC-MS m/e 352 (MH$^+$).

Example 370

1-[6-Methoxy-3-(5-methyl-1H-pyrazol-3-ylamino)-isoquinolin-1-ylmethyl]-piperidin-2-one

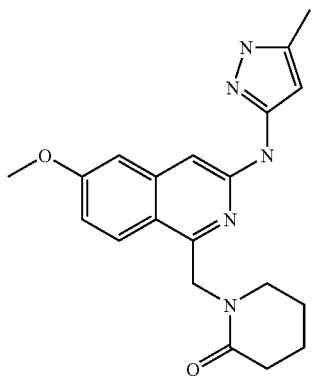

Similar procedure as described in the example 369d was used, starting from Methanesulfonic acid 3-(1-methanesulfonyl-5-methyl-1H-pyrazol-3-ylamino)-6-methoxy-isoquinolin-1-ylmethyl ester and Piperidin-2-one to give 5 mg of 1-[6-Methoxy-3-(5-methyl-1H-pyrazol-3-ylamino)-isoquinolin-1-ylmethyl]-piperidin-2-one as a yellow solid. LC-MS m/e 366 (MH$^+$).

Example 371

3-[6-Methoxy-3-(5-methyl-1H-pyrazol-3-ylamino)-isoquinolin-1-ylmethyl]-oxazolidin-2-one

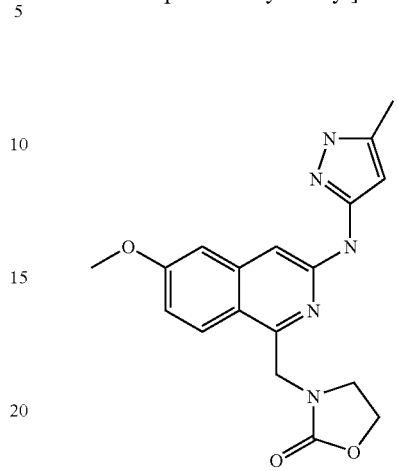

Similar procedure as described in the example 369d was used, starting from Methanesulfonic acid 3-(1-methanesulfonyl-5-methyl-1H-pyrazol-3-ylamino)-6-methoxy-isoquinolin-1-ylmethyl ester and Oxazolidin-2-one to give 5 mg of 3-[6-Methoxy-3-(5-methyl-1H-pyrazol-3-ylamino)-isoquinolin-1-ylmethyl]-oxazolidin-2-one as a yellow solid. LC-MS m/e 354 (MH$^+$).

Example 372

(1-Imidazol-1-ylmethyl-6-methoxy-isoquinolin-3-yl)-(5-methyl-1H-pyrazol-3-yl)-amine

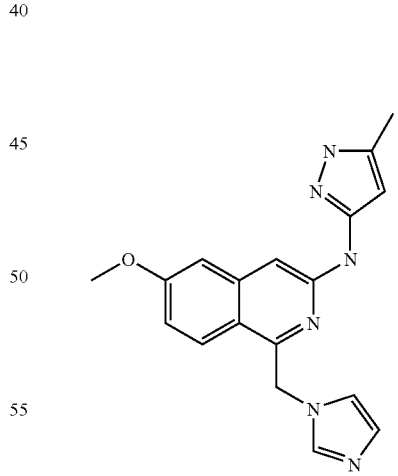

Similar procedure as described in the example 369d was used, starting from Methanesulfonic acid 3-(1-methanesulfonyl-5-methyl-1H-pyrazol-3-ylamino)-6-methoxy-isoquinolin-1-ylmethyl ester and 1H-Imidazole to give 5 mg of (1-Imidazol-1-ylmethyl-6-methoxy-isoquinolin-3-yl)-(5-methyl-1H-pyrazol-3-yl)-amine as a yellow solid. LC-MS m/e 335 (MH$^+$).

Example 373

[1-Isopropoxy-6-(4-methyl-piperazin-1-ylmethyl)-isoquinolin-3-yl]-(5-methyl-1H-pyrazol-3-yl)-amine

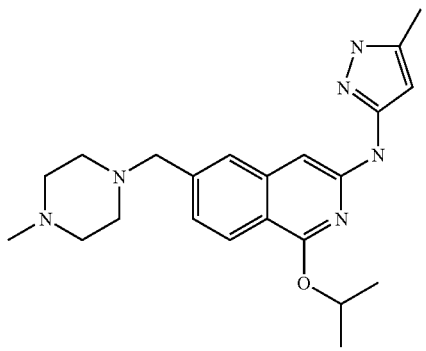

An oven-dried flask was charged with 20 mg [1-Isopropoxy-3-(5-methyl-1H-pyrazol-3-ylamino)-isoquinolin-6-yl]-(4-methyl-piperazin-1-yl)-methanone and then evacuated and filled with Ar three cycles. Excess BH$_3$/THF was added at 0° C. and the solution was stirred at r.t. overnight. After removal of solvent, the residue was dissolved in MeOH and was sent to prep-HPLC to get [1-Isopropoxy-6-(4-methyl-piperazin-1-ylmethyl)-isoquinolin-3-yl]-(5-methyl-1H-pyrazol-3-yl)-amine as a yellow solid. LC-MS m/e 395 (MH$^+$).

Example 374

1-[1-Isopropoxy-3-(5-methyl-1H-pyrazol-3-ylamino)-isoquinolin-6-ylmethyl]-pyrrolidine-2-carboxylic acid amide a) Preparation of 1-Isopropoxy-3-(5-methyl-1H-pyrazol-3-ylamino)-isoquinoline-6-carboxylic acid isopropyl ester

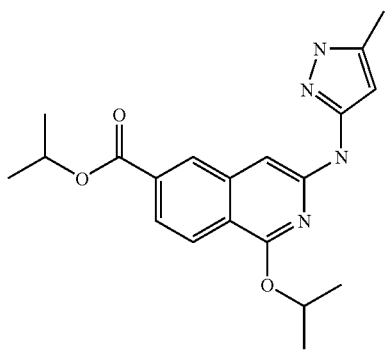

b) [1-Isopropoxy-3-(5-methyl-1H-pyrazol-3-ylamino)-isoquinolin-6-yl]-methanol

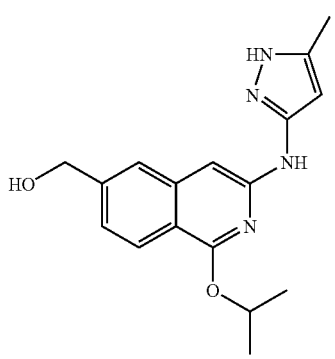

Similar procedure as described in example in 369b was used, starting from 1-Isopropoxy-3-(5-methyl-1H-pyrazol-3-ylamino)-isoquinoline-6-carboxylic acid isopropyl ester to give crude [1-Isopropoxy-3-(5-methyl-1H-pyrazol-3-ylamino)-isoquinolin-6-yl]-methanol for next step without further purification.

c) Preparation of Methanesulfonic acid 1-isopropoxy-3-(1-methanesulfonyl-5-methyl-1H-pyrazol-3-ylamino)-isoquinolin-6-ylmethyl ester

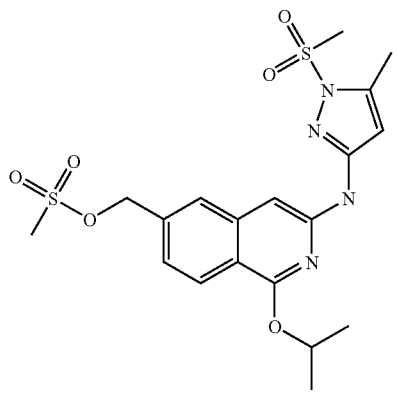

Similar procedure as described in example 369c was used, starting from [1-Isopropoxy-3-(5-methyl-1H-pyrazol-3-ylamino)-isoquinolin-6-yl]-methanol to give crude Methanesulfonic acid 1-isopropoxy-3-(1-methanesulfonyl-5-methyl-1H-pyrazol-3-ylamino)-isoquinolin-6-ylmethyl ester for next step without further purification.

d) Preparation of 1-[1-Isopropoxy-3-(5-methyl-1H-pyrazol-3-ylamino)-isoquinolin-6-ylmethyl]-pyrrolidine-2-carboxylic acid amide

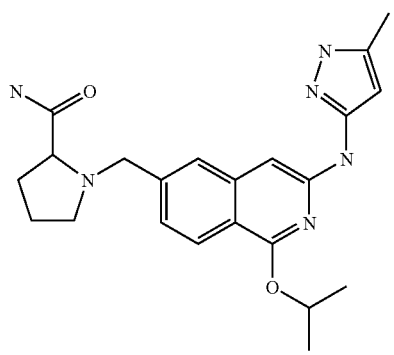

A mixture of 50 mg methanesulfonic acid 1-isopropoxy-3-(1-methanesulfonyl-5-methyl-1H-pyrazol-3-ylamino)-isoquinolin-6-ylmethyl ester, 50 mg pyrrolidine-2-carboxylic acid amide and 54 mg Et$_3$N in 10 mL CH$_3$CN was stirred at r.t overnight. After removal of solvent, the residue in MeOH was sent to prep-HPLC to give 1-[1-Isopropoxy-3-(5-methyl-1H-pyrazol-3-ylamino)-isoquinolin-6-ylmethyl]-pyrrolidine-2-carboxylic acid amide as a yellow solid. LC-MS m/e 409 (MH+).

Example 375

(1-Isopropoxy-6-methoxy-5-methyl-isoquinolin-3-yl)-(5-methyl-1H-pyrazol-3-yl)-amine a) Preparation of 4-Chloromethyl-5-methoxy-indan-1-one

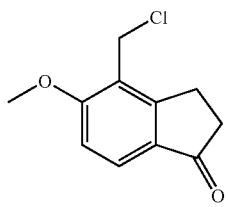

Hydrogen chloride was passed at 45° C. for 8 h, and then at room temperature overnight, through a mixture of 5-methoxy-indan-1-one (16.0 g), paraformaldehyde (6.0 g), and zinc chloride (5.0 g) in concentrated hydrochloric acid (15 mL) and acetic acid (50 mL). Water was then added and the mixture was extracted with dichloromethane. The crude product was purified by flash column chromatography on silica-gel to give 4-Chloromethyl-5-methoxy-indan-1-one.

b) 5-Methoxy-4-methyl-indan-1-one

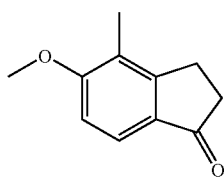

A flask was charged with 3.35 g 4-chloromethyl-5-methoxy-indan-1-one, 0.5 g Pd/C, 2.4 g Et₃N and 2 g CH₃COONa in 50 mL MeOH, and then evacuated and filled with H₂ (1.2 bar) three cycles. The mixture was shaken at r.t. for 6 h. The mixture was concentrated to give the crude product without further purification.

c) Preparation of 5-Methoxy-4-methyl-indan-1,2-dione-2-oxime

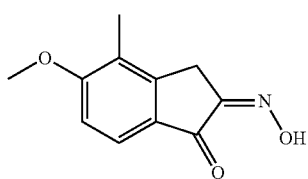

To a solution of 5-Methoxy-4-methyl-indan-1-one (3.1 g) in MeOH at 40° C. was added n-butylnitrite (2.5 mL) followed by concentrated HCl (2.3 ml). The solution was stirred for 30 min during which time a precipitate was formed. The precipitate was collected and dried to yield the crude product as a white solid.

d) Preparation of 2-Cyanomethyl-4-methoxy-3-methyl-benzoic acid

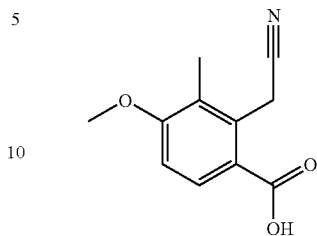

To a solution of 8% 21 mL NaOH was added 5-Methoxy-4-methyl-indan-1,2-dione-2-oxime (2.2 g). The mixture was heated to 50° C. Then p-Toluenesulfonyl chloride (2.77 g) was added in portions to the mixture. The mixture was heated at 80° C. for another 15 min. After cooled to room temperature, the precipitate (a little) was removed from the mixture. Mother liquid was acidified by concentrated HCl to PH=3-4 and precipitate was formed. The precipitate was washed with water and dried for the next reaction.

e) Preparation of 6-Methoxy-5-methyl-3-(5-methyl-1H-pyrazol-3-ylamino)-2H-isoquinolin-1-one

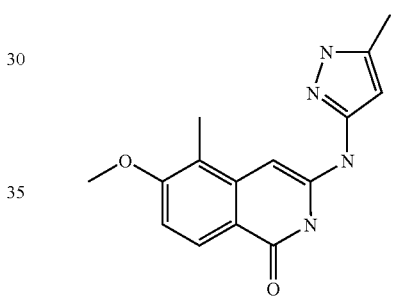

A 10~20 mL process vial was charged with 500 mg 2-Cyanomethyl-4-methoxy-3-methyl-benzoic acid and 5-Methyl-1H-pyrazol-3-ylamine in 15 mL AcOH. The vial was heated at 130° C. for 30 min under microwave irradiation. Most of the solvent was removed under reduced pressure, and the residue was poured into ice-water. The solid was collected and washed with water.

f) Preparation of (1-Chloro-6-methoxy-5-methyl-isoquinolin-3-yl)-(5-methyl-1H-pyrazol-3-yl)-amine

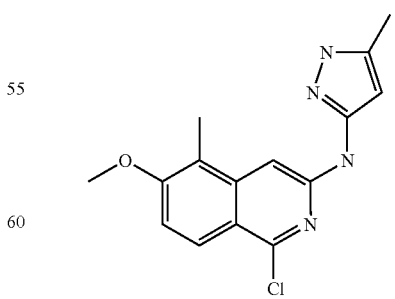

A 10~20 mL process vial was charged with 500 mg 6-Methoxy-5-methyl-3-(5-methyl-1H-pyrazol-3-ylamino)-2H-isoquinolin-1-one in 15 mL POCl₃. The vial was heated at 150° C. for 30 min under microwave irradiation. After cooling, POCl₃ was removed under reduced pressure. MeOH was carefully added to the residue during which the precipitate was formed. The solid was collected as crude product for the next reaction.

g) Preparation of (1-Isopropoxy-6-methoxy-5-methyl-isoquinolin-3-yl)-(5-methyl-1H-pyrazol-3-yl)-amine

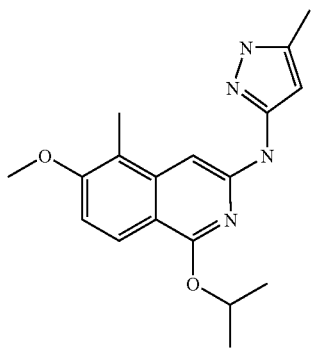

Similar procedure as described in the example 10 was used, starting from (1-Chloro-6-methoxy-5-methyl-isoquinolin-3-yl)-(5-methyl-1H-pyrazol-3-yl)-amine and 2-propanol to give 5 mg of (1-Isopropoxy-6-methoxy-5-methyl-isoquinolin-3-yl)-(5-methyl-1H-pyrazol-3-yl)-amine as a yellow solid. LC-MS m/e 327 (MH⁺).

Example 376

(7-Fluoro-1-isopropoxy-6-methoxy-isoquinolin-3-yl)-(5-methyl-1H-pyrazol-3-yl)-amine

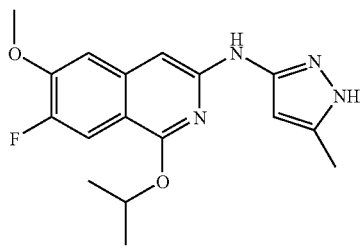

NaH (155 mg) was added to a solution of ispropanol (500 mg) in DME (2 ml) and stirred for 1 hour. 1-Chloro-7-fluoro-6-methoxy-isoquinolin-3-yl)-(5-methyl-1H-pyrazol-3-yl)-amine (100 mg) (example 9B) was added to the mixture, and the mixture was heated at 180° C. for 30 minutes under microwave irradiation. The reaction mixture was acidified to PH=7 with acetic acid and purified by preparative LC-MS to give (7-Fluoro-1-isopropoxy-6-methoxy-isoquinolin-3-yl)-(5-methyl-1H-pyrazol-3-yl)-amine. LC-MS: m/e 331 (MH⁺).

Example 377

(5-Cyclopropyl-1H-pyrazol-3-yl)-(7-fluoro-1-isopropoxy-6-methoxy-isoquinolin-3-yl)-amine

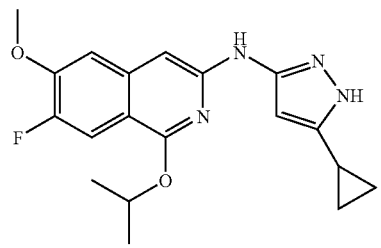

a) Preparation of 3-(5-Cyclopropyl-1H-pyrazol-3-ylamino)-7-fluoro-6-methoxy-isoquinolin-1-ol

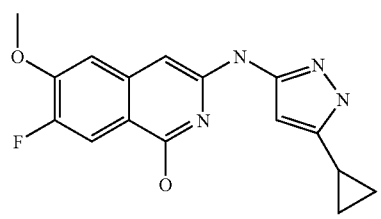

Similar procedure as described in example 9B was used, starting from 2-Cyanomethyl-5-fluoro-4-methoxy-benzoic acid (1.75 g), 3-amino-5-cyclopropylpyrazol, to give 3-(5-Cyclopropyl-1H-pyrazol-3-ylamino)-7-fluoro-6-methoxy-isoquinolin-1-ol. LC-MS: m/e 315 (MH⁺).

b) Preparation of (1-Chloro-7-fluoro-6-methoxy-isoquinolin-3-yl)-(5-cyclopropyl-1H-pyrazol-3-yl)-amine

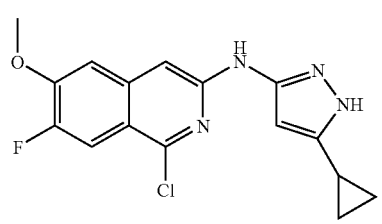

Similar procedure as described in example 9B was used, starting from 3-(5-Cyclopropyl-1H-pyrazol-3-ylamino)-7-fluoro-6-methoxy-isoquinolin-1-ol to give (1-Chloro-7-fluoro-6-methoxy-isoquinolin-3-yl)-(5-cyclopropyl-1H-pyrazol-3-yl)-amine. LC-MS: m/e 33(MH⁺).

c) Preparation of (5-Cyclopropyl-1H-pyrazol-3-yl)-(7-fluoro-1-isopropoxy-6-methoxy-isoquinolin-3-yl)-amine

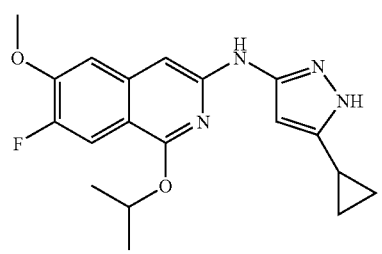

Similar procedure as described in example 376 was used, starting from isopropanol, (1-Chloro-7-fluoro-6-methoxy-isoquinolin-3-yl)-(5-cyclopropyl-1H-pyrazol-3-yl)-amine to give (5-Cyclopropyl-1H-pyrazol-3-yl)-(7-fluoro-1-isopropoxy-6-methoxy-isoquinolin-3-yl)-amine. LC-MS: m/e 357 (MH⁺).

Example 378

[1-Isopropoxy-6-methoxy-7-(2-morpholin-4-yl-ethoxy)-isoquinolin-3-yl]-(5-methyl-1H-pyrazol-3-yl)-amine

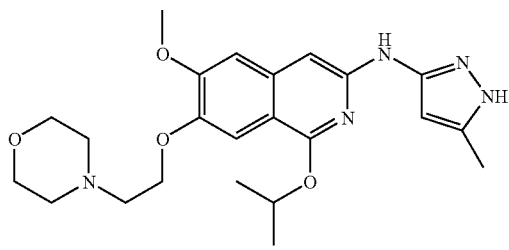

NaH (155 mg) was added to a solution of 2-Morpholin-4-yl-ethanol (2 ml) and stirred for 1 hour. (7-Fluoro-1-isopropoxy-6-methoxy-isoquinolin-3-yl)-(5-methyl-1H-pyrazol-3-yl)-amine (100 mg) was added to the mixture, and the mixture was heated at 180° C. for 1 hour under microwave irradiation. The reaction mixture was acidified to PH=7 with acetic acid and purified by preparative LC-MS to give [1-Isopropoxy-6-methoxy-7-(2-morpholin-4-yl-ethoxy)-isoquinolin-3-yl]-(5-methyl-1H-pyrazol-3-yl)-amine (28 mg). LC-MS: m/e 442(MH⁺).

Example 379

(7-Fluoro-1-isopropoxy-6-morpholin-4-yl-isoquinolin-3-yl)-(5-methyl-1H-pyrazol-3-yl)-amine

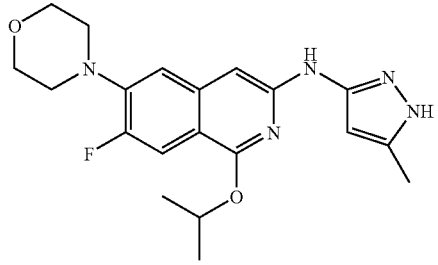

a) Preparation of 1-Bromo-7-fluoro-3-(5-methyl-1H-pyrazol-3-ylamino)-isoquinolin-6-ol

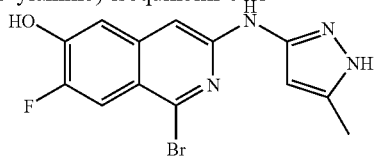

To a solution of (1-Chloro-7-fluoro-6-methoxy-isoquinolin-3-yl)-(5-methyl-1H-pyrazol-3-yl)-amine (1.0 g) in 10 mL acetic acid was added hydrobromic acid (1 mL, 40%). The mixture was heated at 160° C. for 30 min under microwave irradiation. Most of the solvent was removed under reduced pressure, and the residue was dissolved in 100 mL of ethyl acetate and washed with saturated sodium bicarbonate. The organic layer was dried with anhydrous sodium sulfate and concentrated to give oil (0.92 g), which was used for the next reaction without further purification. LC-MS m/e 338 (MH⁺).

b) Preparation of 7-Fluoro-1-isopropoxy-3-(5-methyl-1H-pyrazol-3-ylamino)-isoquinolin-6-ol

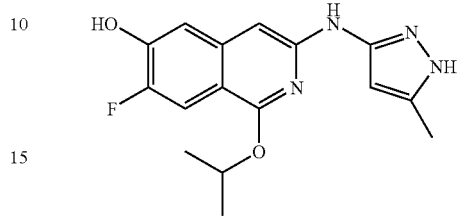

Similar procedure as described in example 376 was used, starting from 1-Bromo-7-fluoro-3-(5-methyl-1H-pyrazol-3-ylamino)-isoquinolin-6-ol, isopropanol, to give 7-Fluoro-1-isopropoxy-3-(5-methyl-1H-pyrazol-3-ylamino)-isoquinolin-6-ol. LC-MS: m/e 317 (MH⁺).

c) Preparation of trifluoro-methanesulfonic acid 7-fluoro-1-isopropoxy-3-(5-methyl-1-trifluoromethanesulfonyl-1H-pyrazol-3-ylamino)-isoquinolin-6-yl ester

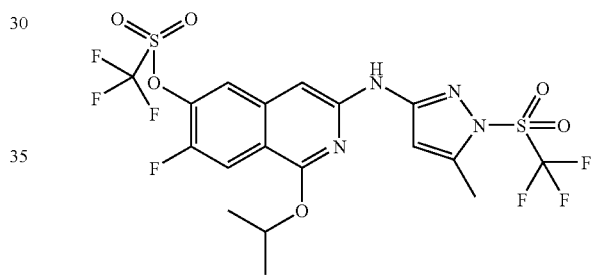

7-Fluoro-1-isopropoxy-3-(5-methyl-1H-pyrazol-3-ylamino)-isoquinolin-6-ol (75 mg), Et₃N (123 ul) was dissolved in 3 ml CH₂Cl₂. Trifluoro-methanesulfonic anhydride was added to this solution at 0° C. Then the mixture was stirred at room temperature for 2 hrs. Another 10 ml CH₂Cl₂ was added, and washed with saturated sodium bicarbonate, brine and dried with anhydrous sodium sulfate, concentrated to give crude product. It was purified by column chromatography (petroleum ether:ethyl acetate=2:1) to give product as brown solid 100 mg. (73% yield) LC-MS: m/e 581 (MH⁺).

d) Preparation of (7-Fluoro-1-isopropoxy-6-morpholin-4-yl-isoquinolin-3-yl)-(5-methyl-1H-pyrazol-3-yl)-amine

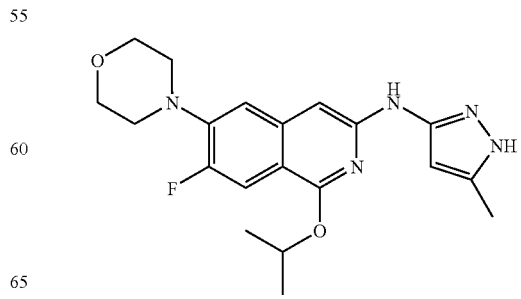

Trifluoro-methanesulfonic acid 7-fluoro-1-isopropoxy-3-(5-methyl-1-trifluoromethanesulfonyl-1H-pyrazol-3-ylamino)-isoquinolin-6-yl ester (100 mg) and morpholine (100 ul) was added to NMP (1 ml). The mixture was heated at 200° C. for 1 hour under microwave irradiation. It was purified by preparative LC-MS to give (7-Fluoro-1-isopropoxy-6-morpholin-4-yl-isoquinolin-3-yl)-(5-methyl-1H-pyrazol-3-yl)-amine (26 mg). LC-MS: m/e 386 (MH$^+$).

Example 380

1-[7-Fluoro-1-isopropoxy-3-(5-methyl-1H-pyrazol-3-ylamino)-isoquinolin-6-yl]-pyrrolidin-2-one

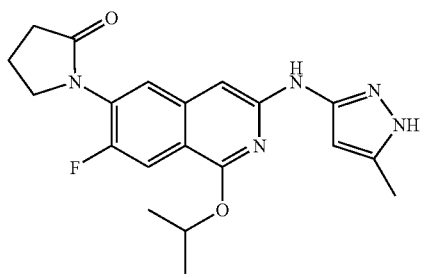

Under Ar, trifluoro-methanesulfonic acid 7-fluoro-1-isopropoxy-3-(5-methyl-1-trifluoromethanesulfonyl-1H-pyrazol-3-ylamino)-isoquinolin-6-yl ester (60 mg), pyrrolidin-2-one, Pd$_2$(dba)$_3$ (4.8 mg), Xantphos (12 mg) and K$_3$PO$_4$ (61.8 mg) were added to dioxane (5 ml), the mixture was heated at 100° C. for 20 hrs. The mixture was filtrated, and the filtrate was concentrated to give crude product. It was purified by preparative LC-MS to give 1-[7-Fluoro-1-isopropoxy-3-(5-methyl-1H-pyrazol-3-ylamino)-isoquinolin-6-yl]-pyrrolidin-2-one (20 mg). LC-MS: m/e 384 (MH$^+$).

Example 381

(5-Chloro-1-isopropoxy-6,7-dimethoxy-isoquinolin-3-yl)-(5-methyl-1H-pyrazol-3-yl)-amine

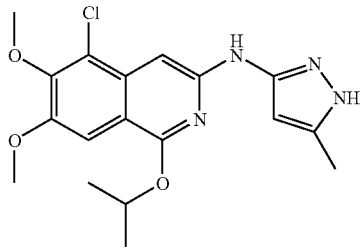

a) Preparation of 3-(2-Chloro-3,4-dimethoxy-phenyl)-acrylic acid

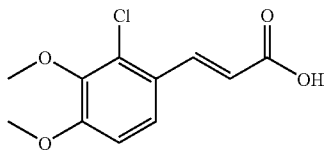

Similar procedure as described in example 9B was used, starting from 2-Chloro-3,4-dimethoxy-benzaldehyde and malonic acid to give 3-(2-Chloro-3,4-dimethoxy-phenyl)-acrylic acid. LC-MS: m/e 241 (M−1).

b) Preparation of 3-(2-Chloro-3,4-dimethoxy-phenyl)-propionic acid

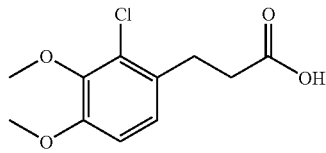

Similar procedure as described in example 9B was used, starting from 3-(2-Chloro-3,4-dimethoxy-phenyl)-acrylic acid and Pd—C to give 3-(2-Chloro-3,4-dimethoxy-phenyl)-propionic acid. LC-MS: m/e 243 (M−1).

c) Preparation of 4-Chloro-5,6-dimethoxy-indan-1-one

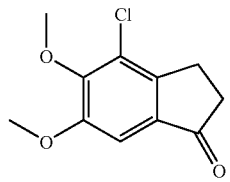

Similar procedure as described in example 9B was used, starting from 3-(2-Chloro-3,4-dimethoxy-phenyl)-propionic acid and Methanesulfonic acid to give 4-Chloro-5,6-dimethoxy-indan-1-one. LC-MS: m/e 227 (MH$^+$).

d) Preparation of 4-Chloro-5,6-dimethoxy-indan-1,2-dione 2-oxime

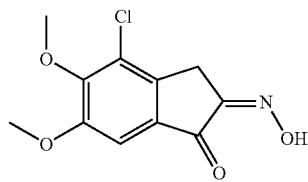

Similar procedure as described in example 9B was used, starting from 4-Chloro-5,6-dimethoxy-indan-1-one and n-butylnitrite to give 4-Chloro-5,6-dimethoxy-indan-1,2-dione 2-oxime. LC-MS: m/e 256 (MH$^+$).

e) Preparation of 3-Chloro-2-cyanomethyl-4,5-dimethoxy-benzoic acid

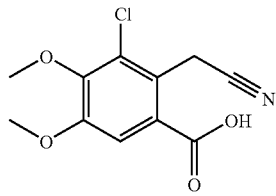

Similar procedure as described in example 9B was used, starting from 4-Chloro-5,6-dimethoxy-indan-1,2-dione 2-oxime and p-Toluenesulfonyl chloride to give 3-Chloro-2-cyanomethyl-4,5-dimethoxy-benzoic acid. LC-MS: m/e 254 (M−1).

f) Preparation of 5-Chloro-6,7-dimethoxy-3-(5-methyl-1H-pyrazol-3-ylamino)-isoquinolin-1-ol

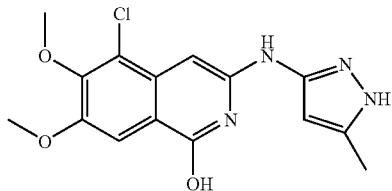

Similar procedure as described in example 9B was used, starting from 3-Chloro-2-cyanomethyl-4,5-dimethoxy-benzoic acid, 3-amino-5-methylpyrazol and acetic acid to give 5-Chloro-6,7-dimethoxy-3-(5-methyl-1H-pyrazol-3-ylamino)-isoquinolin-1-ol. LC-MS: m/e 335 (MH$^+$).

g) Preparation of (1,5-Dichloro-6,7-dimethoxy-isoquinolin-3-yl)-(5-methyl-1H-pyrazol-3-yl)-amine

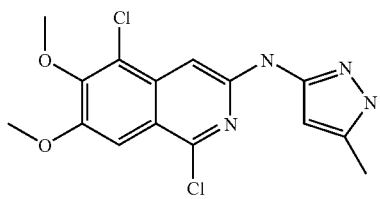

Similar procedure as described in example 9B was used, starting from 5-Chloro-6,7-dimethoxy-3-(5-methyl-1H-pyrazol-3-ylamino)-isoquinolin-1-ol and POCl$_3$ to give (1,5-Dichloro-6,7-dimethoxy-isoquinolin-3-yl)-(5-methyl-1H-pyrazol-3-yl)-amine. LC-MS: m/e 353 (MH$^+$).

h) Preparation of (5-Chloro-1-isopropoxy-6,7-dimethoxy-isoquinolin-3-yl)-(5-methyl-1H-pyrazol-3-yl)-amine

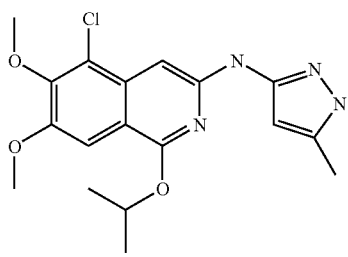

Similar procedure as described in example 376 was used, starting from (1,5-Dichloro-6,7-dimethoxy-isoquinolin-3-yl)-(5-methyl-1H-pyrazol-3-yl)-amine and isopropanol to give (5-Chloro-1-isopropoxy-6,7-dimethoxy-isoquinolin-3-yl)-(5-methyl-1H-pyrazol-3-yl)-amine. LC-MS: m/e 377 (MH$^+$).

Example 382

(5-Chloro-1,6-diisopropoxy-7-methoxy-isoquinolin-3-yl)-(5-methyl-1H-pyrazol-3-yl)-amine

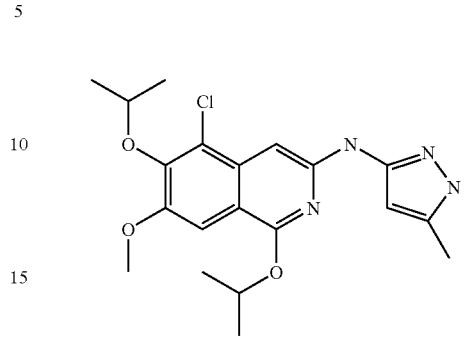

Similar procedure as described in example 376 was used, starting from (1,5-Dichloro-6,7-dimethoxy-isoquinolin-3-yl)-(5-methyl-1H-pyrazol-3-yl)-amine and isopropanol to give (5-Chloro-1,6-diisopropoxy-7-methoxy-isoquinolin-3-yl)-(5-methyl-1H-pyrazol-3-yl)-amine. LC-MS: m/e 405 (MH$^+$).

Example 383

1-Isopropoxy-3-(5-methyl-1H-pyrazol-3-ylamino)-isoquinoline-6-carboxylic acid

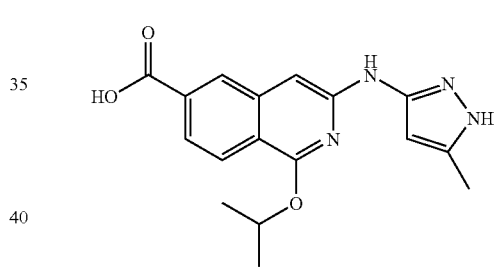

a) Preparation of 5-Bromo-indan-1,2-dione 2-oxime

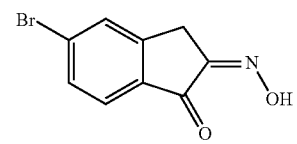

Similar procedure as described in example 9B was used, starting from 5-Bromo-indan-1-one and n-butylnitrite to give 5-Bromo-indan-1,2-dione 2-oxime. LC-MS: m/e 240 (MH$^+$).

b) Preparation of 4-Bromo-2-cyanomethyl-benzoic acid

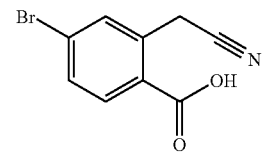

Similar procedure as described in example 9B was used, starting from 5-Bromo-indan-1,2-dione 2-oxime and p-Toluenesulfonyl chloride to give 4-Bromo-2-cyanomethyl-benzoic acid. LC-MS: m/e 238 (M−1).

c) Preparation of 6-Bromo-3-(5-methyl-1H-pyrazol-3-ylamino)-isoquinolin-1-ol

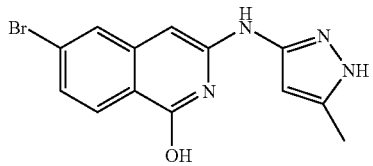

Similar procedure as described in example 9B was used, starting from 4-Bromo-2-cyanomethyl-benzoic acid, 3-amino-5-methylpyrazole and acetic acid to give 6-Bromo-3-(5-methyl-1H-pyrazol-3-ylamino)-isoquinolin-1-ol. LC-MS: m/e 319 (MH$^+$).

d) Preparation of (6-Bromo-1-chloro-isoquinolin-3-yl)-(5-methyl-1H-pyrazol-3-yl)-amine

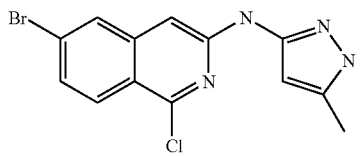

Similar procedure as described in example 9B was used, starting from 6-Bromo-3-(5-methyl-1H-pyrazol-3-ylamino)-isoquinolin-1-ol and POCl$_3$ to give (6-Bromo-1-chloro-isoquinolin-3-yl)-(5-methyl-1H-pyrazol-3-yl)-amine. LC-MS: m/e 337 (MH$^+$).

e) Preparation of (6-Bromo-1-isopropoxy-isoquinolin-3-yl)-(5-methyl-1H-pyrazol-3-yl)-amine

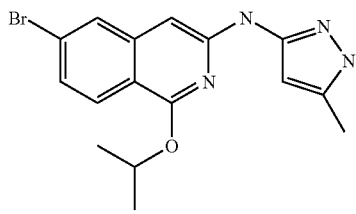

Similar procedure as described in example 376 was used, starting from (6-Bromo-1-chloro-isoquinolin-3-yl)-(5-methyl-1H-pyrazol-3-yl)-amine and isopropanol to give (6-Bromo-1-isopropoxy-isoquinolin-3-yl)-(5-methyl-1H-pyrazol-3-yl)-amine. LC-MS: m/e 361 (MH$^+$).

f) Preparation of 1-Isopropoxy-3-(5-methyl-1H-pyrazol-3-ylamino)-isoquinoline-6-carboxylic acid isopropyl ester

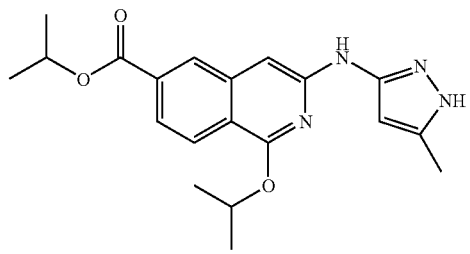

(6-Bromo-1-isopropoxy-isoquinolin-3-yl)-(5-methyl-H-pyrazol-3-yl)-amine (100 mg), Pd(OAc)$_2$ (6 mg), Pd(PPh$_3$)$_4$ (3 mg), DPPP (14 mg), Cs$_2$CO$_3$ (230 mg), in isopropanol and DMF (2:1, 60 ml) was placed in a Parr apparatus. The mixture was stirred under 30 psi of CO at room temperature for 2 hrs, then it was heated to 50° C. for 2 hrs, and 90° C. for 15 hrs. The catalyst was filtered and the filtrate was concentrated in vacuo. The crude product was purified by column chromatography to give 98 mg of yellow solid (96% yield). LC-MS: m/e 369 (MH$^+$).

g) Preparation of 1-Isopropoxy-3-(5-methyl-1H-pyrazol-3-ylamino)-isoquinoline-6-carboxylic acid

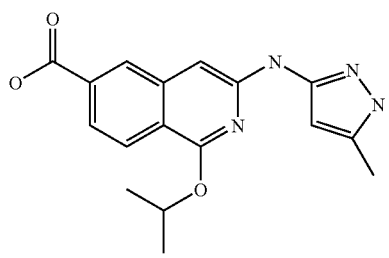

Isopropoxy-3-(5-methyl-1H-pyrazol-3-ylamino)-isoquinoline-6-carboxylic acid isopropyl ester (300 mg) was dissolved in KOH and MeOH (1:1, 10 ml), the mixture was stirred at room temperature for 20 hrs, the MeOH was evaporated and neutralized with concentrated HCl (PH=3). The solid was collected to give 240 mg of desired product (91% yield). LC-MS: m/e 325 (M−1).

Example 384

1-Isopropoxy-3-(5-methyl-1H-pyrazol-3-ylamino)-isoquinoline-6-carboxylic acid diethylamide

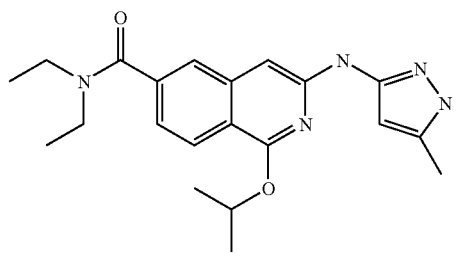

Diethylamine (14 ul) and triethylamine (17 ul) in CH₂Cl₂ (5 ml) was added to 1-Isopropoxy-3-(5-methyl-1H-pyrazol-3-ylamino)-isoquinoline-6-carboxylic acid (33 mg), HOBt (18 mg), EDCI (25 mg) at 0° C. in order. The mixture was stirred at room temperature for 3 hrs and washed with 8% NaOH, water and brine, dried with anhydrous sodium sulfate and concentrated. The residue was purified by preparative LC-MS to give 31 mg of product as yellow solid. (80% yield). LC-MS: m/e 382 (MH⁺).

Example 385

1-Isopropoxy-3-(5-methyl-1H-pyrazol-3-ylamino)-isoquinoline-6-carboxylic acid isopropylamide

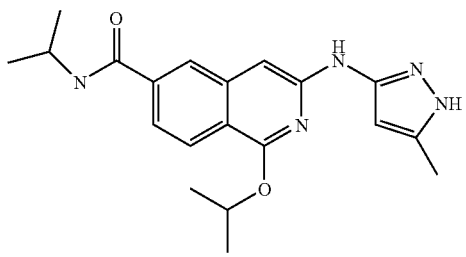

Similar procedure as described in example 384 was used, starting from 1-Isopropoxy-3-(5-methyl-1H-pyrazol-3-ylamino)-isoquinoline-6-carboxylic acid and isopropylamine to give 1-Isopropoxy-3-(5-methyl-1H-pyrazol-3-ylamino)-isoquinoline-6-carboxylic acid isopropylamide. LC-MS: m/e 368 (MH⁺).

Example 386

1-Isopropoxy-3-(5-methyl-1H-pyrazol-3-ylamino)-isoquinoline-6-carboxylic acid cyclohexyl-methyl-amide

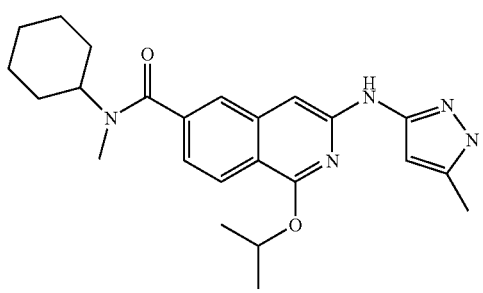

Similar procedure as described in example 384 was used, starting from 1-Isopropoxy-3-(5-methyl-1H-pyrazol-3-ylamino)-isoquinoline-6-carboxylic acid and Cyclohexyl-methyl-amine to give 1-Isopropoxy-3-(5-methyl-1H-pyrazol-3-ylamino)-isoquinoline-6-carboxylic acid cyclohexyl-methyl-amide. LC-MS: m/e 422 (MH⁺).

Example 387

[1-Isopropoxy-3-(5-methyl-1H-pyrazol-3-ylamino)-isoquinolin-6-yl]-(4-methyl-piperazin-1-yl)-methanone

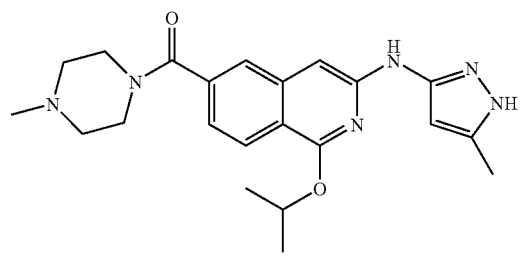

Similar procedure as described in example 384 was used, starting from 1-Isopropoxy-3-(5-methyl-1H-pyrazol-3-ylamino)-isoquinoline-6-carboxylic acid and 1-Methyl-piperazine to give [1-Isopropoxy-3-(5-methyl-1H-pyrazol-3-ylamino)-isoquinolin-6-yl]-(4-methyl-piperazin-1-yl)-methanone. LC-MS: m/e 409 (MH⁺).

Example 388

1-Isopropoxy-3-(5-methyl-1H-pyrazol-3-ylamino)-isoquinoline-6-carboxylic acid methyl-(2-piperidin-1-yl-ethyl)-amide

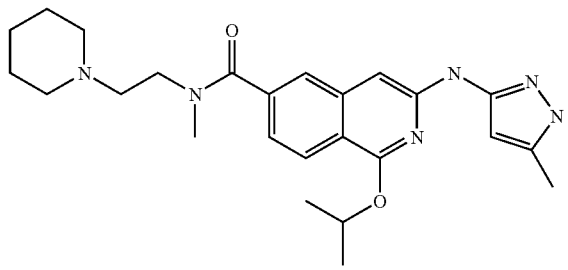

Similar procedure as described in example 384 was used, starting from 1-Isopropoxy-3-(5-methyl-1H-pyrazol-3-ylamino)-isoquinoline-6-carboxylic acid and Methyl-(2-piperidin-1-yl-ethyl)-amine to give 1-Isopropoxy-3-(5-methyl-1H-pyrazol-3-ylamino)-isoquinoline-6-carboxylic acid methyl-(2-piperidin-1-yl-ethyl)-amide. LC-MS: m/e 451 (MH⁺).

Example 389

1-{4-[1-Isopropoxy-3-(5-methyl-1H-pyrazol-3-ylamino)-isoquinoline-6-carbonyl]-piperazin-1-yl}-ethanone

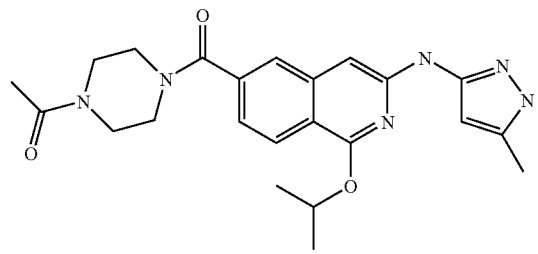

Similar procedure as described in example 384 was used, starting from 1-Isopropoxy-3-(5-methyl-1H-pyrazol-3-ylamino)-isoquinoline-6-carboxylic acid and 1-acetylpiperazine to give 1-{4-[1-Isopropoxy-3-(5-methyl-1H-pyrazol-3-ylamino)-isoquinoline-6-carbonyl]-piperazin-1-yl}-ethanone. LC-MS: m/e 437 (MH⁺).

Example 390

1-Isopropoxy-3-(5-methyl-1H-pyrazol-3-ylamino)-isoquinoline-6-carboxylic acid methyl-(3-piperidin-1-yl-propyl)-amide

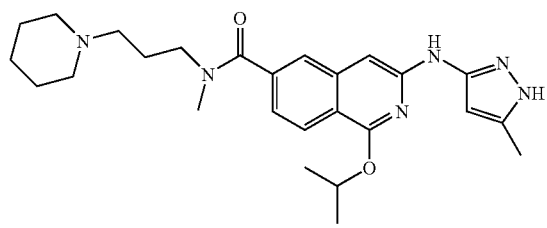

Similar procedure as described in example 384 was used, starting from 1-Isopropoxy-3-(5-methyl-1H-pyrazol-3-ylamino)-isoquinoline-6-carboxylic acid and Methyl-(3-piperidin-1-yl-propyl)-amine to give 1-Isopropoxy-3-(5-methyl-1H-pyrazol-3-ylamino)-isoquinoline-6-carboxylic acid methyl-(3-piperidin-1-yl-propyl)-amide. LC-MS: m/e 465 (MH⁺).

Example 391

[1-Isopropoxy-3-(5-methyl-1H-pyrazol-3-ylamino)-isoquinolin-6-yl]-(4-methanesulfonyl-piperazin-1-yl)-methanone

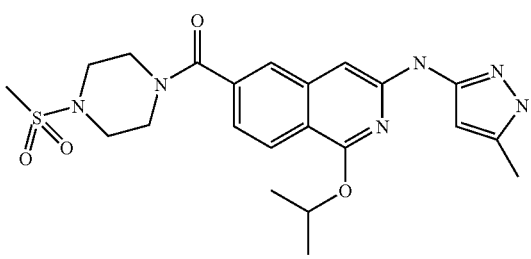

Similar procedure as described in example 384 was used, starting from 1-Isopropoxy-3-(5-methyl-1H-pyrazol-3-ylamino)-isoquinoline-6-carboxylic acid and 1-Methanesulfonyl-piperazine to give [1-Isopropoxy-3-(5-methyl-1H-pyrazol-3-ylamino)-isoquinolin-6-yl]-(4-methanesulfonyl-piperazin-1-yl)-methanone. LC-MS: m/e 473 (MH⁺).

Example 392

1-Isopropoxy-3-(5-methyl-1H-pyrazol-3-ylamino)-isoquinoline-6-carboxylic acid methyl-(tetrahydro-pyran-2-ylmethyl)-amide

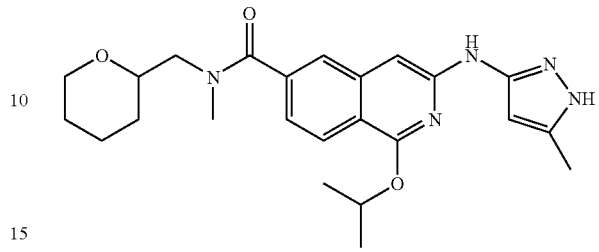

Similar procedure as described in example 384 was used, starting from 1-Isopropoxy-3-(5-methyl-1H-pyrazol-3-ylamino)-isoquinoline-6-carboxylic acid and Methyl-(tetrahydro-pyran-2-ylmethyl)-amine to give 1-Isopropoxy-3-(5-methyl-1H-pyrazol-3-ylamino)-isoquinoline-6-carboxylic acid methyl-(tetrahydro-pyran-2-ylmethyl)-amide. LC-MS: m/e 438 (MH⁺).

Example 393

(3,5-Dimethyl-piperazin-1-yl)-[1-isopropoxy-3-(5-methyl-1H-pyrazol-3-ylamino)-isoquinolin-6-yl]-methanone

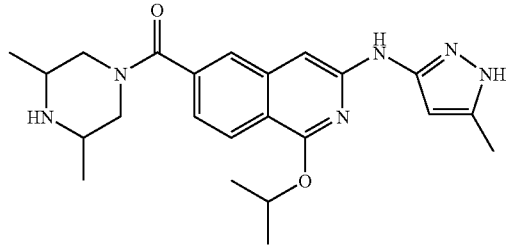

Similar procedure as described in example 384 was used, starting from 1-Isopropoxy-3-(5-methyl-1H-pyrazol-3-ylamino)-isoquinoline-6-carboxylic acid and 2,6-Dimethyl-piperazine to give (3,5-Dimethyl-piperazin-1-yl)-[1-isopropoxy-3-(5-methyl-1H-pyrazol-3-ylamino)-isoquinolin-6-yl]-methanone. LC-MS: m/e 423 (MH⁺).

Example 394

[1-Isopropoxy-3-(5-methyl-1H-pyrazol-3-ylamino)-isoquinolin-6-yl]-[4-(2-methoxy-ethyl)-piperazin-1-yl]-methanone

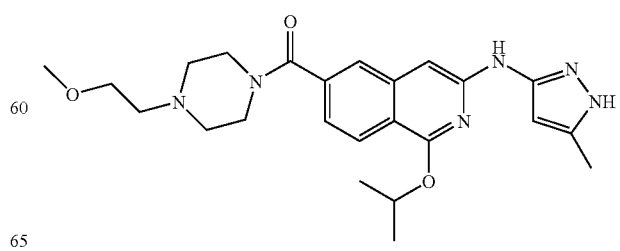

Similar procedure as described in example 384 was used, starting from 1-Isopropoxy-3-(5-methyl-1H-pyrazol-3-ylamino)-isoquinoline-6-carboxylic acid and 1-(2-Methoxyethyl)-piperazine to give [1-Isopropoxy-3-(5-methyl-1H-pyrazol-3-ylamino)-isoquinolin-6-yl]-[4-(2-methoxyethyl)-piperazin-1-yl]-methanone. LC-MS: m/e 453 (MH⁺).

Example 395

[1-Isopropoxy-3-(5-methyl-1H-pyrazol-3-ylamino)-isoquinolin-6-yl]-(4-methoxy-piperidin-1-yl)-methanone

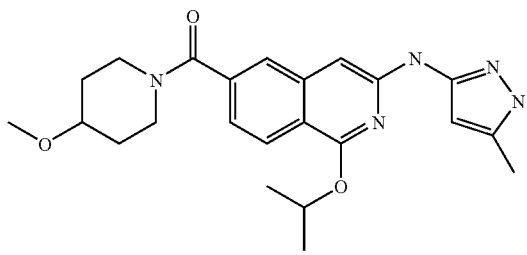

Similar procedure as described in example 384 was used, starting from 1-Isopropoxy-3-(5-methyl-1H-pyrazol-3-ylamino)-isoquinoline-6-carboxylic acid and 4-Methoxy-piperidine to give [1-Isopropoxy-3-(5-methyl-1H-pyrazol-3-ylamino)-isoquinolin-6-yl]-(4-methoxy-piperidin-1-yl)-methanone. LC-MS: m/e 424 (MH⁺).

Example 396

(4-Hydroxy-piperidin-1-yl)-[1-isopropoxy-3-(5-methyl-1H-pyrazol-3-ylamino)-isoquinolin-6-yl]-methanone

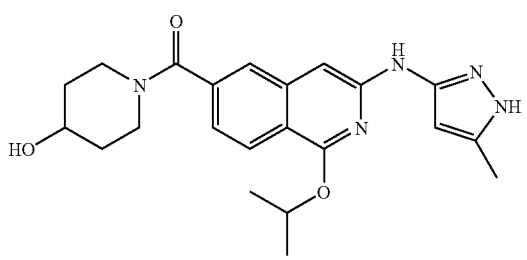

Similar procedure as described in example 384 was used, starting from 1-Isopropoxy-3-(5-methyl-1H-pyrazol-3-ylamino)-isoquinoline-6-carboxylic acid and Piperidin-4-ol to give (4-Hydroxy-piperidin-1-yl)-[1-isopropoxy-3-(5-methyl-1H-pyrazol-3-ylamino)-isoquinolin-6-yl]-methanone. LC-MS: m/e 410 (MH⁺).

Example 397

[1-Isopropoxy-3-(5-methyl-1H-pyrazol-3-ylamino)-isoquinolin-6-yl]-pyrrolidin-1-yl-methanone

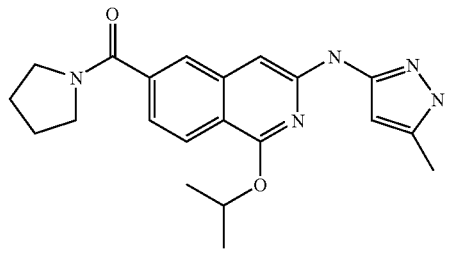

Similar procedure as described in example 384 was used, starting from 1-Isopropoxy-3-(5-methyl-1H-pyrazol-3-ylamino)-isoquinoline-6-carboxylic acid and Pyrrolidine to give [1-Isopropoxy-3-(5-methyl-1H-pyrazol-3-ylamino)-isoquinolin-6-yl]-pyrrolidin-1-yl-methanone. LC-MS: m/e 394 (MH⁺).

Example 398

(7-Bromo-1-isopropoxy-6-methoxy-isoquinolin-3-yl)-(5-methyl-1H-pyrazol-3-yl)-amine

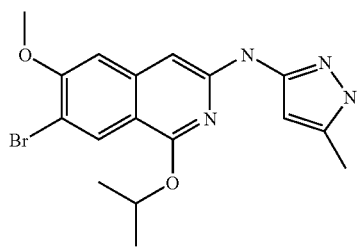

a) Preparation of 6-Bromo-5-methoxy-indan-1-one

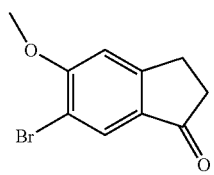

To a mixture of 5-methoxy-1-inanone (52 g, 0.32 mol), acetic acid (600 ml), and water (2 ml), was added sodium acetate (26.32 g, 0.32 mol), followed by dropwise addition of bromine (51.36 g, 0.32 mol) in acetic acid (100 ml). The mixture was stirred at room temperature for two days. The resulting precipitate filtered and filtrate was evaporated. Then it was neutralized with solution of NaOH, extracted with ethyl acetate. The organic layer was washed with water, brine, dried with sodium sulfate and concentrated in vacuo. The residue was purified by column chromatography (petroleum: ethyl acetate=10:1) to give the desire compound 20 g. LC-MS: m/e 241 (MH⁺).

b) Preparation of 6-Bromo-5-methoxy-indan-1,2-dione 2-oxime

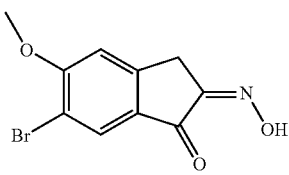

Similar procedure as described in example 9B was used, starting from 6-Bromo-5-methoxy-indan-1-one and n-butylnitrite to give 6-Bromo-5-methoxy-indan-1,2-dione 2-oxime. LC-MS: m/e 270 (MH+).

c) Preparation of 5-Bromo-2-cyanomethyl-4-methoxy-benzoic acid

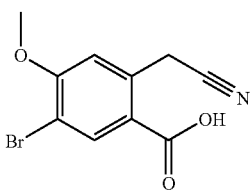

Similar procedure as described in example 9B was used, starting from 6-Bromo-5-methoxy-indan-1,2-dione 2-oxime and p-Toluenesulfonyl chloride to give 5-Bromo-2-cyanomethyl-4-methoxy-benzoic acid. LC-MS: m/e 268 (M−1).

d) Preparation of 7-Bromo-6-methoxy-3-(5-methyl-1H-pyrazol-3-ylamino)-isoquinolin-1-ol

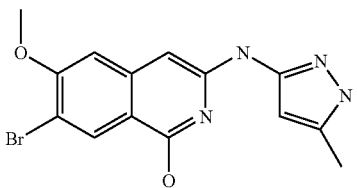

Similar procedure as described in example 9B was used, starting from 5-Bromo-2-cyanomethyl-4-methoxy-benzoic acid, 3-amino-5-methylpyrazol and acetic acid to give 7-Bromo-6-methoxy-3-(5-methyl-1H-pyrazol-3-ylamino)-isoquinolin-1-ol. LC-MS: m/e 349 (MH+).

e) Preparation of (7-Bromo-1-chloro-6-methoxy-isoquinolin-3-yl)-(5-methyl-1H-pyrazol-3-yl)-amine

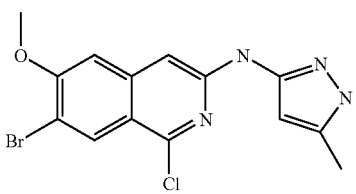

Similar procedure as described in example 9B was used, starting from 7-Bromo-6-methoxy-3-(5-methyl-1H-pyrazol-3-ylamino)-isoquinolin-1-ol and POCl₃ to give (7-Bromo-1-chloro-6-methoxy-isoquinolin-3-yl)-(5-methyl-1H-pyrazol-3-yl)-amine. LC-MS: m/e 367 (MH+).

f) Preparation of (7-Bromo-1-isopropoxy-6-methoxy-isoquinolin-3-yl)-(5-methyl-1H-pyrazol-3-yl)-amine

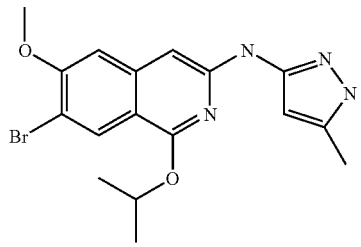

Similar procedure as described in example 376 was used, starting from (7-Bromo-1-chloro-6-methoxy-isoquinolin-3-yl)-(5-methyl-1H-pyrazol-3-yl)-amine and isopropanol to give (7-Bromo-1-isopropoxy-6-methoxy-isoquinolin-3-yl)-(5-methyl-1H-pyrazol-3-yl)-amine. LC-MS: m/e 391 (MH+).

Example 399

(7-Bromo-1-isopropoxy-isoquinolin-3-yl)-(5-methyl-1H-pyrazol-3-yl)-amine

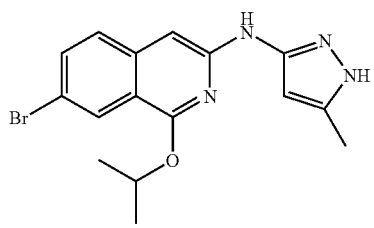

a) Preparation of 6-Bromo-indan-1,2-dione 2-oxime

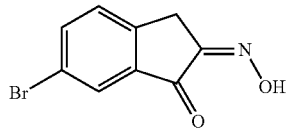

Similar procedure as described in example 9B was used, starting from 6-Bromo-indan-1-one and n-butylnitrite to give 6-Bromo-indan-1,2-dione 2-oxime. LC-MS: m/e 240 (MH+).

b) Preparation of 5-Bromo-2-cyanomethyl-benzoic acid

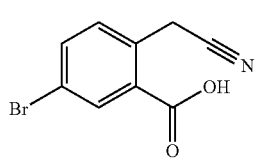

Similar procedure as described in example 9B was used, starting from 6-Bromo-indan-1,2-dione 2-oxime and p-Toluenesulfonyl chloride to give 5-Bromo-2-cyanomethyl-benzoic acid. LC-MS: m/e: 238 (M−1).

c) Preparation of 7-Bromo-3-(5-methyl-1H-pyrazol-3-ylamino)-isoquinolin-1-ol

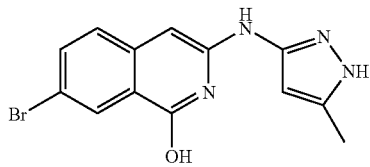

Similar procedure as described in example 9B was used, starting from 5-Bromo-2-cyanomethyl-benzoic acid, 3-amino-5-methylpyrazol and acetic acid to give 7-Bromo-3-(5-methyl-1H-pyrazol-3-ylamino)-isoquinolin-1-ol. LC-MS: m/e 319 (MH+).

d) Preparation of (7-Bromo-1-chloro-isoquinolin-3-yl)-(5-methyl-1H-pyrazol-3-yl)-amine

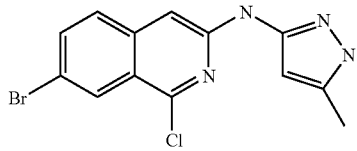

Similar procedure as described in example 9B was used, starting from 7-Bromo-3-(5-methyl-1H-pyrazol-3-ylamino)-isoquinolin-1-ol and POCl₃ to give (7-Bromo-1-chloro-isoquinolin-3-yl)-(5-methyl-1H-pyrazol-3-yl)-amine. LC-MS: m/e 337 (MH+).

e) Preparation of (7-Bromo-1-isopropoxy-isoquinolin-3-yl)-(5-methyl-1H-pyrazol-3-yl)-amine

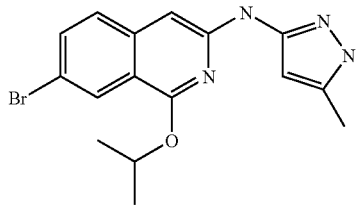

Similar procedure as described in example 376 was used, starting from (7-Bromo-1-chloro-isoquinolin-3-yl)-(5-methyl-1H-pyrazol-3-yl)-amine and isopropanol to give (7-Bromo-1-isopropoxy-isoquinolin-3-yl)-(5-methyl-1H-pyrazol-3-yl)-amine. LC-MS: m/e 361 (MH+).

Example 400

[1-Isopropoxy-6-methoxy-7-(2-methoxy-ethoxy)-isoquinolin-3-yl]-(5-methyl-1H-pyrazol-3-yl)-amine

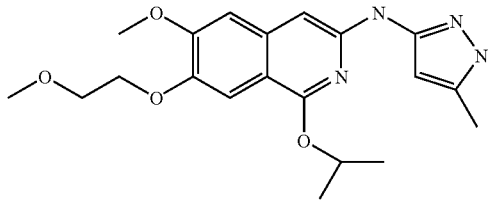

NaH (0.33 g, 8.25 mmol) was added to 2-propanol (4 ml) in a microwave process vial (5 ml), and the mixture was stirred for half an hour at room temperature. [1-Chloro-6-methoxy-7-(2-methoxy-ethoxy)-isoquinolin-3-yl]-(5-methyl-1H-pyrazol-3-yl)-amine (0.3 g, 0.826 mmol) (example 9C) was then added to the mixture, and heated at 140° C. for 30 minutes under microwave irradiation. The reaction mixture was neutralized with acetic acid, and sent to prep. LC-MS. 130 mg of 1-isopropoxy-6-methoxy-7-(2-methoxy-ethoxy)-isoquinolin-3-yl]-(5-methyl-1H-pyrazol-3-yl)-amine was yielded. LC-MS: m/e 387(MH+).

Example 401

[1-Cyclobutoxy-6-methoxy-7-(2-methoxy-ethoxy)-isoquinolin-3-yl]-(5-methyl-1H-pyrazol-3-yl)-amine

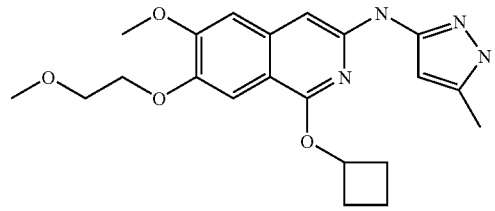

Similar procedure as described in example 400 was used, starting from cyclobutanol and [1-Chloro-6-methoxy-7-(2-methoxy-ethoxy)-isoquinolin-3-yl]-(5-methyl-1H-pyrazol-3-yl)-amine to give [1-Cyclobutoxy-6-methoxy-7-(2-methoxy-ethoxy)-isoquinolin-3-yl]-(5-methyl-1H-pyrazol-3-yl)-amine. LC-MS: m/e 399(MH+).

Example 402

[6-Methoxy-7-(2-methoxy-ethoxy)-1-(tetrahydro-furan-3-yloxy)-isoquinolin-3-yl]-(5-methyl-1H-pyrazol-3-yl)-amine

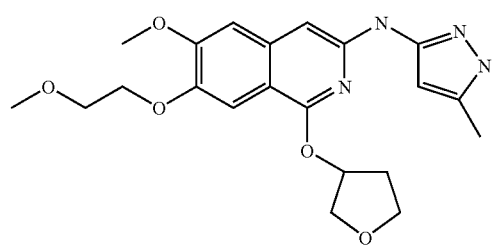

Similar procedure as described in example 400 was used, starting from 3-hydroxy-tetrahydrofuran and [1-Chloro-6-methoxy-7-(2-methoxy-ethoxy)-isoquinolin-3-yl]-(5-methyl-1H-pyrazol-3-yl)-amine to give [6-Methoxy-7-(2-methoxy-ethoxy)-1-(tetrahydro-furan-3-yloxy)-isoquinolin-3-yl]-(5-methyl-1H-pyrazol-3-yl)-amine. LC-MS: m/e 415(MH+).

Example 403

[6-Methoxy-7-(2-methoxy-ethoxy)-1-(oxetan-3-yloxy)-isoquinolin-3-yl]-(5-methyl-1H-pyrazol-3-yl)-amine

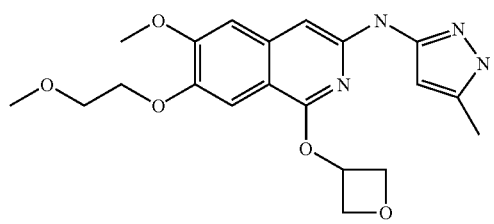

Similar procedure as described in example 400 was used, starting from oxetan-3-ol and [1-Chloro-6-methoxy-7-(2-methoxy-ethoxy)-isoquinolin-3-yl]-(5-methyl-1H-pyrazol-3-yl)-amine to give [6-Methoxy-7-(2-methoxy-ethoxy)-1-(oxetan-3-yloxy)-isoquinolin-3-yl]-(5-methyl-1H-pyrazol-3-yl)-amine. LC-MS: m/e 401 (MH$^+$).

Example 404

[1-Isopropyl-6-methoxy-7-(2-methoxy-ethoxy)-isoquinolin-3-yl]-(5-methyl-1H-pyrazol-3-yl)-amine a) Preparation of [1-Isopropenyl-6-methoxy-7-(2-methoxy-ethoxy)-isoquinolin-3-yl]-(5-methyl-1H-pyrazol-3-yl)-amine

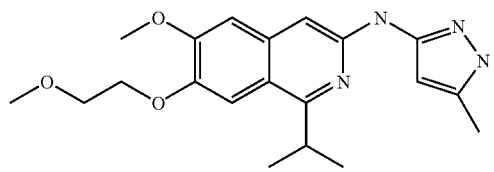

A mixture of [1-Chloro-6-methoxy-7-(2-methoxy-ethoxy)-isoquinolin-3-yl]-(5-methyl-1H-pyrazol-3-yl)-amine (150 mg), isopropenyl boronic acid pinacol ester (70 μl), Na$_2$CO$_3$ (70 mg), Tetrakis(triphenylphosphine)palladium(0) (10 mg), DMF (0.5 ml) and water (0.5 ml) was heated at 180° C. for 30 minutes under microwave irradiation. After reaction finished, the reaction mixture was purified by preparative LC-MS to give [1-Isopropenyl-6-methoxy-7-(2-methoxy-ethoxy)-isoquinolin-3-yl]-(5-methyl-1H-pyrazol-3-yl)-amine (120 mg). LC-MS: m/e 369(MH$^+$).

b) Preparation of [1-Isopropyl-6-methoxy-7-(2-methoxy-ethoxy)-isoquinolin-3-yl]-(5-methyl-1H-pyrazol-3-yl)-amine

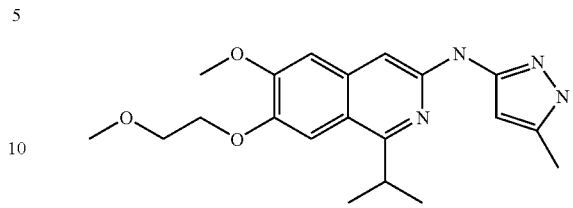

A mixture of [1-Isopropenyl-6-methoxy-7-(2-methoxy-ethoxy)-isoquinolin-3-yl]-(5-methyl-1H-pyrazol-3-yl)-amine (120 mg) and 10% Pt/C (12 mg) was sealed in high-pressure bottle under 40 psi of H$_2$ and stirred overnight at room temperature. Then the mixture was filtered and the organic layer was concentrated to give [1-Isopropyl-6-methoxy-7-(2-methoxy-ethoxy)-isoquinolin-3-yl]-(5-methyl-1H-pyrazol-3-yl)-amine. LC-MS: 371 (MH$^+$).

Example 405

[1-Isopropoxy-6,7-bis-(2-methoxy-ethoxy)-isoquinolin-3-yl]-(5-methyl-1H-pyrazol-3-yl)-amine

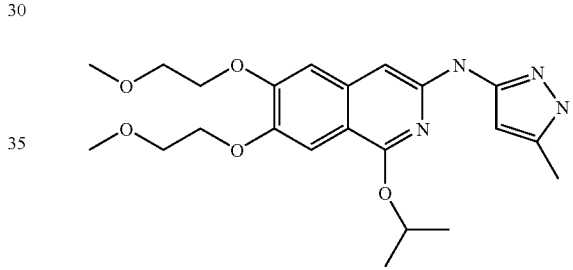

Similar procedure as described in example 400 was used, starting from isopropyl alcohol and [1-Chloro-6,7-bis-(2-methoxy-ethoxy)-isoquinolin-3-yl]-(5-methyl-1H-pyrazol-3-yl)-amine (Example 9E) to give [1-Isopropoxy-6,7-bis-(2-methoxy-ethoxy)-isoquinolin-3-yl]-(5-methyl-1H-pyrazol-3-yl)-amine. LC-MS: m/e 431(MH$^+$).

Example 406

Isopropoxy-6,8-dimethoxy-isoquinolin-3-yl)-(5-methyl-1H-pyrazol-3-yl)-amine

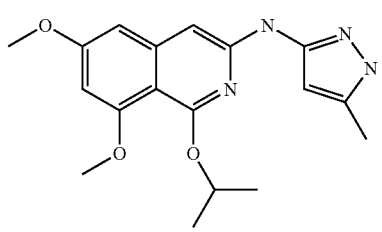

Similar procedure as described in example 400 was used, starting from isopropyl alcohol and (1-Chloro-6,8-dimethoxy-isoquinolin-3-yl)-(5-methyl-1H-pyrazol-3-yl)-amine (example 9F) to give (1-Isopropoxy-6,8-dimethoxy-isoquinolin-3-yl)-(5-methyl-1H-pyrazol-3-yl)-amine. LC-MS: m/e 343(MH⁺).

Example 407

[1-(4-Fluoro-phenoxy)-6,8-dimethoxy-isoquinolin-3-yl]-(5-methyl-1H-pyrazol-3-yl)-amine

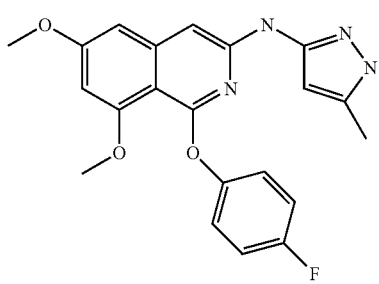

Similar procedure as described in example 400 was used, starting from 4-Fluorophenol and (1-Chloro-6,8-dimethoxy-isoquinolin-3-yl)-(5-methyl-1H-pyrazol-3-yl)-amine to give [1-(4-Fluoro-phenoxy)-6,8-dimethoxy-isoquinolin-3-yl]-(5-methyl-1H-pyrazol-3-yl)-amine. LC-MS: m/e 395(MH⁺).

Example 408

1-Isopropoxy-6-methoxy-3-(5-methyl-1H-pyrazol-3-ylamino)-isoquinoline-7-carboxylic acid dimethylamide

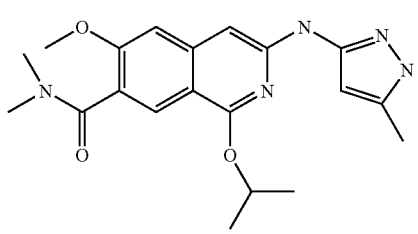

Similar procedure as described in example 400 was used, starting from isopropyl alcohol and 1-Chloro-6-methoxy-3-(5-methyl-1H-pyrazol-3-ylamino)-isoquinoline-7-carboxylic acid dimethylamide (example 9G) to give 1-Isopropoxy-6-methoxy-3-(5-methyl-1H-pyrazol-3-ylamino)-isoquinoline-7-carboxylic acid dimethylamide. LC-MS: m/e 384(MH⁺).

Example 409

1-Cyclobutoxy-6-methoxy-3-(5-methyl-1H-pyrazol-3-ylamino)-isoquinoline-7-carboxylic acid dimethylamide

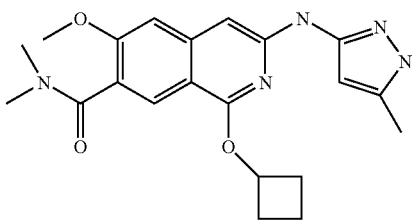

Similar procedure as described in example 400 was used, starting from cyclobutanol and 1-Chloro-6-methoxy-3-(5-methyl-1H-pyrazol-3-ylamino)-isoquinoline-7-carboxylic acid dimethylamide to give 1-Cyclobutoxy-6-methoxy-3-(5-methyl-1H-pyrazol-3-ylamino)-isoquinoline-7-carboxylic acid dimethylamide, LC-MS: m/e 396(MH⁺).

Example 410

1-Cyclopentyloxy-6-methoxy-3-(5-methyl-1H-pyrazol-3-ylamino)-isoquinoline-7-carboxylic acid dimethylamide

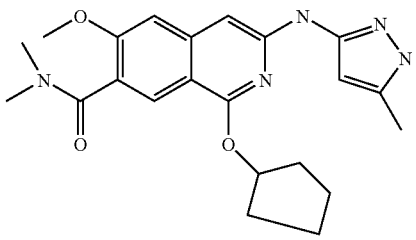

Similar procedure as described in example 400 was used, starting from cyclopentanol and of 1-Chloro-6-methoxy-3-(5-methyl-1H-pyrazol-3-ylamino)-isoquinoline-7-carboxylic acid dimethylamide to give 1-Cyclopentyloxy-6-methoxy-3-(5-methyl-1H-pyrazol-3-ylamino)-isoquinoline-7-carboxylic acid dimethylamide, LC-MS: m/e 410(MH⁺).

Example 411

Isopropoxy-6-methoxy-3-(5-methyl-1H-pyrazol-3-ylamino)-isoquinoline-7-carbonitrile

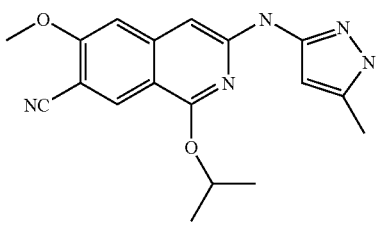

Similar procedure as described in example 400 was used, starting from isopropyl alcohol and 1-Chloro-6-methoxy-3-(5-methyl-1H-pyrazol-3-ylamino)-isoquinoline-7-carbonitrile (example 9H) to give 1-Isopropoxy-6-methoxy-3-(5-methyl-1H-pyrazol-3-ylamino)-isoquinoline-7-carbonitrile. LC-MS: m/e 338(MH$^+$).

Example 412

6-Methoxy-3-(5-methyl-1H-pyrazol-3-ylamino)-1-(tetrahydro-furan-3-yloxy)-isoquinoline-7-carbonitrile

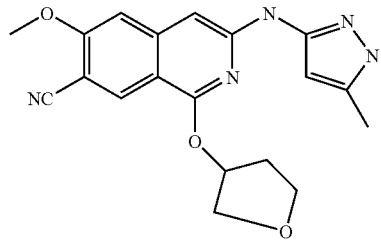

Similar procedure as described in example 400 was used, starting from 3-hydroxy-tetrahydrofuran and of 1-Chloro-6-methoxy-3-(5-methyl-1H-pyrazol-3-ylamino)-isoquinoline-7-carbonitrile to give 6-Methoxy-3-(5-methyl-1H-pyrazol-3-ylamino)-1-(tetrahydro-furan-3-yloxy)-isoquinoline-7-carbonitrile. LC-MS: m/e 366(MH$^+$).

Example 413

[1-Isopropoxy-6-methoxy-7-(2-piperidin-1-yl-ethoxy)-isoquinolin-3-yl]-(5-methyl-1H-pyrazol-3-yl)-amine

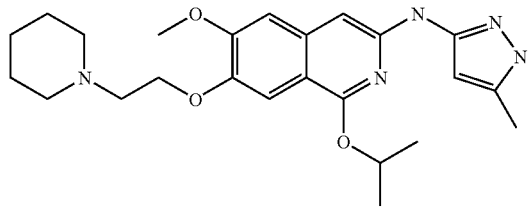

Similar procedure as described in example 378 was used, starting from 2-Piperidin-1-yl-ethanol and (7-Fluoro-1-isopropoxy-6-methoxy-isoquinolin-3-yl)-(5-methyl-1H-pyrazol-3-yl)-amine to give [1-Isopropoxy-6-methoxy-7-(2-piperidin-1-yl-ethoxy)-isoquinolin-3-yl]-(5-methyl-1H-pyrazol-3-yl)-amine. LC-MS: m/e 440(MH$^+$).

Example 414

(1-Cyclopropyl-6-methoxy-isoquinolin-3-yl)-(5-methyl-1H-pyrazol-3-yl)-amine

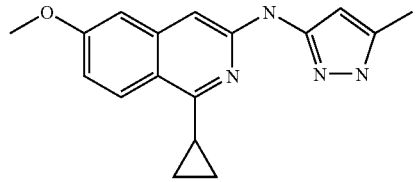

To a mixture of (1-Chloro-6-methoxy-isoquinolin-3-yl)-(5-methyl-1H-pyrazol-3-yl)-amine (0.2887 g 1 mmol), cyclopropyl boronic acid (0.1718 g, 2 mmol), PdCl$_2$ (0.0177 g, 10% mmol), and K$_3$PO$_4$ (0.5307 g, 2.5 mmol) under Argon was added Dioxane/H$_2$O=10:1(1 ml) and P(tBu)$_3$ (20% mmol). The mixture was heated to 130° C. and stirred overnight. The product was purified by preparative HPLC to give 2.5 mg of solid. LC-MS: m/e 295 (MH$^+$).

Example 415

(1-Cyclobutoxy-6-methoxy-isoquinolin-3-yl)-(5-methyl-1H-pyrazol-3-yl)-amine

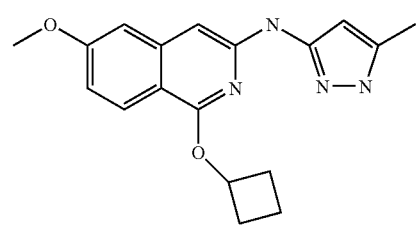

Similar procedure as described in example 10 was used, starting from (1-Chloro-6-methoxy-isoquinolin-3-yl)-(5-methyl-1H-pyrazol-3-yl)-amine and cyclobutanol to give (1-Cyclobutoxy-6-methoxy-isoquinolin-3-yl)-(5-methyl-1H-pyrazol-3-yl)-amine. LC-MS: m/e 325 (MH$^+$).

Example 416

(1-Benzyl-6-methoxy-isoquinolin-3-yl)-(5-methyl-1H-pyrazol-3-yl)-amine

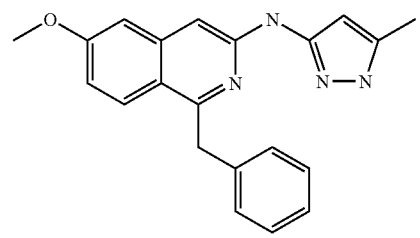

To a solution of (1-Chloro-6-methoxy-isoquinolin-3-yl)-(5-methyl-1H-pyrazol-3-yl)-amine (0.2543 g 1 equiv) in dry THF (2 ml) and NMP (0.2 ml) under Argon was added Fe(acac)$_3$ (acac=acetylacetonate) (46.8 mg 0.15 equiv). The mixture was stirred for 10 min, and then Benzylmagnesium chloride (2M in THF, 0.792 ml 1.8 equiv) was added dropwise. The mixture was stirred at room temperature overnight. The product was purified by HPLC to give 11.5 mg of solid. LC-MS: m/e 345 (MH$^+$).

Example 417

(1-Cyclohexyl-6-methoxy-isoquinolin-3-yl)-(5-methyl-1H-pyrazol-3-yl)-amine

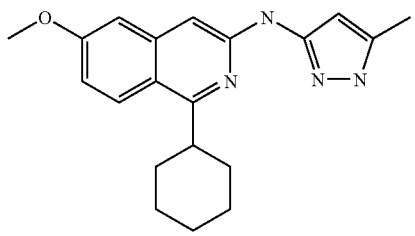

Similar procedure as described in example 416 was used, staring from (1-Chloro-6-methoxy-isoquinolin-3-yl)-(5-methyl-1H-pyrazol-3-yl)-amine and cyclohexylmagnesium bromide to give (1-Cyclohexyl-6-methoxy-isoquinolin-3-yl)-(5-methyl-1H-pyrazol-3-yl)-amine. LC-MS: m/e 337 (MH$^+$).

Example 418

1-[1-Isopropoxy-3-(5-methyl-1H-pyrazol-3-ylamino)-isoquinolin-6-yl]-pyrrolidin-2-one

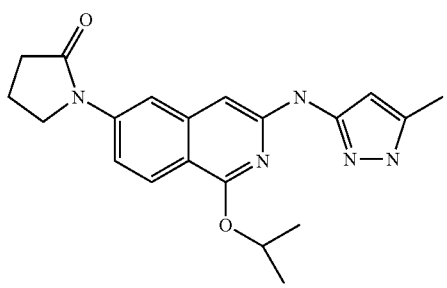

To a mixture of (6-bromo-1-isopropoxy-isoquinolin-3-yl)-(5-methyl-1H-pyrazol-3-yl)-amine (0.1882 g, 0.5 mmol, 1 equiv), 1H-prrolidin-2-one (1.2 equiv), Xantphos (15% equiv), Pd(OAc)$_2$ (10% equiv), Cs$_2$CO$_3$ (1.5 equiv) under Argon was added dry dioxane (1.5 ml). The mixture was heated at 125° C. overnight. The product was purified by prep. HPLC to give 5.0 mg of solid. LC-MS: m/e 366 (MH$^+$).

Example 419

(1-Cyclopentyl-6-methoxy-isoquinolin-3-yl)-(5-methyl-1H-pyrazol-3-yl)-amine

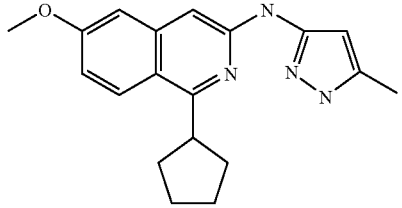

Similar procedure as described in example 416 was used, staring from (1-Chloro-6-methoxy-isoquinolin-3-yl)-(5-methyl-1H-pyrazol-3-yl)-amine and cyclopentyl-lmagnesium bromide to give (1-Cyclopentyl-6-methoxy-isoquinolin-3-yl)-(5-methyl-1H-pyrazol-3-yl)-amine. LC-MS: m/e 323 (MH$^+$).

Example 420

(1-Isobutyl-6-methoxy-isoquinolin-3-yl)-(5-methyl-1H-pyrazol-3-yl)-amine

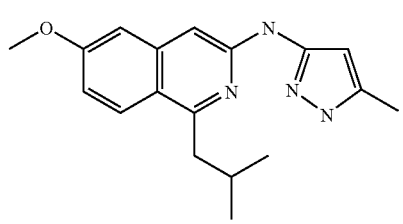

Similar procedure as described in example 416 was used, staring from (1-Chloro-6-methoxy-isoquinolin-3-yl)-(5-methyl-1H-pyrazol-3-yl)-amine and isobutyl-magnesium bromide to give (1-Isobutyl-6-methoxy-isoquinolin-3-yl)-(5-methyl-1H-pyrazol-3-yl)-amine. LC-MS: m/e 311 (MH$^+$).

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A compound according to

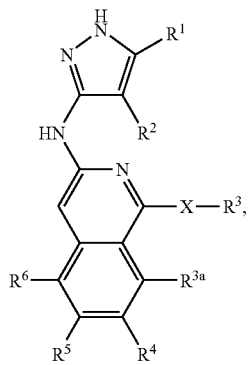

formula I wherein:
(a) R$^1$ is selected from the group consisting of: hydrogen, alkyl, and cycloalkyl;
(b) R$^2$ is hydrogen or alkyl;
(c) R$^3$ is selected from the group consisting of:
  (1) unsubstituted alkyl,
  (2) alkyl which is substituted one or two times with —C(O)O-alkyl, heteroaryl, phenyl, heterocyclyl or cycloalkyl,
  (3) alkyl wherein one or more —CH$_2$— groups are replaced by oxygen,
  (4) aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR$_2$, (5) heteroaryl which is optionally substituted one or more times with alkyl,
(6) cycloalkyl, and
(7) heterocyclyl;
(d) $R^{3a}$ is selected from the group consisting of: hydrogen, alkyl, and alkoxy;
(e) $R^4$ is selected from the group consisting of: hydrogen, alkyl, alkoxy, halogen, cyano, —C(O)NR$_2$, —(CH$_2$)$_n$—Y—R$^7$, and Z-R$^8$;
(f) $R^5$ is selected from the group consisting of: hydrogen, alkyl, alkoxy, halogen, cyano, —C(O)NR$_2$, —(CH$_2$)$_n$—Y—R$^7$, and Z-R$^8$; and $R^6$ is selected from the group consisting of: hydrogen, alkyl, alkoxy, halogen, and cyano; or alternatively, $R^5$ and $R^6$ form, together with the carbon atoms to which they are attached, a 5- or 6-membered heterocyclic ring;
(g) X is selected from the group consisting of: a single bond, —NR—, —O—, —S—, —C(O)—, and —C(O)NR—;
(h) Y is selected from the group consisting of: —O—, —NR—, —S—, —S(O)$_2$NR—, —NRC(O)—, —NRC(O)O—, and —C(O)NR—;
(i) Z is selected from the group consisting of: —C(O)—, —O—, a single bond, and alkylene;
(j) $R^7$ is cycloalkyl; or alkyl, which is optionally substituted one or more times by alkoxy, hydroxyl, alkylsulfonyl, heterocyclyl or NR$_2$;
(k) $R^8$ is heterocyclyl;
(l) R is hydrogen or alkyl; and
(m) n is 0, 1, 2 or 3;
or a pharmaceutically-acceptable salt or ester thereof.

2. A compound according to claim 1, wherein $R^3$ is selected from the group consisting of: unsubstituted alkyl, cycloalkyl, and heterocyclyl.

3. A compound according to claim 1, wherein:
(a) $R^3$ is selected from the group consisting of: unsubstituted alkyl, cycloalkyl, and heterocyclyl; and
(b) X is a single bond or —O—.

4. A compound according to claim 1, wherein:
(a) $R^3$ is unsubstituted alkyl or cycloalkyl; and
(b) X is a single bond or —O—.

5. A compound according to claim 1, wherein $R^3$ is unsubstituted alkyl.

6. A compound according to claim 1 wherein
(a) $R^3$ is unsubstituted alkyl; and
(b) X is a single bond or —O—.

7. A compound according to claim 1, wherein:
(a) $R^3$ is unsubstituted alkyl; and
(b) X is a single bond.

8. A compound according to claim 1 selected from the group consisting of:
(1-Isopropyl-6-methoxy-isoquinolin-3-yl)-(5-methyl-1H-pyrazol-3-yl)-amine;
(5-Cyclopropyl-1H-pyrazol-3-yl)-(1-isopropyl-6,7-dimethoxy-isoquinolin-3-yl)-amine;
[1-Isopropyl-6-(2-methoxy-ethoxy)-isoquinolin-3-yl]-(5-methyl-1H-pyrazol-3-yl)-amine;
[1-Isopropyl-6-(2-morpholin-4-yl-ethoxy)-isoquinolin-3-yl]-(5-methyl-1H-pyrazol-3-yl)-amine;
1-Isopropyl-3-(5-methyl-1H-pyrazol-3-ylamino)-isoquinoline-6-carboxylic acid (3-methoxy-propyl)-amide;
1-{4-[1-Isopropyl-3-(5-methyl-1H-pyrazol-3-ylamino)-isoquinoline-6-carbonyl]-piperazin-1-yl}-ethanone; and
(1-Isopropyl-6,7-dimethoxy-isoquinolin-3-yl)-(5-methyl-1H-pyrazol-3-yl)-amine.

9. A compound according to claim 1 selected from the group consisting of:
(1-Isopropyl-5-methoxy-isoquinolin-3-yl)-(5-methyl-1H-pyrazol-3-yl)-amine;
(1-Ethyl-6-methoxy-isoquinolin-3-yl)-(5-methyl-1H-pyrazol-3-yl)-amine;
(8-Isopropyl-2,3-dihydro-1,4-dioxa-7-aza-phenanthren-6-yl)-(5-methyl-1H-pyrazol-3-yl)-amine;
(1-Isopropyl-6-morpholin-4-yl-isoquinolin-3-yl)-(5-methyl-1H-pyrazol-3-yl)-amine;
[1-Isopropyl-6-(4-methyl-piperazin-1-yl)-isoquinolin-3-yl]-(5-methyl-1H-pyrazol-3-yl)-amine;
[1-Isopropyl-6-methoxy-7-(2-methoxy-ethoxy)-isoquinolin-3-yl]-(5-methyl-1H-pyrazol-3-yl)-amine; and
(1-Isobutyl-6-methoxy-isoquinolin-3-yl)-(5-methyl-1H-pyrazol-3-yl)-amine.

10. A compound according to claim 1, wherein:
(a) $R^3$ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy or alikoxy substituted by heterocyclyl or —NR$^2$; and
(b) X is a single bond.

11. A compound according to claim 1 selected from the group consisting of:
(5-Methyl-1H-pyrazol-3-yl)-(1-phenyl-isoquinolin-3-yl)-amine;
[1-(4-Fluoro-phenyl)-isoquinolin-3-yl]-(5-methyl-1H-pyrazol-3-yl)-amine;
4-[3-(5-Methyl-1H-pyrazol-3-ylamino)-isoquinolin-1-yl]-benzonitrile;
[1-(4-Methoxy-phenyl)-isoquinolin-3-yl]-(5-methyl-1H-pyrazol-3-yl)-amine;
(5-Methyl-1H-pyrazol-3-yl)-[1-(4-trifluoromethyl-phenyl)-isoquinolin-3-yl]-amine;
(5-Methyl-1H-pyrazol-3-yl)-(1-p-tolyl-isoquinolin-3-yl)-amine;
[1-(4-Chloro-phenyl)-isoquinolin-3-yl]-(5-methyl-1H-pyrazol-3-yl)-amine;
[1-(3-Chloro-phenyl)-isoquinolin-3-yl]-(5-methyl-1H-pyrazol-3-yl)-amine;
[1-(3-Fluoro-phenyl)-isoquinolin-3-yl]-(5-methyl-1H-pyrazol-3-yl)-amine; and
3-[3-(5-Methyl-1H-pyrazol-3-ylamino)-isoquinolin-1-yl]-benzonitrile.

12. A compound according to claim 1 selected from the group consisting of:
[1-(3-Methoxy-phenyl)-isoquinolin-3-yl]-(5-methyl-1H-pyrazol-3-yl)-amine;
(5-Methyl-1H-pyrazol-3-yl)-[1-(3-trifluoromethyl-phenyl)-isoquinolin-3-yl]-amine;
(5-Methyl-1H-pyrazol-3-yl)-(1-m-tolyl-isoquinolin-3-yl)-amine;
1-{3-[3-(5-Methyl-1H-pyrazol-3-ylamino)-isoquinolin-1-yl]-phenyl}-ethanone;
1-{4-[3-(5-Methyl-1H-pyrazol-3-ylamino)-isoquinolin-1-yl]-phenyl}-ethanone;
[1-(2-Fluoro-phenyl)-isoquinolin-3-yl]-(5-methyl-1H-pyrazol-3-yl)-amine;
[1-(2-Methoxy-phenyl)-isoquinolin-3-yl]-(5-methyl-1H-pyrazol-3-yl)-amine;
[1-(2,4-Difluoro-phenyl)-6,7-dimethoxy-isoquinolin-3-yl]-(5-methyl-1H-pyrazol-3-yl)-amine;
(5-Methyl-1H-pyrazol-3-yl)-(1-naphthalen-2-yl-isoquinolin-3-yl)-amine; and
[1-(4-tert-Butyl-phenyl)-isoquinolin-3-yl]-(5-methyl-1H-pyrazol-3-yl)-amine.

13. A compound according to claim 1 selected from the group consisting of:
- [1-(2,4-Difluoro-phenyl)-isoquinolin-3-yl]-(5-methyl-1H-pyrazol-3-yl)-amine;
- [1-(3,4-Difluoro-phenyl)-isoquinolin-3-yl]-(5-methyl-1H-pyrazol-3-yl)-amine;
- [1-(3,4-Dimethoxy-phenyl)-isoquinolin-3-yl]-(5-methyl-1H-pyrazol-3-yl)-amine;
- N-{4-[3-(5-Methyl-1H-pyrazol-3-ylamino)-isoquinolin-1-yl]-phenyl}-acetamide;
- (6-Methoxy-1-phenyl-isoquinolin-3-yl)-(5-methyl-1H-pyrazol-3-yl)-amine;
- [1-(4-Fluoro-phenyl)-6-methoxy-isoquinolin-3-yl]-(5-methyl-1H-pyrazol-3-yl)-amine;
- 4-[6-Methoxy-3-(5-methyl-1H-pyrazol-3-ylamino)-isoquinolin-1-yl]-benzonitrile;
- [1-(4-Ethoxy-phenyl)-6-methoxy-isoquinolin-3-yl]-(5-methyl-1H-pyrazol-3-yl)-amine;
- [6-Methoxy-1-(4-trifluoromethyl-phenyl)-isoquinolin-3-yl]-(5-methyl-1H-pyrazol-3-yl)-amine; and
- (6-Methoxy-1-p-tolyl-isoquinolin-3-yl)-(5-methyl-1H-pyrazol-3-yl)-amine.

14. A compound according to claim 1 selected from the group consisting of:
- [1-(4-Chloro-phenyl)-6-methoxy-isoquinolin-3-yl]-(5-methyl-1H-pyrazol-3-yl)-amine;
- [1-(3-Chloro-phenyl)-6-methoxy-isoquinolin-3-yl]-(5-methyl-1H-pyrazol-3-yl)-amine;
- [1-(3-Fluoro-phenyl)-6-methoxy-isoquinolin-3-yl]-(5-methyl-1H-pyrazol-3-yl)-amine;
- 3-[6-Methoxy-3-(5-methyl-1H-pyrazol-3-ylamino)-isoquinolin-1-yl]-benzonitrile;
- [6-Methoxy-1-(3-methoxy-phenyl)-isoquinolin-3-yl]-(5-methyl-1H-pyrazol-3-yl)-amine;
- [6-Methoxy-1-(3-trifluoromethyl-phenyl)-isoquinolin-3-yl]-(5-methyl-1H-pyrazol-3-yl)-amine;
- (6-Methoxy-1-m-tolyl-isoquinolin-3-yl)-(5-methyl-1H-pyrazol-3-yl)-amine;
- 1-{3-[6-Methoxy-3-(5-methyl-1H-pyrazol-3-ylamino)-isoquinolin-1-yl]-phenyl}-ethanone;
- [1-{4-[6-Methoxy-3-(5-methyl-1H-pyrazol-3-ylamino)-isoquinolin-1-yl]-phenyl}-ethanone; and
- [1-(2-Fluoro-phenyl)-6-methoxy-isoquinolin-3-yl]-(5-methyl-1H-pyrazol-3-yl)-amine.

15. A compound according to claim 1 selected from the group consisting of:
- [6-Methoxy-1-(2-methoxy-phenyl)-isoquinolin-3-yl]-(5-methyl-1H-pyrazol-3-yl)-amine;
- (6-Methoxy-1-naphthalen-2-yl-isoquinolin-3-yl)-(5-methyl-1H-pyrazol-3-yl)-amine;
- [1-(4-tert-Butyl-phenyl)-6-methoxy-isoquinolin-3-yl]-(5-methyl-1H-pyrazol-3-yl)-amine;
- [1-(2,4-Difluoro-phenyl)-6-methoxy-isoquinolin-3-yl]-(5-methyl-1H-pyrazol-3-yl)-amine;
- [1-(3,4-Difluoro-phenyl)-6-methoxy-isoquinolin-3-yl]-(5-methyl-1H-pyrazol-3-yl)-amine;
- [1-(3,4-Dimethoxy-phenyl)-6-methoxy-isoquinolin-3-yl]-(5-methyl-1H-pyrazol-3-yl)-amine;
- N-{4-[6-Methoxy-3-(5-methyl-1H-pyrazol-3-ylamino)-isoquinolin-1-yl]-phenyl}-acetamide;
- [1-(2-Fluoro-phenyl)-5-methoxy-isoquinolin-3-yl]-(5-methyl-1H-pyrazol-3-yl)-amine;
- [5-Methoxy-1-(3-methoxy-phenyl)-isoquinolin-3-yl]-(5-methyl-1H-pyrazol-3-yl)-amine; and
- 3-[5-Methoxy-3-(5-methyl-1H-pyrazol-3-ylamino)-isoquinolin-1-yl]-benzonitrile.

16. A compound according to claim 1 selected from the group consisting of:
- (5-Methoxy-1-phenyl-isoquinolin-3-yl)-(5-methyl-1H-pyrazol-3-yl)-amine;
- [1-(2-Fluoro-phenyl)-7-methoxy-isoquinolin-3-yl]-(5-methyl-1H-pyrazol-3-yl)-amine;
- [7-Methoxy-1-(3-methoxy-phenyl)-isoquinolin-3-yl]-(5-methyl-1H-pyrazol-3-yl)-amine;
- 3-[7-Methoxy-3-(5-methyl-1H-pyrazol-3-ylamino)-isoquinolin-1-yl]-benzonitrile;
- (7-Methoxy-1-phenyl-isoquinolin-3-yl)-(5-methyl-1H-pyrazol-3-yl)-amine;
- [1-(2,4-Difluoro-phenyl)-5-methoxy-isoquinolin-3-yl]-(5-methyl-1H-pyrazol-3-yl)-amine;
- [1-(2,4-Difluoro-phenyl)-7-methoxy-isoquinolin-3-yl]-(5-methyl-1H-pyrazol-3-yl)-amine;
- [1-(2-Fluoro-phenyl)-6,7-dimethoxy-isoquinolin-3-yl]-(5-methyl-1H-pyrazol-3-yl)-amine;
- [6,7-Dimethoxy-1-(3-methoxy-phenyl)-isoquinolin-3-yl]-(5-methyl-1H-pyrazol-3-yl)-amine; and
- (6,7-Dimethoxy-1-phenyl-isoquinolin-3-yl)-(5-methyl-1H-pyrazol-3-yl)-amine.

17. A compound according to claim 1 selected from the group consisting of:
- [1-(2-Fluoro-phenyl)-5,6-dimethoxy-isoquinolin-3-yl]-(5-methyl-1H-pyrazol-3-yl)-amine;
- [5,6-Dimethoxy-1-(3-methoxy-phenyl)-isoquinolin-3-yl]-(5-methyl-1H-pyrazol-3-yl)-amine;
- (5,6-Dimethoxy-1-phenyl-isoquinolin-3-yl)-(5-methyl-1H-pyrazol-3-yl)-amine;
- (1-Phenyl-isoquinolin-3-yl)-(1H-pyrazol-3-yl)-amine;
- [1-(2-Methoxy-phenyl)-isoquinolin-3-yl]-(1H-pyrazol-3-yl)-amine;
- (1H-Pyrazol-3-yl)-[1-(4-trifluoromethyl-phenyl)-isoquinolin-3-yl]-amine;
- [1-(3-Fluoro-phenyl)-isoquinolin-3-yl]-(1H-pyrazol-3-yl)-amine;
- 3-[3-(1H-Pyrazol-3-ylamino)-isoquinolin-1-yl]-benzoic acid ethyl ester;
- [1-(4-Fluoro-phenyl)-isoquinolin-3-yl]-(1H-pyrazol-3-yl)-amine; and
- [1-(3-Methoxy-phenyl)-isoquinolin-3-yl]-(1H-pyrazol-3-yl)-amine.

18. A compound according to claim 1 selected from the group consisting of:
- 4-[3-(1H-Pyrazol-3-ylamino)-isoquinolin-1-yl]-benzoic acid;
- [1-(2-Fluoro-phenyl)-isoquinolin-3-yl]-(1H-pyrazol-3-yl)-amine;
- [1-(3,4-Difluoro-phenyl)-isoquinolin-3-yl]-(1H-pyrazol-3-yl)-amine;
- [1-(2,4-Difluoro-phenyl)-isoquinolin-3-yl]-(1H-pyrazol-3-yl)-amine;
- (1H-Pyrazol-3-yl)-[1-(3-trifluoromethyl-phenyl)-isoquinolin-3-yl]-amine;
- (1-Naphthalen-2-yl-isoquinolin-3-yl)-(1H-pyrazol-3-yl)-amine;
- 3-[3-(1H-Pyrazol-3-ylamino)-isoquinolin-1-yl]-benzonitrile;
- (1H-Pyrazol-3-yl)-(1-p-tolyl-isoquinolin-3-yl)-amine;
- (1H-Pyrazol-3-yl)-(1-m-tolyl-isoquinolin-3-yl)-amine; and
- [1-(4-tert-Butyl-phenyl)-isoquinolin-3-yl]-(1H-pyrazol-3-yl)-amine.

19. A compound according to claim 1 selected from the group consisting of:

1-{4-[3-(1H-Pyrazol-3-ylamino)-isoquinolin-1-yl]-phenyl}-ethanone;
1-{3-[3-(1H-Pyrazol-3-ylamino)-isoquinolin-1-yl]-phenyl}-ethanone;
[1-(4-Chloro-phenyl)-isoquinolin-3-yl]-(1H-pyrazol-3-yl)-amine;
[1-(3,4-Dimethoxy-phenyl)-isoquinolin-3-yl]-(1H-pyrazol-3-yl)-amine;
[1-(4-Ethoxy-phenyl)-isoquinolin-3-yl]-(1H-pyrazol-3-yl)-amine;
4-[3-(1H-Pyrazol-3-ylamino)-isoquinolin-1-yl]-benzonitrile;
N-{4-[3-(1H-Pyrazol-3-ylamino)-isoquinolin-1-yl]-phenyl}-acetamide;
(6-Methoxy-1-phenyl-isoquinolin-3-yl)-(1H-pyrazol-3-yl)-amine;
[1-(4-Fluoro-phenyl)-6-methoxy-isoquinolin-3-yl]-(1H-pyrazol-3-yl)-amine; and
1-{3-[6-Methoxy-3-(1H-pyrazol-3-ylamino)-isoquinolin-1-yl]-phenyl}-ethanone.

20. A compound according to claim 1 selected from the group consisting of:
1-{4-[6-Methoxy-3-(1H-pyrazol-3-ylamino)-isoquinolin-1-yl]-phenyl}-ethanone;
[1-(2-Fluoro-phenyl)-6-methoxy-isoquinolin-3-yl]-(1H-pyrazol-3-yl)-amine;
[6-Methoxy-1-(3-methoxy-phenyl)-isoquinolin-3-yl]-(1H-pyrazol-3-yl)-amine;
[6-Methoxy-1-(4-trifluoromethyl-phenyl)-isoquinolin-3-yl]-(1H-pyrazol-3-yl)-amine;
[1-(4-Chloro-phenyl)-6-methoxy-isoquinolin-3-yl]-(1H-pyrazol-3-yl)-amine;
3-[6-Methoxy-3-(1H-pyrazol-3-ylamino)-isoquinolin-1-yl]-benzonitrile;
[6-Methoxy-1-(3-trifluoromethyl-phenyl)-isoquinolin-3-yl]-(1H-pyrazol-3-yl)-amine;
[1-(2,4-Difluoro-phenyl)-6-methoxy-isoquinolin-3-yl]-(1H-pyrazol-3-yl)-amine;
[1-(3,4-Difluoro-phenyl)-6-methoxy-isoquinolin-3-yl]-(1H-pyrazol-3-yl)-amine; and
[1-(3,5-Difluoro-phenyl)-6-methoxy-isoquinolin-3-yl]-(1H-pyrazol-3-yl)-amine.

21. A compound according to claim 1 selected from the group consisting of:
[6-Methoxy-1-(2-methoxy-phenyl)-isoquinolin-3-yl]-(1H-pyrazol-3-yl)-amine;
(6-Methoxy-1-p-tolyl-isoquinolin-3-yl)-(1H-pyrazol-3-yl)-amine;
[1-(3-Fluoro-phenyl)-6-methoxy-isoquinolin-3-yl]-(1H-pyrazol-3-yl)-amine;
(6-Methoxy-1-naphthalen-2-yl-isoquinolin-3-yl)-(1H-pyrazol-3-yl)-amine;
[1-(4-Ethoxy-phenyl)-6-methoxy-isoquinolin-3-yl]-(1H-pyrazol-3-yl)-amine;
(6-Methoxy-1-m-tolyl-isoquinolin-3-yl)-(1H-pyrazol-3-yl)-amine;
[1-(3,4-Dimethoxy-phenyl)-6-methoxy-isoquinolin-3-yl]-(1H-pyrazol-3-yl)-amine;
N-{4-[6-Methoxy-3-(1H-pyrazol-3-ylamino)-isoquinolin-1-yl]-phenyl}-acetamide;
(5-Methyl-1H-pyrazol-3-yl)-[6-(2-morpholin-4-yl-ethoxy)-1-phenyl-isoquinolin-3-yl]-amine; and
[1-(3-Methoxy-phenyl)-6-(2-morpholin-4-yl-ethoxy)-isoquinolin-3-yl]-(5-methyl-1H-pyrazol-3-yl)-amine.

22. A compound according to claim 1 selected from the group consisting of:
[1-(2,4-Difluoro-phenyl)-3-(5-methyl-1H-pyrazol-3-ylamino)-isoquinolin-6-yl]-morpholin-4-yl-methanone;
1-(2,4-Difluoro-phenyl)-3-(5-methyl-1H-pyrazol-3-ylamino)-isoquinoline-6-carboxylic acid (3-methoxy-propyl)-amide;
[1-(2,4-Difluoro-phenyl)-6-(2-methoxy-ethoxy)-isoquinolin-3-yl]-(5-methyl-1H-pyrazol-3-yl)-amine;
3-[5,6-Dimethoxy-3-(5-methyl-1H-pyrazol-3-ylamino)-isoquinolin-1-yl]-benzonitrile;
3-[6,7-Dimethoxy-3-(5-methyl-1H-pyrazol-3-ylamino)-isoquinolin-1-yl]-benzonitrile;
{6-Methoxy-1-[3-(2-morpholin-4-yl-ethoxy)-phenyl]-isoquinolin-3-yl}-(5-methyl-1H-pyrazol-3-yl)-amine;
{5-Methoxy-1-[3-(2-morpholin-4-yl-ethoxy)-phenyl]-isoquinolin-3-yl}-(5-methyl-1H-pyrazol-3-yl)-amine;
[1-(4-Fluoro-phenoxy)-6-isopropoxy-isoquinolin-3-yl]-(5-methyl-1H-pyrazol-3-yl)-amine; and
{1-[3-(2-Dimethylamino-ethoxy)-phenyl]-isoquinolin-3-yl}-(5-methyl-1H-pyrazol-3-yl)-amine.

23. A compounds according to claim 1, wherein:
(a) $R^3$ is heteroaryl which is optionally substituted one or more times with alkyl; and
(b) X is a single bond.

24. A compound according to claim 1 selected from the group consisting of:
(6-Methoxy-1-pyridin-4-yl-isoquinolin-3-yl)-(1H-pyrazol-3-yl)-amine;
(6-Methoxy-1-pyridin-3-yl-isoquinolin-3-yl)-(1H-pyrazol-3-yl)-amine;
[6-Methoxy-1-(1-methyl-1H-pyrazol-4-yl)-isoquinolin-3-yl]-(1H-pyrazol-3-yl)-amine;
(5-Methyl-1H-pyrazol-3-yl)-[1-(4-methyl-thiophen-3-yl)-isoquinolin-3-yl]-amine;
(5-Methyl-1H-pyrazol-3-yl)-(1-thiophen-3-yl-isoquinolin-3-yl)-amine;
(1-Benzo[b]thiophen-3-yl-isoquinolin-3-yl)-(5-methyl-1H-pyrazol-3-yl)-amine;
(5-Methyl-1H-pyrazol-3-yl)-(1-pyridin-3-yl-isoquinolin-3-yl)-amine;
(5-Methyl-1H-pyrazol-3-yl)-(1-pyridin-4-yl-isoquinolin-3-yl)-amine;
(5-Methyl-1H-pyrazol-3-yl)-[1-(1H-pyrazol-4-yl)-isoquinolin-3-yl]-amine; and
(5-Methyl-1H-pyrazol-3-yl)-[1-(1-methyl-1H-pyrazol-4-yl)-isoquinolin-3-yl]-amine.

25. A compound according to claim 1 selected from the group consisting of:
[6-Methoxy-1-(1H-pyrazol-4-yl)-isoquinolin-3-yl]-(1H-pyrazol-3-yl)-amine;
[6-Methoxy-1-(4-methyl-thiophen-3-yl)-isoquinolin-3-yl]-(5-methyl-1H-pyrazol-3-yl)-amine;
(6-Methoxy-1-thiophen-3-yl-isoquinolin-3-yl)-(5-methyl-1H-pyrazol-3-yl)-amine;
(1-Benzo[b]thiophen-3-yl-6-methoxy-isoquinolin-3-yl)-(5-methyl-1H-pyrazol-3-yl)-amine;
N-{4-[6-Methoxy-3-(5-methyl-1H-pyrazol-3-ylamino)-isoquinolin-1-yl]-phenyl}-acetamide;
(6-Methoxy-1-pyridin-3-yl-isoquinolin-3-yl)-(5-methyl-1H-pyrazol-3-yl)-amine;
(6-Methoxy-1-pyridin-4-yl-isoquinolin-3-yl)-(5-methyl-1H-pyrazol-3-yl)-amine;
[6-Methoxy-1-(1H-pyrazol-4-yl)-isoquinolin-3-yl]-(5-methyl-1H-pyrazol-3-yl)-amine;
[6-Methoxy-1-(1-methyl-1H-pyrazol-4-yl)-isoquinolin-3-yl]-(5-methyl-1H-pyrazol-3-yl)-amine; and

[5-Methoxy-1-(1-methyl-1H-pyrazol-4-yl)-isoquinolin-3-yl]-(5-methyl-1H-pyrazol-3-yl)-amine.

26. A compound according to claim 1 selected from the group consisting of:
   (5-Methoxy-1-pyridin-3-yl-isoquinolin-3-yl)-(5-methyl-1H-pyrazol-3-yl)-amine;
   (5-Methoxy-1-thiophen-3-yl-isoquinolin-3-yl)-(5-methyl-1H-pyrazol-3-yl)-amine;
   [7-Methoxy-1-(1-methyl-1H-pyrazol-4-yl)-isoquinolin-3-yl]-(5-methyl-1H-pyrazol-3-yl)-amine;
   (7-Methoxy-1-pyridin-3-yl-isoquinolin-3-yl)-(5-methyl-1H-pyrazol-3-yl)-amine;
   (7-Methoxy-1-thiophen-3-yl-isoquinolin-3-yl)-(5-methyl-1H-pyrazol-3-yl)-amine;
   (1-Benzo[b]thiophen-3-yl-isoquinolin-3-yl)-(1H-pyrazol-3-yl)-amine; and
   (1H-Pyrazol-3-yl)-(1-thiophen-3-yl-isoquinolin-3-yl)-amine.

27. A compound according to claim 1 selected from the group consisting of:
   (1H-Pyrazol-3-yl)-[1-(1H-pyrazol-4-yl)-isoquinolin-3-yl]-amine;
   [1-(1-Methyl-1H-pyrazol-4-yl)-isoquinolin-3-yl]-(1H-pyrazol-3-yl)-amine;
   (1H-Pyrazol-3-yl)-(1-pyridin-3-yl-isoquinolin-3-yl)-amine;
   (1H-Pyrazol-3-yl)-(1-pyridin-4-yl-isoquinolin-3-yl)-amine;
   (6-Methoxy-1-thiophen-3-yl-isoquinolin-3-yl)-(1H-pyrazol-3-yl)-amine;
   [6-Methoxy-1-(4-methyl-thiophen-3-yl)-isoquinolin-3-yl]-(1H-pyrazol-3-yl)-amine; and
   (1-Benzo[b]thiophen-3-yl-6-methoxy-isoquinolin-3-yl)-(1H-pyrazol-3-yl)-amine.

28. A compounds according to claim 1, wherein:
   (a) $R^3$ is alkyl which is substituted one or two times with heteroaryl, phenyl, heterocyclyl or cycloalkyl; and
   (b) X is a single bond.

29. A compound according to claim 1 selected from the group consisting of:
   (6-Methoxy-1-piperidin-1-ylmethyl-isoquinolin-3-yl)-(5-methyl-1H-pyrazol-3-yl)-amine;
   1-[6-Methoxy-3-(5-methyl-1H-pyrazol-3-ylamino)-isoquinolin-1-ylmethyl]-piperidin-2-one;
   3-[6-Methoxy-3-(5-methyl-1H-pyrazol-3-ylamino)-isoquinolin-1-ylmethyl]-oxazolidin-2-one;
   (6-Methoxy-1-pyrazol-1-ylmethyl-isoquinolin-3-yl)-(5-methyl-1H-pyrazol-3-yl)-amine; and
   (1-Benzyl-6-methoxy-isoquinolin-3-yl)-(5-methyl-1H-pyrazol-3-yl)-amine.

30. A compounds according to claim 1, wherein:
   (a) $R^3$ is cycloalkyl; and
   (b) X is a single bond.

31. A compound according to claim 1 selected from the group consisting of:
   (1-Cyclopropyl-6-methoxy-isoquinolin-3-yl)-(5-methyl-1H-pyrazol-3-yl)-amine;
   (1-Cyclohexyl-6-methoxy-isoquinolin-3-yl)-(5-methyl-1H-pyrazol-3-yl)-amine; and
   (1-Cyclopentyl-6-methoxy-isoquinolin-3-yl)-(5-methyl-1H-pyrazol-3-yl)-amine.

32. A compounds according to claim 1, wherein:
   (a) $R^3$ is alkyl which is substituted one time with phenyl; and
   (b) X is —NR—.

33. A compound according to claim 1 selected from the group consisting of:
   $N^1$-Benzyl-$N^3$-(5-methyl-1H-pyrazol-3-yl)-isoquinoline-1,3-diamine; and
   $N^3$-(5-Methyl-1H-pyrazol-3-yl)-$N^1$-((R)-1-phenyl-ethyl)-isoquinoline-1,3-diamine.

34. A compounds according to claim 1, wherein:
   (a) $R^3$ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR$_2$; and
   (b) X is —NR—.

35. A compound according to claim 1 selected from the group consisting of:
   4-[6-Methoxy-3-(5-methyl-1H-pyrazol-3-ylamino)-isoquinolin-1-ylamino]-benzonitrile;
   4-[3-(5-Methyl-1H-pyrazol-3-ylamino)-isoquinolin-1-ylamino]-benzonitrile;
   $N^1$-(4-Bromo-phenyl)-6-methoxy-$N^3$-(5-methyl-1H-pyrazol-3-yl)-isoquinoline-1,3-diamine;
   $N^1$-(4-Chloro-phenyl)-6-methoxy-$N^3$-(5-methyl-1H-pyrazol-3-yl)-isoquinoline-1,3-diamine;
   $N^1$-(4-Fluoro-phenyl)-6-methoxy-$N^3$-(5-methyl-1H-pyrazol-3-yl)-isoquinoline-1,3-diamine;
   4-[6,7-Dimethoxy-3-(5-methyl-1H-pyrazol-3-ylamino)-isoquinolin-1-ylamino]-benzonitrile;
   4-[5,6-Dimethoxy-3-(5-methyl-1H-pyrazol-3-ylamino)-isoquinolin-1-ylamino]-benzonitrile;
   $N^1$-(4-Butoxy-phenyl)-$N^3$-(5-methyl-1H-pyrazol-3-yl)-isoquinoline-1,3-diamine;
   $N^1$-(4-Butoxy-phenyl)-6-methoxy-$N^3$-(5-methyl-1H-pyrazol-3-yl)-isoquinoline-1,3-diamine;
   $N^1$-(4-Butoxy-phenyl)-6-methoxy-$N^3$-(1H-pyrazol-3-yl)-isoquinoline-1,3-diamine; and
   $N^1$-(3,4-Dimethoxy-phenyl)-$N^3$-(1H-pyrazol-3-yl)-isoquinoline-1,3-diamine.

36. A compound according to claim 1 selected from the group consisting of:
   $N^1$-(3,5-Dimethoxy-phenyl)-$N^3$-(1H-pyrazol-3-yl)-isoquinoline-1,3-diamine;
   $N^1$-(3-Ethyl-phenyl)-$N^3$-(5-methyl-1H-pyrazol-3-yl)-isoquinoline-1,3-diamine;
   $N^1$-(3-Ethyl-phenyl)-6-methoxy-$N^3$-(5-methyl-1H-pyrazol-3-yl)-isoquinoline-1,3-diamine;
   $N^1$-(3-Chloro-phenyl)-N-3-(5-methyl-1H-pyrazol-3-yl)-isoquinoline-1,3-diamine;
   $N^1$-(3-Chloro-phenyl)-6-methoxy-$N^3$-(5-methyl-1H-pyrazol-3-yl)-isoquinoline-1,3-diamine;
   $N^1$-(3-Ethyl-phenyl)-6-methoxy-$N^3$-(1H-pyrazol-3-yl)-isoquinoline-1,3-diamine;
   4-[5-Methoxy-3-(5-methyl-1H-pyrazol-3-ylamino)-isoquinolin-1-ylamino]-benzonitrile;
   4-[7-Methoxy-3-(5-methyl-1H-pyrazol-3-ylamino)-isoquinolin-1-ylamino]-benzonitrile;
   $N^3$-(5-Methyl-1H-pyrazol-3-yl)-$N^1$-phenyl-isoquinoline-1,3-diamine; and
   $N^1$-(4-Butoxy-phenyl)-$N^3$-(1H-pyrazol-3-yl)-isoquinoline-1,3-diamine.

37. A compounds according to claim 1, wherein:
   (a) $R^3$ is heteroaryl which is optionally substituted one or more times with alkyl; and
   (b) X is —NR—.

38. A compound according to claim 1 selected from the group consisting of:
   $N^3$-(5-Methyl-1H-pyrazol-3-yl)-$N^1$-pyridin-4-yl-isoquinoline-1,3-diamine;

6-Methoxy-N$^3$-(5-methyl-1H-pyrazol-3-yl)-N$^1$-pyridin-4-yl-isoquinoline-1,3-diamine;

N$^3$-(1H-Pyrazol-3-yl)-N$^1$-pyridin-4-yl-isoquinoline-1,3-diamine;

6-Methoxy-N$^3$-(5-methyl-1H-pyrazol-3-yl)-N$^1$-pyridin-2-yl-isoquinoline-1,3-diamine;

N$^3$-(1H-Pyrazol-3-yl)-N$^1$-pyridin-2-yl-isoquinoline-1,3-diamine;

N$^3$-(5-Methyl-1H-pyrazol-3-yl)-N$^1$-pyridin-3-yl-isoquinoline-1,3-diamine; and 6-Methoxy-N$^3$-(5-methyl-1H-pyrazol-3-yl)-N$^1$-pyridin-3-yl-isoquinoline-1,3-diamine.

39. A compounds according to claim 1, wherein:
(a) R$^3$ is selected from the group consisting of:
(1) alkyl which is substituted one to two times with phenyl, heterocyclyl, or cycloalkyl; and
(2) alkyl wherein one or more —CH$_2$— groups are replaced by oxygen; and
(b) X is —O—.

40. A compound according to claim 1 selected from the group consisting of:
(1-Benzyloxy-isoquinolin-3-yl)-(5-methyl-1H-pyrazol-3-yl)-amine;
{-[2-(2-Ethoxy-ethoxy)-ethoxy]-isoquinolin-3-yl}-(5-methyl-1H-pyrazol-3-yl)-amine;
(5-Methyl-1H-pyrazol-3-yl)-[1-(2-morpholin-4-yl-ethoxy)-isoquinolin-3-yl]-amine;
(5-Methyl-1H-pyrazol-3-yl)-[1-(2-piperidin-1-yl-ethoxy)-isoquinolin-3-yl]-amine;
(1-Benzyloxy-6-methoxy-isoquinolin-3-yl)-(5-methyl-1H-pyrazol-3-yl)-amine;
[6-Methoxy-1-(2-piperidin-1-yl-ethoxy)-isoquinolin-3-yl]-(5-methyl-1H-pyrazol-3-yl)-amine; and
{-[2-(2-Ethoxy-ethoxy)-ethoxy]-6-methoxy-isoquinolin-3-yl}-(5-methyl-1H-pyrazol-3-yl)-amine.

41. A compound according to claim 1 selected from the group consisting of:
[6-Methoxy-1-(2-morpholin-4-yl-ethoxy)-isoquinolin-3-yl]-(5-methyl-1H-pyrazol-3-yl)-amine;
[1-(4-Methoxy-phenoxy)-5-methyl-isoquinolin-3-yl]-(5-methyl-1H-pyrazol-3-yl)-amine;
(5-Methyl-1H-pyrazol-3-yl)-(1,6,7-trimethoxy-isoquinolin-3-yl)-amine;
(5-Methyl-1H-pyrazol-3-yl)-(1,5,6-trimethoxy-isoquinolin-3-yl)-amine;
(1-Benzyloxy-isoquinolin-3-yl)-(1H-pyrazol-3-yl)-amine;
{1-[2-(2-Ethoxy-ethoxy)-ethoxy]-isoquinolin-3-yl}-(1H-pyrazol-3-yl)-amine;
(1-Benzyloxy-6-methoxy-isoquinolin-3-yl)-(1H-pyrazol-3-yl)-amine; and
(1-Cyclopropylmethoxy-6,7-dimethoxy-isoquinolin-3-yl)-(5-methyl-1H-pyrazol-3-yl)-amine.

42. A compounds according to claim 1, wherein:
(a) R$^3$ is unsubstituted alkyl; and
(b) X is —O—.

43. A compound according to claim 1 selected from the group consisting of:
(1-Methoxy-isoquinolin-3-yl)-(5-methyl-1H-pyrazol-3-yl)-amine;
(1-Isobutoxy-isoquinolin-3-yl)-(5-methyl-1H-pyrazol-3-yl)-amine;
(1-Isopropoxy-isoquinolin-3-yl)-(5-methyl-1H-pyrazol-3-yl)-amine;
(1,6-Dimethoxy-isoquinolin-3-yl)-(5-methyl-1H-pyrazol-3-yl)-amine;
(1-Isobutoxy-6-methoxy-isoquinolin-3-yl)-(5-methyl-1H-pyrazol-3-yl)-amine;
(1-Isopropoxy-isoquinolin-3-yl)-(1H-pyrazol-3-yl)-amine;
(1-Isopropoxy-6-methoxy-isoquinolin-3-yl)-(5-methyl-1H-pyrazol-3-yl)-amine;
(1-Isopropoxy-5-methoxy-isoquinolin-3-yl)-(5-methyl-1H-pyrazol-3-yl)-amine;
(1,5-Dimethoxy-isoquinolin-3-yl)-(5-methyl-1H-pyrazol-3-yl)-amine; and
(1-Isopropoxy-7-methoxy-isoquinolin-3-yl)-(5-methyl-1H-pyrazol-3-yl)-amine.

44. A compound according to claim 1 selected from the group consisting of:
(1,7-Dimethoxy-isoquinolin-3-yl)-(5-methyl-1H-pyrazol-3-yl)-amine;
(1-Methoxy-5-methyl-isoquinolin-3-yl)-(5-methyl-1H-pyrazol-3-yl)-amine;
(1-Isopropoxy-6,7-dimethoxy-isoquinolin-3-yl)-(5-methyl-1H-pyrazol-3-yl)-amine;
(1-Ethoxy-6,7-dimethoxy-isoquinolin-3-yl)-(5-methyl-1H-pyrazol-3-yl)-amine;
(1-Isopropoxy-5,6-dimethoxy-isoquinolin-3-yl)-(5-methyl-1H-pyrazol-3-yl)-amine;
(1-Methoxy-isoquinolin-3-yl)-(1H-pyrazol-3-yl)-amine;
(1-Isobutoxy-isoquinolin-3-yl)-(1H-pyrazol-3-yl)-amine;
(1-Isobutoxy-6-methoxy-isoquinolin-3-yl)-(1H-pyrazol-3-yl)-amine;
(1-Isopropoxy-6-methoxy-isoquinolin-3-yl)-(1H-pyrazol-3-yl)-amine; and
(5-Cyclopropyl-1H-pyrazol-3-yl)-(1-ethoxy-6,7-dimethoxy-isoquinolin-3-yl)-amine.

45. A compound according to claim 1 selected from the group consisting of:
(5-Cyclopropyl-1H-pyrazol-3-yl)-(1-isopropoxy-6,7-dimethoxy-isoquinolin-3-yl)-amine;
[1-Isopropoxy-6-(2-methoxy-ethoxy)-isoquinolin-3-yl]-(5-methyl-1H-pyrazol-3-yl)-amine;
[1-Isopropoxy-6-(2-morpholin-4-yl-ethoxy)-isoquinolin-3-yl]-(5-methyl-1H-pyrazol-3-yl)-amine;
(1-Isopropoxy-5-methyl-isoquinolin-3-yl)-(5-methyl-1H-pyrazol-3-yl)-amine;
[1-Isopropoxy-7-methoxy-6-(2-methoxy-ethoxy)-isoquinolin-3-yl]-(5-methyl-1H-pyrazol-3-yl)-amine;
[1-Isopropoxy-7-methoxy-6-(2-morpholin-4-yl-ethoxy)-isoquinolin-3-yl]-(5-methyl-1H-pyrazol-3-yl)-amine;
[1-Isopropoxy-7-methoxy-6-(tetrahydro-pyran-4-yloxy)-isoquinolin-3-yl]-(5-methyl-1H-pyrazol-3-yl)-amine;
1-Isopropoxy-7-methoxy-3-(5-methyl-1H-pyrazol-3-ylamino)-isoquinoline-6-carboxylic acid (3-methoxy-propyl)-amide;
[1-Isopropoxy-7-methoxy-3-(5-methyl-1H-pyrazol-3-ylamino)-isoquinolin-6-yl]-morpholin-4-yl-methanone; and
1-Isopropoxy-7-methoxy-3-(5-methyl-1H-pyrazol-3-ylamino)-isoquinoline-6-carboxylic acid dimethylamide.

46. A compound according to claim 1 selected from the group consisting of:
(8-Isopropoxy-2,3-dihydro-1,4-dioxa-7-aza-phenanthren-6-yl)-(5-methyl-1H-pyrazol-3-yl)-amine;
[1,6-Diethoxy-7-(2-methoxy-ethoxy)-isoquinolin-3-yl]-(5-methyl-1H-pyrazol-3-yl)-amine;
[1,6-Diisopropoxy-7-(2-methoxy-ethoxy)-isoquinolin-3-yl]-(5-methyl-1H-pyrazol-3-yl)-amine;

[1-Isopropoxy-7-(2-methoxy-ethoxy)-6-(tetrahydro-furan-3-yloxy)-isoquinolin-3-yl]-(5-methyl-1H-pyrazol-3-yl)-amine;
3-[1-Isopropoxy-7-(2-methoxy-ethoxy)-3-(5-methyl-1H-pyrazol-3-ylamino)-isoquinolin-6-yloxy]-propane-1,2-diol;
[1-Isopropoxy-3-(5-methyl-1H-pyrazol-3-ylamino)-isoquinolin-6-yl]-morpholin-4-yl-methanone;
1-Isopropoxy-3-(5-methyl-1H-pyrazol-3-ylamino)-isoquinoline-6-carboxylic acid dimethylamide;
1-Isopropoxy-3-(5-methyl-1H-pyrazol-3-ylamino)-isoquinoline-6-carboxylic acid (3-methoxy-propyl)-amide; and
1-Isopropoxy-3-(5-methyl-1H-pyrazol-3-ylamino)-isoquinoline-6-carboxylic acid (3-dimethylamino-propyl)-methyl-amide.

47. A compound according to claim 1 selected from the group consisting of:
[1-Isopropoxy-3-(5-methyl-1H-pyrazol-3-ylamino)-isoquinolin-6-yl]-piperidin-1-yl-methanone;
[1-Isopropoxy-6-(4-methyl-piperazin-1-yl)-isoquinolin-3-yl]-(5-methyl-1H-pyrazol-3-yl)-amine;
(1-Isopropoxy-6-morpholin-4-yl-isoquinolin-3-yl)-(5-methyl-1H-pyrazol-3-yl)-amine;
(1-Isopropoxy-6-piperidin-1-yl-isoquinolin-3-yl)-(5-methyl-1H-pyrazol-3-yl)-amine;
(1-Isopropoxy-6-pyrrolidin-1-yl-isoquinolin-3-yl)-(5-methyl-1H-pyrazol-3-yl)-amine;
[1-Isopropoxy-6-(4-methyl-piperazin-1-ylmethyl)-isoquinolin-3-yl]-(5-methyl-1H-pyrazol-3-yl)-amine;
(S)-1-[1-Isopropoxy-3-(5-methyl-1H-pyrazol-3-ylamino)-isoquinolin-6-ylmethyl]-pyrrolidine-2-carboxylic acid amide;
(1-Isopropoxy-6-methoxy-5-methyl-isoquinolin-3-yl)-(5-methyl-1H-pyrazol-3-yl)-amine;
(7-Fluoro-1-isopropoxy-6-methoxy-isoquinolin-3-yl)-(5-methyl-1H-pyrazol-3-yl)-amine; and
(5-Cyclopropyl-1H-pyrazol-3-yl)-(7-fluoro-1-isopropoxy-6-methoxy-isoquinolin-3-yl)-amine.

48. A compound according to claim 1 selected from the group consisting of:
[1-Isopropoxy-6-methoxy-7-(2-morpholin-4-yl-ethoxy)-isoquinolin-3-yl]-(5-methyl-1H-pyrazol-3-yl)-amine;
(7-Fluoro-1-isopropoxy-6-morpholin-4-yl-isoquinolin-3-yl)-(5-methyl-1H-pyrazol-3-yl)-amine;
1-[7-Fluoro-1-isopropoxy-3-(5-methyl-1H-pyrazol-3-ylamino)-isoquinolin-6-yl]-pyrrolidin-2-one;
(5-Chloro-1-isopropoxy-6,7-dimethoxy-isoquinolin-3-yl)-(5-methyl-1H-pyrazol-3-yl)-amine;
(5-Chloro-1,6-diisopropoxy-7-methoxy-isoquinolin-3-yl)-(5-methyl-1H-pyrazol-3-yl)-amine;
(6-Bromo-1-isopropoxy-isoquinolin-3-yl)-(5-methyl-1H-pyrazol-3-yl)-amine;
1-Isopropoxy-3-(5-methyl-1H-pyrazol-3-ylamino)-isoquinoline-6-carboxylic acid diethylamide;
1-Isopropoxy-3-(5-methyl-1H-pyrazol-3-ylamino)-isoquinoline-6-carboxylic acid isopropylamide;
1-Isopropoxy-3-(5-methyl-1H-pyrazol-3-ylamino)-isoquinoline-6-carboxylic acid cyclohexyl-methyl-amide; and
[1-Isopropoxy-3-(5-methyl-1H-pyrazol-3-ylamino)-isoquinolin-6-yl]-(4-methyl-piperazin-1-yl)-methanone.

49. A compound according to claim 1 selected from the group consisting of:
1-Isopropoxy-3-(5-methyl-1H-pyrazol-3-ylamino)-isoquinoline-6-carboxylic acid methyl-(2-piperidin-1-yl-ethyl)-amide;
1-{4-[1-Isopropoxy-3-(5-methyl-1H-pyrazol-3-ylamino)-isoquinoline-6-carbonyl]-piperazin-1-yl}-ethanone;
1-Isopropoxy-3-(5-methyl-1H-pyrazol-3-ylamino)-isoquinoline-6-carboxylic acid methyl-(3-piperidin-1-yl-propyl)-amide;
[1-Isopropoxy-3-(5-methyl-1H-pyrazol-3-ylamino)-isoquinolin-6-yl]-(4-methanesulfonyl-piperazin-1-yl)-methanone;
1-Isopropoxy-3-(5-methyl-1H-pyrazol-3-ylamino)-isoquinoline-6-carboxylic acid methyl-(tetrahydro-pyran-2-ylmethyl)-amide;
(3,5-Dimethyl-piperazin-1-yl)-[1-isopropoxy-3-(5-methyl-1H-pyrazol-3-ylamino)-isoquinolin-6-yl]-methanone;
[1-Isopropoxy-3-(5-methyl-1H-pyrazol-3-ylamino)-isoquinolin-6-yl]-[4-(2-methoxy-ethyl)-piperazin-1-yl]-methanone;
[1-Isopropoxy-3-(5-methyl-1H-pyrazol-3-ylamino)-isoquinolin-6-yl]-(4-methoxy-piperidin-1-yl)-methanone;
(4-Hydroxy-piperidin-1-yl)-[1-isopropoxy-3-(5-methyl-1H-pyrazol-3-ylamino)-isoquinolin-6-yl]-methanone; and
[1-Isopropoxy-3-(5-methyl-1H-pyrazol-3-ylamino)-isoquinolin-6-yl]-pyrrolidin-1-yl-methanone.

50. A compound according to claim 1 selected from the group consisting of:
(7-Bromo-1-isopropoxy-6-methoxy-isoquinolin-3-yl)-(5-methyl-1H-pyrazol-3-yl)-amine;
(7-Bromo-1-isopropoxy-isoquinolin-3-yl)-(5-methyl-1H-pyrazol-3-yl)-amine;
[1-Isopropoxy-6-methoxy-7-(2-methoxy-ethoxy)-isoquinolin-3-yl]-(5-methyl-1H-pyrazol-3-yl)-amine;
[1-Isopropoxy-6,7-bis-(2-methoxy-ethoxy)-isoquinolin-3-yl]-(5-methyl-1H-pyrazol-3-yl)-amine;
(1-Isopropoxy-6,8-dimethoxy-isoquinolin-3-yl)-(5-methyl-1H-pyrazol-3-yl)-amine;
1-Isopropoxy-6-methoxy-3-(5-methyl-1H-pyrazol-3-ylamino)-isoquinoline-7-carboxylic acid dimethylamide;
1-Isopropoxy-6-methoxy-3-(5-methyl-1H-pyrazol-3-ylamino)-isoquinoline-7-carbonitrile;
[1-Isopropoxy-6-methoxy-7-(2-piperidin-1-yl-ethoxy)-isoquinolin-3-yl]-(5-methyl-1H-pyrazol-3-yl)-amine; and
1-[1-Isopropoxy-3-(5-methyl-1H-pyrazol-3-ylamino)-isoquinolin-6-yl]-pyrrolidin-2-one.

51. A compounds according to claim 1, wherein:
(a) $R^3$ is aryl which is optionally substituted one or more times with halogen, alkyl, halogenated alkyl, halogenated alkoxy, cyano, —C(O)-alkyl, —NH—C(O)-alkyl, —C(O)OH, —C(O)O-alkyl, unsubstituted alkoxy, alkoxy substituted by heterocyclyl, or —NR$_2$; and
(b) X is —O—.

52. A compound according to claim 1 selected from the group consisting of:
[1-(4-Methoxy-phenoxy)-isoquinolin-3-yl]-(5-methyl-1H-pyrazol-3-yl)-amine;
(5-Methyl-1H-pyrazol-3-yl)-(1-phenoxy-isoquinolin-3-yl)-amine;
[1-(4-Fluoro-phenoxy)-isoquinolin-3-yl]-(5-methyl-1H-pyrazol-3-yl)-amine;
(5-Methyl-1H-pyrazol-3-yl)-(1-p-tolyloxy-isoquinolin-3-yl)-amine;
4-[3-(5-Methyl-1H-pyrazol-3-ylamino)-isoquinolin-1-yloxy]-benzonitrile;
[1-(4-Chloro-phenoxy)-isoquinolin-3-yl]-(5-methyl-1H-pyrazol-3-yl)-amine;

(5-Methyl-1H-pyrazol-3-yl)-(1-m-tolyloxy-isoquinolin-3-yl)-amine;
[1-(3-Fluoro-phenoxy)-isoquinolin-3-yl]-(5-methyl-1H-pyrazol-3-yl)-amine;
[1-(3-Chloro-phenoxy)-isoquinolin-3-yl]-(5-methyl-1H-pyrazol-3-yl)-amine; and
[1-(3-Methoxy-phenoxy)-isoquinolin-3-yl]-(5-methyl-1H-pyrazol-3-yl)-amine.

53. A compound according to claim 1 selected from the group consisting of:
(5-Methyl-1H-pyrazol-3-yl)-(1-o-tolyloxy-isoquinolin-3-yl)-amine;
[1-(2-Fluoro-phenoxy)-isoquinolin-3-yl]-(5-methyl-1H-pyrazol-3-yl)-amine;
[1-(2-Chloro-phenoxy)-isoquinolin-3-yl]-(5-methyl-1H-pyrazol-3-yl)-amine;
[1-(2-Methoxy-phenoxy)-isoquinolin-3-yl]-(5-methyl-1H-pyrazol-3-yl)-amine;
3-[3-(5-Methyl-1H-pyrazol-3-ylamino)-isoquinolin-1-yloxy]-benzonitrile;
(5-Methyl-1H-pyrazol-3-yl)-[1-(3-trifluoromethyl-phenoxy)-isoquinolin-3-yl]-amine;
[6-Methoxy-1-(4-methoxy-phenoxy)-isoquinolin-3-yl]-(5-methyl-1H-pyrazol-3-yl)-amine;
(6-Methoxy-1-phenoxy-isoquinolin-3-yl)-(5-methyl-1H-pyrazol-3-yl)-amine;
[1-(4-Fluoro-phenoxy)-6-methoxy-isoquinolin-3-yl]-(5-methyl-1H-pyrazol-3-yl)-amine; and
(6-Methoxy-1-p-tolyloxy-isoquinolin-3-yl)-(5-methyl-1H-pyrazol-3-yl)-amine.

54. A compound according to claim 1 selected from the group consisting of:
4-[6-Methoxy-3-(5-methyl-1H-pyrazol-3-ylamino)-isoquinolin-1-yloxy]-benzonitrile;
[1-(4-Chloro-phenoxy)-6-methoxy-isoquinolin-3-yl]-(5-methyl-1H-pyrazol-3-yl)-amine;
(6-Methoxy-1-m-tolyloxy-isoquinolin-3-yl)-(5-methyl-1H-pyrazol-3-yl)-amine;
[1-(3-Fluoro-phenoxy)-6-methoxy-isoquinolin-3-yl]-(5-methyl-1H-pyrazol-3-yl)-amine;
[1-(3-Chloro-phenoxy)-6-methoxy-isoquinolin-3-yl]-(5-methyl-1H-pyrazol-3-yl)-amine;
[6-Methoxy-1-(3-methoxy-phenoxy)-isoquinolin-3-yl]-(5-methyl-1H-pyrazol-3-yl)-amine;
(6-Methoxy-1-o-tolyloxy-isoquinolin-3-yl)-(5-methyl-1H-pyrazol-3-yl)-amine;
[1-(2-Fluoro-phenoxy)-6-methoxy-isoquinolin-3-yl]-(5-methyl-1H-pyrazol-3-yl)-amine;
[1-(2-Chloro-phenoxy)-6-methoxy-isoquinolin-3-yl]-(5-methyl-1H-pyrazol-3-yl)-amine; and
[1-(4-Methoxy-phenoxy)-isoquinolin-3-yl]-(1H-pyrazol-3-yl)-amine.

55. A compound according to claim 1 selected from the group consisting of:
N-{4-[6-Methoxy-3-(5-methyl-1H-pyrazol-3-ylamino)-isoquinolin-1-yloxy]-phenyl}-acetamide;
N-{4-[3-(5-Methyl-1H-pyrazol-3-ylamino)-isoquinolin-1-yloxy]-phenyl}-acetamide;
N-{4-[5-Methoxy-3-(5-methyl-1H-pyrazol-3-ylamino)-isoquinolin-1-yloxy]-phenyl}-acetamide;
N-{4-[7-Methoxy-3-(5-methyl-1H-pyrazol-3-ylamino)-isoquinolin-1-yloxy]-phenyl}-acetamide;
[5-Methoxy-1-(4-methoxy-phenoxy)-isoquinolin-3-yl]-(5-methyl-1H-pyrazol-3-yl)-amine;
(5-Methoxy-1-phenoxy-isoquinolin-3-yl)-(5-methyl-1H-pyrazol-3-yl)-amine;
[1-(4-Fluoro-phenoxy)-5-methoxy-isoquinolin-3-yl]-(5-methyl-1H-pyrazol-3-yl)-amine;
(5-Methoxy-1-p-tolyloxy-isoquinolin-3-yl)-(5-methyl-1H-pyrazol-3-yl)-amine;
4-[5-Methoxy-3-(5-methyl-1H-pyrazol-3-ylamino)-isoquinolin-1-yloxy]-benzonitrile; and
[1-(4-Chloro-phenoxy)-5-methoxy-isoquinolin-3-yl]-(5-methyl-1H-pyrazol-3-yl)-amine.

56. A compound according to claim 1 selected from the group consisting of:
[7-Methoxy-1-(4-methoxy-phenoxy)-isoquinolin-3-yl]-(5-methyl-1H-pyrazol-3-yl)-amine;
(7-Methoxy-1-phenoxy-isoquinolin-3-yl)-(5-methyl-1H-pyrazol-3-yl)-amine;
[1-(4-Fluoro-phenoxy)-7-methoxy-isoquinolin-3-yl]-(5-methyl-1H-pyrazol-3-yl)-amine;
N-{4-[6-Methoxy-3-(1H-pyrazol-3-ylamino)-isoquinolin-1-yloxy]-phenyl}-acetamide;
4-[7-Methoxy-3-(5-methyl-1H-pyrazol-3-ylamino)-isoquinolin-1-yloxy]-benzonitrile;
[1-(4-Chloro-phenoxy)-7-methoxy-isoquinolin-3-yl]-(5-methyl-1H-pyrazol-3-yl)-amine;
(5-Methyl-1-phenoxy-isoquinolin-3-yl)-(5-methyl-1H-pyrazol-3-yl)-amine;
[1-(4-Fluoro-phenoxy)-5-methyl-isoquinolin-3-yl]-(5-methyl-1H-pyrazol-3-yl)-amine;
(5-Methyl-1H-pyrazol-3-yl)-(5-methyl-1-p-tolyloxy-isoquinolin-3-yl)-amine; and
[1-(4-Chloro-phenoxy)-5-methyl-isoquinolin-3-yl]-(5-methyl-1H-pyrazol-3-yl)-amine.

57. A compound according to claim 1 selected from the group consisting of:
(6,7-Dimethoxy-1-phenoxy-isoquinolin-3-yl)-(5-methyl-1H-pyrazol-3-yl)-amine;
[1-(4-Fluoro-phenoxy)-6,7-dimethoxy-isoquinolin-3-yl]-(5-methyl-1H-pyrazol-3-yl)-amine;
N-{4-[3-(1H-Pyrazol-3-ylamino)-isoquinolin-1-yloxy]-phenyl}-acetamide;
N-{4-[6,7-Dimethoxy-3-(5-methyl-1H-pyrazol-3-ylamino)-isoquinolin-1-yloxy]-phenyl}-acetamide;
(5,6-Dimethoxy-1-phenoxy-isoquinolin-3-yl)-(5-methyl-1H-pyrazol-3-yl)-amine;
[1-(4-Fluoro-phenoxy)-5,6-dimethoxy-isoquinolin-3-yl]-(5-methyl-1H-pyrazol-3-yl)-amine;
4-[5,6-Dimethoxy-3-(5-methyl-1H-pyrazol-3-ylamino)-isoquinolin-1-yloxy]-benzonitrile;
[1-(4-Chloro-phenoxy)-5,6-dimethoxy-isoquinolin-3-yl]-(5-methyl-1H-pyrazol-3-yl)-amine;
N-{4-[5,6-Dimethoxy-3-(5-methyl-1H-pyrazol-3-ylamino)-isoquinolin-1-yloxy]-phenyl}-acetamide; and
(1H-Pyrazol-3-yl)-(1-m-tolyloxy-isoquinolin-3-yl)-amine.

58. A compound according to claim 1 selected from the group consisting of:
(1H-Pyrazol-3-yl)-(1-p-tolyloxy-isoquinolin-3-yl)-amine;
(1H-Pyrazol-3-yl)-(1-o-tolyloxy-isoquinolin-3-yl)-amine;
[1-(3-Methoxy-phenoxy)-isoquinolin-3-yl]-(1H-pyrazol-3-yl)-amine;
[1-(2-Methoxy-phenoxy)-isoquinolin-3-yl]-(1H-pyrazol-3-yl)-amine;
[1-(2-Fluoro-phenoxy)-isoquinolin-3-yl]-(H-pyrazol-3-yl)-amine;
[1-(3-Fluoro-phenoxy)-isoquinolin-3-yl]-(1H-pyrazol-3-yl)-amine;

3-[3-(1H-Pyrazol-3-ylamino)-isoquinolin-1-yloxy]-benzonitrile;
4-[3-(1H-Pyrazol-3-ylamino)-isoquinolin-1-yloxy]-benzonitrile;
[1-(4-Chloro-phenoxy)-isoquinolin-3-yl]-(1H-pyrazol-3-yl)-amine; and
[1-(3-Chloro-phenoxy)-isoquinolin-3-yl]-(1H-pyrazol-3-yl)-amine.

59. A compound according to claim 1 selected from the group consisting of:
[1-(2-Chloro-phenoxy)-isoquinolin-3-yl]-(1H-pyrazol-3-yl)-amine;
(1-Phenoxy-isoquinolin-3-yl)-(1H-pyrazol-3-yl)-amine;
[1-(4-Fluoro-phenoxy)-isoquinolin-3-yl]-(1H-pyrazol-3-yl)-amine;
(6-Methoxy-1-phenoxy-isoquinolin-3-yl)-(1H-pyrazol-3-yl)-amine;
[1-(4-Fluoro-phenoxy)-6-methoxy-isoquinolin-3-yl]-(1H-pyrazol-3-yl)-amine;
[1-(3-Fluoro-phenoxy)-6-methoxy-isoquinolin-3-yl]-(1H-pyrazol-3-yl)-amine;
[1-(2-Fluoro-phenoxy)-6-methoxy-isoquinolin-3-yl]-(1H-pyrazol-3-yl)-amine; and
(6-Methoxy-1-p-tolyloxy-isoquinolin-3-yl)-(1H-pyrazol-3-yl)-amine.

60. A compound according to claim 1 selected from the group consisting of:
(6-Methoxy-1-m-tolyloxy-isoquinolin-3-yl)-(1H-pyrazol-3-yl)-amine;
[6-Methoxy-1-(4-methoxy-phenoxy)-isoquinolin-3-yl]-(1H-pyrazol-3-yl)-amine;
[6-Methoxy-1-(3-methoxy-phenoxy)-isoquinolin-3-yl]-(1H-pyrazol-3-yl)-amine;
[1-(4-Chloro-phenoxy)-6-methoxy-isoquinolin-3-yl]-(1H-pyrazol-3-yl)-amine;
[1-(3-Chloro-phenoxy)-6-methoxy-isoquinolin-3-yl]-(1H-pyrazol-3-yl)-amine;
[1-(4-Fluoro-phenoxy)-3-(5-methyl-1H-pyrazol-3-ylamino)-isoquinolin-6-yl]-morpholin-4-yl-methanone; and
[1-(4-Fluoro-phenoxy)-6,8-dimethoxy-isoquinolin-3-yl]-(5-methyl-1H-pyrazol-3-yl)-amine.

61. A compounds according to claim 1, wherein $R^3$ is cycloalkyl and X is —O—.

62. A compound according to claim 1 selected from the group consisting of:
(1-Cyclohexyloxy-isoquinolin-3-yl)-(5-methyl-1H-pyrazol-3-yl)-amine;
(1-Cyclohexyloxy-6-methoxy-isoquinolin-3-yl)-(5-methyl-1H-pyrazol-3-yl)-amine;
(1-Cyclopentyloxy-6,7-dimethoxy-isoquinolin-3-yl)-(5-methyl-1H-pyrazol-3-yl)-amine;
(1-Cyclobutoxy-6,7-dimethoxy-isoquinolin-3-yl)-(5-methyl-1H-pyrazol-3-yl)-amine;
(1-Cyclobutoxy-6,7-dimethoxy-isoquinolin-3-yl)-(5-cyclopropyl-1H-pyrazol-3-yl)-amine;
[1-Cyclobutoxy-6-methoxy-7-(2-methoxy-ethoxy)-isoquinolin-3-yl]-(5-methyl-1H-pyrazol-3-yl)-amine;
1-Cyclobutoxy-6-methoxy-3-(5-methyl-1H-pyrazol-3-ylamino)-isoquinoline-7-carboxylic acid dimethylamide;
1-Cyclopentyloxy-6-methoxy-3-(5-methyl-1H-pyrazol-3-ylamino)-isoquinoline-7-carboxylic acid dimethylamide; and
1-Cyclobutoxy-6-methoxy-isoquinolin-3-yl)-(5-methyl-1H-pyrazol-3-yl)-amine.

63. A compounds according to claim 1, wherein $R^3$ is heterocyclyl and X is —O—.

64. A compound according to claim 1 selected from the group consisting of:
{6,7-Dimethoxy-1-[(R)-(tetrahydro-furan-3-yl)oxy]-isoquinolin-3-yl}-(5-methyl-1H-pyrazol-3-yl)-amine;
{6,7-Dimethoxy-1-[(S)-(tetrahydro-furan-3-yl)oxy]-isoquinolin-3-yl}-(5-methyl-1H-pyrazol-3-yl)-amine;
[6,7-Dimethoxy-1-(tetrahydro-furan-3-yloxy)-isoquinolin-3-yl]-(5-methyl-1H-pyrazol-3-yl)-amine;
[6-Methoxy-7-(2-methoxy-ethoxy)-1-(tetrahydro-furan-3-yloxy)-isoquinolin-3-yl]-(5-methyl-1H-pyrazol-3-yl)-amine;
[6-Methoxy-7-(2-methoxy-ethoxy)-1-(oxetan-3-yloxy)-isoquinolin-3-yl]-(5-methyl-1H-pyrazol-3-yl)-amine; and
6-Methoxy-3-(5-methyl-1H-pyrazol-3-ylamino)-1-(tetrahydro-furan-3-yloxy)-isoquinoline-7-carbonitrile.

65. A compounds according to claim 1, wherein:
(a) $R^3$ is selected from the group consisting of:
(1) alkyl which is substituted one time with —C(O)O-alkyl; and
(2) aryl which is optionally substituted one or more times with halogen, alkyl or unsubstituted alkoxy; and
(b) X is —S—.

66. A compound according to claim 1 selected from the group consisting of:
(5-Methyl-1H-pyrazol-3-yl)-(1-phenylsulfanyl-isoquinolin-3-yl)-amine;
[1-(3-Methoxy-phenylsulfanyl)-isoquinolin-3-yl]-(5-methyl-1H-pyrazol-3-yl)-amine;
[6-Methoxy-1-(3-methoxy-phenylsulfanyl)-isoquinolin-3-yl]-(5-methyl-1H-pyrazol-3-yl)-amine;
[1-(4-Chloro-phenylsulfanyl)-isoquinolin-3-yl]-(5-methyl-1H-pyrazol-3-yl)-amine;
[1-(4-Chloro-phenylsulfanyl)-6-methoxy-isoquinolin-3-yl]-(5-methyl-1H-pyrazol-3-yl)-amine;
[1-(3-Fluoro-phenylsulfanyl)-isoquinolin-3-yl]-(5-methyl-1H-pyrazol-3-yl)-amine;
[1-(3-Fluoro-phenylsulfanyl)-6-methoxy-isoquinolin-3-yl]-(5-methyl-1H-pyrazol-3-yl)-amine;
[1-(4-Fluoro-phenylsulfanyl)-isoquinolin-3-yl]-(5-methyl-1H-pyrazol-3-yl)-amine;
[1-(4-Fluoro-phenylsulfanyl)-6-methoxy-isoquinolin-3-yl]-(5-methyl-1H-pyrazol-3-yl)-amine;
[1-(2-Fluoro-phenylsulfanyl)-isoquinolin-3-yl]-(5-methyl-1H-pyrazol-3-yl)-amine; and
[1-(2-Fluoro-phenylsulfanyl)-6-methoxy-isoquinolin-3-yl]-(5-methyl-1H-pyrazol-3-yl)-amine.

67. A compound according to claim 1 selected from the group consisting of:
(6-Methoxy-1-phenylsulfanyl-isoquinolin-3-yl)-(5-methyl-1H-pyrazol-3-yl)-amine;
(5-Methyl-1H-pyrazol-3-yl)-(1-p-tolylsulfanyl-isoquinolin-3-yl)-amine;
(6-Methoxy-1-p-tolylsulfanyl-isoquinolin-3-yl)-(5-methyl-1H-pyrazol-3-yl)-amine;
(5-Methyl-1H-pyrazol-3-yl)-(1-m-tolylsulfanyl-isoquinolin-3-yl)-amine;
(6-Methoxy-1-m-tolylsulfanyl-isoquinolin-3-yl)-(5-methyl-1H-pyrazol-3-yl)-amine;
[1-(3-Chloro-phenylsulfanyl)-isoquinolin-3-yl]-(5-methyl-1H-pyrazol-3-yl)-amine;
[1-(3-Chloro-phenylsulfanyl)-6-methoxy-isoquinolin-3-yl]-(5-methyl-1H-pyrazol-3-yl)-amine;
[1-(2-Chloro-phenylsulfanyl)-isoquinolin-3-yl]-(5-methyl-1H-pyrazol-3-yl)-amine;

[1-(2-Chloro-phenylsulfanyl)-6-methoxy-isoquinolin-3-yl]-(5-methyl-1H-pyrazol-3-yl)-amine; and

[3-(5-Methyl-1H-pyrazol-3-ylamino)-isoquinolin-1-ylsulfanyl]-acetic acid ethyl ester.

68. A compounds according to claim 1, wherein $R^3$ is heterocyclyl and X is —C(O)—.

69. A compound according to claim 1 selected from the group consisting of:

[6-Methoxy-3-(5-methyl-1H-pyrazol-3-ylamino)-isoquinolin-1-yl]-morpholin-4-yl-methanone;

1-{4-[6-Methoxy-3-(5-methyl-1H-pyrazol-3-ylamino)-isoquinoline-1-carbonyl]-piperazin-1-yl}-ethanone; and

[6-Methoxy-3-(5-methyl-1H-pyrazol-3-ylamino)-isoquinolin-1-yl]-piperidin-1-yl-methanone.

70. A compounds according to claim 1, wherein:
(a) $R^3$ is selected from the group consisting of:
  (1) unsubstituted alkyl,
  (2) alkyl which is substituted one or two times with phenyl or cycloalkyl,
  (3) aryl, or
  (4) cycloalkyl; and
(b) X is —C(O)NR—.

71. A compounds according to claim 1 selected from the group consisting of:

6-Methoxy-3-(5-methyl-1H-pyrazol-3-ylamino)-isoquinoline-1-carboxylic acid cyclopropylmethyl-amide;

6-Methoxy-3-(5-methyl-1H-pyrazol-3-ylamino)-isoquinoline-1-carboxylic acid dimethylamide;

6-Methoxy-3-(5-methyl-1H-pyrazol-3-ylamino)-isoquinoline-1-carboxylic acid phenylamide;

6-Methoxy-3-(5-methyl-1H-pyrazol-3-ylamino)-isoquinoline-1-carboxylic acid cyclohexylamide;

6-Methoxy-3-(5-methyl-1H-pyrazol-3-ylamino)-isoquinoline-1-carboxylic acid benzylamide; and 6-Methoxy-3-(5-methyl-1H-pyrazol-3-ylamino)-isoquinoline-1-carboxylic acid cyclopropylamide.

72. A process for the preparation of a compound according to claim 1, comprising the step of:

reacting a compound of formula II:

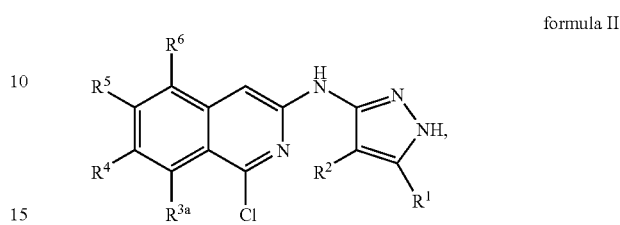

formula II wherein $R^1$, $R^2$, $R^4$, $R^5$ and $R^1$ are defined according to formula I in claim 1;

with a compound of formula III:

formula III wherein $R^3$ has the significance given above for formula I in claim 1 and X is a single bond, —NR—, —O— or —S—.

73. A pharmaceutical composition comprising a therapeutically effective amount of a compound of claim 1 and a pharmaceutically acceptable carrier.

74. A method of treating cancer comprising administering to a person in need thereof a therapeutically effective amount of a compound of claim 1 wherein the cancer is colon cancer.

* * * * *